(12) United States Patent
Kobayashi

(10) Patent No.: US 8,470,199 B2
(45) Date of Patent: Jun. 25, 2013

(54) FIVE-RING LIQUID CRYSTAL COMPOUND, LIQUID CRYSTAL COMPOSITION AND LIQUID CRYSTAL DISPLAY DEVICE

(75) Inventor: Masahide Kobayashi, Chiba (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 0 days.

(21) Appl. No.: 13/376,383

(22) PCT Filed: Jun. 2, 2010

(86) PCT No.: PCT/JP2010/059346
§ 371 (c)(1),
(2), (4) Date: Dec. 6, 2011

(87) PCT Pub. No.: WO2010/146992
PCT Pub. Date: Dec. 23, 2010

(65) Prior Publication Data
US 2012/0074355 A1  Mar. 29, 2012

(30) Foreign Application Priority Data
Jun. 15, 2009  (JP) .................... 2009-142305

(51) Int. Cl.
C09K 19/00 (2006.01)
C09K 19/06 (2006.01)
C09K 19/34 (2006.01)
C09K 19/52 (2006.01)
C07C 22/00 (2006.01)

(52) U.S. Cl.
USPC ............. 252/299.63; 252/299.01; 252/299.6; 428/1.1; 428/1.3; 570/101; 570/123; 570/124; 570/127; 570/129; 349/1; 349/182

(58) Field of Classification Search
USPC ............. 252/299.01, 299.6, 299.63; 428/1.1, 428/1.3; 570/101, 123, 124, 127, 129; 349/1, 349/182
See application file for complete search history.

(56) References Cited

U.S. PATENT DOCUMENTS
5,310,501 A  5/1994  Huynh-Ba et al.
5,576,867 A  11/1996  Baur et al.

FOREIGN PATENT DOCUMENTS
| CN | 1434331 | 8/2003 |
| JP | 2002-193853 | 7/2002 |
| WO | 91/02779 | 3/1991 |
| WO | 91/10936 | 7/1991 |
| WO | 2008/090780 | 7/2008 |
| WO | 2009/031437 | 3/2009 |

Primary Examiner — Geraldina Visconti
(74) Attorney, Agent, or Firm — Jianq Chyun IP Office

(57) ABSTRACT

The invention provides a liquid crystal compound having a high stability to heat, light or the like, a nematic phase in a wide temperature range, a small viscosity, a suitable optical anisotropy (especially, a relatively small optical anisotropy), a large elastic constant $K_{33}$ and a suitable dielectric anisotropy (especially, a relatively large dielectric anisotropy), which is represented by formula (1-1).

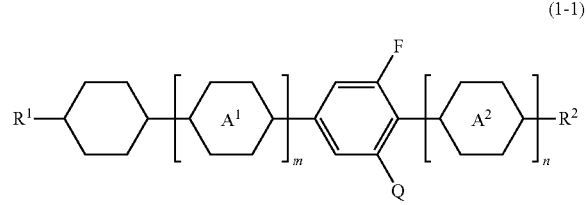

(1-1)

For example, $R^1$ and $R^2$ are alkyl having 1 to 10 carbons, alkenyl having 2 to 10 carbons or alkoxy having 1 to 9 carbons; the ring $A^1$ and the ring $A^2$ is 1,4-phenylene, 2-fluoro-1,4-phenylene, 3-fluoro-1,4-phenylene or 3,5-difluoro-1,4-phenylene; and m and n are 0, 1, 2 or 3, and the sum of m and n is 3.

8 Claims, No Drawings

FIVE-RING LIQUID CRYSTAL COMPOUND, LIQUID CRYSTAL COMPOSITION AND LIQUID CRYSTAL DISPLAY DEVICE

CROSS-REFERENCE TO RELATED APPLICATION

This application is a 371 of international application of PCT application serial no. PCT/JP2010/059364, filed on Jun. 2, 2010, which claims the priority benefit of Japan application no. 2009-142305, filed on Jun. 15, 2009. The entirety of each of the above-mentioned patent applications is hereby incorporated by reference herein and made a part of this specification.

TECHNICAL FIELD

The invention relates to a new liquid crystal compound that is useful as a material for use in a liquid crystal display device, and a liquid crystal composition including this compound. More specifically, the invention relates to a liquid crystal compound that has a small viscosity and an excellent compatibility with other liquid crystal compounds and further has a suitable refractive index anisotropy and dielectric anisotropy, and that gives steep electro-optic characteristics when it is used for a liquid crystal display device, and relates to a liquid crystal composition including this compound and a liquid crystal display device containing the liquid crystal composition.

TECHNICAL BACKGROUND

A display device utilizing a liquid crystal compound (in this patent application, a liquid crystal compound is used as a generic term for a compound that exhibits a liquid crystal phase and a compound that exhibits no liquid crystal phases but useful as a component of a liquid crystal composition) has been widely used for the display of a watch, a calculator, a word processor or the like. The display device utilizes the refractive index anisotropy, the dielectric anisotropy and so forth of the liquid crystal compound.

A liquid crystal phase includes a nematic liquid crystal phase, a smectic liquid crystal phase and a cholestric liquid crystal phase, and the nematic liquid crystal phase is most widely applied. A display mode includes a DS (dynamic scattering) mode, a DAP (deformation of aligned phases) mode, a GH (guest-host) mode, a TN (twisted nematic) mode, a STN (super twisted nematic) mode, a TFT (thin film transistor) mode, a VA (vertical alignment) mode, an IPS (in-plane switching) mode and a PSA (polymer sustained alignment) mode.

The display device operated in each mode described above contains a liquid crystal composition. A liquid crystal compound included in the liquid crystal composition is required to have a high clearing point and a large elastic constant $K_{33}$ ($K_{33}$: a bend elastic constant) in order to further improve characteristics described above. The liquid crystal compound is required to have a high safety when it is used as a component of a liquid crystal composition in which a high insulation (specific resistance) is required for use in a liquid crystal display device having a thin-film transistor mode or the like.

A variety of liquid crystal compounds in which hydrogen on the benzene ring is replaced by fluorine have conventionally been studied as a component of a liquid crystal composition having a high clearing point and a large elastic constant $K_{33}$ that is usable for liquid crystal display devices having these operating modes (see, Patent documents No. 1 to 3).

For example, the compounds (A) and (B) having a cyclohexane ring and a benzene ring (See, Patent document No. 1). However, these kinds of compounds do not have such a sufficiently high clearing point and a high elastic constant $K_{33}$ that satisfies market demand. They also do not have a sufficiently wide temperature range of nematic phase.

The compound (C) in which hydrogen on a benzene ring is replaced by methyl is studied (See, Patent document No. 2). However, this compound does not have such a sufficiently high clearing point and a large elastic constant $K_{33}$ that satisfies market demand.

The compound (D) in which hydrogen on a benzene ring is replaced by fluorine is studied (See, Patent document No. 3). However, it does not have such a sufficiently high clearing point and a large elastic constant $K_{33}$ that satisfies market demand.

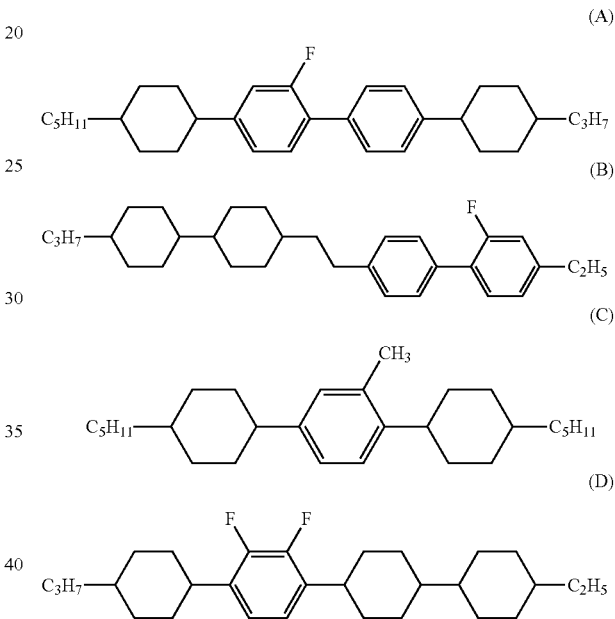

PRIOR ART

Patent Document

Patent document No. 1: JP H04-501581 A (1992).
Patent document No. 2: U.S. Pat. No. 5,310,501 (1994).
Patent document No. 3: JP 2002-193853 A (2002).

OUTLINE OF THE INVENTION

Subject to be Solved by the Invention

A display device operated in each mode described above contains a liquid crystal composition. A liquid crystal compound included in this liquid crystal composition is required to have the following characteristics shown in items (1) to (8), in order to improve the characteristics. That is to say:
(1) a high chemical stability and a high physical stability,
(2) a high clearing point (the transition temperature between a liquid crystal phase and an isotropic phase),
(3) a low minimum temperature of a liquid crystal phase (a nematic phase, a smectic phase and so forth), especially a low minimum temperature of a nematic phase, (4) a small viscosity,
(5) a suitable optical anisotropy,
(6) a suitable dielectric anisotropy,
(7) a large elastic constant $K_{33}$ ($K_{33}$: a bend elastic constant), and
(8) an excellent compatibility with other liquid crystal compounds.

A voltage holding ratio can be increased when a composition including a chemically and physically stable liquid crystal compound, as described in item (1), is used for a display device.

The temperature range of a nematic phase is wide in a composition that includes a liquid crystal compound having a high clearing point or a low minimum temperature of a liquid crystal phase as described in items (2) and (3), and thus the display device can be used in a wide temperature range.

The response speed can be improved, when a composition that includes a compound having a small viscosity as described in item (4) and a compound having a large elastic constant $K_{33}$ as described in item (7) is used for a display device. The contrast of a display device can be improved, when a composition that includes a compound having a suitable optical anisotropy as described in item (5) is used for a display device. Optical anisotropy ranging from small to large is necessary according to the design of a device. Recently, a method to improve the response speed by decreasing the cell thickness has been studied, and thus a liquid crystal composition having a large optical anisotropy becomes necessary. On the other hand, a liquid crystal composition having a small optical anisotropy is also important for a reflection-type display device and so forth because of its structure.

When a liquid crystal compound has a suitable dielectric anisotropy, the threshold voltage of the liquid crystal composition including this compound can be decreased. Hence, the driving voltage of a display device can be decreased and the electric power consumption can also be decreased, when the display device contains a composition that includes a compound having a suitable dielectric anisotropy as described in item (6). The contrast ratio of a display device can be increased, when the display device contains a composition that includes a compound having a large elastic constant $K_{33}$ as described in item (7).

A liquid crystal compound is generally used in the form of a composition prepared by mixing it with many other liquid crystal compounds in order to exhibit characteristics that are difficult to be attained by a single compound. Accordingly, it is desirable that a liquid crystal compound used for a display device has an excellent compatibility with other liquid crystal compounds and so forth, as described in item (8). Since the display device may also be used in a wide temperature range including a lower temperature than the freezing point, the compound that exhibits an excellent compatibility even at a low temperature may be desirable.

The first aim of the invention is to provide a liquid crystal compound having a high stability to heat, light or the like, a wide temperature range of a nematic phase, a small viscosity, a suitable optical anisotropy (especially, a relatively small optical anisotropy), a large elastic constant $K_{33}$ and a suitable dielectric anisotropy (especially, a relatively large dielectric anisotropy).

The second aim of the invention is to provide a liquid crystal compound having a high stability to heat, light or the like, a nematic phase in a wide temperature range, a small viscosity, a suitable optical anisotropy (especially, a relatively small optical anisotropy), a large elastic constant $K_{33}$, a wide temperature range of a nematic phase, and an excellent compatibility with other liquid crystal compounds.

The third aim of the invention is to provide a liquid crystal composition including this compound and having a high stability to heat, light or the like, a small viscosity, a suitable optical anisotropy (especially, a relatively small optical anisotropy), a suitable dielectric anisotropy (especially, a relatively large dielectric anisotropy), a large elastic constant $K_{33}$, a low threshold voltage, a high maximum temperature of a nematic phase (the phase transition temperature between a nematic phase and an isotropic phase), and a low minimum temperature of a nematic phase.

The fourth aim of the invention is to provide a liquid crystal display device containing this composition and having a short response time, low electric power consumption, a low driving voltage, a large contrast and a wide temperature range in which the device can be used.

Means for Solving the Subject

As a result of earnest research on these subjects, the inventors have found that a five-ring liquid crystal compound having a cyclohexane ring and a benzene ring that are arranged in a suitable position has a high stability to heat, light or the like, a nematic phase in a wide temperature range, a small viscosity, a suitable optical anisotropy, a large elastic constant $K_{33}$, a suitable dielectric anisotropy (especially, relatively large dielectric anisotropy), and an excellent compatibility with other liquid crystal compounds; and a liquid crystal composition including this compound has a high stability to heat, light or the like, a small viscosity, a suitable optical anisotropy (especially, a relatively small optical anisotropy), a large elastic constant $K_{33}$, a suitable dielectric anisotropy, a low threshold voltage, a high maximum temperature of a nematic phase and a low minimum temperature of a nematic phase; and a liquid crystal display device containing this composition has a short response time, low electric power consumption, a low driving voltage, a large contrast and a wide temperature range in which the device can be used. Thus, the inventors have completed the invention.

That is to say, the invention includes the following items 1 to 23.

Item 1 A compound represented by formula (1-1).

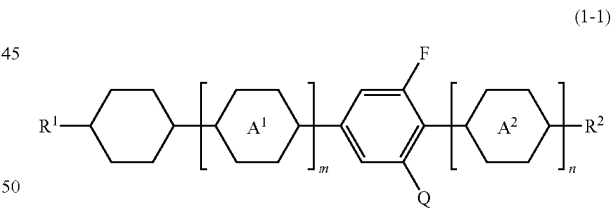

(1-1)

In formula (1-1), $R^1$ is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; $R^2$ is hydrogen, alkyl having 1 to 10 carbons, alkenyl having 2 to 10 carbons, alkoxy having 1 to 9 carbons, alkoxyalkyl having 2 to 9 carbons, alkenyloxy having 2 to 9 carbons, halogen, —C≡N, —SF$_5$, —CF$_3$, —CHF$_2$, —CH$_2$F, —OCF$_3$, —OCHF$_2$ or —OCH$_2$F; the ring A$^1$ and the ring A$^2$ are independently 1,4-phenylene, 2-fluoro-1,4-phenylene, 3-fluoro-1,4-phenylene, 3,5-difluoro-1,4-phenylene, trans-1,4-cyclohexylene, 1,4-cyclohexenylene, tetrahydropyran-2,5-diyl, tetrahydropyran-3,6-diyl, 1,3-dioxane-2,5-diyl or 1,3-dioxane-3,6-diyl; Q is hydrogen or fluorine; and m and n are independently 0, 1, 2 or 3, and the sum of m and n is 3.

Item 2. The compound according to item 1, wherein the compound is represented by formula (1-2).

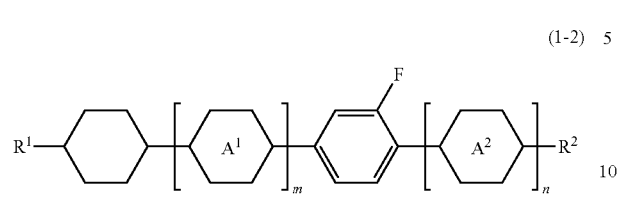
(1-2)

In formula (1-2), $R^1$ and $R^2$ are independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; the ring $A^1$ and the ring $A^2$ are independently 1,4-phenylene, 2-fluoro-1,4-phenylene, 3-fluoro-1,4-phenylene, 3,5-difluoro-1,4-phenylene, trans-1,4-cyclohexylene, 1,4-cyclohexenylene, tetrahydropyran-2,5-diyl, tetrahydropyran-3,6-diyl, 1,3-dioxane-2,5-diyl or 1,3-dioxane-3,6-diyl; and m and n are independently 0, 1, 2 or 3, and the sum of m and n is 3.

Item 3. The compound according to item 1, wherein the compound is represented by formula (1-3) or (1-4).

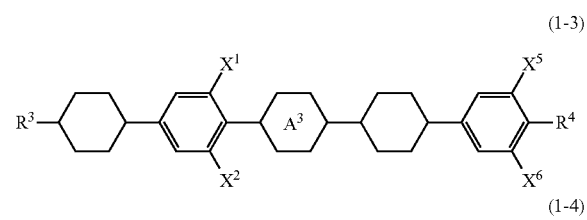
(1-3)
(1-4)

In formulas (1-3) and (1-4), $R^3$ is alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; $R^4$ is alkyl having 1 to 10 carbons, alkenyl having 2 to 10 carbons, alkoxy having 1 to 9 carbons, alkoxyalkyl having 2 to 9 carbons, alkenyloxy having 2 to 9 carbons, fluorine, chlorine, —C≡N, —CF$_3$ or —OCF$_3$; the ring $A^3$ and the ring $A^4$ are independently trans-1,4-cyclohexylene, 1,4-cyclohexenylene, tetrahydropyran-2,5-diyl or 1,3-dioxane-2,5-diyl; $X^1$, $X^2$, $X^3$, $X^4$, $X^5$ and $X^6$ are independently hydrogen or fluorine; and at least one of $X^1$ and $X^2$ is fluorine, and at least one of $X^3$ and $X^4$ is fluorine.

Item 4. The compound according to item 1, wherein the compound is represented by any one of formulas (1-5) to (1-9).

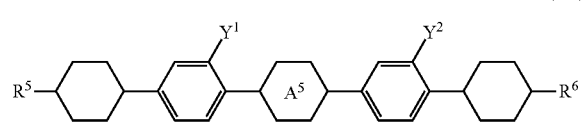
(1-5)

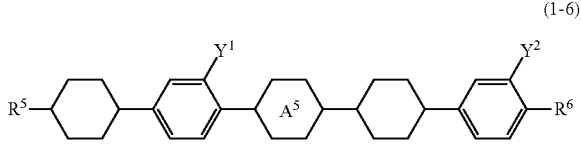
(1-6)

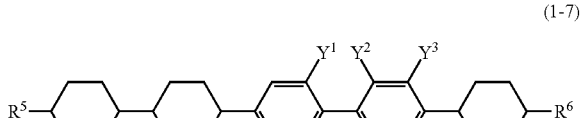
(1-7)

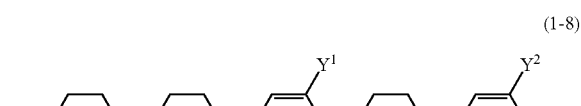
(1-8)

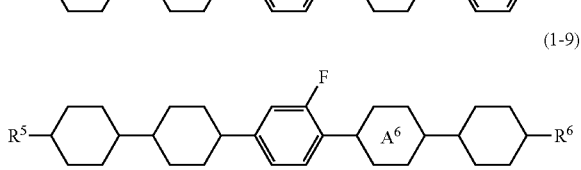
(1-9)

In formulas (1-5) to (1-9), $R^5$ and $R^6$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; the ring $A^5$ and the ring $A^6$ are independently trans-1,4-cyclohexylene, 1,4-cyclohexenylene or tetrahydropyran-2,5-diyl; $Y^1$, $Y^2$ and $Y^3$ are independently hydrogen or fluorine; in formulas (1-5), (1-6) and (1-8), at least one of $Y^1$ and $Y^2$ is fluorine; and in formula (1-7), at least one of $Y^1$, $Y^2$ and $Y^3$ is fluorine, and at least one of $Y^2$ and $Y^3$ is hydrogen.

Item 5. The compound according to item 1, wherein the compound is represented by any one of formulas (1-10) and (1-11).

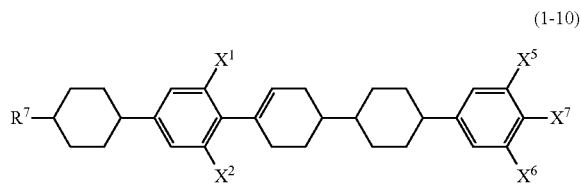
(1-10)
(1-11)

In formulas (1-10) and (1-11), $R^7$ is alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; $X^7$ is fluorine, chlorine, —C≡N, —CF$_3$ or —OCF$_3$; $X^1$, $X^2$, $X^3$, $X^4$, $X^5$ and $X^6$ are independently hydrogen or fluorine; and at least one of $X^1$ and $X^2$ is fluorine, and at least one of $X^3$ and $X^4$ is fluorine.

Item 6. The compound according to item 1, wherein the compound is represented by any one of formulas (1-12) and (1-13).

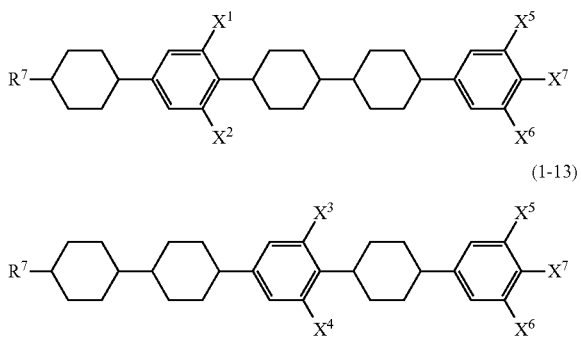

In formulas (1-12) and (1-13), $R^7$ is alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; $X^7$ is fluorine, chlorine, —C≡N, —CF$_3$ or —OCF$_3$; $X^1$, $X^2$, $X^3$, $X^4$, $X^5$ and $X^6$ are independently hydrogen or fluorine; and at least one of $X^1$ and $X^2$ is fluorine, and at least one of $X^3$ and $X^4$ is fluorine.

Item 7. The compound according to item 1, wherein the compound is represented by any one of formulas (1-14) and (1-15).

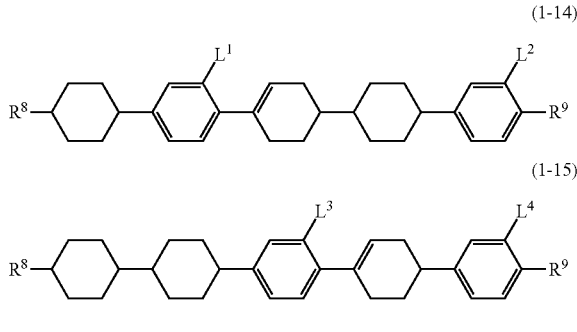

In formulas (1-14) and (1-15), $R^8$ and $R^9$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $L^1$, $L^2$, $L^3$ and $L^4$ are independently hydrogen or fluorine, at least one of $L^1$ and $L^2$ is fluorine, and at least one of $L^3$ and $L^4$ is fluorine.

Item 8. The compound according to item 1, wherein the compound is represented by any one of formulas (1-16) and (1-17).

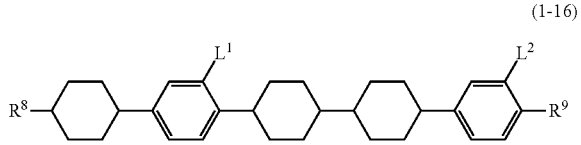

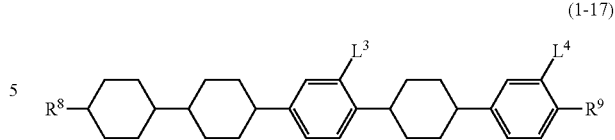

In formulas (1-16) and (1-17), $R^8$ and $R^9$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $L^1$, $L^2$, $L^3$ and $L^4$ are independently hydrogen or fluorine, at least one of $L^1$ and $L^2$ is fluorine, and at least one of $L^3$ and $L^4$ is fluorine.

Item 9. The compound according to item 1, wherein the compound is represented by any one of formulas (1-18) and (1-19).

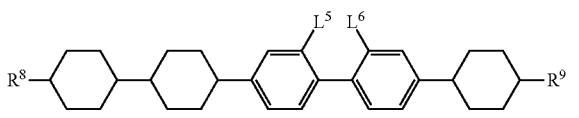

In formulas (1-18) and (1-19), $R^8$ and $R^9$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; $L^5$, $L^6$ and $L^7$ are independently hydrogen or fluorine; in formula (1-18), at least one of $L^5$ and $L^6$ is fluorine; and in formula (1-19), at least one of $L^5$ and $L^7$ is fluorine.

Item 10. The compound according to item 1, wherein the compound is represented by formula (1-20).

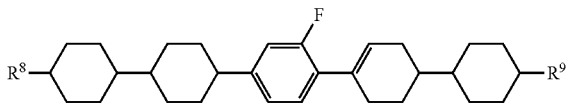

In formula (1-20), $R^8$ and $R^9$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons.

Item 11. The compound according to item 1, wherein the compound is represented by formula (1-21).

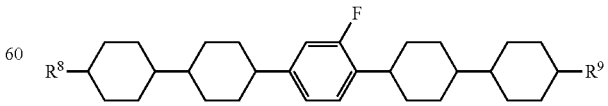

In formula (1-21), $R^8$ and $R^9$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons.

Item 12. The compound according to item 1, wherein the compound is represented by any one of formulas (1-22) to (1-37).
(1-22)
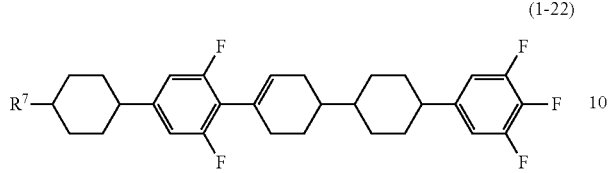
(1-23)
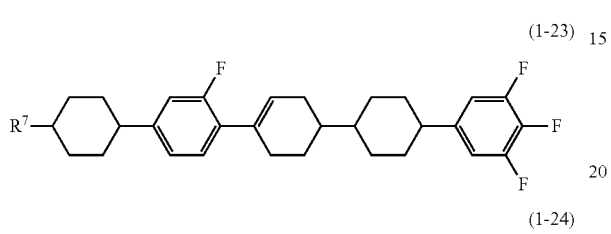
(1-24)
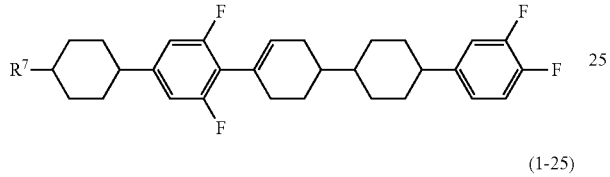
(1-25)
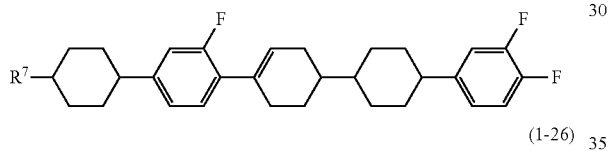
(1-26)
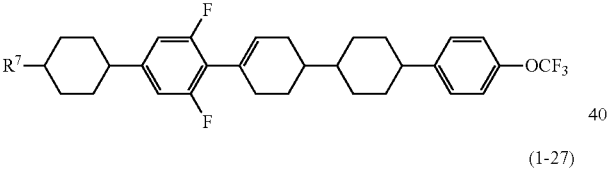
(1-27)
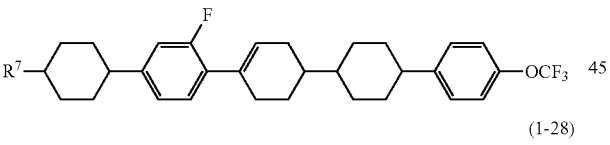
(1-28)
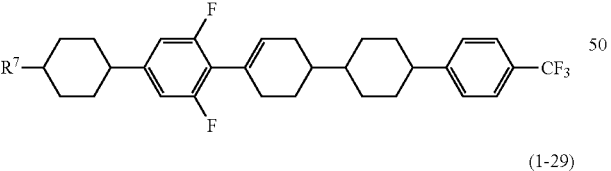
(1-29)
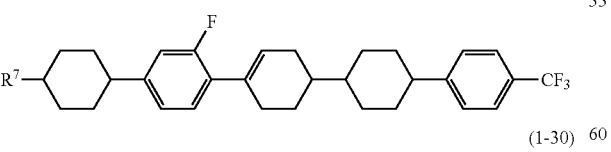
(1-30)
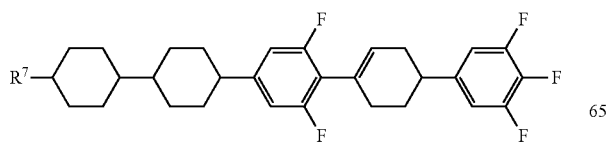
(1-31)
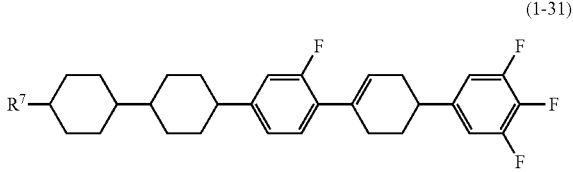
(1-32)
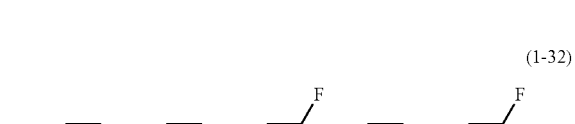
(1-33)
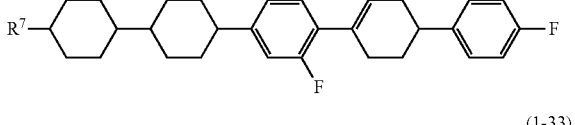
(1-34)
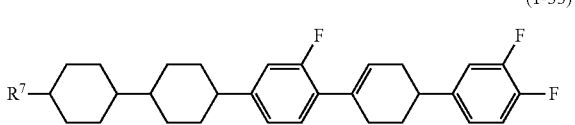
(1-35)
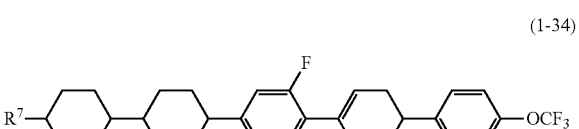
(1-36)
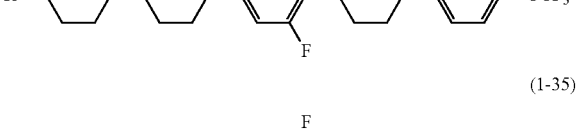
(1-37)
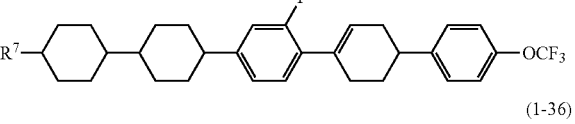
In formulas (1-22) to (1-37), $R^7$ is alkyl having 1 to 10 carbons, alkenyl having 2 to 10 carbons, alkoxy having 1 to 9 carbons, alkoxyalkyl having 2 to 9 carbons or alkenyloxy having 2 to 9 carbons.
Item 13. The compound according to item 1, wherein the compound is represented by any one of formulas (1-38) to (1-53).
(1-38)
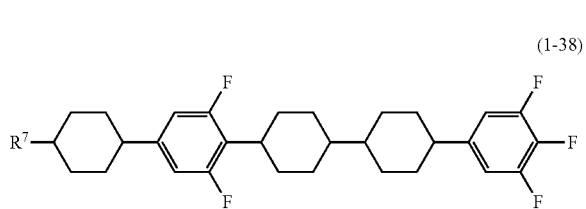

(1-39) 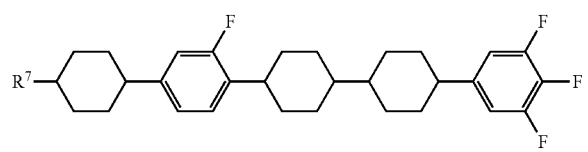

(1-40) 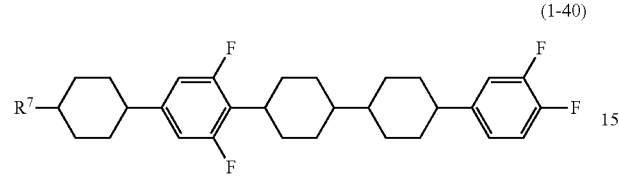

(1-41) 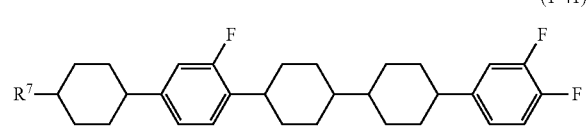

(1-42) 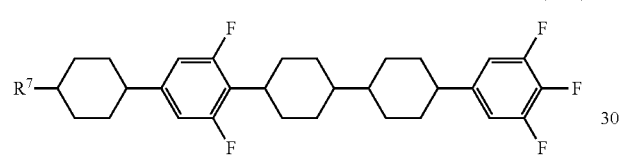

(1-43) 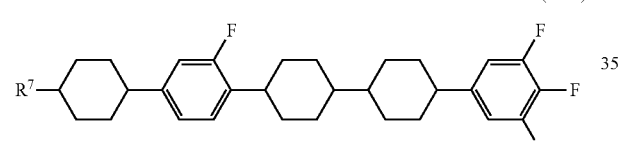

(1-44) 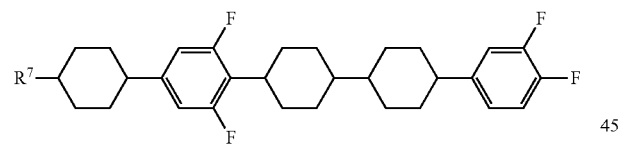

(1-45) 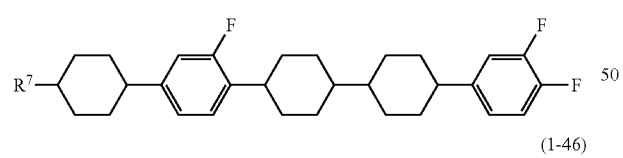

(1-46) 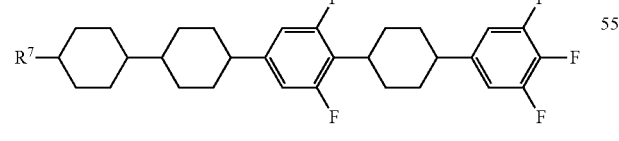

(1-47) 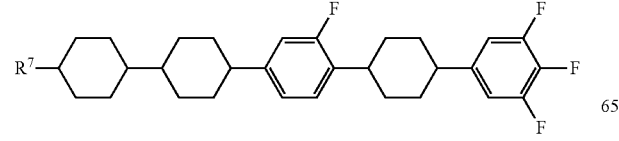

(1-48) 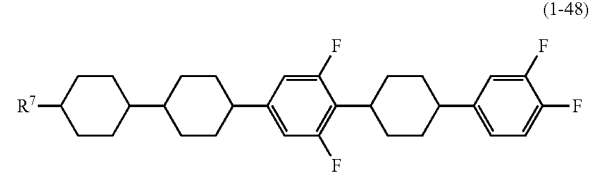

(1-49) 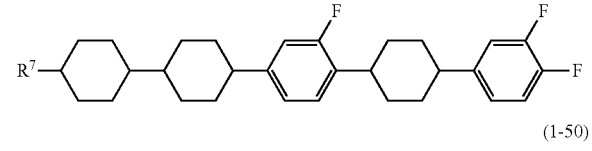

(1-50) 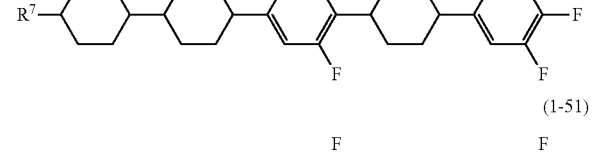

(1-51) 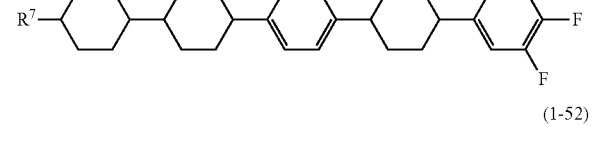

(1-52) 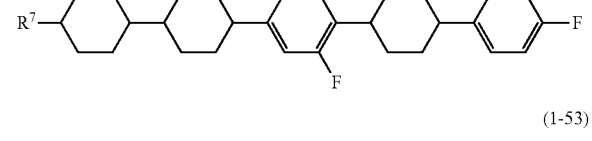

(1-53) 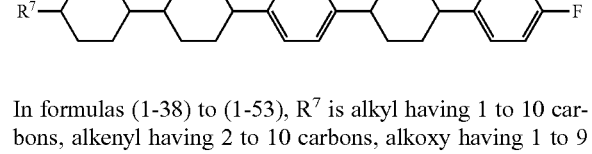

In formulas (1-38) to (1-53), $R^7$ is alkyl having 1 to 10 carbons, alkenyl having 2 to 10 carbons, alkoxy having 1 to 9 carbons, alkoxyalkyl having 2 to 9 carbons or alkenyloxy having 2 to 9 carbons.

Item 14. A liquid crystal composition including a first component and a second component, wherein the first component is at least one compound selected from compounds according to any one of items 1 to 13.

Item 15. The liquid crystal composition according to item 14, including at least one compound selected from the group of compounds represented by formulas (2), (3) and (4), as the second component.

(2) 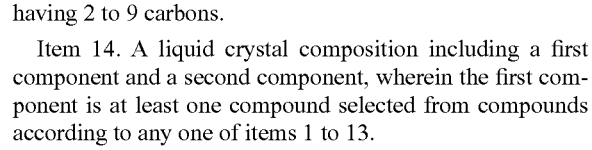

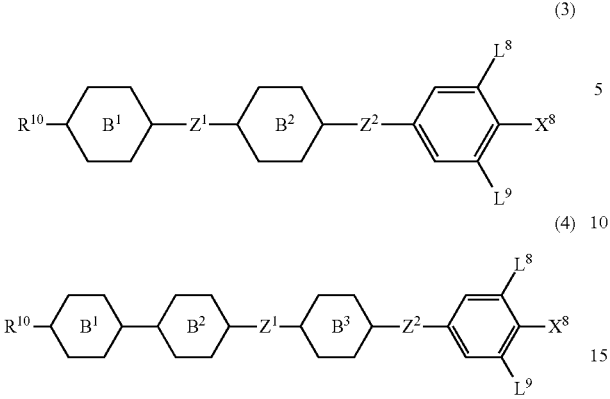

(3)

(4)

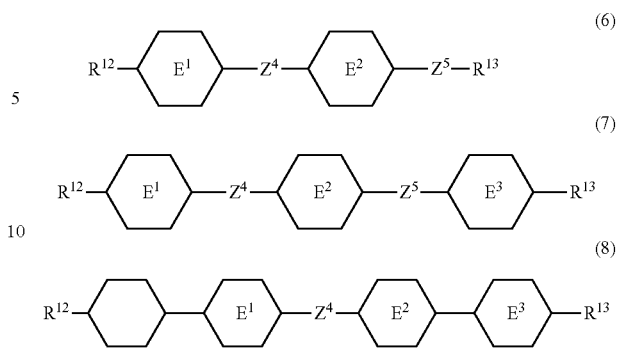

(6)

(7)

(8)

In formulas (2) to (4), $R^{10}$ is alkyl having 1 to 10 carbons or alkenyl having 2 to 10 carbons, and in the alkyl and alkenyl, arbitrary hydrogen may be replaced by fluorine and arbitrary —$CH_2$— may be replaced by —O—; $X^8$ is fluorine, chlorine, —$OCF_3$, —$OCHF_2$, —$CF_3$, —$CHF_2$, —$CH_2F$, —$OCF_2CHF_2$ or —$OCF_2CHFCF_3$; the ring $B^1$, the ring $B^2$ and the ring $B^3$ are independently 1,4-cyclohexylene, 1,3-dioxane-2,5-diyl, pyrimidine-2,5-diyl, 1-tetrahydropyran-2,5-diyl, or 1,4-phenylene in which arbitrary hydrogen may be replaced by fluorine; $Z^1$ and $Z^2$ are independently —$(CH_2)_2$—, —$(CH_2)_4$—, —COO—, —$CF_2O$—, —$OCF_2$—, —CH=CH—, —C≡C—, —$CH_2O$— or a single bond; and $L^8$ and $L^9$ are independently hydrogen or fluorine. In formula (4), the ring $B^3$ is not 1-tetrahydropyran-2,5-diyl when both the ring $B^1$ and the ring $B^2$ are 2,3-difluoro-1,4-phenylene, and the ring $B^1$ is not 1-tetrahydropyran-2,5-diyl when both the ring $B^2$ and the ring $B^3$ are 2,3-difluoro-1,4-phenylene and $Z^1$ is a single bond.

Item 16. The liquid crystal composition according to item 14, including at least one compound selected from the group of compounds represented by formula (5), as the second component.

(5)

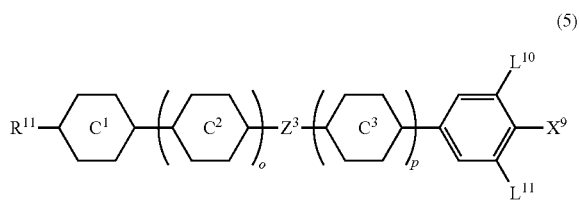

In formula (5), $R^{11}$ is alkyl having 1 to 10 carbons or alkenyl having 2 to 10 carbons, and in the alkyl and alkenyl, arbitrary hydrogen may be replaced by fluorine and arbitrary —$CH_2$— may be replaced by —O—; $X^9$ is —C≡N or —C≡C—C≡N; the ring $C^1$, the ring $C^2$ and the ring $C^3$ are independently 1,4-cyclohexylene, 1,4-phenylene in which arbitrary hydrogen may be replaced by fluorine, 1,3-dioxane-2,5-diyl, 1-tetrahydropyran-2,5-diyl or pyrimidine-2,5-diyl; $Z^3$ is —$(CH_2)_2$—, —COO—, —$CF_2O$—, —$OCF_2$—, —≡C—, —$CH_2O$— or a single bond; $L^{10}$ and $L^{11}$ are independently hydrogen or fluorine; and o is 0, 1 or 2, p is 0 or 1, and the sum of o and p is 2 or less.

Item 17. The liquid crystal composition according to item 14, including at least one compound selected from the group of compounds represented by formulas (6), (7) and (8), as the second component.

In formulas (6) to (8), $R^{12}$ and $R^{13}$ are independently alkyl having 1 to 10 carbons or alkenyl having 2 to 10 carbons, and in the alkyl and alkenyl, arbitrary —$CH_2$— may be replaced by —O—; the ring $E^1$, the ring $E^2$ and the ring $E^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^4$ and $Z^5$ are independently —C≡C—, —COO—, —$(CH_2)_2$—, —CH=CH— or a single bond.

Item 18. The liquid crystal composition according to item 15, further including at least one compound selected from the group of compounds represented by formula (5) according to item 16.

Item 19. The liquid crystal composition according to item 15, further including at least one compound selected from the group of compounds represented by formulas (6), (7) and (8) according to item 17.

Item 20. The liquid crystal composition according to item 16, further including at least one compound selected from the group of compounds represented by formulas (6), (7) and (8) according to item 17.

Item 21. The liquid crystal composition according to any one of items 14 to 20, further including at least one optically active compound and/or at least one polymerizable compound.

Item 22. The liquid crystal composition according to any one of items 14 to 20, further including at least one antioxidant and/or at least one ultraviolet light absorber.

Item 23. A liquid crystal display device containing the liquid crystal composition according to any one of items 14 to 22.

Usage of the terms in this specification is as follows. A liquid crystal compound is a generic term for a compound having a liquid crystal phase such as a nematic phase or a smectic phase, and also for a compound having no liquid crystal phases but useful as a component of a liquid crystal composition. The terms, a liquid crystal compound, a liquid crystal composition and a liquid crystal display device may be abbreviated to a compound, a composition and a device, respectively. A liquid crystal display device is a generic term for a liquid crystal display panel and a liquid crystal display module. The maximum temperature of a nematic phase is the phase transition temperature between a nematic phase and an isotropic phase, and may simply be abbreviated to the clearing point or the maximum temperature. The minimum temperature of the nematic phase may simply be abbreviated to the minimum temperature. The compound represented by formula (1) may be abbreviated to the compound (1). This abbreviation may apply to the compound represented by formula (2) or the like. In formulas (1) to (13), the symbols $A^1$, $B^1$, $C^1$, $E^1$ or the like surrounded by a hexagonal shape correspond to the ring $A^1$, the ring $B^1$, the ring $C^1$, the ring $E^1$ or the like, respectively. The amount of a compound, which is expressed as a percentage, means a weight percentage (% by weight) based on the total weight of the composition. A plurality of the same symbols of the ring $A^1$, $X^1$, $R^1$, $Y^1$ or the like were described in the same or different formulas, where arbitrary two of these same symbols may mean the same or different.

"Arbitrary" is used not only in cases where the position is arbitrary but also in cases where the number is arbitrary. However, it is not used in cases where the number is 0 (zero). The expression "arbitrary A may be replaced by B, C or D" includes cases where arbitrary A is replaced by B, and arbitrary A is replaced by C, and arbitrary A is replaced by D, and also cases where a plurality of A are replaced by at least two of B, C and/or D. For example, "alkyl in which arbitrary —$CH_2$— may be replaced by —O— or —CH=CH—" includes alkyl, alkenyl, alkoxy, alkoxyalkyl, alkoxyalkenyl and alkenyloxyalkyl. Incidentally, it is undesirable in the invention that two successive —$CH_2$— are replaced by —O— to give —O—O—. It is also undesirable that the terminal —$CH_2$— in the alkyl is replaced by —O—. The invention will be further explained below.

Effect of the Invention

The first feature of the liquid crystal compound of the invention is a high stability to heat, light or the like, a nematic phase in a wide temperature range, a small viscosity, a suitable optical anisotropy (especially, a relatively small optical anisotropy), a suitable elastic constant $K_{33}$ ($K_{33}$: a bend elastic constant), and a suitable dielectric anisotropy (especially, a relatively large positive dielectric anisotropy).

The second feature of the liquid crystal compound of the invention is a high stability to heat, light or the like, a nematic phase in a wide temperature range, a small viscosity, a suitable optical anisotropy (especially, a relatively small optical anisotropy), a large elastic constant $K_{33}$ ($K_{33}$: a bend elastic constant), a wide temperature range of a nematic phase and an excellent compatibility with other liquid crystal compounds.

The liquid crystal compound of the invention is excellent in view of a wide temperature range of a nematic phase and a large elastic constant $K_{33}$. Furthermore, it is quite excellent in view of the fact that the dielectric anisotropy has a tendency to increase without an increase in the viscosity.

The liquid crystal composition of the invention has a small viscosity, a large optical anisotropy, a suitable elastic constant $K_{33}$ and a large positive dielectric anisotropy, a low threshold voltage, a high maximum temperature of a nematic phase, and a low minimum temperature of a nematic phase. In particular, the liquid crystal composition of the invention is effective in a device that requires a large optical anisotropy, since it has a large optical anisotropy.

The liquid crystal display device of the invention is characterized by containing this liquid crystal composition, and has a short response time, low electric power consumption, a low driving voltage, a large contrast ratio, a wide temperature range in which the device can be used. Thus, the liquid crystal display device can be used preferably for a display mode such as a PC mode, a TN mode, a STN mode, an ECB mode, an OCB mode, an IPS mode or a PSA mode. It can be suitably used especially for a liquid crystal display device having the IPS mode or the PSA mode.

EMBODIMENT TO CARRY OUT THE INVENTION

The invention will be explained more specifically as follows. Incidentally, the amount of a compound that is expressed as a percentage in the following explanation means a weight percentage (% by weight) based on the total weight of the composition, unless otherwise noted.

The Liquid Crystal Compound (1-1)

The liquid crystal compound of the invention has a structure represented by formula (1-1). Hereinafter, the compound may be abbreviated to "the compound (1-1)".

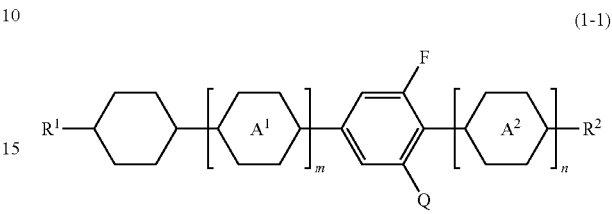

(1-1)

In formula (1-1), $R^1$ is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $R^2$ is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons, halogen, —C≡N, —$SF_5$, —$CF_3$, —$CHF_2$, —$CH_2F$, —$OCF_3$, —$OCHF_2$ or —$OCH_2F$.

The ring $A^1$ and the ring $A^2$ are independently 1,4-phenylene, 2-fluoro-1,4-phenylene, 3-fluoro-1,4-phenylene, 3,5-difluoro-1,4-phenylene, trans-1,4-cyclohexylene, 1,4-cyclohexenylene, tetrahydropyran-2,5-diyl, tetrahydropyran-3,6-diyl, 1,3-dioxane-2,5-diyl or 1,3-dioxane-3,6-diyl; Q is hydrogen or fluorine; and m and n are independently 0, 1, 2 or 3, and the sum of m and n is 3.

The compound (1-1) has a five-ring structure including 1,4-phenylene and trans-1,4-cyclohexylene. The compound has a suitable optical anisotropy, a large elastic constant $K_{33}$, a suitable dielectric anisotropy and an excellent compatibility with other liquid crystal compounds, by the effect of this kind of structure. In particular, the compound is quite excellent in a high maximum temperature of a nematic phase and also a large elastic constant $K_{33}$.

In the formula, $R^1$ is hydrogen, alkyl having 1 to 10 carbons or alkenyl having 2 to 10 carbons, alkoxy having 1 to 9 carbons, alkoxyalkyl having 2 to 9 carbons, alkenyloxy having 2 to 9 carbons; and $R^2$ is hydrogen, alkyl having 1 to 10 carbons, alkenyl having 2 to 10 carbons, alkoxy having 1 to 9 carbons, alkoxyalkyl having 2 to 9 carbons, alkenyloxy having 2 to 9 carbons, halogen, —C≡N, —$SF_5$, —$CF_3$, —$CHF_2$, —$CH_2F$, —$OCF_3$, —$OCHF_2$ or —$OCH_2F$, and those examples are $CH_3(CH_2)_3$, $CH_3(CH_2)_2O$—, $CH_3$—O—$(CH_2)_2$—, $CH_3$—O—$CH_2$—O—, $H_2C$=CH—$(CH_2)_2$—, $CH_3$—CH=CH—$CH_2$—, $CH_3$—CH=CH—O—, —F or —Cl.

However, a group having adjacent oxygens, such as $CH_3$—O—O—$CH_2$—, or a group having adjacent double bond moieties, such as $CH_3$—CH=CH—CH=CH—, is undesirable in consideration of the stability of the compound.

It is desirable that the chain of carbon-carbon bonds in these groups is straight. When the chain of carbon-carbon bonds is straight, the temperature range of a liquid crystal phase can be increased and the viscosity can be decreased. When one of $R^1$ and $R^2$ is an optically active group, the compound is useful as a chiral dopant, and a reverse twisted domain which will occur in a liquid crystal display device can be prevented by the addition of the compound to the liquid crystal composition.

Desirable $R^1$ is alkyl, alkoxy, alkoxyalkyl and alkenyl, and more desirable $R^1$ is alkyl, alkoxy or alkenyl. Desirable $R^2$ is alkyl, alkoxy, alkoxyalkyl, alkenyl, fluorine, chlorine, —C≡N, —$CF_3$ and —$OCF_3$, and more desirable $R^2$ is alkyl, fluorine, —$CF_3$ and —$OCF_3$.

The temperature range of a liquid crystal phase of the liquid crystal compound can be increased when $R^1$ is alkyl, alkoxy or alkenyl and $R^2$ is alkyl, alkoxy, alkenyl, fluorine, —$CF_3$ or —$OCF_3$.

A desirable configuration of —CH═CH— in the alkenyl depends on the position of the double bond.

A trans-configuration is desirable for the configuration of alkenyl having a double bond in the odd position, such as —CH═$CHCH_3$, —CH═$CHC_2H_5$, —CH═$CHC_3H_7$, —CH═$CHC_4H_9$, —$C_2H_4$CH═$CHCH_3$ or —$C_2H_4$CH═$CHC_2H_5$.

On the other hand, a cis-configuration is desirable for the configuration of alkenyl having a double bond in the even position, such as —$CH_2$CH═$CHCH_3$, —$CH_2$CH═$CHC_2H_5$ and —$CH_2$CH═$CHC_3H_7$. An alkenyl compound possessing a desirable configuration described above has a wide temperature range of a liquid crystal phase, a large elastic constant ratio $K_{33}/K_{11}$ ($K_{33}$: a bend elastic constant, $K_{11}$: a splay elastic constant), and a decreased viscosity. When this liquid crystal compound is added to a liquid crystal composition, the maximum temperature ($T_{NI}$) of a nematic phase can be increased.

Specific examples of the alkenyl are —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$ or $C_{10}H_{21}$; specific examples of the alkoxy are —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$ or $OC_9H_{19}$; specific examples of the alkoxyalkyl include —$CH_2OCH_3$, —$CH_2OC_2H_5$, —$CH_2OC_3H_7$, —$(CH_2)_2OCH_3$, —$(CH_2)_2OC_2H_5$, —$(CH_2)_2OC_3H_7$, —$(CH_2)_3OCH_3$, —$(CH_2)_4OCH_3$ or $(CH_2)_5OCH_3$; specific examples of the alkenyl include —CH═$CH_2$, —CH═$CHCH_3$, —$CH_2$CH═$CH_2$, —CH═$CHC_2H_5$, —$CH_2$CH═$CHCH_3$, —$(CH_2)_2$CH═$CH_2$, —CH═$CHC_3H_7$, —$CH_2$CH═$CHC_2H_5$, —$(CH_2)_2$CH═$CHCH_3$ or $(CH_2)_3$CH═$CH_2$; and specific examples of the alkenyloxy include —$OCH_2$CH═$CH_2$, —$OCH_2$CH═$CHCH_3$ or $OCH_2$CH═$CHC_2H_5$.

In the specific example, desirable $R^1$ and $R^2$ are —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$, —$OC_5H_{11}$, —$CH_2OCH_3$, —$(CH_2)_2OCH_3$, —$(CH_2)_3OCH_3$, —$CH_2$CH═$CH_2$, —$CH_2$CH═$CHCH_3$, —$(CH_2)_2$CH═$CH_2$, —$CH_2$CH═$CHC_2H_5$, —$(CH_2)_2$CH═$CHCH_3$, —$(CH_2)_3$CH═$CH_2$, —$(CH_2)_3$CH═$CHCH_3$, —$(CH_2)_3$CH═$CHC_2H_5$, —$(CH_2)_3$CH═$CHC_3H_7$, —$OCH_2$CH═$CH_2$, —$OCH_2$CH═$CHCH_3$ or —$OCH_2$CH═$CHC_2H_5$, and more desirable $R^1$ and $R^2$ are —$CH_3$, —$C_2H_5$, —$C_3H_7$, —$OCH_3$, —$OC_2H_5$, —$OC_3H_7$, —$OC_4H_9$, —$(CH_2)_2$CH═$CH_2$, —$(CH_2)_2$CH═$CHCH_3$ or $(CH_2)_2$CH═$CHC_3H_7$, for increasing the temperature range of a nematic phase.

Furthermore, desirable $R^1$ is —$CH_3$, —$C_2H_5$, —$C_3H_7$, —$C_4H_9$, $C_5H_{11}$, —$OCH_3$, —$OC_2H_5$, —$OC_3H_7$, —$OC_4H_9$, —$OC_5H_{11}$, —$CH_2OCH_3$, —$(CH_2)_2OCH_3$, —$(CH_2)_3OCH_3$, —$CH_2$CH═$CH_2$, —$CH_2$CH═$CHCH_3$, —$(CH_2)_2$CH═$CH_2$, —$CH_2$CH═$CHC_2H_5$, —$(CH_2)_2$CH═$CHCH_3$, —$(CH_2)_3$CH═$CH_2$, —$(CH_2)_3$CH═$CHCH_3$, —$(CH_2)_3$CH═$CHC_2H_5$, —$(CH_2)_3$CH═$CHC_3H_7$, —$OCH_2$CH═$CH_2$, —$OCH_2$CH═$CHCH_3$ or —$OCH_2$CH═$CHC_2H_5$, and more desirable $R^1$ is —$CH_3$, —$C_2H_5$, —$C_3H_7$, —$OCH_3$, —$OC_2H_5$, —$OC_3H_7$, —$OC_4H_9$, —$(CH_2)_2$CH═$CH_2$, —$(CH_2)_2$CH═$CHCH_3$ or $(CH_2)_2$CH═$CHC_3H_7$. Desirable $R^2$ is —F, —Cl, —$SF_5$, —CN, —$CF_3$ or —$OCF_3$, and more desirable $R^2$ is —F, —$CF_3$ or —$OCF_3$.

The ring $A^1$ and the ring $A^2$ are independently 1,4-phenylene, 2-fluoro-1,4-phenylene, 3-fluoro-1,4-phenylene, 3,5-difluoro-1,4-phenylene, trans-1,4-cyclohexylene, 1,4-cyclohexenylene, tetrahydropyran-2,5-diyl, tetrahydropyran-3,6-diyl, 1,3-dioxane-2,5-diyl or 1,3-dioxane-3,6-diyl; and arbitrary two of the ring $A^1$ may be the same or different when m is 2 or 3, and arbitrary two of the ring $A^2$ may be the same or different when n is 2 or 3.

In these rings, 1,4-cyclohexenylene and trans-1,4-cyclohexylene are more desirable, and trans-1,4-cyclohexylene is most desirable, for increasing the temperature range of a nematic phase. 2-Fluoro-1,4-phenylene, 3-fluoro-1,4-phenylene, 3,5-difluoro-1,4-phenylene is desirable, and 3,5-difluoro-1,4-phenylene most desirable, for increasing the dielectric anisotropy.

In particular, the viscosity is decreased when at least one of these rings is trans-1,4-cyclohexylene. Furthermore, the maximum temperature of a nematic phase ($T_{NI}$) is increased by the addition of this liquid crystal compound to a liquid crystal composition.

Incidentally, the compound (1-1) may also contain isotopes such as $^2H$ (deuterium) and $^{13}C$ in a larger amount than the amount of the natural abundance, since such isotopes do not make a major difference in physical properties of the compound.

In the compound (1-1), it is possible to adjust physical properties, such as dielectric anisotropy, to desired values by suitably selecting $R^1$, $R^2$, the ring $A^1$ and the ring $A^2$.

Desirable examples of the compound (1-1) include the compounds (1-2) to (1-53).

(1-2)

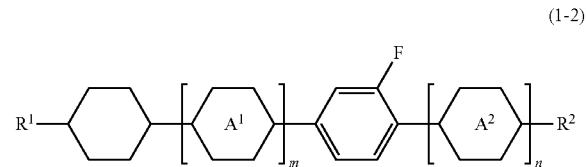

In formula (1-2), $R^1$ and $R^2$ are independently hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; the ring $A^1$ and the ring $A^2$ are independently 1,4-phenylene, 2-fluoro-1,4-phenylene, 3-fluoro-1,4-phenylene, 3,5-difluoro-1,4-phenylene, trans-1,4-cyclohexylene, 1,4-cyclohexenylene, tetrahydropyran-2,5-diyl, tetrahydropyran-3,6-diyl, 1,3-dioxane-2,5-diyl or 1,3-dioxane-3,6-diyl; and m and n are independently 0, 1, 2 or 3, and the sum of m and n is 3.

The compound (1-2) is more desirable in view of, almost without a decrease in the maximum temperature of a nematic phase, a small viscosity, an excellent compatibility, a high stability to heat or light, a lower minimum temperature of a liquid crystal phase, a higher maximum temperature of a nematic phase, a large elastic constant $K_{33}$ and a suitable optical anisotropy (especially, a relatively large optical anisotropy), since it has 3-fluorophenylene and trans-1,4-cyclohexylene, and the structure of the whole compound is asymmetric.

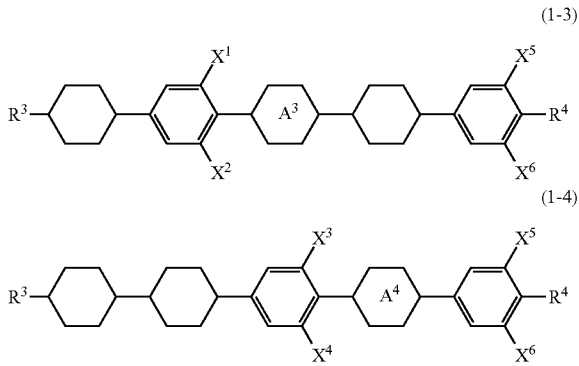
(1-3)

(1-4)

In formulas (1-3) and (1-4), $R^3$ is alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; $R^4$ is alkyl having 1 to 10 carbons, alkenyl having 2 to 10 carbons, alkoxy having 1 to 9 carbons, alkoxyalkyl having 2 to 9 carbons, alkenyloxy having 2 to 9 carbons, fluorine, chlorine, —C≡N, —CF$_3$ or —OCF$_3$; the ring $A^3$ and the ring $A^4$ are independently trans-1,4-cyclohexylene, 1,4-cyclohexenylene, tetrahydropyran-2,5-diyl, 1,3-dioxane-2,5-diyl; $X^1$, $X^2$, $X^3$, $X^4$, $X^5$ and $X^6$ are independently hydrogen or fluorine; and at least one of $X^1$ and $X^2$ is fluorine, and at least one of $X^3$ and $X^4$ is fluorine.

The compounds (1-3) and (1-4) are more desirable in view of, almost without a decrease in the maximum temperature of a nematic phase, a small viscosity, an excellent compatibility, a high stability to heat and light, a lower minimum temperature of a liquid crystal phase, a large elastic constant $K_{33}$, a suitable optical anisotropy (especially, a relatively large optical anisotropy), a higher maximum temperature of a nematic phase (when the number of fluorine is 3 or less), and a large positive dielectric anisotropy (when the number of fluorine is 3 or more), since they have fluorine-substituted phenylene, trans-1,4-cyclohexylene and 1,4-cyclohexenylene, and the structure of the whole compound is asymmetric.

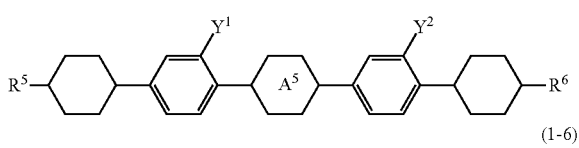
(1-5)

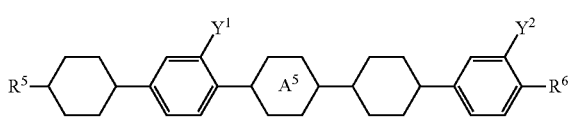
(1-6)

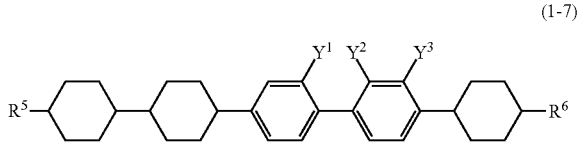
(1-7)

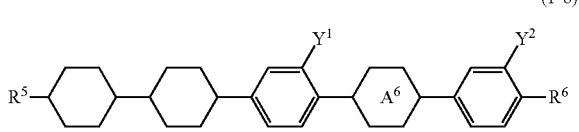
(1-8)

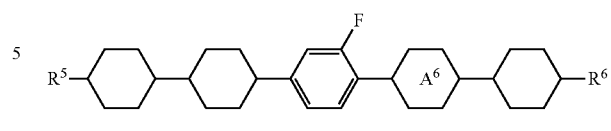
(1-9)

In formulas (1-5) to (1-9), $R^5$ and $R^6$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; the ring $A^5$ and the ring $A^6$ are independently trans-1,4-cyclohexylene, 1,4-cyclohexenylene or tetrahydropyran-2,5-diyl; $Y^1$, $Y^2$ and $Y^3$ are independently hydrogen or fluorine; in formulas (1-5), (1-6) and (1-8), at least one of $Y^1$ and $Y^2$ is fluorine; and in formula (1-7), at least one of $Y^1$, $Y^2$ and $Y^3$ is fluorine, and at least one of $Y^2$ and $Y^3$ is hydrogen.

The compounds (1-5) to (1-9) are desirable in view of an excellent compatibility, a high stability to heat or light, a lower minimum temperature of a liquid crystal phase, a higher maximum temperature of a nematic phase, a suitable optical anisotropy, a large elastic constant $K_{33}$ and a small viscosity, since they have fluorine-substituted phenylene and trans-1,4-cyclohexylene, and the structure of the whole compound is asymmetric.

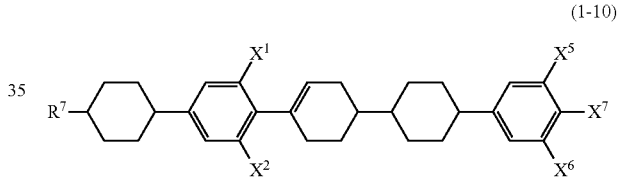
(1-10)

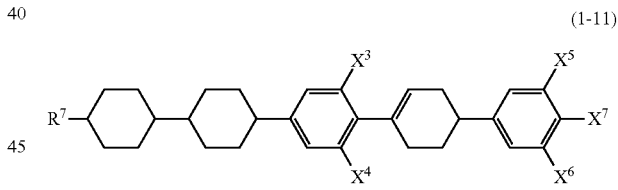
(1-11)

In formulas (1-10) and (1-11), $R^7$ is alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; $X^7$ is fluorine, chlorine, —C≡N, —CF$_3$ or —OCF$_3$; $X^1$, $X^2$, $X^3$, $X^4$, $X^5$ and $X^6$ are independently hydrogen or fluorine; and at least one of $X^1$ and $X^2$ is fluorine, and at least one of $X^3$ and $X^4$ is fluorine.

The compounds (1-10) and (1-11) are more desirable in view of, almost without a decrease in the maximum temperature of a nematic phase, a small viscosity nearly, an excellent compatibility, a high stability to heat or light, a lower minimum temperature of a liquid crystal phase, a higher maximum temperature of a nematic phase, a large elastic constant $K_{33}$, a suitable optical anisotropy (especially, a relatively large optical anisotropy) and a large positive dielectric anisotropy, since they have two fluorine-substituted phenylene, trans-1,4-cyclohexylene and 1,4-cyclohexenylene, and the structure of the whole compound is asymmetric.

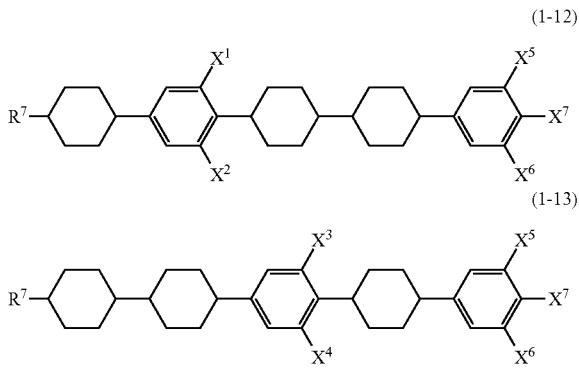

(1-12)

(1-13)

In formulas (1-12) and (1-13), $R^7$ is alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; $X^7$ is fluorine, chlorine, —C≡N, —$CF_3$ or —$OCF_3$; $X^1$, $X^2$, $X^4$, $X^5$ and $X^6$ are independently hydrogen or fluorine; and at least one of $X^1$ and $X^2$ is fluorine, and at least one of $X^3$ and $X^4$ is fluorine.

The compounds (1-12) and (1-13) are more desirable in view of, almost without a decrease in the maximum temperature of a nematic phase, a small viscosity, an excellent compatibility, a high stability to heat or light, a lower minimum temperature of a liquid crystal phase, a higher maximum temperature of a nematic phase, a large elastic constant $K_{33}$, a suitable optical anisotropy (especially, a relatively large optical anisotropy), a large positive dielectric anisotropy, since they have two fluorine-substituted phenylene and trans-1,4-cyclohexylene, and the structure of the whole compound is asymmetric.

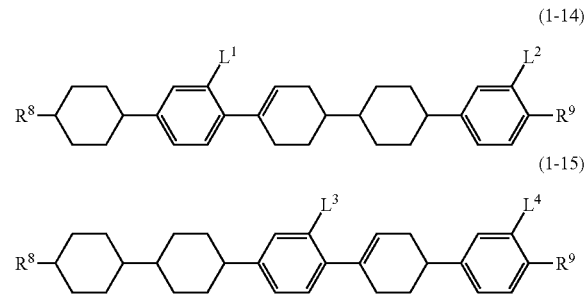

(1-14)

(1-15)

In formulas (1-14) and (1-15), $R^8$ and $R^9$ are alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $L^1$, $L^2$, $L^3$ and $L^4$ are independently hydrogen or fluorine, at least one of $L^1$ and $L^2$ is fluorine, and at least one of $L^3$ and $L^4$ is fluorine.

The compounds (1-14) and (1-15) are more desirable in view of, almost without a decrease in the maximum temperature of a nematic phase, a small viscosity, an excellent compatibility, a high stability to heat or light, a lower minimum temperature of a liquid crystal phase, higher maximum temperature of a nematic phase, a large elastic constant $K_{33}$ and a large optical anisotropy, since they have two fluorine-substituted phenylene, trans-1,4-cyclohexylene and 1,4-cyclohexenylene, and the structure of the whole compound is asymmetric.

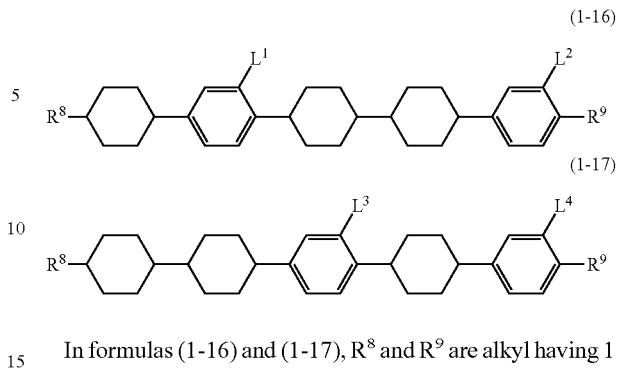

(1-16)

(1-17)

In formulas (1-16) and (1-17), $R^8$ and $R^9$ are alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; and $L^1$, $L^2$, $L^3$ and $L^4$ are independently hydrogen or fluorine, at least one of $L^1$ and $L^2$ is fluorine, and at least one of $L^3$ and $L^4$ is fluorine.

The compounds (1-16) and (1-17) are more desirable in view of an excellent compatibility, a high stability to heat or light, a lower minimum temperature of a liquid crystal phase, a higher maximum temperature of a nematic phase, a suitable optical anisotropy and a large elastic constant $K_{33}$ and a small viscosity, since they have fluorine-substituted phenylene and trans-1,4-cyclohexylene, and the structure of the whole compound is asymmetric.

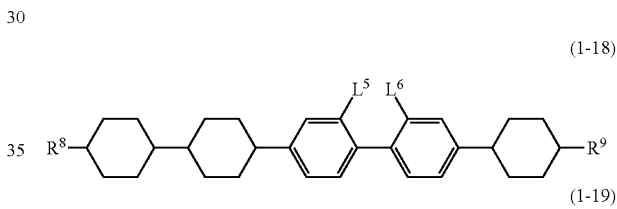

(1-18)

(1-19)

In formulas (1-18) and (1-19), $R^8$ and $R^9$ are alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; $L^5$, $L^6$ and $L^7$ are independently hydrogen or fluorine; in formula (1-18), at least one of $L^5$ and $L^6$ is fluorine; and in formula (1-19), at least one of $L^5$ and $L^7$ is fluorine.

The compounds (1-18) and (1-19) are more desirable in view of an excellent compatibility, a high stability to heat or light, a lower minimum temperature of a liquid crystal phase, a higher maximum temperature of a nematic phase, a large elastic constant $K_{33}$ and a large optical anisotropy, since they have fluorine-substituted phenylene and trans-1,4-cyclohexylene, and the structure of the whole compound is asymmetric.

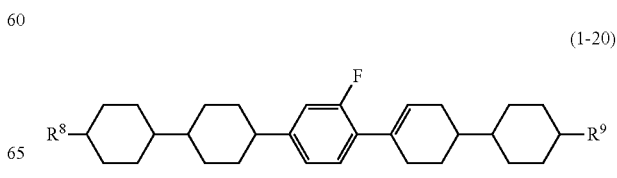

(1-20)

In formula (1-20), $R^8$ and $R^9$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons.

The compound (1-20) is more desirable in view of, almost without a decrease in the maximum temperature of a nematic phase, a small viscosity, an excellent compatibility, a lower minimum temperature of a liquid crystal phase, a higher maximum temperature of a nematic phase, a suitable optical anisotropy and a large elastic constant $K_{33}$ and a small viscosity, since it has fluorine-substituted phenylene, trans-1,4-cyclohexylene and 1,4-cyclohexenylene, and the structure of the whole compound is asymmetric.

(1-21)

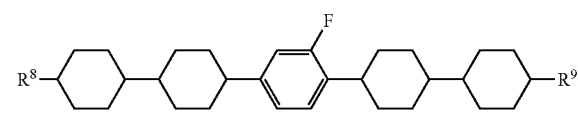

In formula (1-21), $R^8$ and $R^9$ are independently alkyl having 1 to 10 carbons, alkenyl having 2 to 10 carbons, alkoxy having 1 to 9 carbons, alkoxyalkyl having 2 to 9 carbons or alkenyloxy having 2 to 9 carbons.

The compound (1-21) is more desirable in view of a lower minimum temperature of a liquid crystal phase, a higher maximum temperature of a nematic phase, a suitable optical anisotropy, a large elastic constant $K_{33}$ and a small viscosity, since it has of fluorine-substituted phenylene and trans-1,4-cyclohexylene, and the structure of the whole compound is asymmetric.

(1-22)

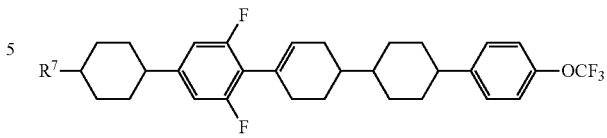

(1-23)

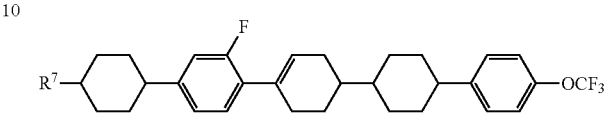

(1-24)

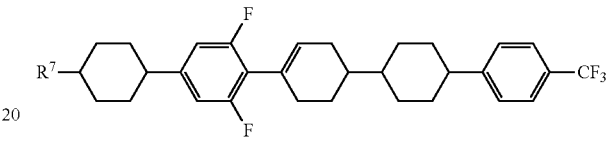

(1-25)

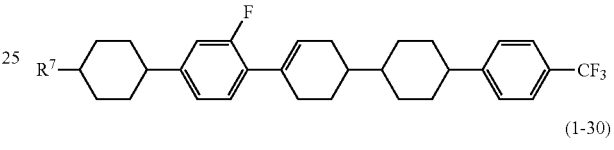

-continued (1-26)

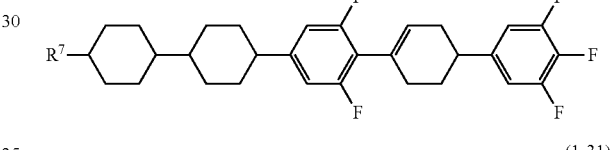

(1-27)

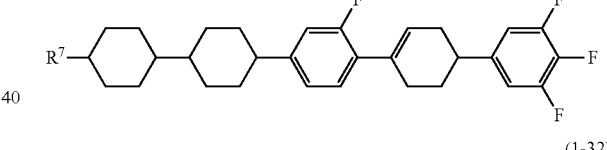

(1-28)

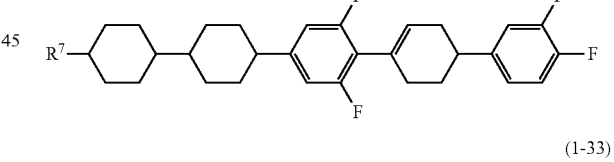

(1-29)

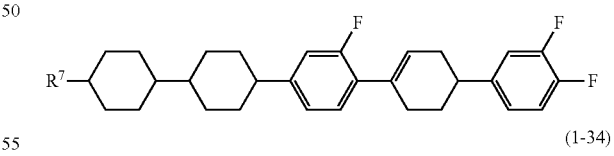

(1-30)

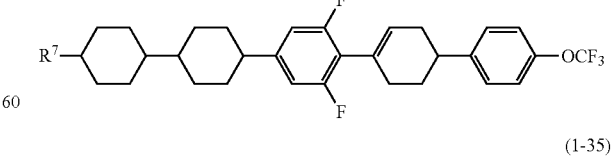

(1-31)

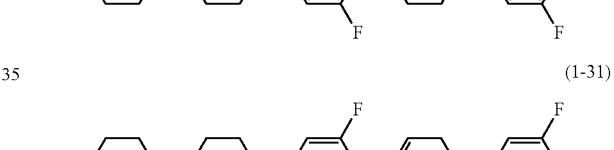

(1-32)

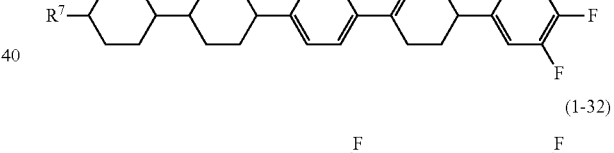

(1-33)

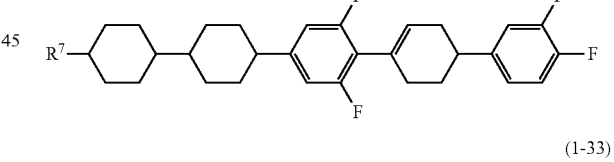

(1-34)

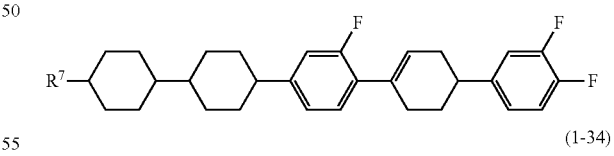

(1-35)

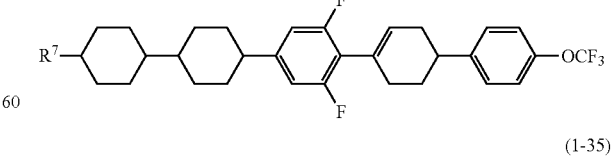

(1-36)
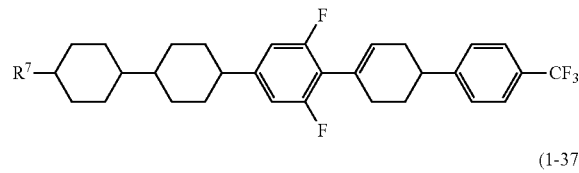

(1-37)
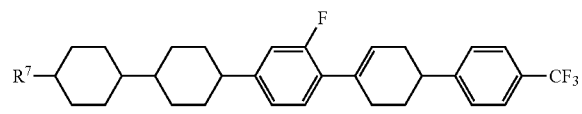

In formulas (1-22) to (1-37), $R^7$ is alkyl having 1 to 10 carbons, alkenyl having 2 to 10 carbons, alkoxy having 1 to 9 carbons, alkoxyalkyl having 2 to 9 carbons or alkenyloxy having 2 to 9 carbons.

The compounds (1-22) to (1-37) are more desirable in view of an excellent compatibility, almost without a decrease in the maximum temperature of a nematic phase, a small viscosity, a high stability to heat or light, a lower minimum temperature of a liquid crystal phase, a higher maximum temperature of a nematic phase, a large elastic constant $K_{33}$, a larger optical anisotropy and a large positive dielectric anisotropy, since they have fluorine-substituted phenylene, two trans-1,4-cyclohexylene and 1,4-cyclohexenylene, the structure of the whole compound is asymmetric, and the polar group is located in the lateral position of the major molecular axis.

(1-38)
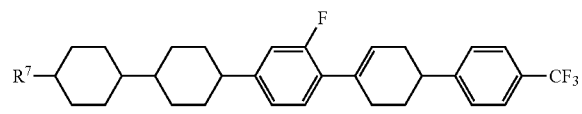

(1-39)
(1-40)
(1-41)
(1-42)

(1-43)
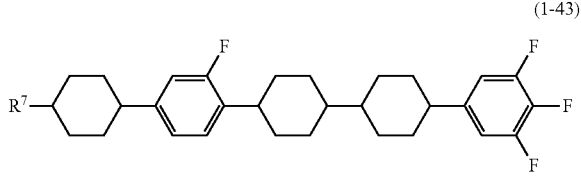

(1-44)
(1-45)
(1-46)
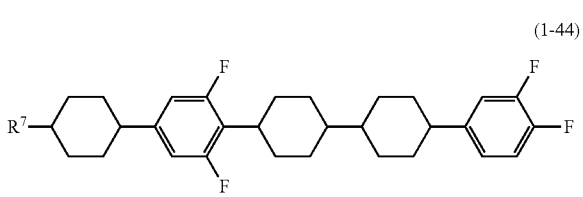

(1-47)
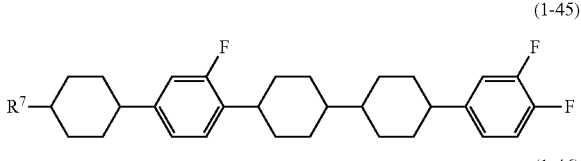

(1-48)
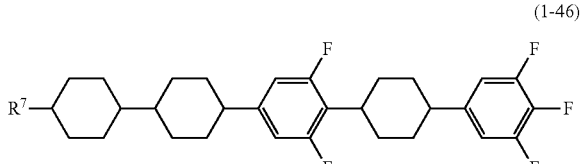

(1-49)
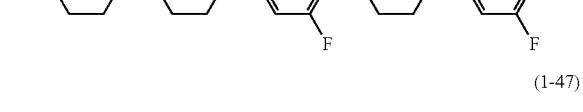

(1-50)
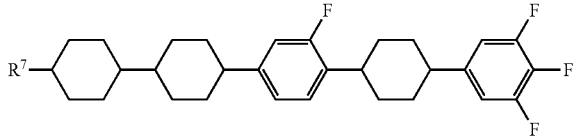

(1-51)
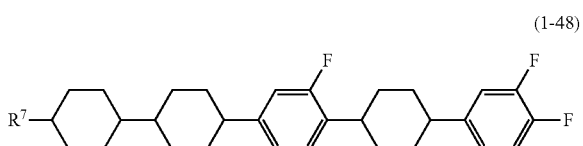

(1-52)

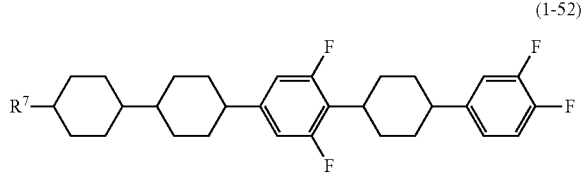

(1-53)

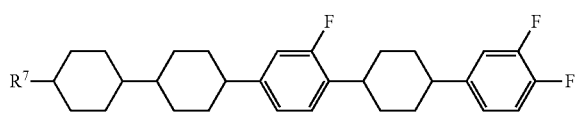

In formulas (1-38) to (1-53), $R^7$ is alkyl having 1 to 10 carbons, alkenyl having 2 to 10 carbons, alkoxy having 1 to 9 carbons, alkoxyalkyl having 2 to 9 carbons or alkenyloxy having 2 to 9 carbons.

The compounds (1-38) to (1-53) are more desirable in view of a high stability to heat or light, a lower minimum temperature of a liquid crystal phase, a higher maximum temperature of a nematic phase, a large elastic constant $K_{33}$, a suitable optical anisotropy, a large positive dielectric anisotropy, since they have two fluorine-substituted phenylene and three trans-1,4-cyclohexylene, the structure of the whole compound is asymmetric, and the polar group is located in the lateral position of the major molecular axis.

When a liquid crystal compound has structures shown by these compounds (1-10) to (1-53), it has quite excellent compatibility with other liquid crystal compounds. It has also a high stability to heat, light or the like, a small viscosity, a large optical anisotropy and a large elastic constant $K_{33}$. A liquid crystal composition including this compound (1-1) is stable under conditions in which a liquid crystal display device is usually used, and this compound does not deposit its crystals (or its smectic phase) even when the composition is kept in storage at a low temperature.

Accordingly, the compound (1-1) can suitably utilized for a liquid crystal composition that is used for a liquid crystal display device having a display mode such as PC, TN, STN, ECB, OCB, IPS or PSA.

Preparation of the Compound (1-1)

The compound (1-1) can be synthesized by a suitable combination of techniques in synthetic organic chemistry. Methods of introducing objective terminal groups, rings and bonding groups into starting materials are described in books such as Organic Syntheses (John Wiley & Sons, Inc), Organic Reactions (John Wiley & Sons, Inc), Comprehensive Organic Synthesis (Pergamon Press) and New Experimental Chemistry Course (Shin Jikken Kagaku Kouza, in Japanese) (Maruzen Co., Ltd.).

Formation of the Ring $A^1$ or the Ring $A^2$

Starting materials are commercially available, or methods are well known, for the formation of rings such as trans-1,4-cyclohexylene, cyclohexene-1,4-diyl, 1,3-dioxane-2,5-diyl, tetrahydropyran-2,5-diyl, 1,4-phenylene, 2-fluoro-1,4-phenylene, 3-fluoro-1,4-phenylene, 2,3-difluoro-1,4-phenylene, pyrimidine-2,5-diyl and pyridine-2,5-diyl.

The Method for Preparing the Compound (1-1)

An example of the preparation of the compound (1-1), the liquid crystal compound represented by the general formula (1-1), is as follows.

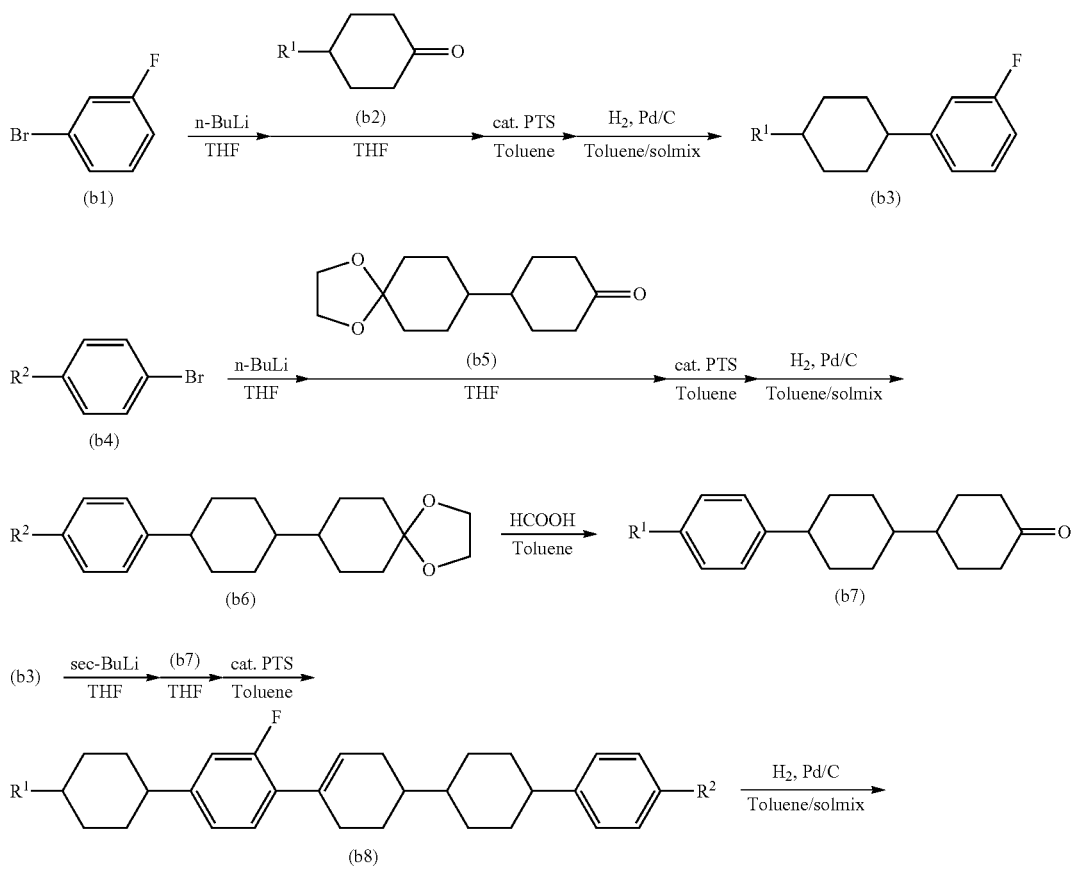

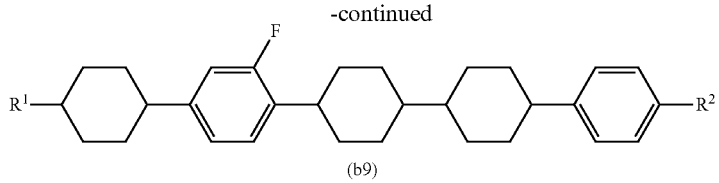

(b9)

First, a lithium salt is prepared by the reaction of the compound (b1) and n-BuLi. The lithium salt is allowed to react with the carbonyl derivative (b2) to give the alcohol derivative, which is then dehydrated to give the cyclohexene derivative in the presence of an acid catalyst such as p-toluenesulfonic acid. This compound is hydrogenated to give the compound (b3) in the presence of a catalyst such as Pd/C. In a separate run, a lithium salt is prepared by the reaction of the compound (b4) with n-BuLi. The lithium salt is allowed to react with the carbonyl derivative (b5) to give the alcohol derivative, which is hydrated to give the cyclohexene in the presence of an acid catalyst such as p-toluenesulfonic acid derivative. The derivative is hydrogenated to give the compound (b6) in the presence of a catalyst such as Pd/C. The resulting compound (b6) is allowed to react with formic acid or the like to give the carbonyl derivative (b7).

A lithium salt is prepared by the reaction of the compound (b3) obtained in the procedure described above, with sec-BuLi. This lithium salt is allowed to react with the carbonyl derivative (b7) to give the alcohol derivative, which is then dehydrated in the presence of an acid catalyst such as p-toluenesulfonic acid to give the compound (b8), which is one example of the liquid crystal compound (1-1) of the invention. The compound (b8) is hydrogenated in the presence of a catalyst such as Pd/C to give the compound (b9) that is one example of the liquid crystal compound (1-1) of the invention.

The Liquid Crystal Composition

The liquid crystal composition of the invention will be explained below. This liquid crystal composition is characterized by including at least one of the liquid crystal compounds (1-1) as a component. The composition may include two or more of the liquid crystal compound (1-1). When the liquid crystal composition of the invention is prepared, its components can be selected, for example, by taking into consideration the dielectric anisotropy of the liquid crystal compound (1-1). The liquid crystal composition in which the components have been selected has a small viscosity, a large positive dielectric anisotropy, a suitable elastic constant $K_{33}$ and a low threshold voltage, and also has a high maximum temperature of a nematic phase (the phase transition temperature between a nematic phase and an isotropic phase) and a low minimum temperature of a nematic phase.

The Liquid Crystal Composition (1)

The liquid crystal composition of the invention should include the component A consisting of the compound represented by formula (1-1) of the invention, as a first component. This composition may include a liquid crystal compound which is not described in this specification or may include the component B, C or D that will be described below, as a second component.

A desirable second component is the component B consisting of at least one compound selected from the group of formulas (2), (3) and (4) and/or the component C consisting of at least one compound selected from the group of formula (5) described above. The threshold voltage, the temperature range of a liquid crystal phase, the refractive index anisotropy, the dielectric anisotropy, the viscosity and so forth can be adjusted by further addition of the component D consisting of at least one compound selected from the group of formulas (6), (7) and (8).

There are no major differences in physical properties even if each component of the liquid crystal composition of the invention is an analogue composed of isotope of each element.

In the component B, suitable examples of the compound represented by formula (2) include formulas (2-1) to (2-16), suitable examples of the compound represented by formula (3) include formulas (3-1) to (3-112), and suitable examples of the compound represented by formula (4) include formulas (4-1) to (4-54).

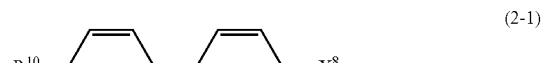

(2-1)

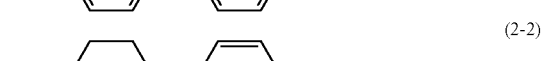

(2-2)

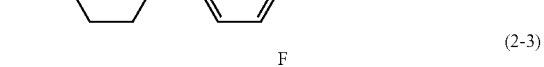

(2-3)

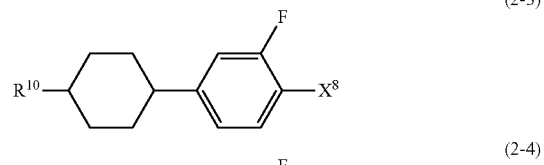

(2-4)

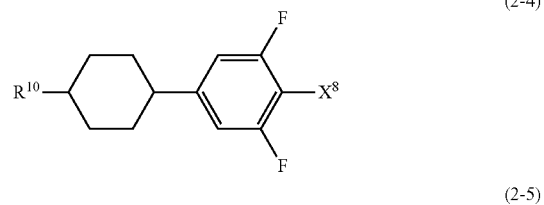

(2-5)

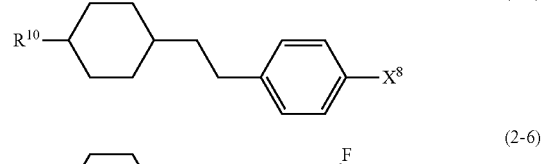

(2-6)

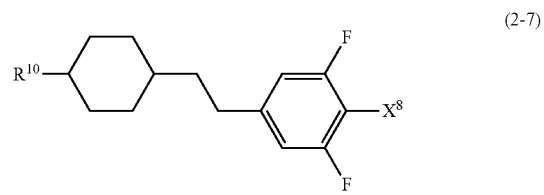

(2-7)

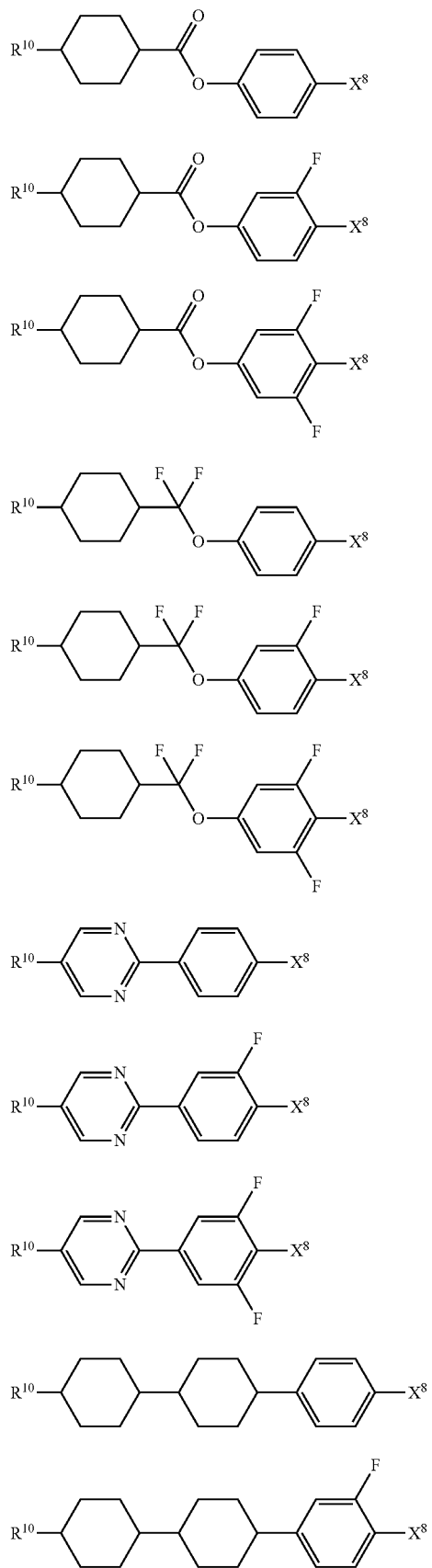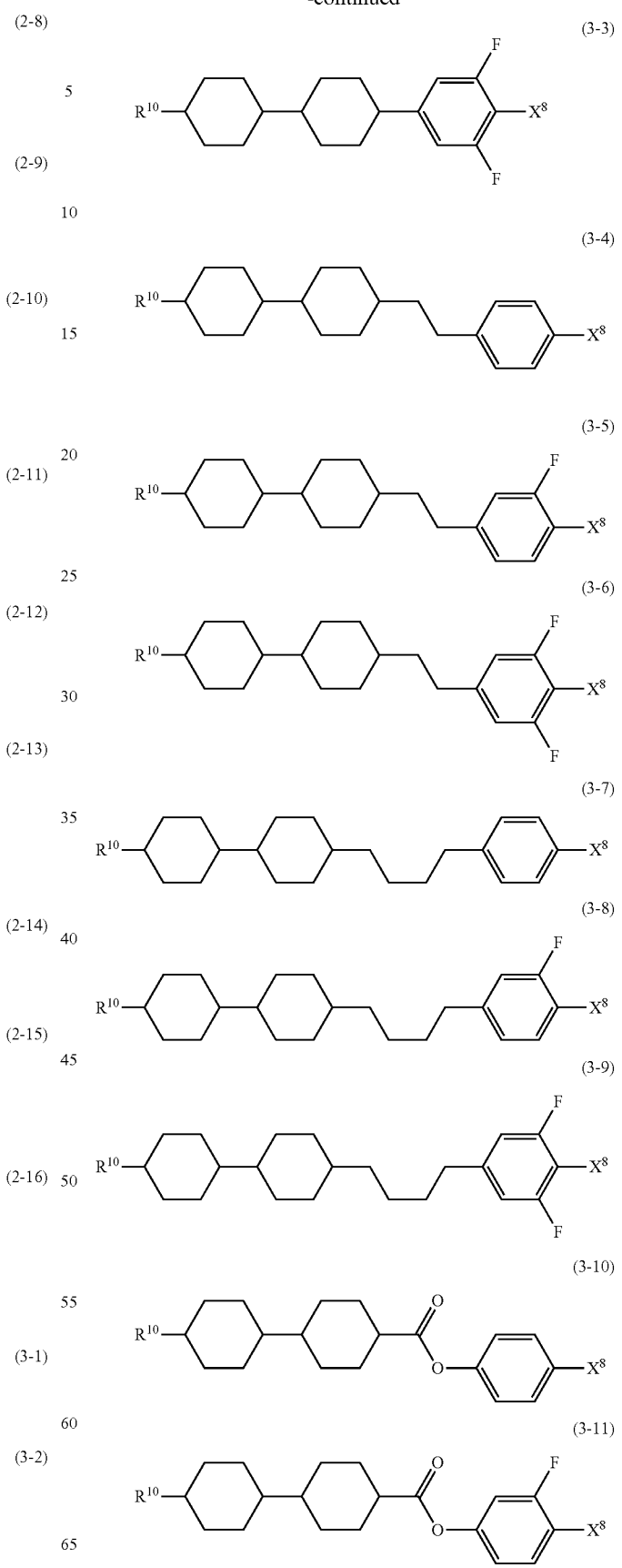

(3-12) 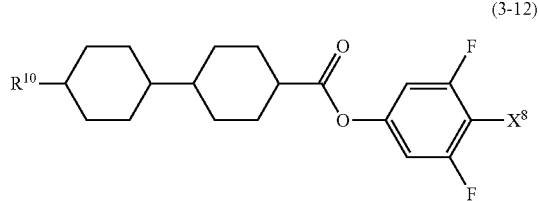
(3-13) 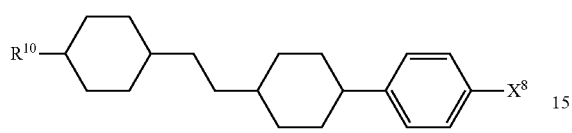
(3-14) 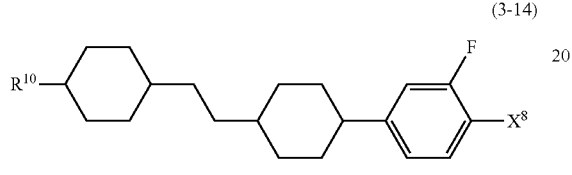
(3-15) 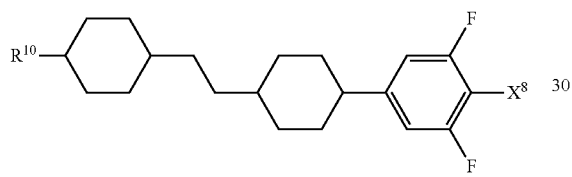
(3-16) 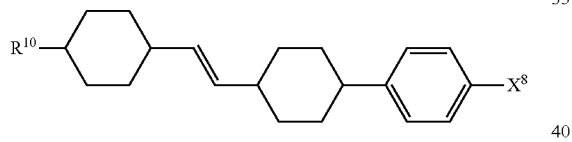
(3-17) 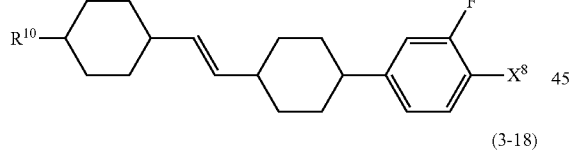
(3-18) 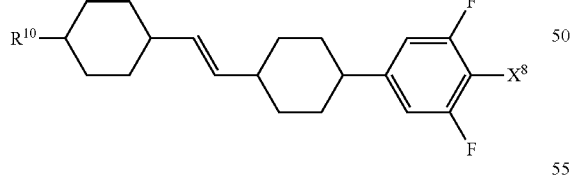
(3-19) 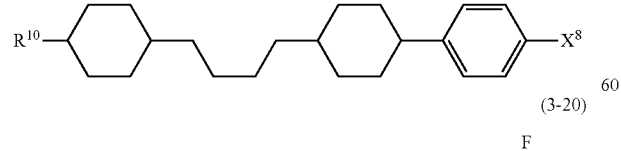
(3-20) 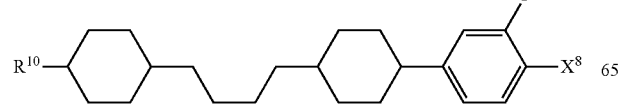
(3-21) 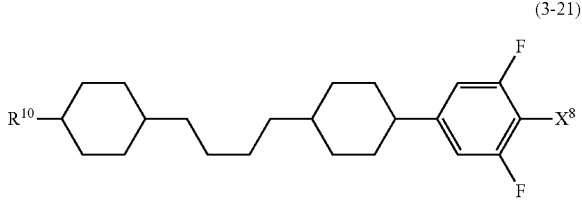
(3-22) 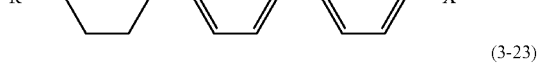
(3-23) 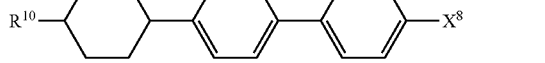
(3-24) 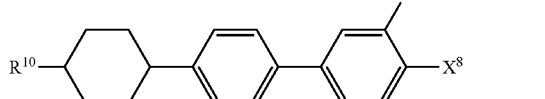
(3-25) 
(3-26) 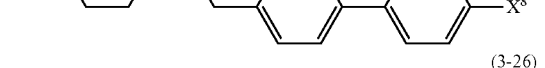
(3-27) 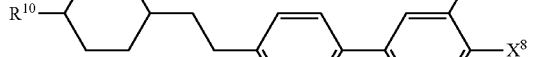
(3-28) 
(3-29) 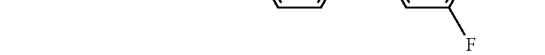
(3-30) 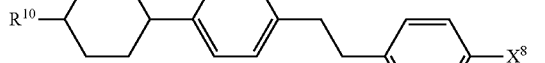

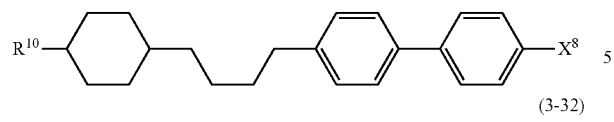
(3-31)
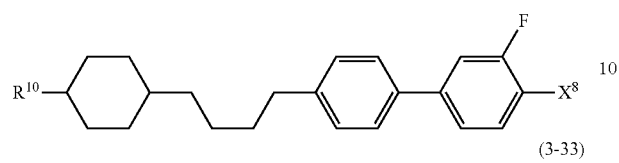
(3-32)
(3-33)
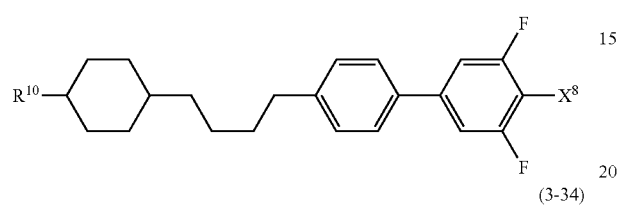
(3-34)
(3-35)
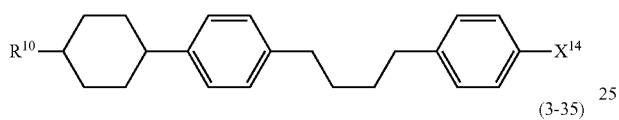
(3-36)
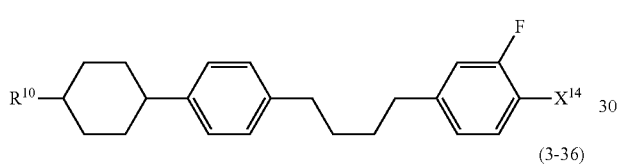
(3-37)
(3-38)
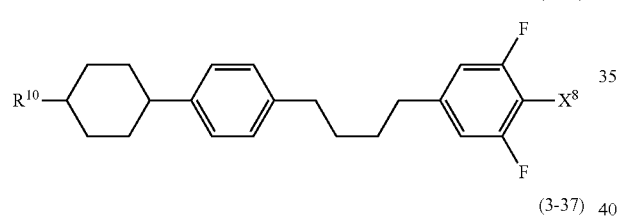
(3-39)
(3-40)
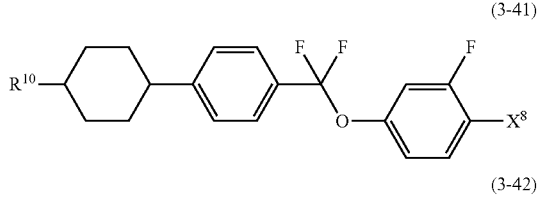
(3-41)
(3-42)
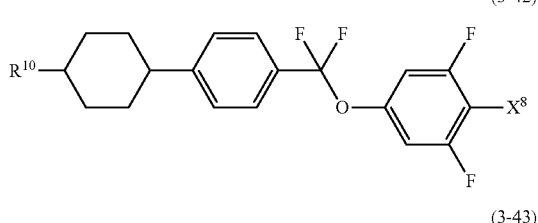
(3-43)
(3-44)
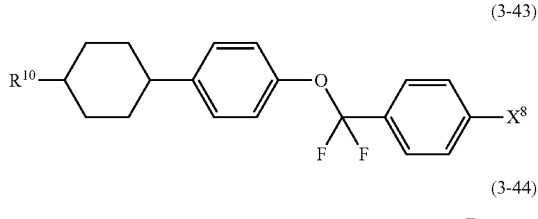
(3-45)
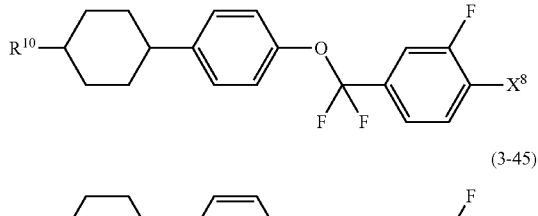
(3-46)
(3-47)
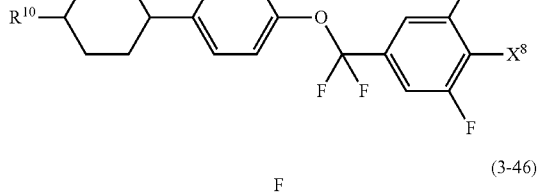
(3-48)
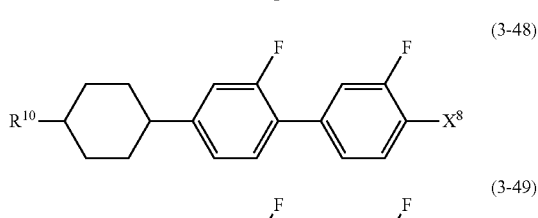
(3-49)

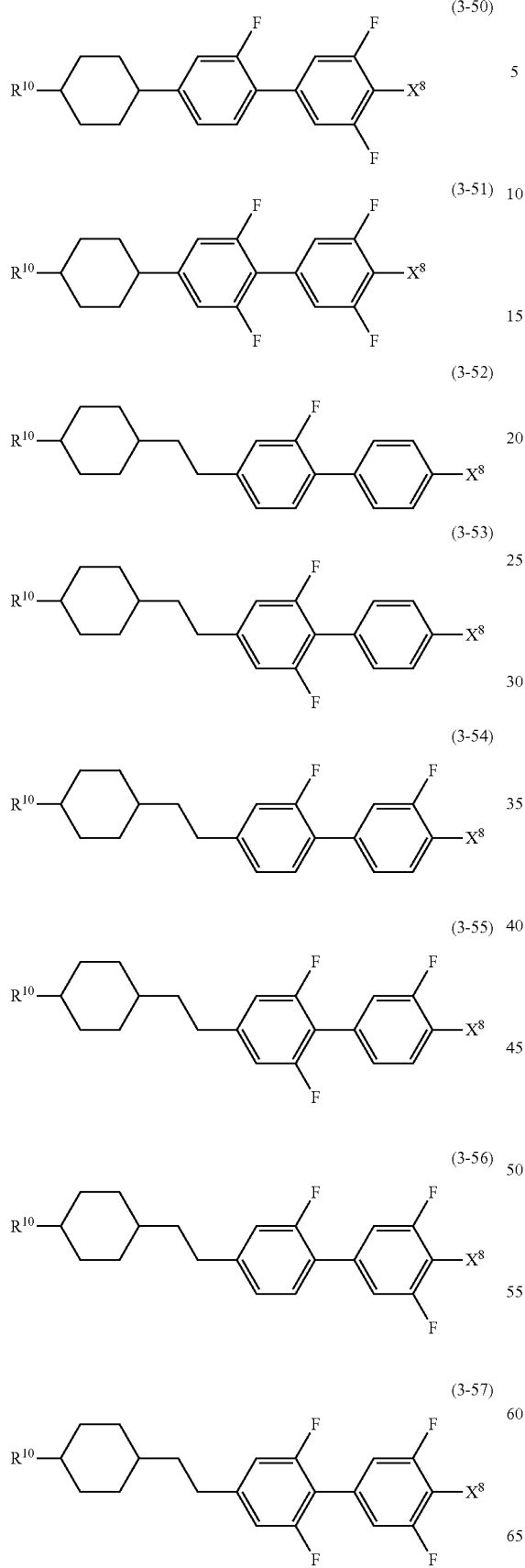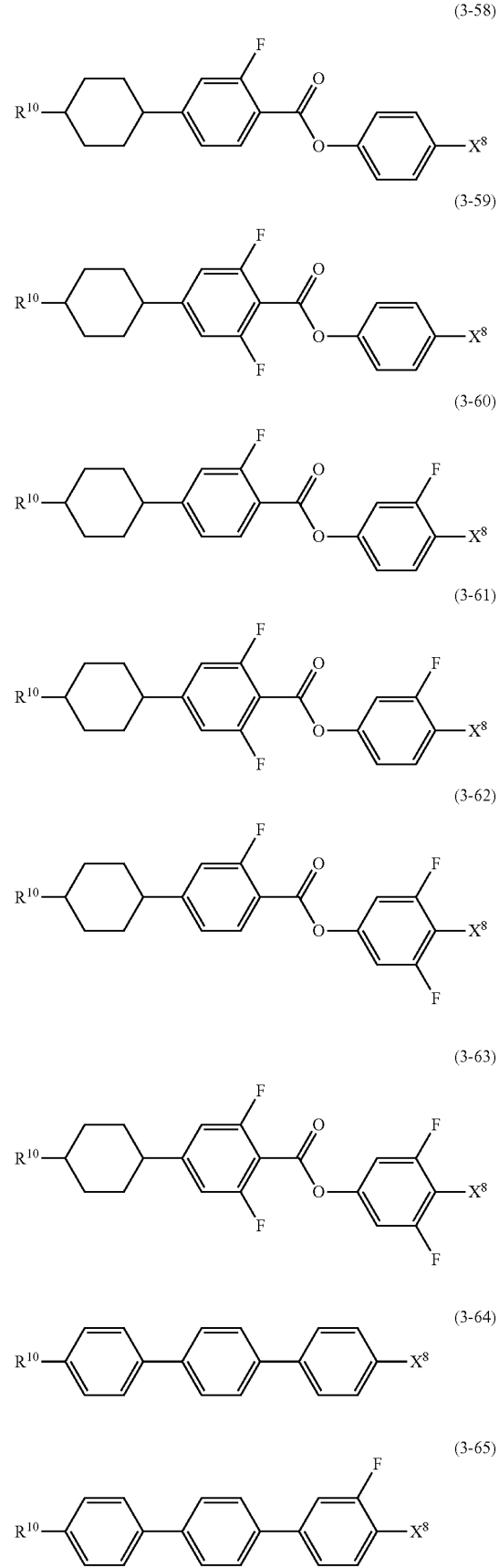

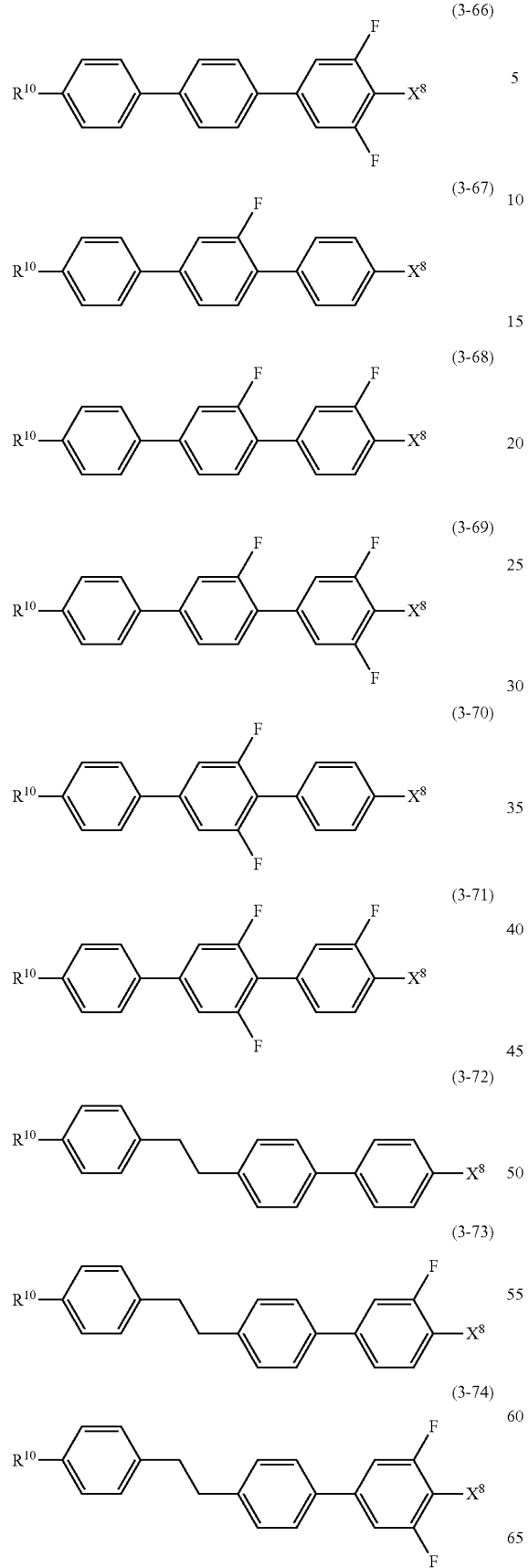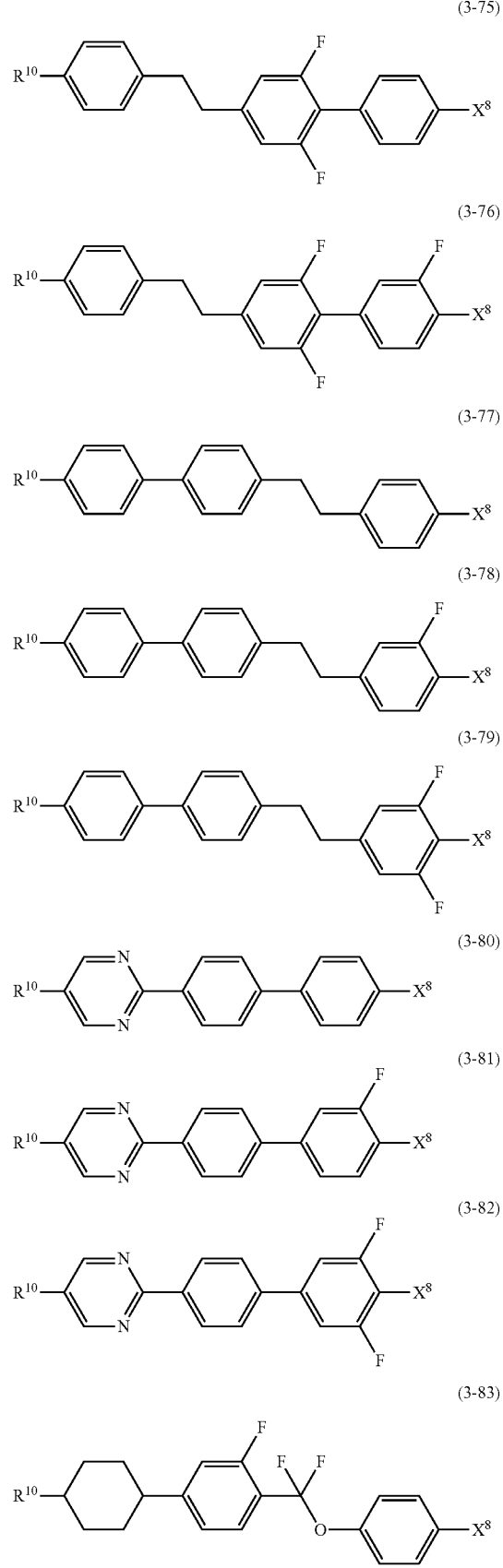

(3-84) 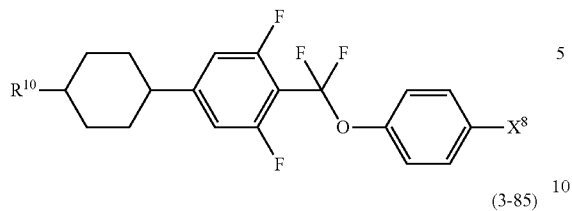
(3-85) 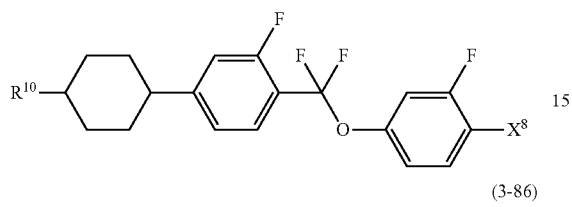
(3-86) 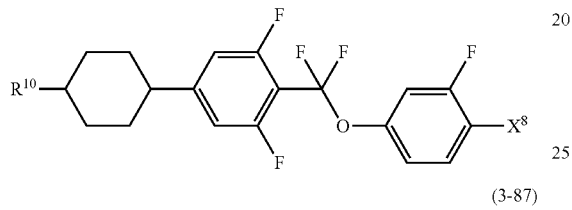
(3-87) 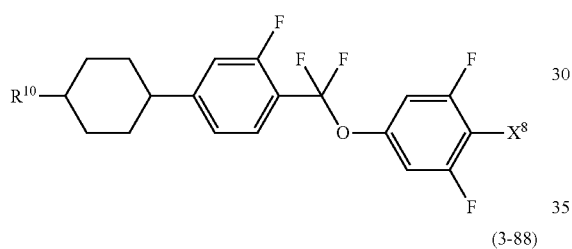
(3-88) 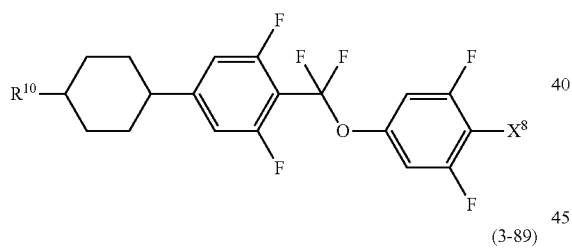
(3-89) 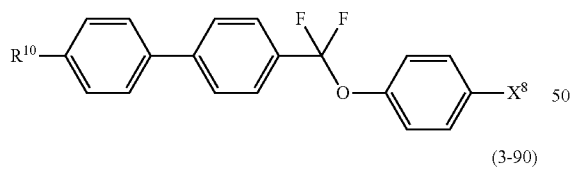
(3-90) 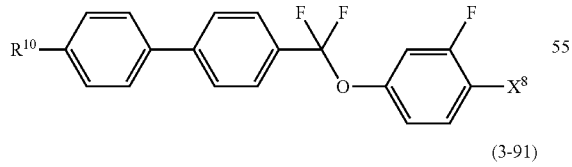
(3-91) 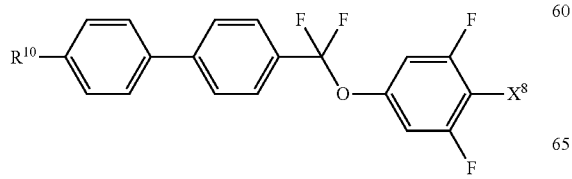
(3-92) 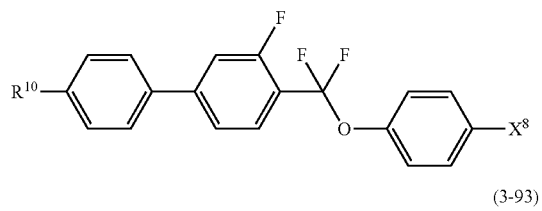
(3-93) 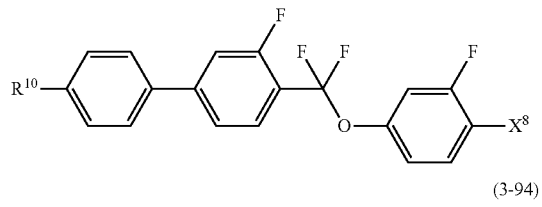
(3-94) 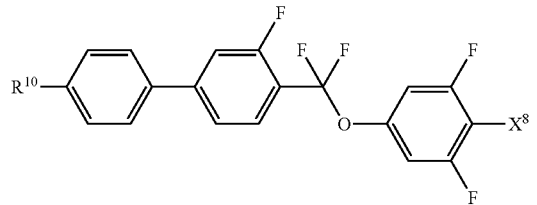
(3-95) 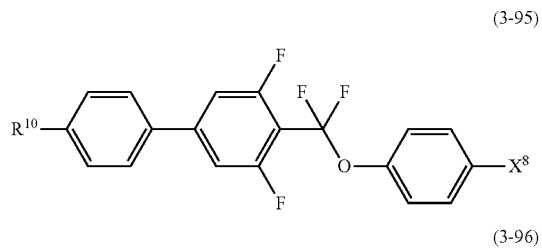
(3-96) 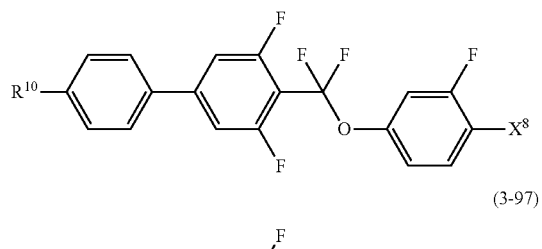
(3-97) 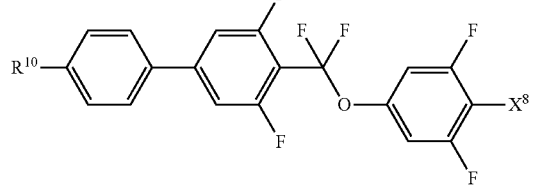
(3-98)
(3-99)
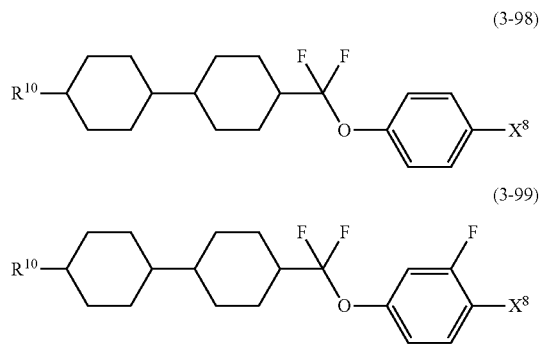

(3-100)
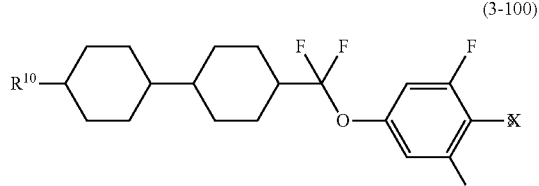
(3-101)
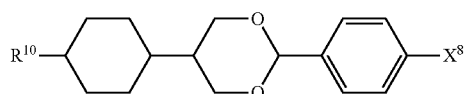
(3-102)
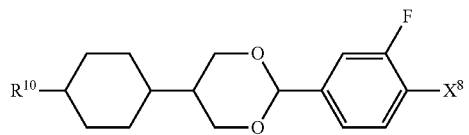
(3-103)
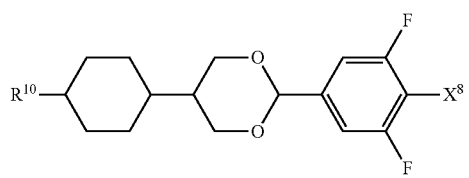
(3-104)
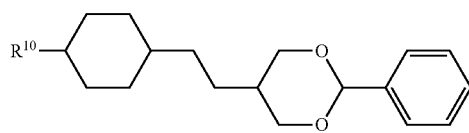
(3-105)
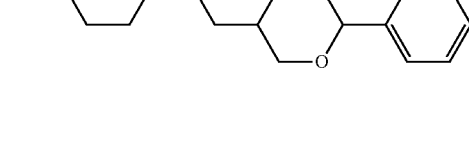
(3-106)
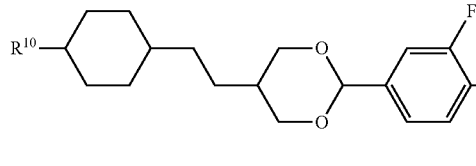
(3-107)
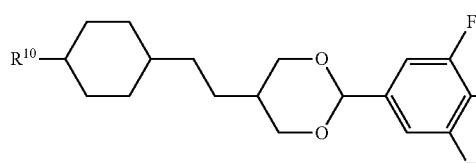
(3-108)
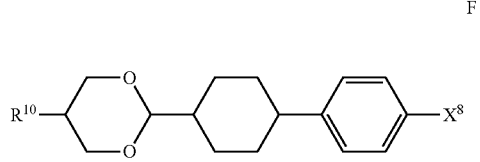
(3-109)
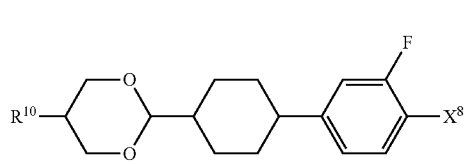
(3-110)
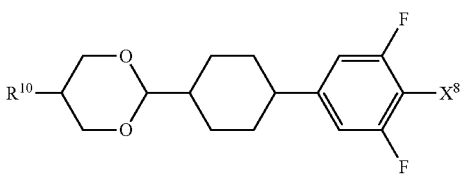
(3-111)
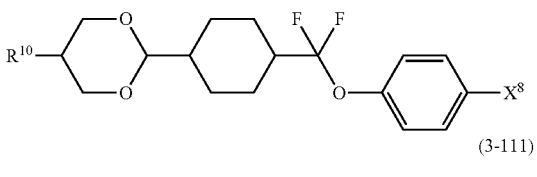
(3-112)
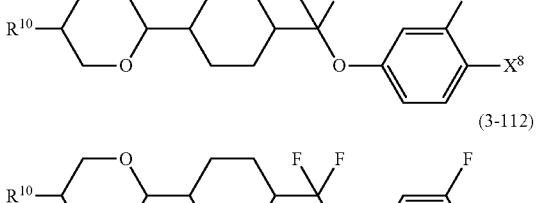
(4-1)
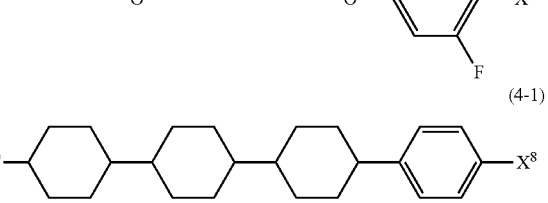
(4-2)
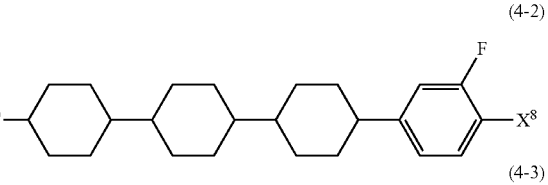
(4-3)
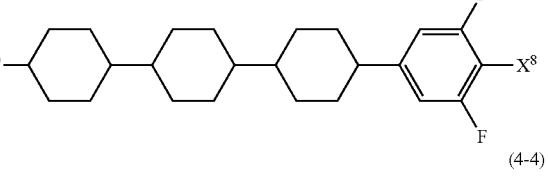
(4-4)
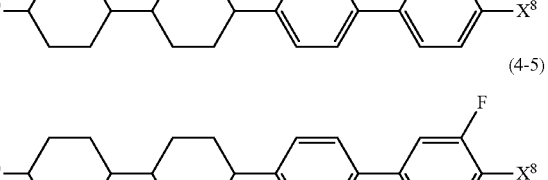
(4-5)
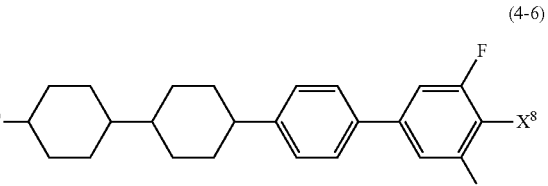
(4-6)

(4-7) 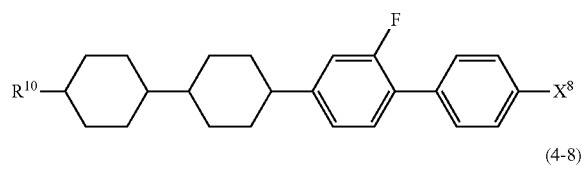
(4-8) 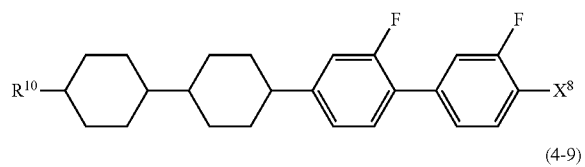
(4-9) 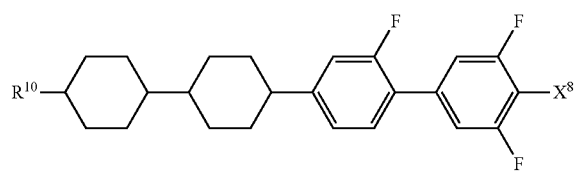
(4-10) 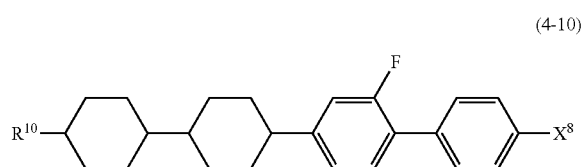
(4-11) 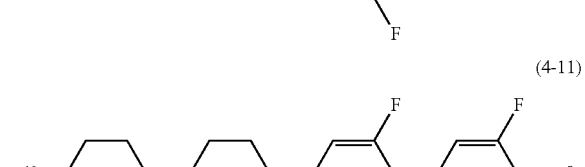
(4-12) 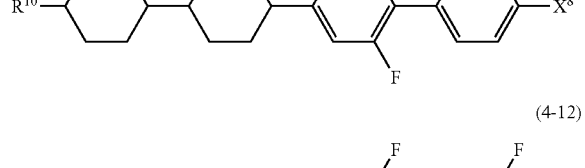
(4-13) 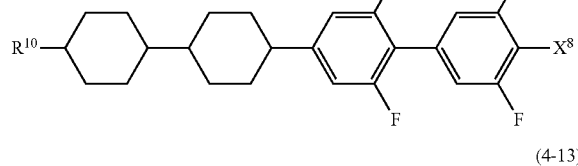
(4-14) 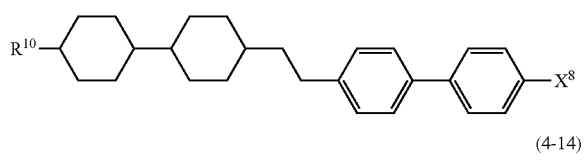
(4-15) 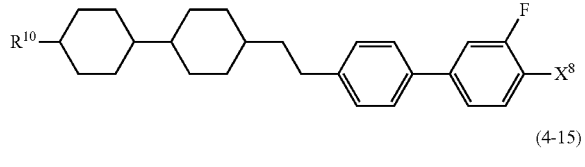
(4-16) 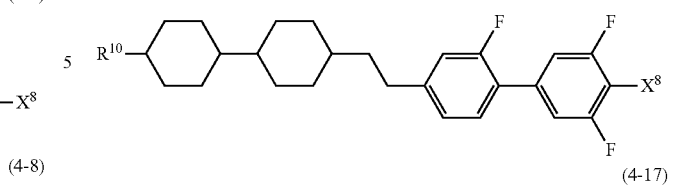
(4-17) 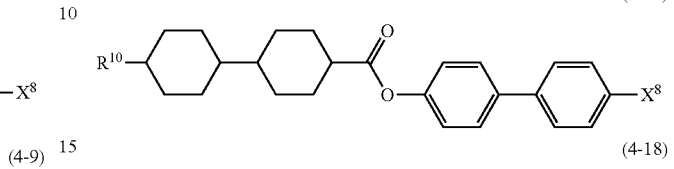
(4-18) 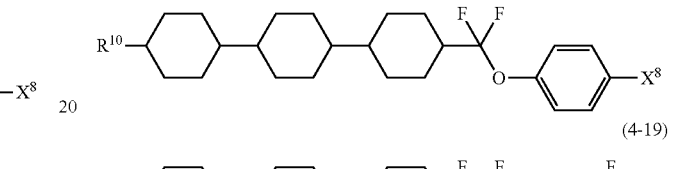
(4-19) 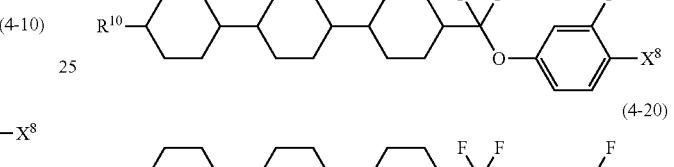
(4-20) 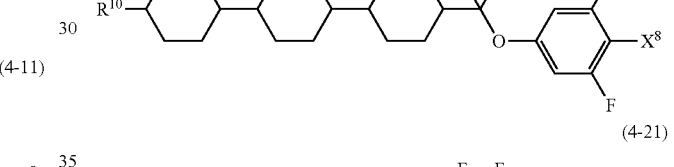
(4-21) 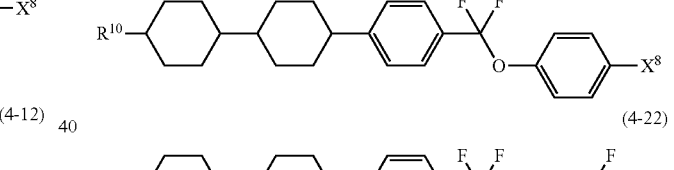
(4-22) 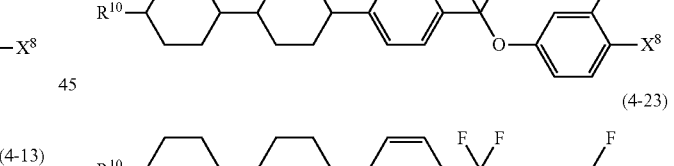
(4-23) 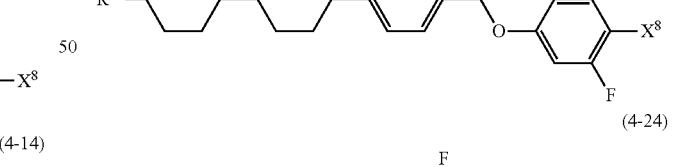
(4-24) 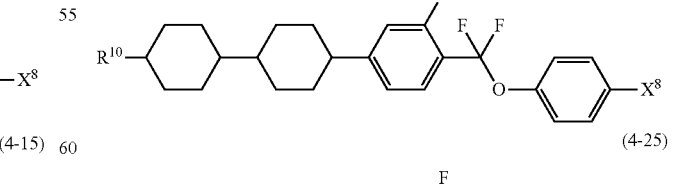
(4-25)

(4-26) 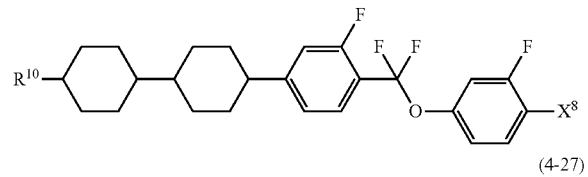
(4-27) 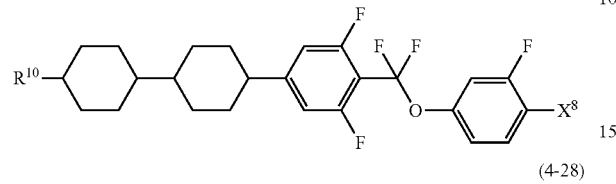
(4-28) 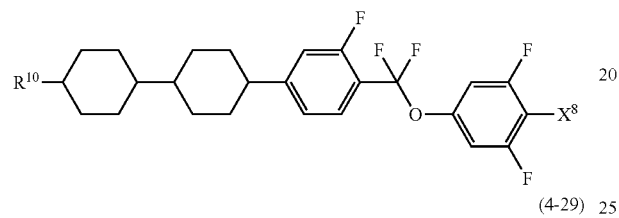
(4-29) 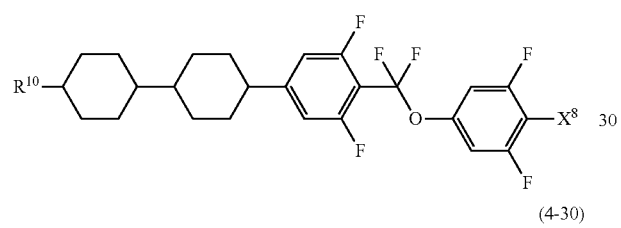
(4-30) 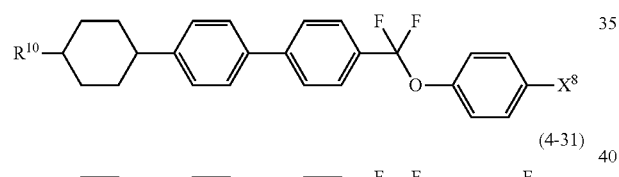
(4-31) 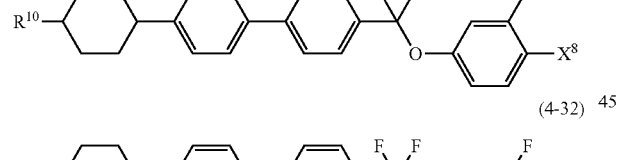
(4-32) 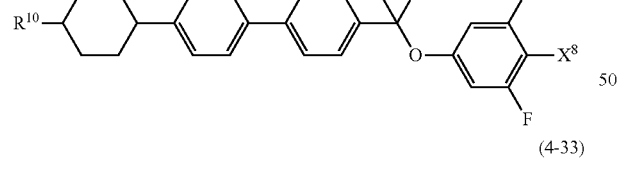
(4-33) 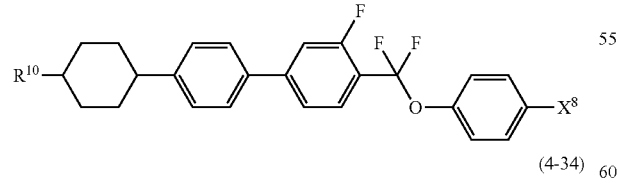
(4-34) 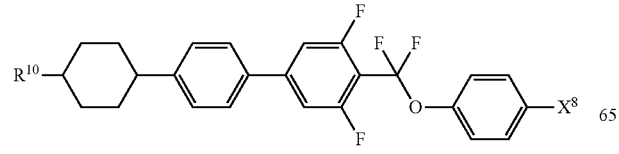
(4-35) 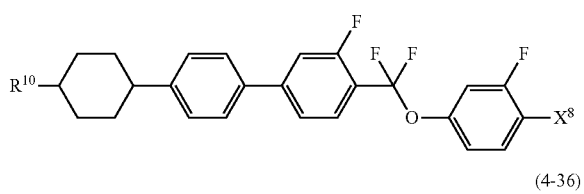
(4-36) 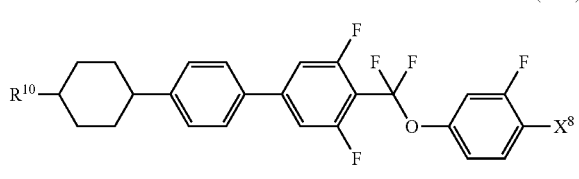
(4-37) 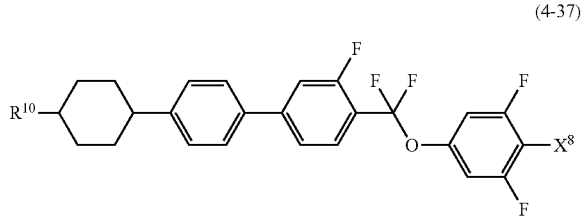
(4-38) 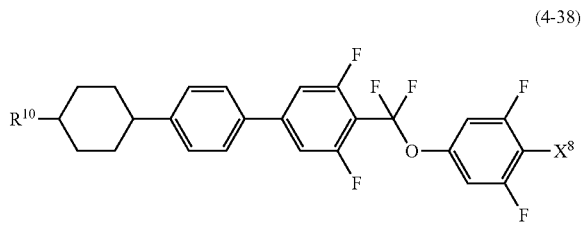
(4-39) 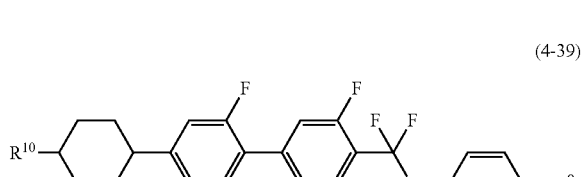
(4-40) 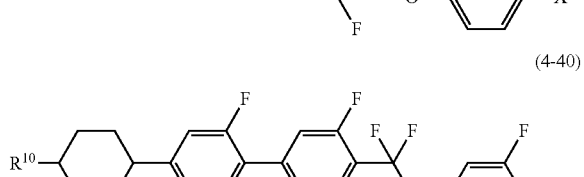
(4-41) 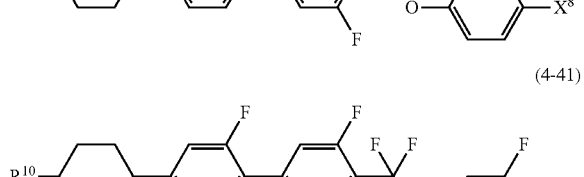
(4-42) 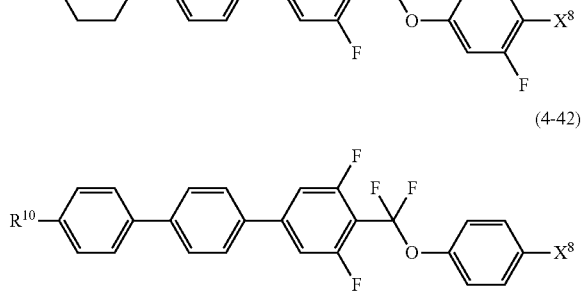

(4-43)
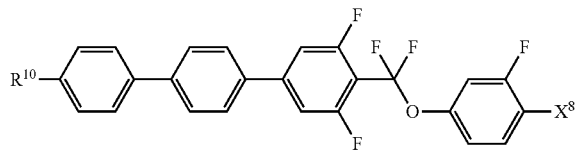

(4-44)
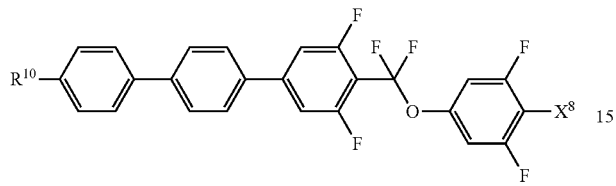

(4-45)
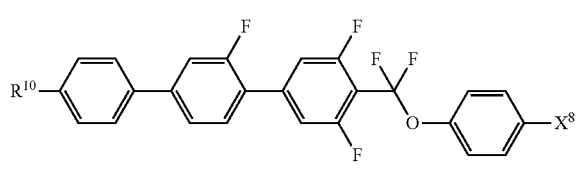

(4-46)
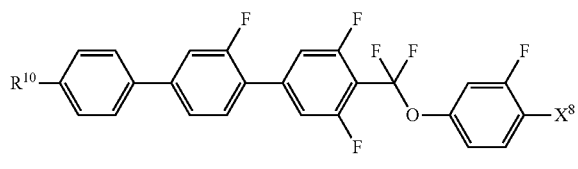

(4-47)
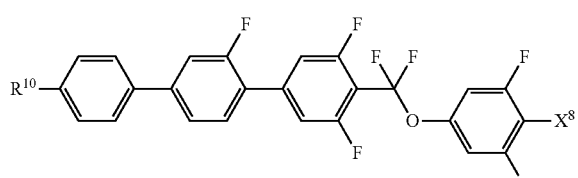

(4-48)
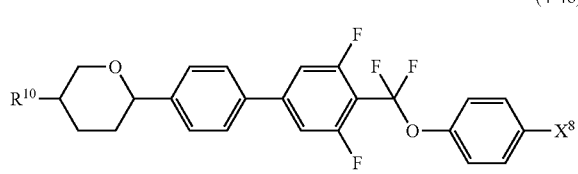

(4-49)
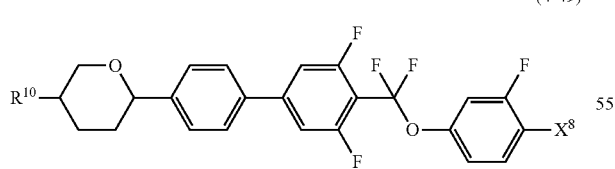

(4-50)
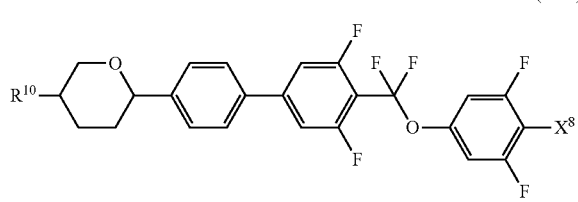

(4-51)
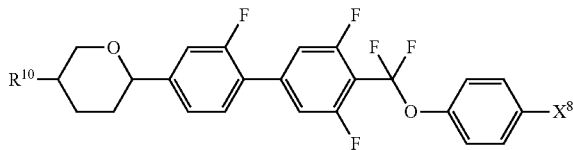

(4-52)
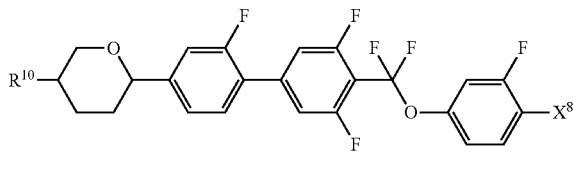

(4-53)
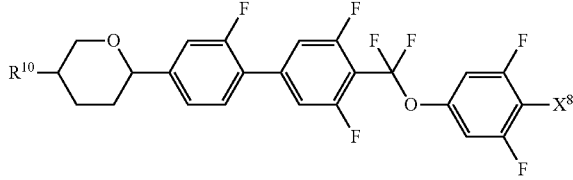

(4-54)
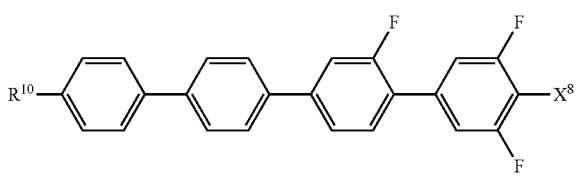

In the formulas, $R^{10}$ and $X^8$ have the same meanings as described above.

The compounds represented by these formulas (2) to (4), that is to say the component B, is used for the preparation of a liquid crystal composition for use in TFT and PSA, since the dielectric anisotropy is positive, and the thermal stability or the chemical stability is quite excellent. The content of the component B in the liquid crystal composition of the invention is suitably in the range of 1% to 99% by weight, preferably in the range of 10% to 97% by weight, and more preferably 40% to 95% by weight, based on the total weight of the liquid crystal composition. The viscosity can be adjusted by the further addition of the compound represented by formulas (6) to (8), that is to say the component D.

Suitable examples of the compound represented by formula (5), that is to say the component C, include formulas (5-1) to (5-64).

(5-1)
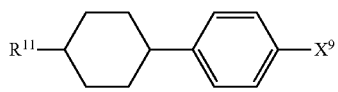

(5-2)
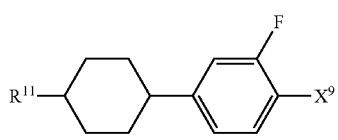

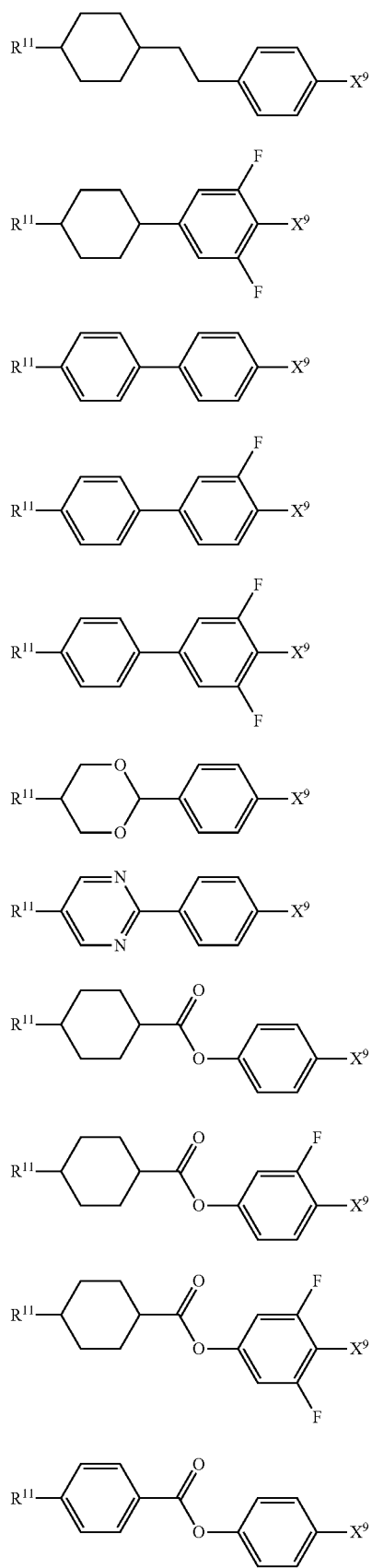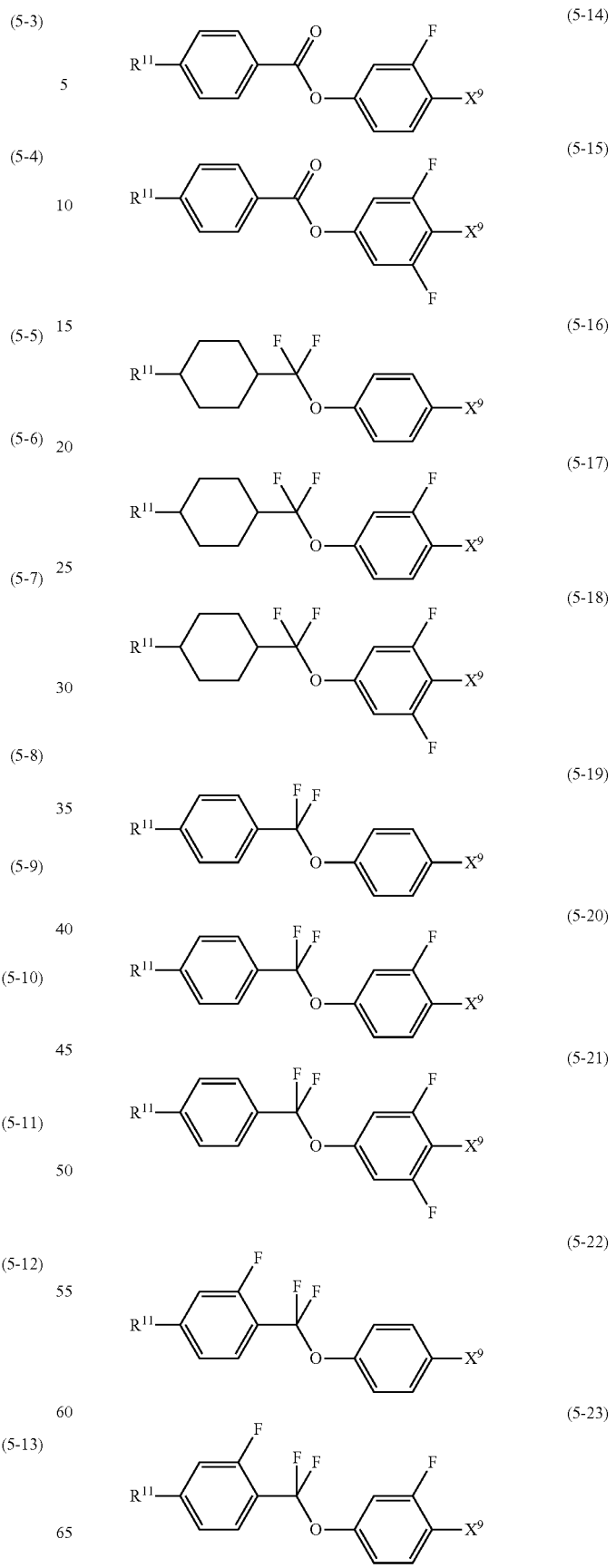

-continued
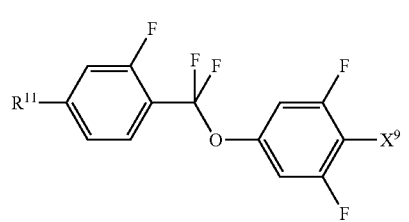
(5-24)
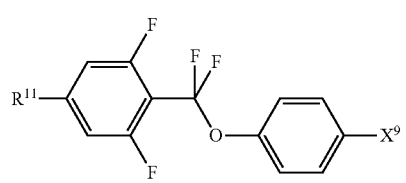
(5-25)
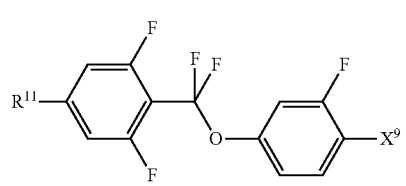
(5-26)
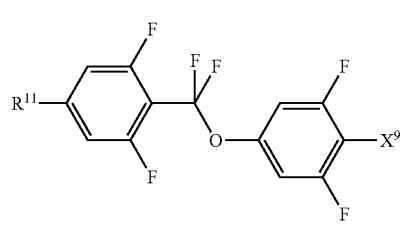
(5-27)
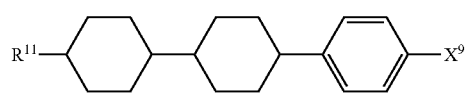
(5-28)
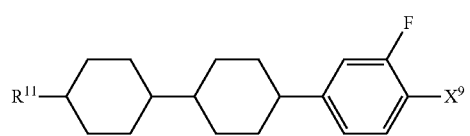
(5-29)
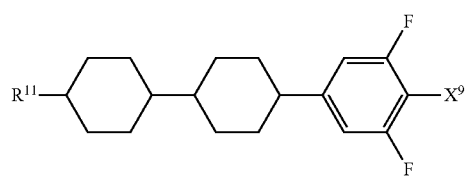
(5-30)
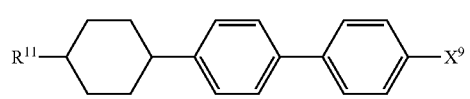
(5-31)
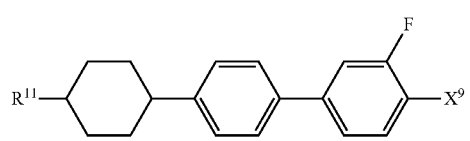
(5-32)
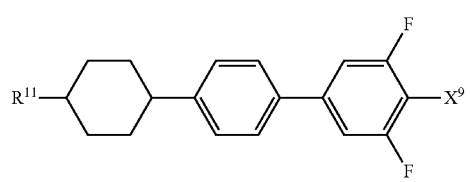
(5-33)
-continued
(5-34)
(5-35)
(5-36)
(5-37)
(5-38)
(5-39)
(5-40)
(5-41)
(5-42)
(5-43)

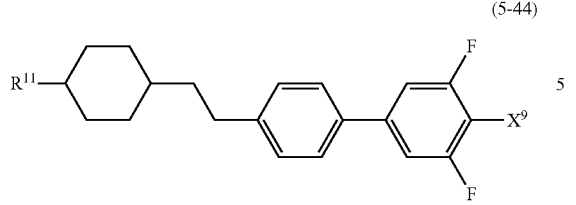
(5-44)
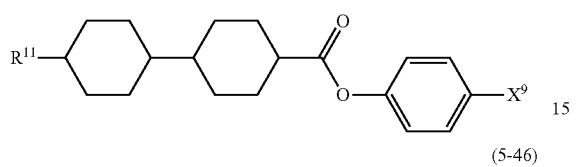
(5-45)
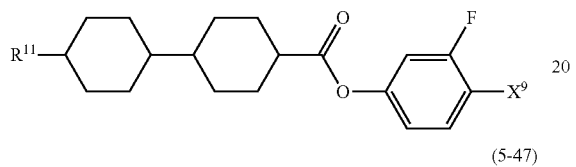
(5-46)
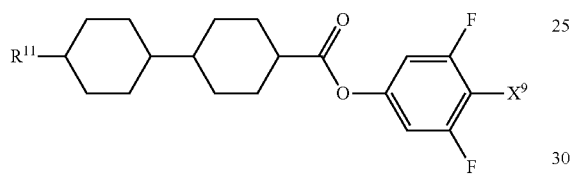
(5-47)
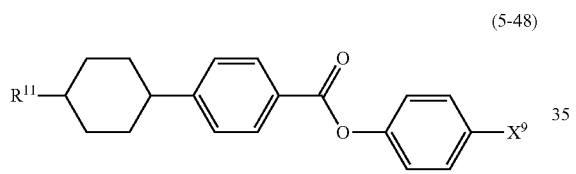
(5-48)
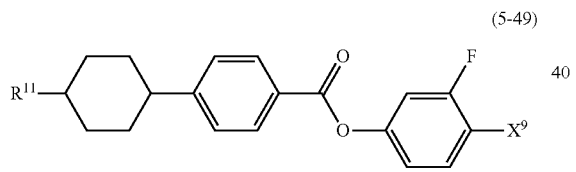
(5-49)
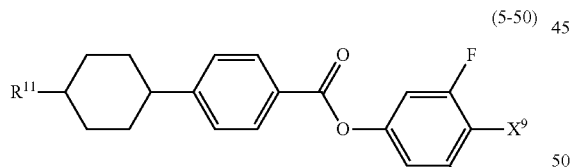
(5-50)
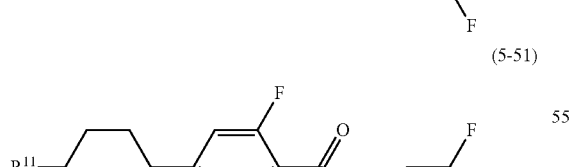
(5-51)
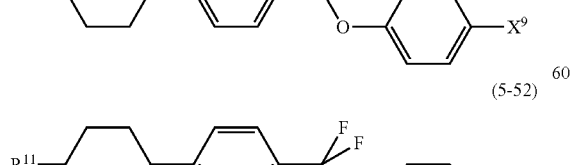
(5-52)
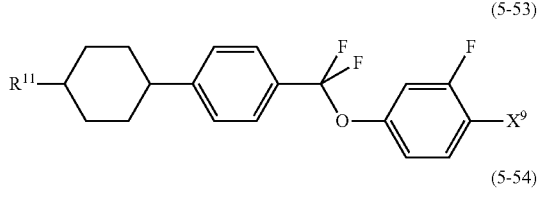
(5-53)
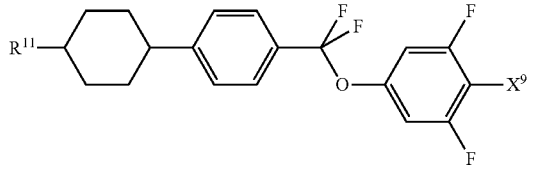
(5-54)
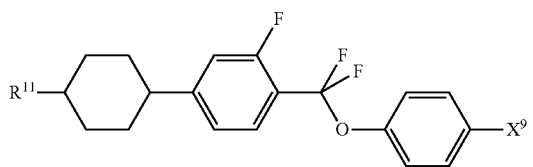
(5-55)
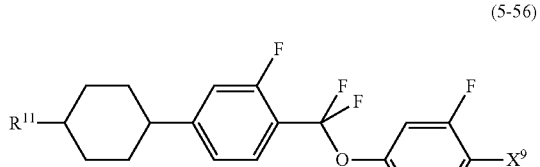
(5-56)
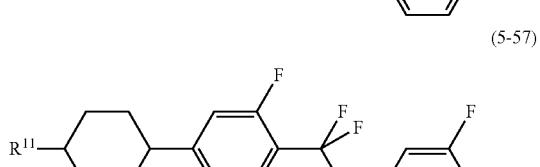
(5-57)
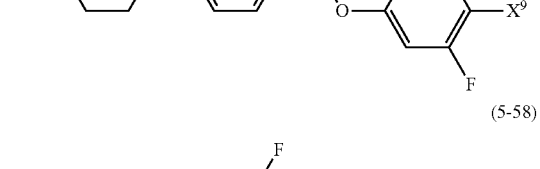
(5-58)
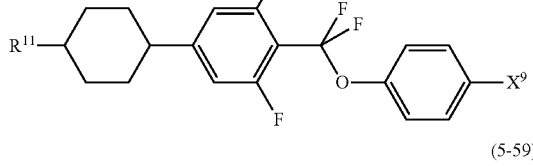
(5-59)
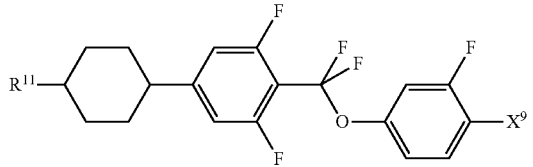
(5-60)
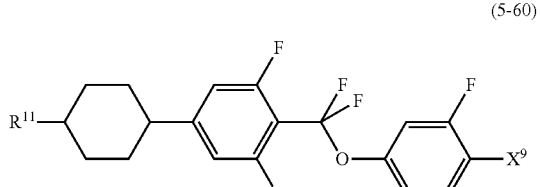

(5-61)

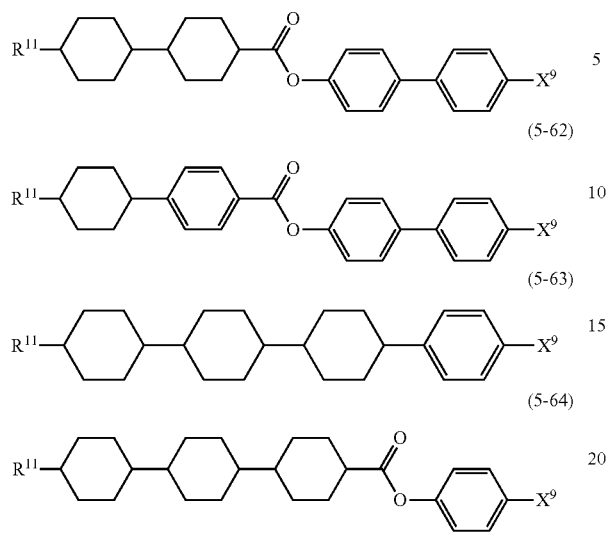

(5-62)

(5-63)

(5-64)

In the formulas, $R^{11}$ and $X^9$ have the same meanings as described above. In formula (5), two of the ring $C^2$ may be the same or different when o is 2.

The compound represented by formula (5), that is to say the component C, is mainly used in the preparation of a liquid crystal composition for use in STN, TN or PSA, since the dielectric anisotropy is positive, and the value is quite large. The threshold voltage of the composition can be decreased by the addition of the component C. Further, the viscosity can be adjusted, the refractive index anisotropy can be adjusted and the temperature range of a liquid crystal phase can be increased. Furthermore, the component C can be utilized for an improvement of the steepness.

The content of the component C is suitably in the range of 0.1% to 99.9% by weight, preferably in the range of 10% to 97% by weight, and more preferably in the range of 40% to 95% by weight in the preparation of a liquid crystal composition for use in STN or TN. The threshold voltage, the temperature range of a liquid crystal phase, the refractive index anisotropy, the dielectric anisotropy, the viscosity or the like can be adjusted by the addition of a component that will be described below.

Suitable examples of the compounds represented by formulas (6), (7) and (8), that is to say the component D, includes formulas (6-1) to (6-11), (7-1) to (7-19) and (8-1) to (8-6), respectively.

(6-1)

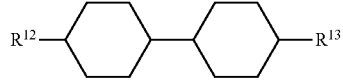

(6-2)

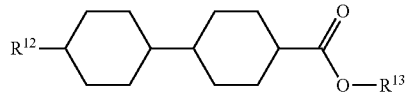

(6-3)

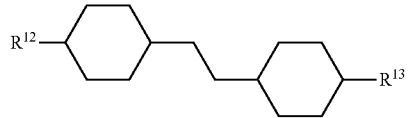

(6-4)

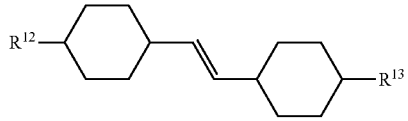

(6-5)

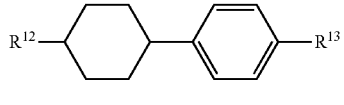

(6-6)

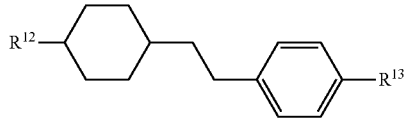

(6-7)

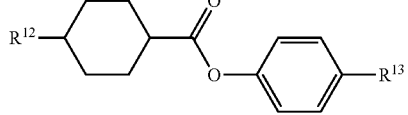

(6-8)

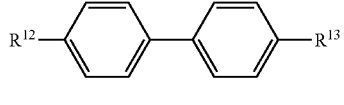

(6-9)

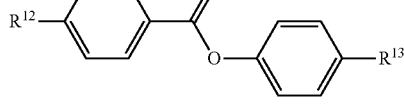

(6-10)

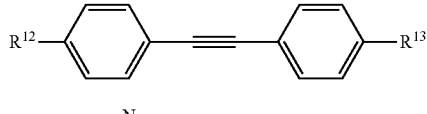

(6-11)

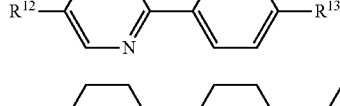

(7-1)

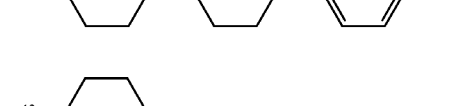

(7-2)

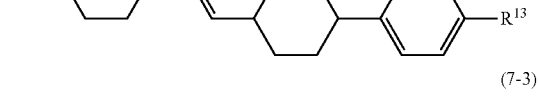

(7-3)

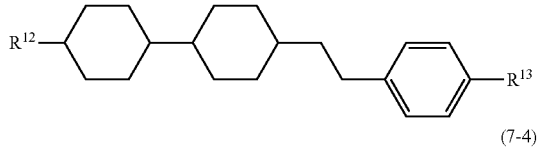

(7-4)

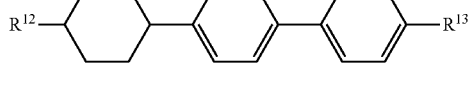

(7-5)

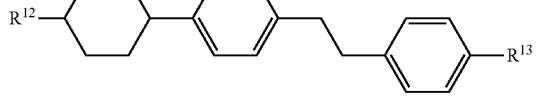

(7-6) 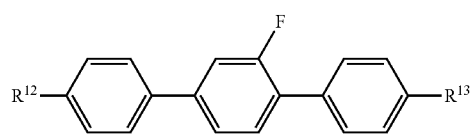
(7-7) 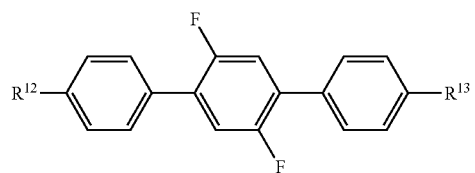
(7-8) 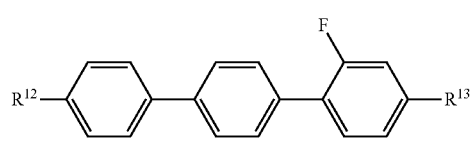
(7-9) 
(7-10) 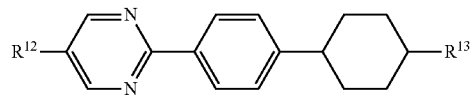
(7-11) 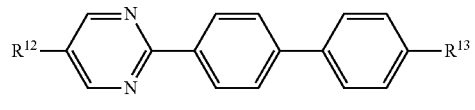
(7-12) 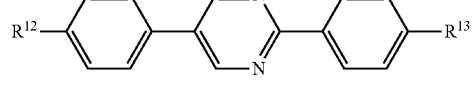
(7-13) 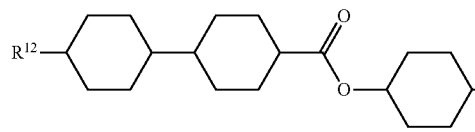
(7-14) 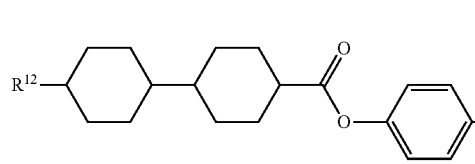
(7-15) 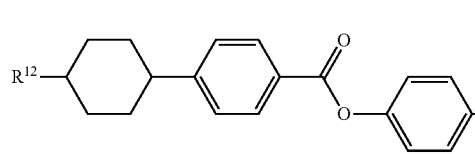
(7-16) 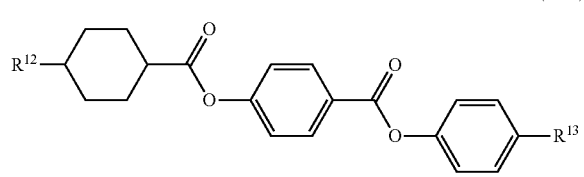

(7-17) 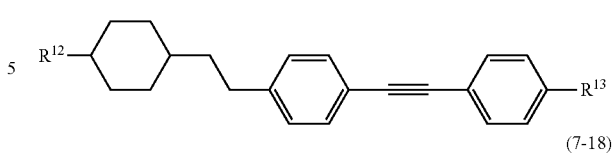
(7-18) 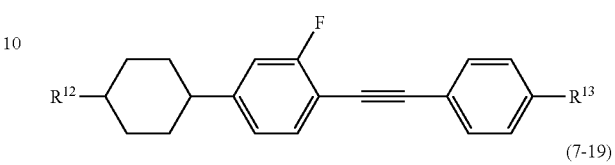
(7-19) 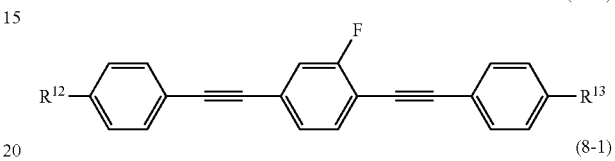
(8-1) 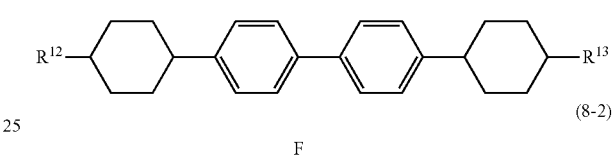
(8-2) 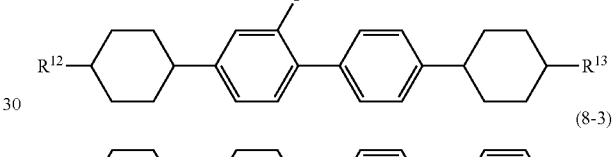
(8-3) 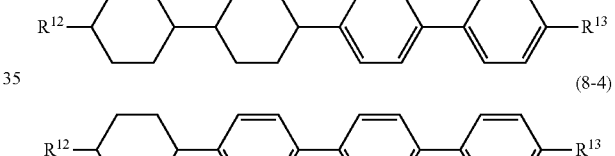
(8-4) 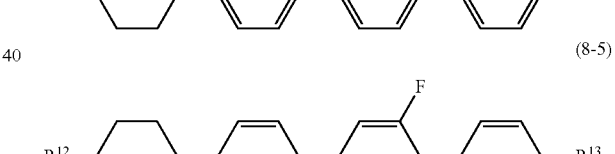
(8-5) 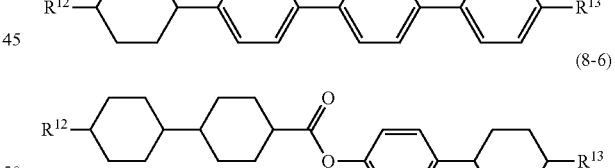
(8-6) 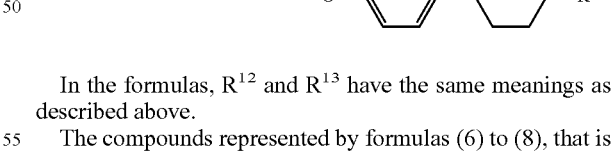

In the formulas, $R^{12}$ and $R^{13}$ have the same meanings as described above.

The compounds represented by formulas (6) to (8), that is to say the component D, have a small absolute value of the dielectric anisotropy, and are close to neutral. The compound represented by formula (6) is mainly effective in adjusting the viscosity or adjusting the refractive index anisotropy. The compounds represented by formulas (7) and (8) are effective in increasing the temperature range of a nematic phase, such as increasing the clearing point, or adjusting the refractive index anisotropy.

As the content of the component D is increased, the threshold voltage of the liquid crystal composition increases and the viscosity decreases. Accordingly, it is desirable that the content increases as long as the required value of the threshold voltage of the liquid crystal composition is satisfied. The content of the component D is preferably 30% by weight or more, and more preferably 50% by weight or more based on the total amount of the composition, in the preparation of the liquid crystal composition for use in TFT or PSA. The content of the component D is preferably 30% by weight or more, and more preferably 40% by weight or more based on the total amount of the composition, in the preparation of the liquid crystal composition for use in TN, STN or PSA.

It is desirable that the liquid crystal composition of the invention includes at least one of compounds of the invention that is represented by formula (1-1), that is to say the component A, in the range of 0.1% to 99% by weight for exhibiting excellent characteristics.

The liquid crystal composition of the invention is generally prepared according to known methods such as the mutual dissolution of necessary components at a high temperature.

An additive that is well-known to a person skilled in the art may be added to the composition depending on its intended use. For example, a liquid crystal composition of the invention including an optically active compound, which will be described below, or a polymerizable compound and a polymerization initiator, or a liquid crystal composition for use in GH, to which a dye is added, can be prepared. The additive is generally well known to a person skilled in the art, and is described in the literature and so forth in detail.

In the liquid crystal composition of the invention, the liquid crystal composition of the invention described above may further include one or more optically active compounds.

A known chiral dopant can be added as an optically active compound. The chiral dopant is effective in inducing a helical structure in liquid crystals, adjusting a necessary twist angle and thus preventing a reverse twist. Examples of the chiral dopant include the following optically active compounds (Op-1) to (Op-13).

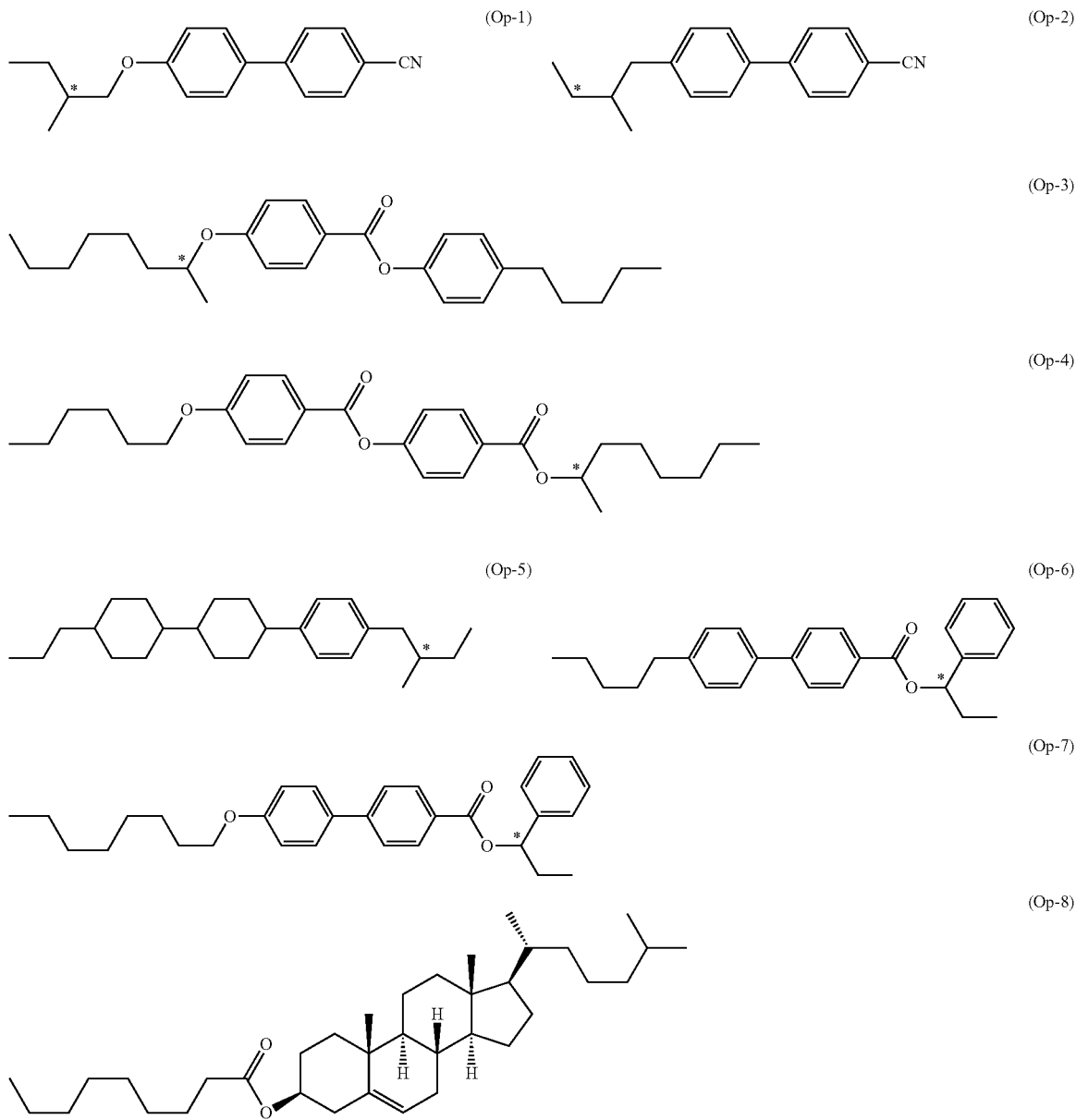

-continued

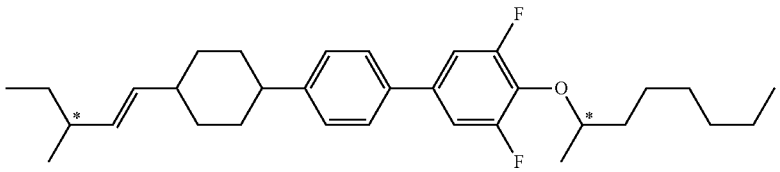
(Op-9)

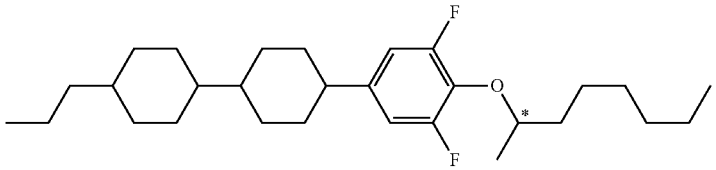
(Op-10)

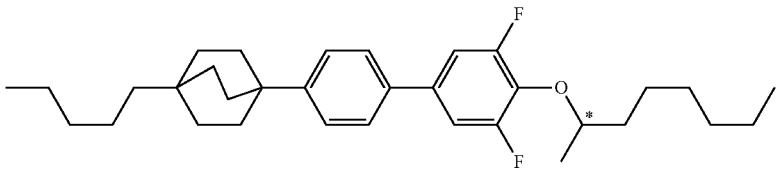
(Op-11)

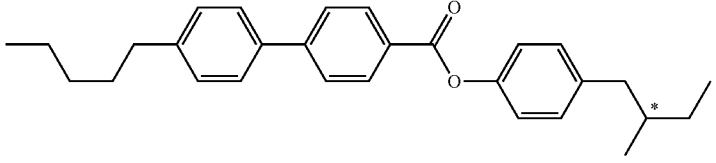
(Op-12)

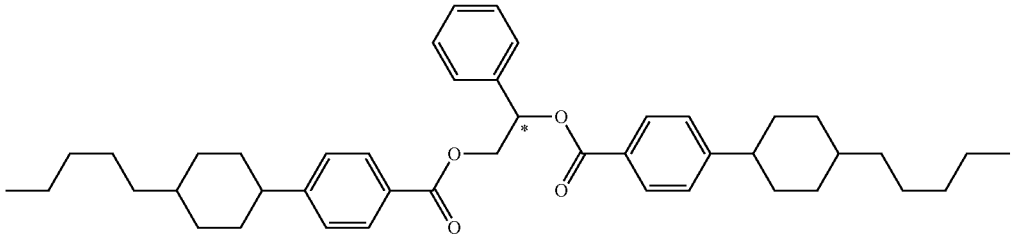
(Op-13)

A helical pitch is usually adjusted by the addition of this optically active compound to the liquid crystal composition of the invention. It is desirable to adjust the helical pitch to the range of 40 to 200 micrometers in a liquid crystal composition for use in TFT and TN. It is desirable to adjust the helical pitch to the range of 6 to 20 micrometers in a liquid crystal composition for use in STN. It is desirable to adjust the helical pitch to the range of 1.5 to 4 micrometers in a liquid crystal composition for use in BTN (bistable TN). Two or more optically active compounds may be added for the purpose of adjusting the temperature dependence of the helical pitch.

The liquid crystal composition of the invention can be used for GH by the addition of a dichroic dye such as a merocyanine, stylyl, azo, azomethine, azoxy, quinophthalone, anthraquinone or tetrazine compound.

The liquid crystal composition of the invention can be used for NCAP prepared by micro-encapsulating nematic liquid crystals, and for PDLCD (a polymer-distributed liquid crystal display device) prepared by forming a three-dimensional network polymer in liquid crystals, such as PNLCD (a polymer network liquid crystal display device), and also for ECB (electrically controlled birefringence) or DS.

The liquid crystal composition of the invention can be used as a liquid crystal composition for use in PSA (polymer sustained alignment) by the addition of a polymerizable compound. Examples of the polymerizable compound include compounds having polymerizable groups such as acrylates, methacrylates, vinyl compounds, vinyloxy compounds, propenyl ethers, epoxy compounds, vinyl ketones and oxetanes. The polymerizable compound is polymerized on irradiation with ultraviolet light or the like, preferably in the presence of a suitable initiator such as a photopolymerization initiator. Suitable conditions for the polymerization, and a suitable type and a suitable amount of the initiator are known to a person skilled in the art and are described in the literature. For example, Irgacure 651 (registered trademark), Irgacure 184 (registered trademark) or Darocure 1173 (registered trademark) (Ciba Japan K. K.), each of which is a photopolymerization initiator, is suitable for radical polymerization.

Method for the Preparation of the Liquid Crystal Composition

When each of component compounds in the liquid crystal composition of the invention is a liquid, for example, the composition is prepared by mixing and shaking the compounds. When solids are included, the composition is prepared by mixing each compound, and then shaking after the compounds have been heated and liquefied. Moreover, the liquid crystal composition of the invention can also be prepared according to other known methods.

Physical Properties of the Liquid Crystal Composition

In the liquid crystal composition of the invention, the temperature range of the nematic phase is wide, since the maximum temperature of a nematic phase can be adjusted to 70° C. or higher and the minimum temperature of the nematic phase can be adjusted to −20° C. or lower. Accordingly, the liquid crystal display device containing this liquid crystal composition can be used in a wide temperature range.

In the liquid crystal composition of the invention, the optical anisotropy can be adjusted to the range of 0.10 to 0.13, and to the range of 0.05 to 0.18, by suitably varying the components and their ratios.

In the liquid crystal composition of the invention, the liquid crystal composition having the dielectric anisotropy usually in the range of 2.0 to 15.0, and preferably in the range of 2.0 to 11.0 can be obtained. The liquid crystal composition having the dielectric anisotropy in the range of 2.0 to 11.0 can be suitably used for a liquid crystal display device operated in a PC mode, a TN mode, a STN mode, an OCB mode or a PSA mode.

The Liquid Crystal Display Device

The liquid crystal composition of the invention can be used not only for a liquid crystal display device having an operating mode such as a PC mode, a TN mode, a STN mode, an OCB mode or a PSA mode, which is driven by means of an AM mode, but also for a liquid crystal display device having an operating mode such as a PC mode, a TN mode, a STN mode, an OCB mode or an IPS mode, which is driven by means of a PM (passive matrix) mode.

The liquid crystal display devices having the AM and PM modes can be applied to any of liquid crystal displays and so forth that have a reflection type, a transmission type, and a semi-transmission type.

Moreover, the liquid crystal composition of the invention can also be used for a dynamic scattering (DS) mode-device containing the liquid crystal composition to which a conducting agent is added, and a nematic curvilinear aligned phase (NCAP) device containing the liquid crystal composition microencapsulated, and a polymer dispersed (PD) device having a three-dimensional network polymer formed in the liquid crystal composition, for example, a polymer network (PN) device.

Since the liquid crystal composition of the invention has the characteristics described above, it can be suitably used for the liquid crystal display device having an AM mode which is driven by means of an operating mode such as a PC mode, a TN mode, a STN mode, an OCB mode or a PSA mode, wherein the liquid crystal composition having positive dielectric anisotropy is used, and especially for the liquid crystal display device having an AM mode which is driven by means of a STN mode or an IPS mode.

Incidentally, the direction of an electric field is perpendicular to the liquid crystal layer in a liquid crystal display device which is driven by means of the TN mode. On the other hand, the direction of an electric field is parallel to the liquid crystal layer in a liquid crystal display device which is driven by means of the IPS mode or the like. The structure of the liquid crystal display device which is driven by means of the IPS mode is reported in WO 1991-010936 A (patent family: U.S. Pat. No. 5,576,867).

EXAMPLES

Example of the Compound (1-1)

The invention will be explained below in more detail based on examples. However, the invention is not limited to the examples. Incidentally, the term "%" means "% by weight," unless otherwise noted.

The resulting compounds herein were identified on the basis of nuclear magnetic resonance spectra obtained by means of $^1$H-NMR analysis, gas chromatograms obtained by means of gas chromatography (GC) analysis and so forth. Thus, analytical methods will be explained first.

$^1$H-NMR Analysis

A model DRX-500 apparatus (made by Bruker BioSpin Corporation) was used for measurement. A sample was dissolved in a deuterated solvent such as $CDCl_3$ in which the sample was soluble, and the measurement was carried out under the conditions of room temperature, 500 MHz and thirty-two times of accumulation. In the explanation of the nuclear magnetic resonance spectra obtained, the symbols s, d, t, q, quin, sex, m and br stand for a singlet, a doublet, a triplet, a quartet, a quintet, a sextet, a multiplet and line-broadening, respectively. Tetramethylsilane (TMS) was used as the standard reference material for the zero point of the chemical shift (δ values).

GC Analysis

A Gas Chromatograph Model GC-14B made by Shimadzu Corporation was used for measurement. A capillary column CBP1-M25-025 (length 25 m, bore 0.22 mm, film thickness 0.25 micrometer; dimethylpolysiloxane as a stationary liquid phase; non-polar) made by Shimadzu Corporation was used. Helium was used as a carrier gas, and its flow rate was adjusted to 1 ml per minute. The temperature of the sample injector was set at 280° C. and the temperature of the detector (FID) was set at 300° C.

A sample was dissolved in toluene to give a 1% by weight solution, and then 1 microliter of the solution obtained was injected into the sample injector.

Chromatopac Model C-R6A made by Shimadzu Corporation or its equivalent was used as a recorder. The obtained gas chromatogram showed the retention time of the peaks and the values of the peak areas corresponding to the component compounds.

Chloroform or hexane, for example, may also be used as a solvent for diluting the sample. The following capillary columns may also be used: DB-1 (length 30 m, bore 0.32 mm, film thickness 0.25 micrometer) made by Agilent Technologies Inc., HP-1 (length 30 m, bore 0.32 mm, film thickness 0.25 micrometer) made by Agilent Technologies Inc., Rtx-1 (length 30 m, bore 0.32 mm, film thickness 0.25 micrometer) made by Restek Corporation, BP-1 (length 30 m, bore 0.32 mm, film thickness 0.25 micrometer) made by SGE International Pty. Ltd, and so forth.

The ratio of the peak areas in the gas chromatogram corresponds to the ratio of component compounds. In general, the percentage by weight of each component compound in an analytical sample is not completely the same as the percentage of each peak area in the analytical sample. In the invention, however, the percentage by weight of the component compound in the analytical sample corresponds substantially to the percentage of the peak area in the analytical sample, because the correction coefficient is essentially 1 (one) when the columns described above are used. This is because there is no significant difference among the correction coefficients of the liquid crystal compounds as components. An internal standard method using gas chromatograms is used in order to determine the composition ratio of the liquid crystal compounds in the liquid crystal composition more accurately by means of the gas chromatograms. Each liquid crystal compound (test-component) weighed accurately in a fixed amount and a liquid crystal compound serving as a standard (standard reference material) are analyzed simultaneously by means of gas chromatography, and the relative intensity is calculated in advance from the ratio of the peak area of the test-component to that of the standard reference material. Then, the composition ratio of the liquid crystal compounds in the liquid crystal composition can be determined more accurately by means of the gas-chromatographic analysis using the correction method based on the relative intensity of the peak area of each component to that of the standard reference material.

Samples for Measurement of Physical Properties of Compounds and so Forth

Two kinds of samples were used for measuring physical properties of a compound: one was the compound itself, and the other was a mixture of the compound and mother liquid crystals.

In the case using a sample in which the compound was mixed with mother liquid crystals, the measurement was carried out according to the following method. First, the sample was prepared by mixing 15% by weight of the compound obtained and 85% by weight of the mother liquid crystals. Then, extrapolated values were calculated from the measured values of the resulting sample by means of an extrapolation method according to the following formula. The extrapolated values were regarded as physical properties of this compound.

(Extrapolated value)=[100×(Measured value of sample)−(% by weight of mother liquid crystals)×(Measured value of mother liquid crystals)]/(% by weight of liquid crystal compound)

When a smectic phase or crystals deposits even at this ratio of the compound to the mother liquid crystals at 25° C., the ratio of the liquid crystal compound to the mother liquid crystals was changed in the order of (10% by weight:90% by weight), (5% by weight:95% by weight) and (1% by weight: 99% by weight). Physical property values of the sample were measured at the ratio in which the smectic phase or the crystals did not deposit at 25° C. Extrapolated values were determined according to the above equation, and regarded as physical property values of the liquid crystal compound.

There are a variety of mother liquid crystals used for measurement and, for example, the formulation (% by weight) of the mother liquid crystals (i) is shown below. The mother liquid crystals (i):

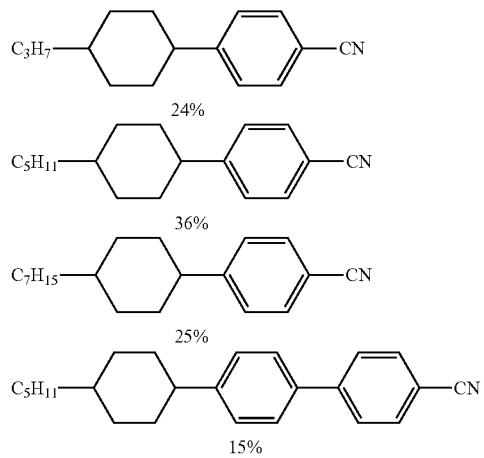

Incidentally, in the case where the physical properties of a liquid crystal composition were measured, the composition itself was used as a sample.

Methods for the Measurement of Physical Properties of a Compound and so Forth

Physical property values were measured according to the following methods. Most were methods described in the Standard of Electronic Industries Association of Japan, EIAJ•ED-2521A, or the modified methods. No TFT was attached to a TN device or a VA device used for measurement.

The physical properties of a liquid crystal compound itself as a sample were measured. The physical properties of a liquid crystal composition itself as a sample were measured. The both measured values were described here as an experimental data. When a sample was prepared by mixing the compound with mother liquid crystals, the values calculated from the measured value according to the extrapolation method were regarded as physical property values.

Phase Structure and Transition Temperature (° C.)

Measurements were carried out according to the following methods (1) and (2).

(1) A compound was placed on a hot plate of a melting point apparatus (Hot Stage Model FP-52 made by Mettler Toledo International Inc.) equipped with a polarizing microscope, and the phase conditions and their changes were observed with the polarizing microscope while the compound was heated at the rate of 3° C. per minute, and the kinds of phases were specified.

(2) A sample was heated and then cooled at a rate of 3° C. per minute using a Perkin-Elmer differential scanning calorimeter, a DSC-7 System or a Diamond DSC System. The starting point of an endothermic peak or an exothermic peak caused by a phase change of the sample was obtained by means of the extrapolation (on set), and thus the phase transition temperature was determined.

Hereinafter, the symbol C stood for crystals, which were expressed as $C_1$ and $C_2$ when the kinds of crystals were distinguishable. The symbols S and N stood for a smectic phase and a nematic phase, respectively. The symbol I stood for a liquid (isotropic). When a smectic B phase and a smectic A phase were distinguishable in the smectic phases, they were expressed as $S_B$ and $S_A$, respectively. Phase transition temperatures were expressed, for example, as "C 50.0 N 100.0 I", which means that the phase transition temperature from crystals to a nematic phase (CN) is 50.0° C., and the phase transition temperature from the nematic phase to a liquid (NI) is 100.0° C. The same applied to the other descriptions.

Maximum Temperature of a Nematic Phase ($T_{NI}$; ° C.)

A sample (a liquid crystal composition, or a mixture of a liquid crystal compound and mother liquid crystals) was placed on a hot plate of a melting point apparatus (Hot Stage Model FP-52 made by Mettler Toledo International Inc.) equipped with a polarizing microscope, and was observed with the polarizing microscope while being heated at the rate of 1° C. per minute. The maximum temperature of a nematic phase meant a temperature measured when part of the sample began to change from a nematic phase to an isotropic liquid. Hereinafter, the maximum temperature of a nematic phase may simply be abbreviated to "the maximum temperature."

Compatibility at Low Temperature

Samples were prepared by mixing a liquid crystal compound with mother liquid crystals so that the amount of the liquid crystal compound became 20% by weight, 15% by weight, 10% by weight, 5% by weight, 3% by weight and 1% by weight, and placed in glass vials. After these glass vials had been kept in a freezer at −10° C. or −20° C. for a certain period of time, they were observed as to whether or not crystals or a smectic phase had been deposited.

Viscosity (Bulk Viscosity; η; Measured at 20° C.; mPa·s)

An E-type viscometer was used for measurement.

Viscosity (Rotational Viscosity; γ1; Measured at 25° C.; mPa·s)

Measurement was carried out according to the method described in M. Imai, et al., Molecular Crystals and Liquid Crystals, Vol. 259, p. 37 (1995). A sample (a liquid crystal composition, or a mixture of a liquid crystal compound and mother liquid crystals) was put in a VA device in which the distance between the two glass substrates (cell gap) was 20 micrometers. A voltage in the range of 30 V to 50 V was applied stepwise with an increment of 1 volt to the device. After a period of 0.2 second with no voltage, a voltage was applied repeatedly under the conditions of only one rectangular wave (rectangular pulse; 0.2 second) and no voltage (2 seconds). The peak current and the peak time of the transient current generated by the applied voltage were measured. The value of rotational viscosity was obtained from the measured values and the calculating equation (8) on page 40 of the paper presented by M. Imai, et al. Incidentally, the value of the dielectric anisotropy necessary for the present calculation was obtained by the method described below, under the heading "Dielectric Anisotropy."

Optical Anisotropy (Refractive Index Anisotropy; Δn; Measured at 25° C.)

Measurement was carried out using an Abbe refractometer with a polarizing plate attached to the ocular, on irradiation with light at a wavelength of 589 nanometers. The surface of the main prism was rubbed in one direction, and then a sample (a liquid crystal composition, a liquid crystal composition, or a mixture of a liquid crystal compound and mother liquid crystals) was dropped onto the main prism. The refractive index (n∥) was measured when the direction of the polarized light was parallel to that of the rubbing. The refractive index (n⊥) was measured when the direction of polarized light was perpendicular to that of the rubbing. The value of the refractive index anisotropy (Δn) was calculated from the equation:

$$\Delta n = n_{\parallel} - n_{\perp}.$$

Dielectric Anisotropy (Δ∈; Measured at 25° C.)

Dielectric anisotropy was measured by the following method. An ethanol (20 mL) solution of octadecyltriethoxysilane (0.16 mL) was applied to a well-washed glass substrate. The glass substrate was rotated with a spinner, and then heated at 150° C. for 1 hour. A VA device in which the distance (cell gap) was 20 micrometers was assembled from the two glass substrates.

A polyimide alignment film was prepared on glass substrates in a similar manner. After a rubbing-treatment to the alignment film formed on the glass substrates, a TN device in which the distance between the two glass substrates was 9 micrometers and the twist angle was 80 degrees was assembled.

A sample (a liquid crystal composition, or a mixture of a liquid crystal compound and mother liquid crystals) was put in the VA device obtained, a voltage of 0.5 V (1 kHz, sine waves) was applied to the sample, and then the dielectric constant (∈∥) in the major axis direction of the liquid crystal molecules was measured.

The sample (the liquid crystal composition, or the mixture of the liquid crystal compound and the mother liquid crystals) was put in the TN device obtained, a voltage of 0.5 V (1 kHz, sine waves) was applied to the sample, and then the dielectric constant (∈⊥) in the minor axis direction of the liquid crystal molecules was measured.

The value of the dielectric anisotropy was calculated from the equation of $\Delta \in = \in_{\parallel} - \in_{\perp}$.

Voltage Holding Ratio (VHR; Measured at 25° C.; %)

A TN device used for measurement had a polyimide-alignment film and the distance between the two glass substrates (cell gap) was 6 micrometers. A sample (a liquid crystal composition, or a mixture of a liquid crystal compound and mother liquid crystals) was put in the device, and then the device was sealed with an adhesive polymerizable on irradiation with ultraviolet light. The TN device was charged by applying pulse voltage (60 microseconds at 5 V). Decreasing voltage was measured for 16.7 milliseconds with a High Speed Voltmeter, and the area A between a voltage curve and a horizontal axis in a unit period was measured. The area B was an area without the decrease. The voltage holding ratio was expressed as the percentage of the area A to the area B.

Elastic Constant ($K_{11}$ and $K_{33}$; Measured at 25° C.)

An elastic constant measurement system Model EC-1 made by Toyo Corporation was used for measurement. A sample was put in a homeotropic cell in which the distance between the two glass substrates (cell gap) was 20 micrometers. An electric charge of 20 volts to 0 volts was applied to the cell, and the electrostatic capacity and the applied voltage were measured. The measured values of the electrostatic capacity (C) and the applied voltage (V) were fitted to the equation (2.98) and the equation (2.101) in page 75 of the "Liquid Crystal Device Handbook" (Ekisho Debaisu Handobukku, in Japanese; The Nikkan Kogyo Shimbun, Ltd.) and the value of the elastic constant was obtained from the equation (2.100).

Example 1

Preparation of 1-(4-(trans-4-(4-ethylphenyl)cyclohexyl)cyclohex-1-enyl)-2-fluoro-4-(trans-4-pentylcyclohexyl)benzene (No. 213)

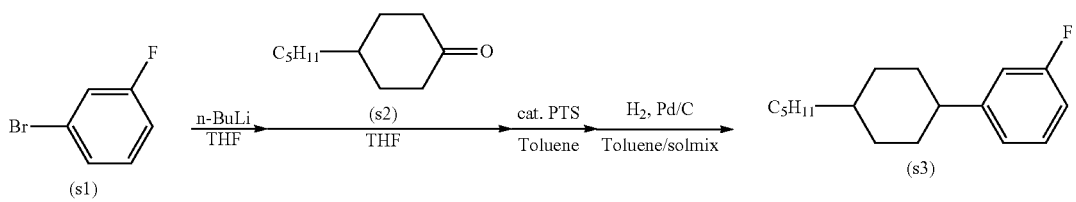

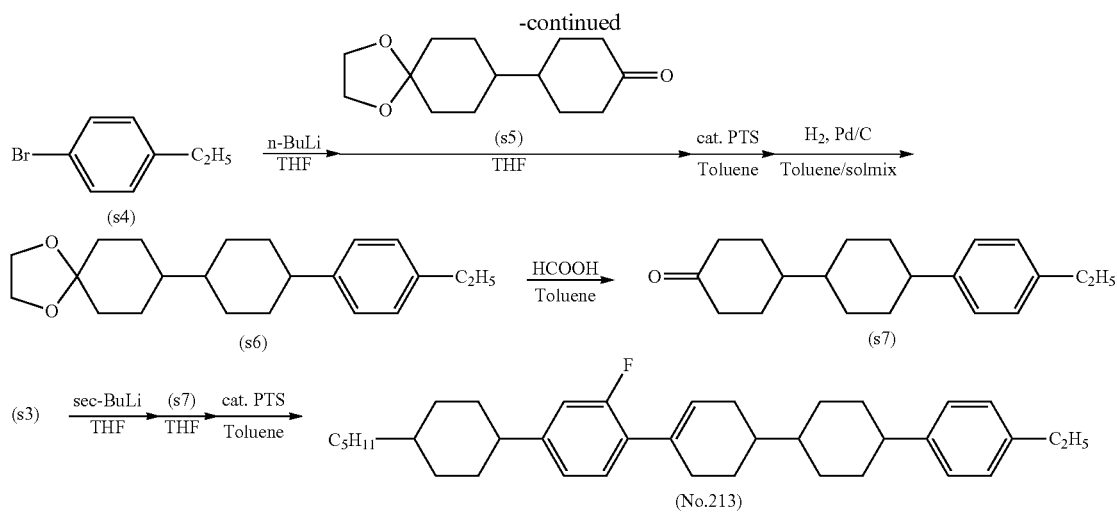

First Step:

1-Bromo-3-fluorobenzene (s1) (60.0 g) and THF (1,000 ml) were placed in a reaction vessel under an atmosphere of nitrogen, and cooled to −74° C. n-Butyllithium (1.57M in n-hexane; 218 ml) was added dropwise in the temperature range of −74° C. to −70° C., and the stirring was continued for another 2 hours. 4-Pentylcyclohexanone (s2) (57.7 g) dissolved in THF (150 ml) was added dropwise in the temperature range of −75° C. to −70° C., and the stirring was continued for another 8 hours while the mixture was allowed to come to 25° C. The resulting reaction mixture was poured into a vessel containing an aqueous solution of ammonium chloride (500 ml) and ethyl acetate (500 ml), and mixed with them. The mixture was allowed to stand and separate into organic and aqueous layers, and the latter was extracted. The separated organic layers were washed with water, a saturated aqueous solution of sodium hydrogencarbonate and water, and dried over anhydrous magnesium sulfate. The solvent was distilled under reduced pressure. p-Toluenesulfonic acid (2.4 g) and toluene (250 ml) were added to the residue, and the mixture was heated to reflux for 2 hours, while distilled water was removed. After the reaction mixture had been cooled to 30° C., water (500 ml) and toluene (900 ml) were added and mixed with it. The mixture was allowed to stand and separate into two layers of organic and aqueous layers, and the latter was extracted. The separated organic layers were washed with a saturated aqueous solution of sodium hydrogencarbonate and water, and then dried over anhydrous magnesium sulfate. The resulting solution was purified by fractionation using column chromatography with heptane as an eluent and silica gel as a stationary phase powder, and dried. The product was dissolved in toluene (150 ml) and Solmix A-11 (150 ml), to which Pd/C (0.8 g) was added. The mixture was stirred at room temperature under a hydrogen atmosphere until hydrogen absorption had ceased. After the reaction had been completed, Pd/C was removed, and then solvent was distilled off. The resulting residue was purified by fractionation using column chromatography with heptane as an eluent and silica gel as a stationary phase powder, and by recrystallization from Solmix A-11, and then dried to give 1-fluoro-3-(trans-4-pentyl cyclohexyl)benzene (s3) (58.4 g). The yield based on the compound (s1) was 68.6%.

Second Step:

4-Bromoethylbenzene (s4) (30.0 g) and THF (1,000 ml) were placed in a reaction vessel under an atmosphere of nitrogen, and cooled to −74° C. n-Butyllithium (1.57M in n-hexane; 124 ml) was added dropwise in the temperature range of −74° C. to −70° C., and the stirring was continued for another 2 hours. 4-(1,4-Dioxaspiro[4.5]decan-8-yl)-cyclohexanone (s5) (38.6 g) in THF (200 ml) solution was added dropwise in the temperature range of −75° C. to −70° C., and the stirring was continued for another 8 hours while the mixture was allowed to come to 25° C. The resulting reaction mixture was poured into a vessel containing an aqueous solution of ammonium chloride (500 ml) and ethyl acetate (500 ml), and mixed with them. The mixture was allowed to stand and separate into organic and aqueous layers, and the latter was extracted. The separated organic layers were washed with water, a saturated aqueous solution of sodium hydrogencarbonate and water, and dried over anhydrous magnesium sulfate. The solvent was distilled under reduced pressure. p-Toluenesulfonic acid (1.6 g) and toluene (300 ml) were added to the residue, and the mixture was heated to reflux for 2 hours, while distilled water was removed. After the reaction mixture had been cooled to 30° C., water (500 ml) and toluene (900 ml) were added and mixed with it. The mixture was allowed to stand and separate into two layers of organic and aqueous layers, and the latter was extracted. The organic layers were washed with a saturated aqueous solution of sodium hydrogencarbonate and water, and then dried over anhydrous magnesium sulfate. The resulting solution was purified by fractionation using column chromatography with toluene as an eluent and silica gel as a stationary phase powder. The product was dissolved in a mixed solvent of toluene (250 ml) and Solmix A-11 (250 ml), to which Pd/C (0.3 g) was added. The mixture was stirred at room temperature under a hydrogen atmosphere until hydrogen absorption had ceased. After the reaction had been completed, Pd/C was removed, and then solvent was distilled off. The resulting residue was purified by fractionation using column chromatography with toluene as an eluent and silica gel as a stationary phase powder, and by recrystallization from heptane, and then dried to give 8-(trans-4-(4-ethylphenyl)cyclohexyl)-1,4-dioxaspiro[4.5]decane (s6) (33.2 g). The yield based on the compound (s1) was 62.3%.

Third Step:

The compound (s6) (33.2 g), formic acid (87%; 23.3 ml) and toluene (200 ml) were mixed, and the mixture was heated to reflux for 2 hours. After the reaction mixture had been cooled to 30° C., water (500 ml) and toluene (500 ml) were added and mixed with it. The mixture was allowed to stand and separate into two layers of organic and aqueous layers, and the latter was extracted. The separated organic layers were washed with water, a saturated aqueous solution of sodium hydrogencarbonate and water, and then dried over anhydrous magnesium sulfate. The solvent was distilled off under reduced pressure. The resulting residue was purified by fractionation using column chromatography with toluene as an eluent and silica gel as a stationary phase powder, and by recrystallization from heptane, and then dried to give 4'-(4-ethylphenyl) bicyclohexan-4-one (s7) (12.0 g). The yield based on the compound (s6) was 41.7%.

Fourth Step:

The compound (s3) (7.0 g) and THF (200 ml) were placed in a reaction vessel under an atmosphere of nitrogen, and cooled to −74° C. sec-Butyllithium (1.00M in n-hexane and cyclohexane; 34 ml) was added dropwise in the temperature range of −74° C. to −70° C., and the stirring was continued for another 2 hours. The compound (s7) (8.0 g) in THF (100 ml) solution was added dropwise in the temperature range of −75° C. to −70° C., and the stirring was continued for another 8 hours while the mixture was allowed to come to 25° C. The resulting reaction mixture was poured into a vessel containing an aqueous solution of ammonium chloride (300 ml) and ethyl acetate (500 ml), and mixed with them. The mixture was allowed to stand and separate into organic and aqueous layers, and the latter was extracted. The separated organic layers were washed with water, a saturated aqueous solution of sodium hydrogencarbonate and water, and dried over anhydrous magnesium sulfate. The solvent was distilled under reduced pressure. p-Toluenesulfonic acid (0.21 g) and toluene (200 ml) were added to the residue, and the mixture was heated to reflux for two hours, while distilled water was removed. After the reaction mixture had been cooled to 30° C., water (300 ml) and toluene (500 ml) were added and mixed with it. The mixture was allowed to stand and separate into two layers of organic and aqueous layers, and the latter was extracted. The separated organic layers were washed with a saturated aqueous solution of sodium hydrogencarbonate and water, and then dried over anhydrous magnesium sulfate. The resulting solution was purified by fractionation using column chromatography with toluene as an eluent and silica gel as a stationary phase powder. The residue was further purified by recrystallization from a mixed solvent of ethyl acetate and Solmix A-11 (ethyl acetate: Solmix A-11=2:1 by volume), and then dried to give 1-(4-(trans-4-(4-ethylphenyl)cyclohexyl)cyclohex-1-enyl)-2-fluoro-4-(trans-4-pentylcyclohexyl)benzene (No. 213) (5.7 g). The yield based on the compound (s7) was 39.3%.

The chemical shift (δ; ppm) in $^1$H-NMR analysis was described below, and the resulting compound was identified as 1-(4-(trans-4-(4-ethylphenyl)cyclohexyl)cyclohex-1-enyl)-2-fluoro-4-(trans-4-pentylcyclohexyl)benzene (No. 213). The solvent for measurement was $CDCl_3$.

Chemical shift (δ ppm): 7.15 (m, 5H), 6.93 (d, 1H), 6.87 (d, 1H), 5.94 (m, 1H), 2.64 (q, 2H), 2.53-2.37 (m, 4H), 2.33-2.24 (m, 1H), 2.05-1.84 (m, 10H), 1.54-1.14 (m, 21H), 1.10-1.00 (m, 2H) and 0.91 (t, 3H).

The transition temperature was expressed in terms of measured values of the compound itself. The maximum temperature ($T_{NI}$), the dielectric anisotropy (Δ∈) and the optical anisotropy (Δn) were expressed in terms of calculated values according to the extrapolation described above from measured values of a sample in which the compound was mixed with the mother liquid crystals (i). The physical property-values of the compound (No. 213) were as follows. Transition temperature: C 96.9 $S_B$ 288.0 N>350 I. $T_{NI}$=247.7° C., Δ∈=1.8, Δn=0.177, η=65.3 mPa·s, $K_{33}$=25.38 pN.

Example 2

Preparation of 1-(trans-4-(trans-4-(4-ethylphenyl) cyclohexyl)-cyclohexyl)-2-fluoro-4-(trans-4-pentyl-cyclohexyl)benzene (No. 203)

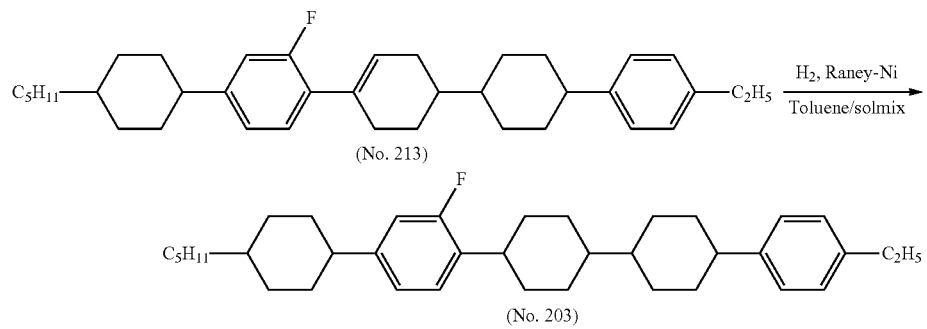

First Step:

The compound (No. 232) (4.5 g) was dissolved in a mixed solvent of toluene (150 ml) and Solmix A-11 (150 ml), to which Raney nickel (0.45 g) was added. The mixture was stirred at room temperature under a hydrogen atmosphere until hydrogen absorption had ceased. After the reaction had been completed, Raney nickel was removed, and then solvent was distilled off. The resulting residue was purified by fractionation using column chromatography with a mixed solvent of heptane and toluene (heptane:toluene=1:2 by volume) as an eluent and silica gel as a stationary phase powder, and by recrystallization from a mixed solvent of ethyl acetate and Solmix A-11 (ethyl acetate:Solmix=1:2 by volume), and then dried to give 1-(trans-4-(trans-4-(4-ethylphenyl)cyclohexyl) cyclohexyl)-2-fluoro-4-(trans-4-pentyl cyclohexyl)benzene (No. 203) (1.5 g). The yield based on the compound (No. 232) was 33.9%.

The chemical shift (δ; ppm) in $^1$H-NMR analysis was described below, and the resulting compound was identified as 1-(trans-4-(trans-4-(4-ethylphenyl)cyclohexyl)cyclohexyl)-2-fluoro-4-(trans-4-pentylcyclohexyl)benzene (No. 203). The solvent for measurement was $CDCl_3$.

Chemical shift δ ppm): 7.13 (m, 5H), 6.91 (d, 1H), 6.84 (d, 1H), 2.77 (m, 1H), 2.64 (q, 2H), 2.43 (m, 2H), 1.97-1.82 (m, 12H), 1.52-1.14 (m, 24H), 1.07-0.97 (m, 2H) and 0.90 (t, 3H).

Transition temperature was expressed in terms of measured values of the compound itself. The maximum temperature ($T_{NI}$), the dielectric anisotropy ($\Delta\in$) and the optical anisotropy ($\Delta n$) were expressed in terms of calculated values according to the extrapolation described above from measured values of a sample in which the compound was mixed with the mother liquid crystals (i). The physical property-values of the compound (No. 203) were as follows. Transition temperature: C 74.8 $S_B$ 323.1 N>350 I. $T_{NI}$=245.0° C.; $\Delta\in$=5.13; $\Delta n$=0.170; $\eta$=70.2 mPa·s.

Example 3

Preparation of trans-4-(4-(4-(trans-4-ethylcyclohexyl)cyclohex-1-enyl)-3-fluorophenyl)-4'-pentylbicyclohexane (No. 13)

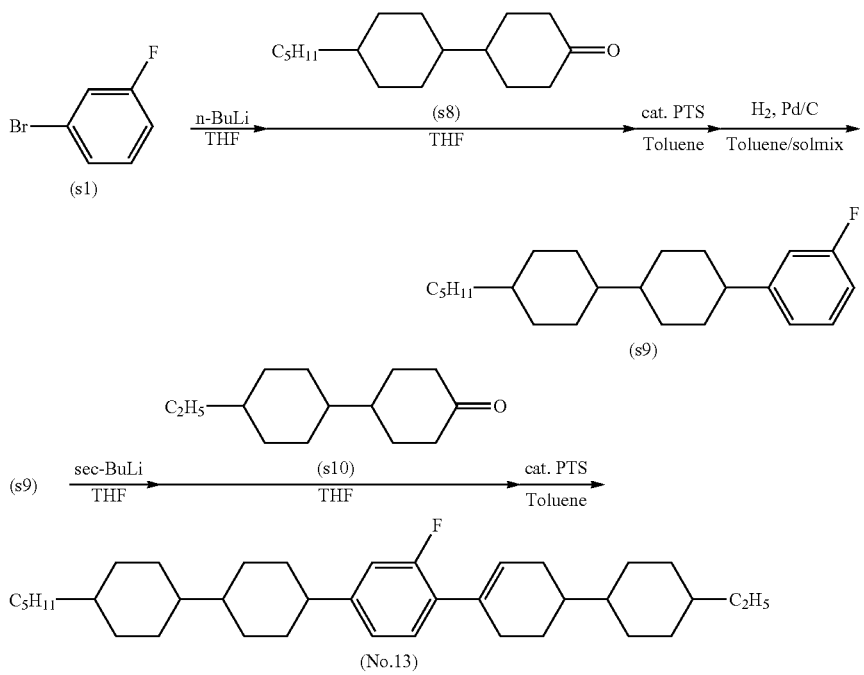

First Step:

1-Bromo-3-fluorobenzene (s1) (100.0 g) and THF (1,000 ml) were placed in a reaction vessel under an atmosphere of nitrogen, and cooled to −74° C. n-Butyllithium (1.57M in n-hexane; 437 ml) was added dropwise in the temperature range of −74° C. to −70° C., and the stirring was continued for another 2 hours. trans-4-Pentyl-4'-bicyclohexanone (s8) (143.1 g) dissolved in THF (150 ml) was added dropwise in the temperature range of −75° C. to −70° C., and the stirring was continued for another 8 hours while the mixture was allowed to come to 25° C. The resulting reaction mixture was poured into a vessel containing an aqueous solution of ammonium chloride (500 ml) and ethyl acetate (500 ml), and mixed with them. The mixture was allowed to stand and separate into organic and aqueous layers, and the latter was extracted. The separated organic layers were washed with water, a saturated aqueous solution of sodium hydrogencarbonate and water, and dried over anhydrous magnesium sulfate. The solvent was distilled under reduced pressure. p-Toluene-sulfonic acid (3.0 g) and toluene (250 ml) were added to the residue, and the mixture was heated to reflux for 2 hours, while distilled water was removed. After the reaction mixture had been cooled to 30° C., water (500 ml) and toluene (900 ml) were added and mixed with it. The mixture was allowed to stand and separate into two layers of organic and aqueous layers, and the latter was extracted. The separated organic layers were washed with a saturated aqueous solution of sodium hydrogencarbonate and water, and then dried over anhydrous magnesium sulfate. The resulting solution was purified by fractionation using column chromatography with heptane as an eluent and silica gel as a stationary phase powder, and dried. The product was dissolved in toluene (150 ml) and Solmix A-11 (150 ml), to which Pd/C (1.0 g) was added. The mixture was stirred at room temperature under a hydrogen atmosphere until hydrogen absorption had ceased. After the reaction had been completed, Pd/C was removed, and then solvent was distilled off. The resulting residue was purified by fractionation using column chromatography with heptane as an eluent and silica gel as a stationary phase powder, and by recrystallization from Solmix A-11, and then dried to give trans-4-(3-fluorophenyl)-4'-pentylbicyclohexyl (s9) (66.0 g). The yield based on the compound (s1) was 34.9%.

Second Step:

The compound (s9) (10.0 g) and THF (200 ml) were placed in a reaction vessel under an atmosphere of nitrogen, and cooled to −74° C. sec-Butyllithium (1.00M in n-hexane and cyclohexane; 36 ml) was added dropwise in the temperature range of −74° C. to −70° C., and the stirring was continued for another 2 hours. trans-4-Ethyl-4'-bicyclohexanone (s10) (6.3 g) in THF (100 ml) solution was added dropwise in the temperature range of −75° C. to −70° C., and the stirring was continued for another 8 hours while the mixture was allowed to come to 25° C. The resulting reaction mixture was poured into a vessel containing an aqueous solution of ammonium chloride (300 ml) and ethyl acetate (500 ml), and mixed with them. The mixture was allowed to stand and separate into organic and aqueous layers, and the latter was extracted. The separated organic layers were washed with water, a saturated aqueous solution of sodium hydrogencarbonate and water, and dried over anhydrous magnesium sulfate. The solvent was distilled under reduced pressure. p-Toluenesulfonic acid (0.5 g) and toluene (200 ml) were added to the residue, and the mixture was heated to reflux for 2 hours, while distilled water was removed. After the reaction mixture had been cooled to 30° C., water (300 ml) and toluene (500 ml) were added and mixed with it. The mixture was allowed to stand and separate into two layers of organic and aqueous layers, and the latter was extracted. The separated organic layers were washed with a saturated aqueous solution of sodium hydrogencarbonate and water, and then dried over anhydrous magnesium sulfate. The resulting solution was purified by fractionation using column chromatography with toluene as an eluent and silica gel as a stationary phase powder. The residue was further purified by recrystallization from a mixed solvent of ethyl acetate and Solmix A-11 (ethyl acetate:Solmix A-11=2:1 by volume), and then dried to give trans-4-(4-(4-(trans-4-ethylcyclohexyl)cyclohex-1-enyl)-3-fluorophenyl)-4'-pentyl bicyclohexane (No. 13) (8.0 g). The yield based on the compound (s9) was 50.8%.

The chemical shift ($\delta$; ppm) in $^1$H-NMR analysis was described below, and the resulting compound was identified as trans-4-(4-(4-(trans-4-ethylcyclohexyl)cyclohex-1-enyl)-3-fluorophenyl)-4'-pentylbicyclohexane (No. 13). The solvent for measurement was $CDCl_3$.

Chemical shift $\delta$ ppm): 7.12 (m, 1H), 6.90 (d, 1H), 6.84 (d, 1H), 5.90 (m, 1H), 2.47-2.33 (m, 3H), 2.27-2.17 (m, 1H), 1.98-1.69 (m, 14H), 1.46-0.93 (m, 25H) and 0.93-0.79 (m, 10H).

The transition temperature was expressed in terms of measured values of the compound itself. The maximum temperature ($T_{NI}$), the dielectric anisotropy ($\Delta\epsilon$) and the optical anisotropy ($\Delta n$) were expressed in terms of calculated values according to the extrapolation described above from measured values of a sample in which the compound was mixed with the mother liquid crystals (i). The physical property-values of the compound (No. 13) were as follows. Transition temperature: C 22.4 $S_B$ 325.5 N>350 I. $T_{NI}$=254.7° C.; $\Delta\epsilon$=2.28; $\Delta n$=0.151; $\eta$=88.4 mPa·s; $K_{33}$=25.16 pN.

Example 4

Preparation of trans-4-(4-(4-(trans-4-ethylcyclohexyl)cyclohexyl)-3-fluorophenyl)-4'-pentylbicyclohexane (No. 3)

First Step:

The compound (No. 13) (5.3 g) was dissolved in a mixed solvent of toluene (150 ml) and Solmix A-11 (150 ml), to which Raney nickel (0.53 g) was added. The mixture was stirred at room temperature under a hydrogen atmosphere until hydrogen absorption had ceased. After the reaction had been completed, Raney nickel was removed, and then solvent was distilled off. The resulting residue was purified by fractionation using column chromatography with a mixed solvent of heptane and toluene (heptane:toluene=1:2 by volume) as an eluent and silica gel as a stationary phase powder, and by recrystallization from a mixed solvent of ethyl acetate and Solmix A-11 (ethyl acetate:Solmix=1:2 by volume), and then dried to give 1-(trans-4-(trans-4-(4-ethylphenyl)cyclohexyl)cyclohexyl)-2-fluoro-4-(trans-4-pentyl cyclohexyl)benzene (No. 3) (2.5 g). The yield based on the compound (No. 13) was 46.0%.

The chemical shift ($\delta$; ppm) in $^1$H-NMR analysis was described below, and the resulting compound was identified as trans-4-(4-(4-(trans-4-ethylcyclohexyl)cyclohexyl)-3-fluorophenyl)-4'-pentyl bicyclohexane (No. 3). The solvent for measurement was $CDCl_3$.

Chemical shift ($\delta$ ppm): 7.10 (t, 1H), 6.90 (d, 1H), 6.83 (d, 1H), 2.74 (m, 1H), 2.39 (m, 1H), 1.94-1.68 (m, 16H), 1.48-0.94 (m, 28H) and 0.93-0.79 (m, 10H).

The transition temperature was expressed in terms of measured values of the compound itself. The maximum temperature ($T_{NI}$), the dielectric anisotropy ($\Delta\epsilon$) and the optical anisotropy ($\Delta n$) were expressed in terms of calculated values according to the extrapolation described above from measured values of a sample in which the compound was mixed with the mother liquid crystals (i). The physical property-values of the compound (No. 3) were as follows. Transition temperature: C 37.5 $S_B$ 342.6 N>350 I. $T_{NI}$=251.7° C.; $\Delta\epsilon$=1.74; $\Delta n$=0.109; $K_{33}$=27.83 pN.

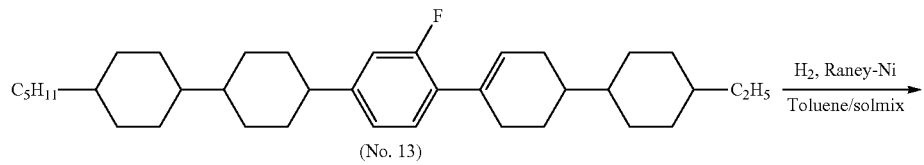

(No. 13)

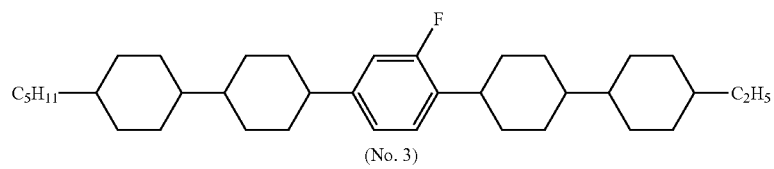

(No. 3)

Example 5

Preparation of trans-4-(2,2'-difluoro-4'-(trans-4-pentyl cyclohexyl)biphenyl-4-yl)-trans-4'-propylbicyclohexane (No. 164)

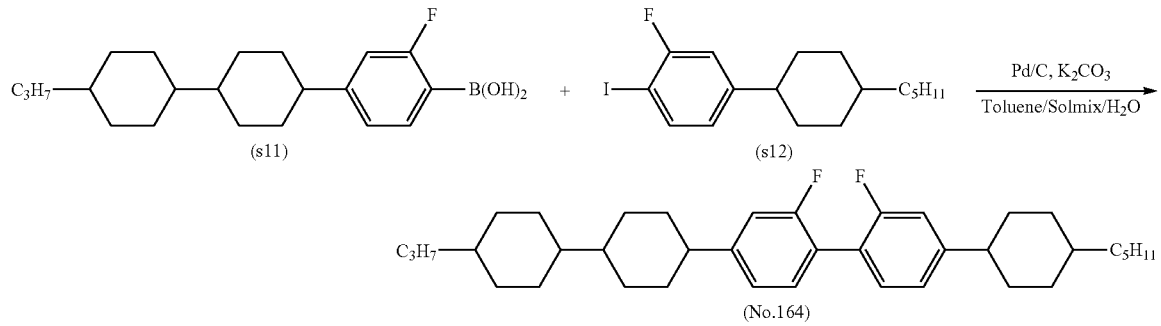

First Step:

trans-4-Pentyl-(3-fluoro-4-iodophenyl)cyclohexane (s12) (3.0 g), 2-fluoro-4-(trans-4'-propylbicyclohexane-trans-4-yl) phenylboronic acid (s11) (2.5 g), potassium carbonate (3.7 g), Pd/C (NX-type) (0.34 g), toluene (100 ml), Solmix A-11 (100 ml) and water (100 ml) were placed in a reaction vessel under an atmosphere of nitrogen, and the mixture was heated to reflux for 2 hours. After the reaction mixture had been cooled to 25° C., it was poured into water (300 ml) and toluene (300 ml), and the mixture was mixed. The mixture was allowed to stand and separate into two layers of organic and aqueous layers, and the latter was extracted. The separated organic layers were washed with water, and then dried over anhydrous magnesium sulfate. The resulting solution was concentrated under reduced pressure. The resulting residue was purified by fractionation using column chromatography with a mixed solvent of toluene and heptane (toluene:heptane=1:5 by volume) as an eluent and silica gel as a stationary phase powder. The residue was further purified by recrystallization from a mixed solvent of ethyl acetate/Solmix A-11 (ethyl acetate:Solmix A-11=1:2 by volume) and then dried to give trans-4-(2,2'-difluoro-4'-(trans-4-pentyl cyclohexyl)biphenyl-4-yl)-trans-4'-propylbicyclohexane (No. 164) (3.4 g). The yield based on the compound (s12) was 89.5%.

The chemical shift (δ; ppm) in $^1$H-NMR analysis was described below, and the resulting compound was identified as trans-4-(2,2'-difluoro-4'-(trans-4-pentylcyclohexyl)biphenyl-4-yl)-trans-4'-propylbicyclohexane (No. 164). The solvent for measurement was $CDCl_3$.

Chemical shift (δ ppm): 7.10 (t, 1H), 6.90 (d, 1H), 6.83 (d, 1H), 2.74 (m, 1H), 2.39 (m, 1H), 1.94-1.68 (m, 16H), 1.48-0.94 (m, 28H) and 0.93-0.79 (m, 10H).

The transition temperature was expressed in terms of measured values of the compound itself. The maximum temperature ($T_{NI}$), the dielectric anisotropy (Δ∈) and the optical anisotropy (Δn) were expressed in terms of calculated values according to the extrapolation described above from measured values of a sample in which the compound was mixed with the mother liquid crystals (i). The physical property-values of the compound (No. 164) were as follows. Transition temperature: C 58.3 $S_X$ 92.7 $S_B$ 226.5 N>350 I. $T_{NI}$=237.7° C., Δ∈=3.80, Δn=0.177.

Example 6

A variety of compounds were prepared using the corresponding starting materials according to the methods shown in Examples 1 to 5, and they were identified as the expected compounds.

(1) trans-4-(4-(4-(4-Ethylphenyl)cyclohex-1-enyl)-3-fluorophenyl)-4'-pentylbicyclohexane (No. 33)

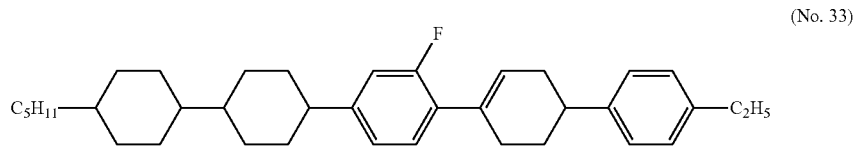

Chemical shift (δ ppm): 7.28 (m, 2H), 7.04 (d, 2H), 7.00 (m, 2H), 2.49 (m, 2H), 1.99-1.82 (m, 8H), 1.75 (t, 4H), 1.50-1.37 (m, 4H), 1.37-1.11 (m, 16H), 1.11-0.95 (m, 6H) and 0.92-0.80 (m, 8H).

The transition temperature was expressed in terms of measured values of the compound itself. The maximum temperature ($T_{NI}$), the dielectric anisotropy (Δ∈) and the optical anisotropy (Δn) were expressed in terms of calculated values according to the extrapolation described above from measured values of a sample in which the compound was mixed with the mother liquid crystals (i). The physical property-values of the compound (No. 33) were as follows. Transition temperature: C 23.9 $S_B$ 291.5 N>350 I. $T_{NI}$=245.7° C.; Δ∈=2.47; Δn=0.164; η=74.0 mPa·s; $K_{33}$=29.83 pN.

(2) trans-4-(4-(4-(4-Ethylphenyl)cyclohexyl)-3-fluoro phenyl)-4'-pentylbicyclohexane (No. 23)

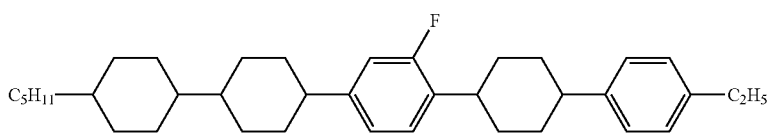

(No. 23)

Chemical shift (δ ppm): 7.16 (m, 5H), 6.93 (d, 1H), 6.86 (d, 1H), 2.90 (m, 1H), 2.67-2.54 (m, 3H), 2.41 (m, 1H), 2.04-1.95 (m, 4H), 1.94-1.88 (m, 2H), 1.88-1.80 (m, 2H), 1.80-1.70 (m, 4H), 1.70-1.58 (m, 4H), 1.44-1.34 (m, 2H), 1.34-1.20 (m, 9H), 1.20-1.08 (m, 6H), 1.08-0.95 (m, 3H) and 0.92-0.78 (m, 5H).

The transition temperature was expressed in terms of measured values of the compound itself. The maximum temperature ($T_{NI}$), the dielectric anisotropy (Δ∈) and the optical anisotropy (Δn) were expressed in terms of calculated values according to the extrapolation described above from measured values of a sample in which the compound was mixed with the mother liquid crystals (i). The physical property-values of the compound (No. 23) were as follows. Transition temperature: C 87.6 $S_B$ 326.3 N>350 I. $T_{NI}$=241.7° C.; Δ∈=1.70; Δn=0.204; η=63.7 mPa·s; $K_{33}$=26.03 pN.

(3) trans-4-(3-Fluoro-4-(4-(3,4,5-trifluorophenyl)cyclohex-1-enyl)phenyl)-4'-pentylbicyclohexane (No. 116)

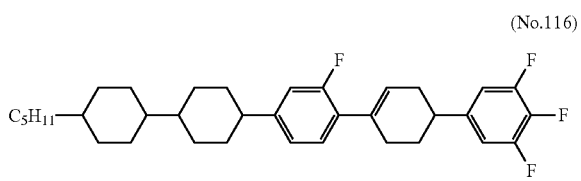

(No.116)

Chemical shift (δ ppm): 7.15 (t, 1H), 6.93 (d, 1H), 6.91-6.84 (m, 3H), 5.96 (m, 1H), 2.90-2.82 (m, 1H), 2.63-2.52 (m, 1H), 2.52-2.38 (m, 3H), 2.28-2.19 (m, 1H), 2.06-1.99 (m, 1H), 1.94-1.88 (m, 2H), 1.88-1.70 (m, 7H), 1.45-1.34 (m, 2H), 1.34-1.20 (m, 6H), 1.20-1.09 (m, 6H), 1.09-0.95 (m, 3H) and 0.91-0.81 (m, 5H).

The transition temperature was expressed in terms of measured values of the compound itself. The maximum temperature ($T_{NI}$), the dielectric anisotropy (Δ∈) and the optical anisotropy (Δn) were expressed in terms of calculated values according to the extrapolation described above from measured values of a sample in which the compound was mixed with the mother liquid crystals (i). The physical property-values of the compound (No. 116) were as follows. Transition temperature: C 116.7 $S_B$ 153.1 N 309.3 I. $T_{NI}$=226.4° C.; Δ∈=7.80; Δn=0.150; η=103.9 mPa·s; $K_{33}$=22.17 pN.

(4) trans-4-(3-Fluoro-4-(4-(3,4,5-trifluorophenyl)cyclohexyl)phenyl)-4'-pentylbicyclohexane (No. 96)

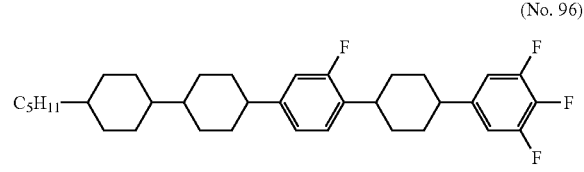

(No. 96)

Chemical shift (δ ppm): 7.13 (t, 1H), 6.93 (d, 1H), 6.89-6.82 (m, 3H), 5.92 (m, 1H), 2.87 (m, 1H), 2.54 (m, 1H), 2.41 (m, 1H), 2.03-1.95 (m, 4H), 1.94-1.87 (m, 2H), 1.87-1.80 (m, 2H), 1.80-1.70 (m, 4H), 1.68-1.50 (m, 4H), 1.44-1.33 (m, 2H), 1.33-1.19 (m, 6H), 1.19-1.08 (m, 3H), 1.08-0.94 (m, 3H) and 0.92-0.80 (m, 5H).

The transition temperature was expressed in terms of measured values of the compound itself. The maximum temperature ($T_{NI}$), the dielectric anisotropy (Δ∈) and the optical anisotropy (Δn) were expressed in terms of calculated values according to the extrapolation described above from measured values of a sample in which the compound was mixed with the mother liquid crystals (i). The physical property-values of the compound (No. 96) were as follows. Transition temperature: C 126.8 $S_B$ 179.3 N 343.7 I. $T_{NI}$=217.7° C.; Δ∈=9.92; Δn=0.133; η=97.2 mPa·s; $K_{33}$=22.29 pN.

(5) 1-(4-(trans-4-(3,4-Difluorophenyl)cyclohexyl)cyclohex-1-enyl)-2-fluoro-4-(trans-4-pentylcyclohexyl)benzene (No. 293)

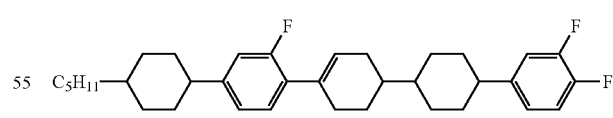

(No. 293)

Chemical shift (δ ppm): 7.14 (t, 1H), 7.08-6.97 (m, 2H), 6.94-6.88 (m, 2H), 6.85 (d, 1H), 5.92 (m, 1H), 2.50-2.35 (m, 4H), 2.30-2.22 (m, 1H), 2.02-1.77 (m, 10H), 1.52-1.11 (m, 19H), 1.08-0.97 (m, 2H) and 0.89 (t, 3H).

The transition temperature was expressed in terms of measured values of the compound itself. The maximum temperature ($T_{NI}$), the dielectric anisotropy (Δ∈) and the optical anisotropy (Δn) were expressed in terms of calculated values according to the extrapolation described above from measured values of a sample in which the compound was mixed with the mother liquid crystals (i). The physical property-values of the compound (No. 293) were as follows. Transition temperature: C 78.2 $S_B$ 171.1 $S_A$ 189.6 N 330.7 I. $T_{NI}$=238.4° C.; $\Delta\varepsilon$=5.80; $\Delta n$=0.164; $\eta$=86.6 mPa·s; $K_{33}$=28.66 pN.

(6) 1-(trans-4-(4-(3,4-Difluorophenyl)bicyclohexyl)-2-fluoro-4-(trans-4-pentylcyclohexyl)benzene (No. 273)

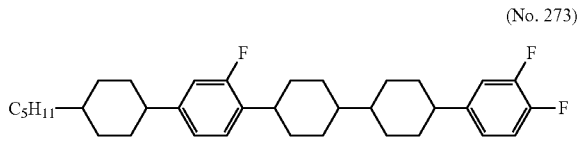

(No. 273)

Chemical shift ($\delta$ ppm): 7.12 (t, 1H), 7.14-6.96 (m, 2H), 6.94-6.88 (m, 2H), 6.84 (d, 1H), 2.77 (t, 1H), 2.42 (t, 2H), 1.95-1.82 (m, 11H), 1.53-1.12 (m, 20H), 1.08-0.97 (m, 2H) and 0.89 (t, 3H).

The transition temperature was expressed in terms of measured values of the compound itself. The maximum temperature ($T_{NI}$), the dielectric anisotropy ($\Delta\varepsilon$) and the optical anisotropy ($\Delta n$) were expressed in terms of calculated values according to the extrapolation described above from measured values of a sample in which the compound was mixed with the mother liquid crystals (i). The physical property-values of the compound (No. 273) were as follows. Transition temperature: C 66.2 $S_B$ 172.0 N 324.6 I. $T_{NI}$=198.7° C.; $\Delta\varepsilon$=5.80; $\Delta n$=0.127; $\eta$=105.1 mPa·s; $K_{33}$=27.41 pN.

(7) 1-(4-(trans-4-(3,4,5-Trifluorophenyl)cyclohexyl) cyclohex-1-enyl)-2-fluoro-4-(trans-4-pentylcyclohexyl)benzene (No. 296)

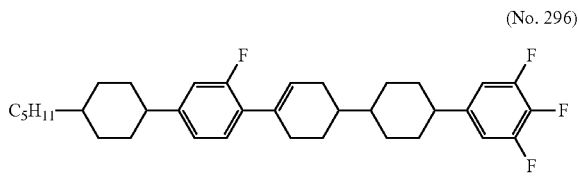

(No. 296)

Chemical shift ($\delta$ ppm): 7.13 (t, 1H), 6.91 (d, 1H), 6.86 (d, 1H), 6.81 (t, 2H), 5.92 (m, 1H), 2.50-2.35 (m, 4H), 2.30-2.22 (m, 1H), 2.02-1.82 (m, 10H), 1.52-1.11 (m, 18H), 1.08-0.98 (m, 2H) and 0.90 (t, 3H).

The transition temperature was expressed in terms of measured values of the compound itself. The maximum temperature ($T_{NI}$), the dielectric anisotropy ($\Delta\varepsilon$) and the optical anisotropy ($\Delta n$) were expressed in terms of calculated values according to the extrapolation described above from measured values of a sample in which the compound was mixed with the mother liquid crystals (i). The physical property-values of the compound (No. 296) were as follows. Transition temperature: C 120.2 $S_B$ 127.7 $S_A$ 152.2 N 303.0 I. $T_{NI}$=219.7° C.; $\Delta\varepsilon$=9.13; $\Delta n$=0.150; $\eta$=99.2 mPa·s; $K_{33}$=23.26 pN.

(8) 1-(trans-4-(4-(3,4,5-Trifluorophenyl) bicyclohexyl)-2-fluoro-4-(trans-4-pentylcyclohexyl)benzene (No. 276)

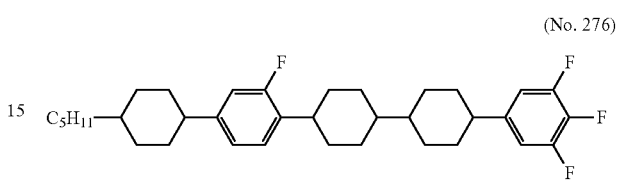

(No. 276)

Chemical shift ($\delta$ ppm): 7.14 (t, 1H), 7.08-6.97 (m, 2H), 6.94-6.88 (m, 2H), 6.85 (d, 1H), 2.77 (t, 1H), 2.42 (t, 2H), 1.95-1.82 (m, 11H), 1.53-1.12 (m, 19H), 1.08-0.97 (m, 2H) and 0.89 (t, 3H).

The transition temperature was expressed in terms of measured values of the compound itself. The maximum temperature ($T_{NI}$), the dielectric anisotropy ($\Delta\varepsilon$) and the optical anisotropy ($\Delta n$) were expressed in terms of calculated values according to the extrapolation described above from measured values of a sample in which the compound was mixed with the mother liquid crystals (i). The physical property-values of the compound (No. 276) were as follows. Transition temperature: C 95.4 $S_B$ 169.0 N 337.3 I. $T_{NI}$=213.7° C.; $\Delta\varepsilon$=8.37; $\Delta n$=0.130; $\eta$=94.3 mPa·s; $K_{33}$=25.16 pN.

(9) 1-(4-(trans-4-(3,4,5-Trifluorophenyl)cyclohexyl) cyclohex-1-enyl)-2,6-difluoro-4-(trans-4-pentylcyclohexyl)benzene (No. 297)

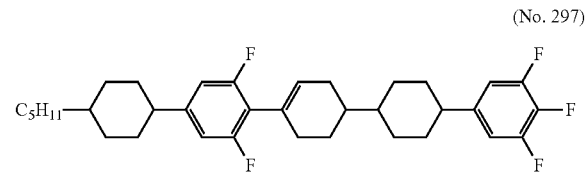

(No. 297)

Chemical shift ($\delta$ ppm): 6.81 (t, 2H), 6.70 (d, 2H), 5.78 (m, 1H), 2.48-2.32 (m, 3H), 2.25 (m, 2H), 2.04-1.82 (m, 10H), 1.48-1.11 (m, 18H), 1.08-0.96 (m, 2H) and 0.91 (t, 3H).

The transition temperature was expressed in terms of measured values of the compound itself. The maximum temperature ($T_{NI}$), the dielectric anisotropy ($\Delta\varepsilon$) and the optical anisotropy ($\Delta n$) were expressed in terms of calculated values according to the extrapolation described above from measured values of a sample in which the compound was mixed with the mother liquid crystals (i). The physical property-values of the compound (No. 297) were as follows. Transition temperature: C 109.9 $S_B$ 126.8 $S_A$ 132.0 N 307.3 I. $T_{NI}$=193.7° C.; $\Delta\varepsilon$=18.1; $\Delta n$=0.147; $\eta$=89.4 mPa·s; $K_{33}$=25.16 pN.

(10) 1-(trans-4-(4-(3,4,5-Trifluorophenyl) bicyclohexyl)-2,6-difluoro-4-(trans-4-pentylcyclohexyl)benzene (No. 277)

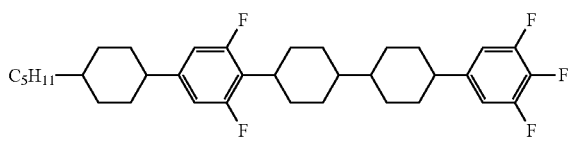
(No. 277)

Chemical shift (δ ppm): 6.82 (t, 2H), 6.67 (d, 2H), 2.90 (t, 1H), 2.40 (m, 2H), 1.96-1.75 (m, 14H), 1.44-1.11 (m, 19H), 1.02 (m, 2H) and 0.90 (t, 3H).

The transition temperature was expressed in terms of measured values of the compound itself. The maximum temperature ($T_{NI}$), the dielectric anisotropy ($\Delta\varepsilon$) and the optical anisotropy ($\Delta n$) were expressed in terms of calculated values according to the extrapolation described above from measured values of a sample in which the compound was mixed with the mother liquid crystals (i). The physical property-values of the compound (No. 277) were as follows. Transition temperature: C 120.5 $S_B$ 145.3 N 341.0 I. $T_{NI}$=201.7° C.; $\Delta\varepsilon$=18.27; $\Delta n$=0.137; η=97.1 mPa·s; $K_{33}$=25.16 pN.

(11) 1-(4-(trans-4-(3,4-Difluorophenyl)cyclohexyl)cyclohex-1-enyl)-2,6-difluoro-4-(trans-4-pentylcyclohexyl)benzene (No. 294)

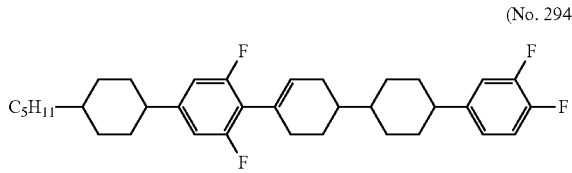
(No. 294)

Chemical shift (δ ppm): 7.09-6.96 (m, 2H), 6.91 (m, 1H), 6.70 (d, 2H), 5.78 (m, 1H), 2.50-2.32 (m, 3H), 2.31-2.21 (m, 2H), 2.04-1.87 (m, 10H), 1.47-1.11 (m, 18H), 1.08-0.97 (m, 2H) and 0.89 (t, 3H).

The transition temperature was expressed in terms of measured values of the compound itself. The maximum temperature ($T_{NI}$), the dielectric anisotropy ($\Delta\varepsilon$) and the optical anisotropy ($\Delta n$) were expressed in terms of calculated values according to the extrapolation described above from measured values of a sample in which the compound was mixed with the mother liquid crystals (i). The physical property-values of the compound (No. 294) were as follows. Transition temperature: C 118.5 $S_B$ 129.0 N 318.0 I. $T_{NI}$=210.7° C.; $\Delta\varepsilon$=12.1; $\Delta n$=0.157; η=83.4 mPa·s; $K_{33}$=28.66 pN.

(12) 1-(trans-4-(4-(3,4-Difluorophenyl) bicyclohexyl)-2,6-difluoro-4-(trans-4-pentylcyclohexyl)benzene (No. 274)

(No. 274)

Chemical shift (δ ppm): 7.09-6.96 (m, 2H), 6.90 (m, 1H), 6.65 (d, 2H), 2.88 (t, 1H), 2.40 (m, 2H), 1.95-1.74 (m, 14H), 1.45-1.10 (m, 19H), 1.01 (m, 2H) and 0.90 (t, 3H).

The transition temperature was expressed in terms of measured values of the compound itself. The maximum temperature ($T_{NI}$), the dielectric anisotropy ($\Delta\varepsilon$) and the optical anisotropy ($\Delta n$) were expressed in terms of calculated values according to the extrapolation described above from measured values of a sample in which the compound was mixed with the mother liquid crystals (i). The physical property-values of the compound (No. 274) were as follows. Transition temperature: C 117.5 $S_B$ 182.0 N>350 I. $T_{NI}$=208.4° C.; $\Delta\varepsilon$=24.73; $\Delta n$=0.170; η=110.9 mPa·s; $K_{33}$=28.36 pN.

(13) trans-4-(4-(4-(4-Trifluoromethoxyphenyl)cyclohex-1-enyl)-3-fluorophenyl)-4'-pentylbicyclohexane (No. 109)

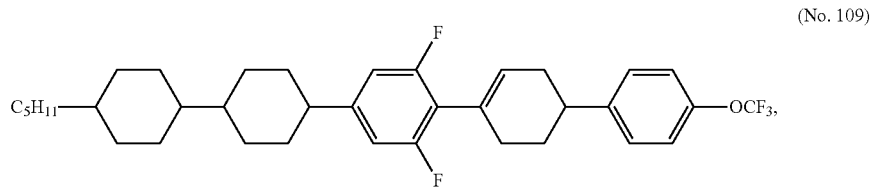
(No. 109)

Chemical shift (δ ppm): 7.27 (d, 2H), 7.16 (m, 3H), 6.93 (d, 1H), 6.87 (d, 1H), 5.99 (m, 1H), 2.93 (m, 1H), 2.65-2.54 (m, 1H), 2.53-2.38 (m, 3H), 2.34-2.25 (m, 1H), 2.08-2.01 (m, 1H), 1.96-1.80 (m, 5H), 1.80-1.68 (m, 4H), 1.45-1.34 (m, 2H), 1.34-1.20 (m, 6H), 1.19-0.94 (m, 9H) and 0.92-0.79 (m, 5H).

The transition temperature was expressed in terms of measured values of the compound itself. The maximum temperature ($T_{NI}$), the dielectric anisotropy ($\Delta\in$) and the optical anisotropy ($\Delta n$) were expressed in terms of calculated values according to the extrapolation described above from measured values of a sample in which the compound was mixed with the mother liquid crystals (i). The physical property-values of the compound (No. 109) were as follows. Transition temperature: C 55.0 $S_B$ 271.3 N 280.9 I. $T_{NI}$=232.4° C.; $\Delta\in$=1.70; $\Delta n$=0.157; η=77.7 mPa·s; $K_{33}$=29.83 pN.

(14) trans-4-(4-(4-(4-Trifluoromethoxyphenyl)cyclohexyl)-3-fluorophenyl)-4'-pentylbicyclohexane (No. 89)

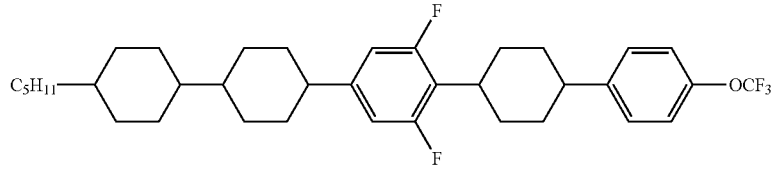

(No. 89)

Chemical shift (δ ppm): 7.26 (m, 2H), 7.15 (m, 3H), 6.93 (d, 1H), 6.87 (d, 1H), 2.90 (m, 1H), 2.61 (m, 1H), 2.42 (m, 1H), 2.00 (d, 4H), 1.91 (d, 2H), 1.83 (m, 1H), 1.75 (m, 4H), 1.63 (m, 4H), 1.45-1.34 (m, 2H), 1.34-1.20 (m, 6H), 1.19-0.94 (m, 10H) and 0.92-0.79 (m, 5H).

The transition temperature was expressed in terms of measured values of the compound itself. The maximum temperature ($T_{NI}$), the dielectric anisotropy ($\Delta\in$) and the optical anisotropy ($\Delta n$) were expressed in terms of calculated values according to the extrapolation described above from measured values of a sample in which the compound was mixed with the mother liquid crystals (i). The physical property-values of the compound (No. 89) were as follows. Transition temperature: C 63.1 $S_B$ 290.1 N>350 I. $T_{NI}$=219.7° C.; $\Delta\in$=3.70; $\Delta n$=0.157; η=58.9 mPa·s; $K_{33}$=26.03 pN.

(15) trans-4-(3,5-Difluoro-4-(4-(3,4,5-trifluorophenyl)cyclohex-1-enyl)phenyl)-4'-pentylbicycloh (No. 117)

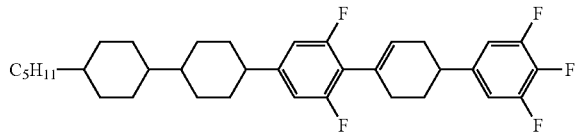

(No. 117)

Chemical shift (δ ppm): 6.89 (t, 2H), 6.71 (d, 2H), 5.84 (m, 1H), 2.90 (m, 1H), 2.54-2.36 (m, 3H), 2.35-2.21 (m, 2H), 2.05-1.97 (m, 1H), 1.94-1.80 (m, 5H), 1.80-1.68 (m, 4H), 1.43-1.19 (m, 8H), 1.19-0.94 (m, 9H) and 0.92-0.70 (m, 5H).

The transition temperature was expressed in terms of measured values of the compound itself. The maximum temperature ($T_{NI}$), the dielectric anisotropy ($\Delta\in$) and the optical anisotropy ($\Delta n$) were expressed in terms of calculated values according to the extrapolation described above from measured values of a sample in which the compound was mixed with the mother liquid crystals (i). The physical property-values of the compound (No. 117) were as follows. Transition temperature: C 166.1 N 288.7 I. $T_{NI}$=189.7° C.; $\Delta\in$=17.6; $\Delta n$=0.137; η=105.2 mPa·s; $K_{33}$=22.17 pN.

(16) trans-4-(3,5-Difluoro-4-(4-(3,4,5-trifluorophenyl)cyclohexyl)phenyl)-4'-pentylbicyclohexane (No. 97)

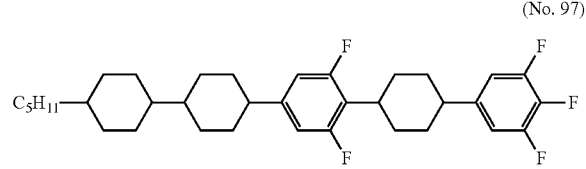

(No. 97)

Chemical shift (δ ppm): 6.84 (t, 2H), 6.68 (d, 2H), 3.00 (m, 1H), 2.58 (t, 1H), 2.38 (t, 1H), 2.05-1.93 (m, 4H), 1.93-1.80 (m, 6H), 1.80-1.68 (m, 4H), 1.56-1.45 (m, 2H), 1.40-1.19 (m, 8H), 1.19-0.93 (m, 9H) and 0.92-0.80 (m, 5H).

The transition temperature was expressed in terms of measured values of the compound itself. The maximum temperature ($T_{NI}$), the dielectric anisotropy ($\Delta\in$) and the optical anisotropy ($\Delta n$) were expressed in terms of calculated values according to the extrapolation described above from measured values of a sample in which the compound was mixed with the mother liquid crystals (i). The physical property-values of the compound (No. 97) were as follows. Transition temperature: C 176.5 N 338.4 I. $T_{NI}$=221.7° C.; $\Delta\in$=17.3; $\Delta n$=0.117; η=106.9 mPa·s; $K_{33}$=22.29 pN.

Example 7

The compounds (No. 1) to (No. 380) shown below can be prepared by synthetic methods similar to those described in Examples 1 to 5. Appended data were measured according to the methods described above. The measured values of the compound itself were used for the transition temperature. Values calculated from the measured values of a sample, in which the compound was mixed with the mother liquid crystals (i), by means of the extrapolation method described above were used for the maximum temperature ($T_{NI}$) the dielectric anisotropy ($\Delta\in$) and the optical anisotropy ($\Delta n$).

In the compounds Nos. 23, 89, 97, 117, 164, 203, 213, 274 and 277, the liquid crystal composition consisting of 95% by weight of the mother liquid crystals and 5% by weight of each compound was prepared, and its physical property values were measured, and then the measured values were extrapolated. In the compounds Nos. 3, 13, 96, 273, 294 and 297, the liquid crystal composition consisting of 90% by weight of the mother liquid crystals and 10% by weight of each compound was prepared, and its physical property values were measured, and then the measured values were extrapolated. In the residual compounds having data, the liquid crystal composition consisting of 85% by weight of the mother liquid crystals and 15% by weight of each compound was prepared, and its physical property values were measured, and then the measured values were extrapolated.

| No. | |
|---|---|
| 1 | 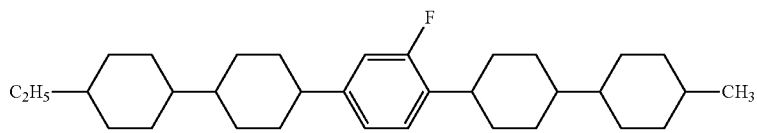 |
| 2 | 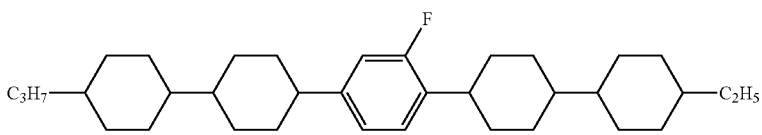 |
| 3 | 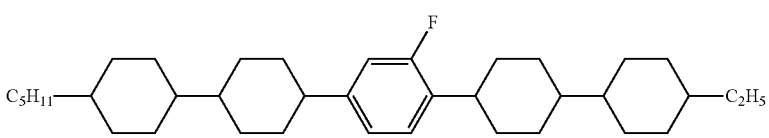<br>C 37.5 S$_B$ 342.6 N >350 I<br>T$_{NI}$; 251.7° C., Δ ∈; 1.74, Δ n; 0.109 |
| 4 | 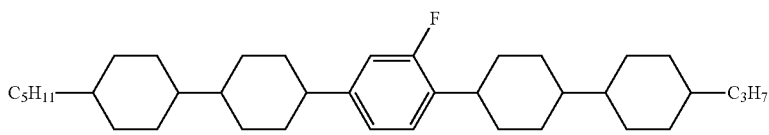 |
| 5 | 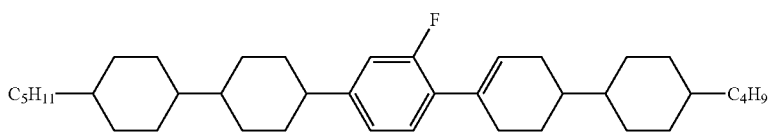 |
| 6 | 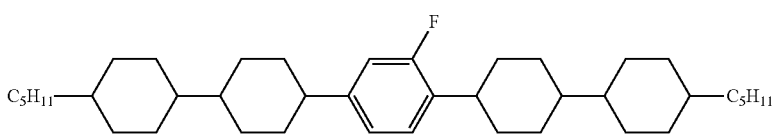 |
| 7 | 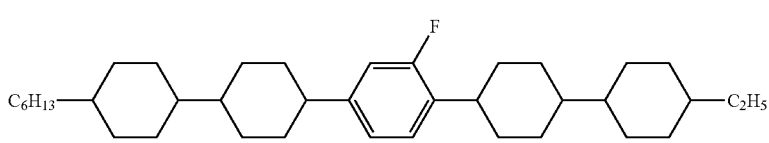 |
| 8 | 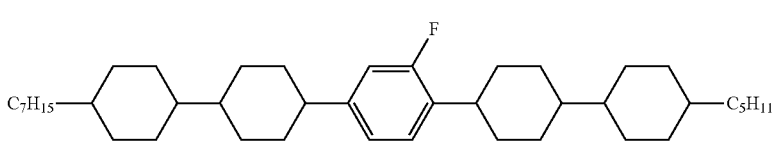 |
| 9 | 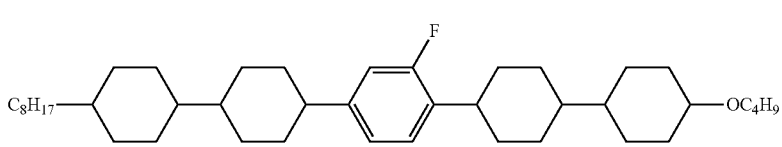 |
| 10 | 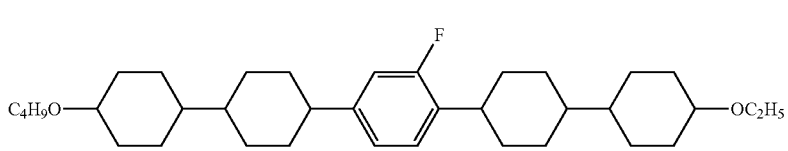 |
| 11 | 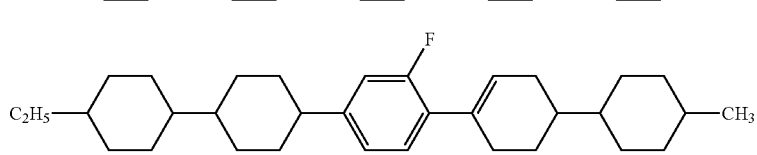 |

-continued
| No. | |
|---|---|
| 12 | 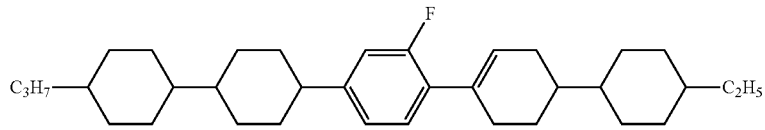 |
| 13 | 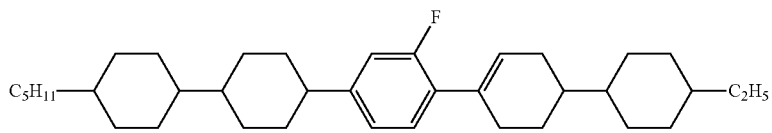<br>C 22.4 S$_B$ 325.5 N >350 I<br>T$_{NI}$; 254.7° C., Δ ϵ; 2.28, Δ n; 0.151 |
| 14 | 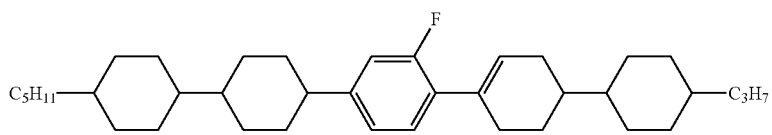 |
| 15 | 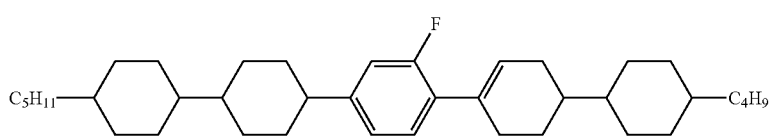 |
| 16 | 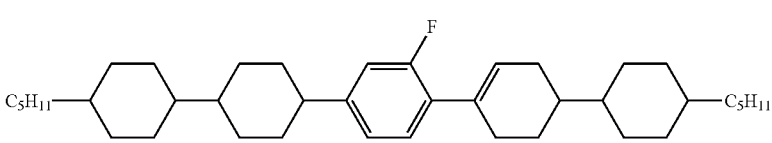 |
| 17 | 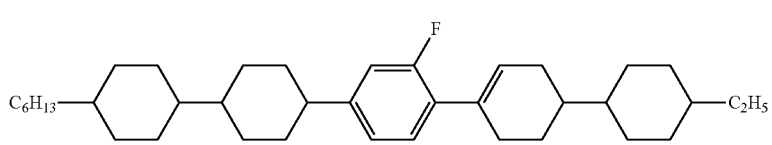 |
| 18 | 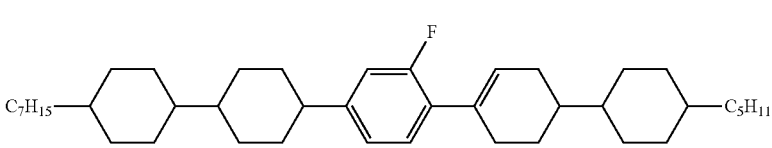 |
| 19 | 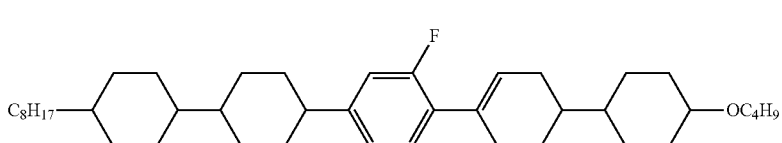 |
| 20 | 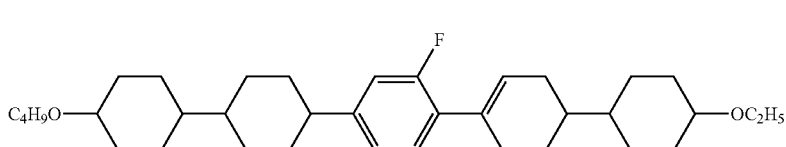 |
| 21 | 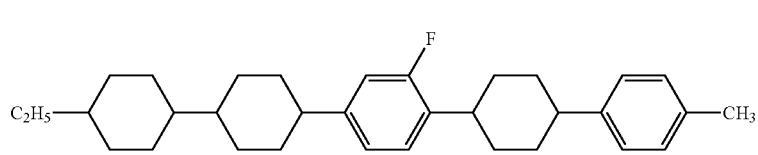 |

-continued
| No. | |
|---|---|
| 22 | 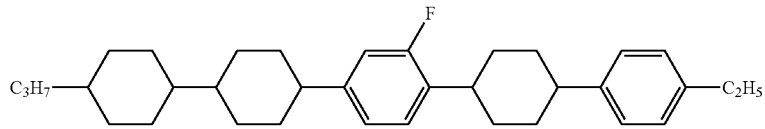 |
| 23 | 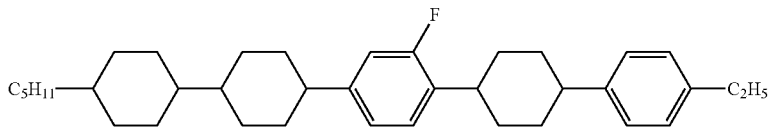<br>C 87.6 S$_B$ 326.3 N >350 I<br>T$_{NI}$; 241.7° C., Δ ε; 1.70, Δ n; 0.204 |
| 24 | 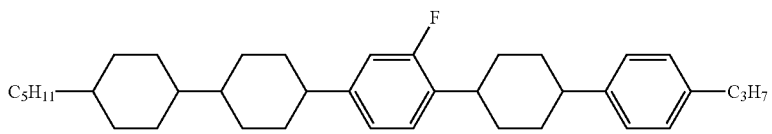 |
| 25 | 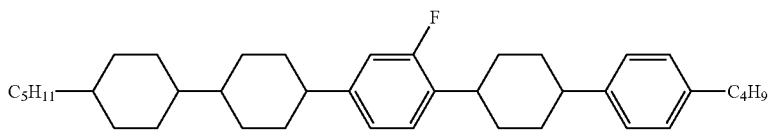 |
| 26 | 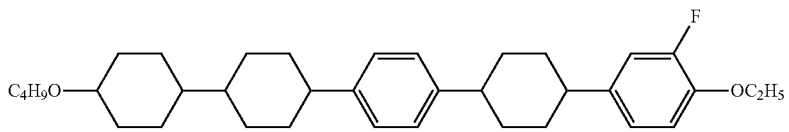 |
| 27 | 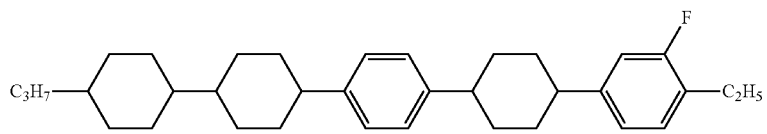 |
| 28 | 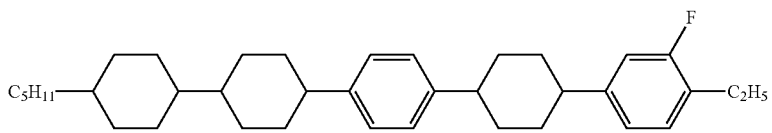 |
| 29 | 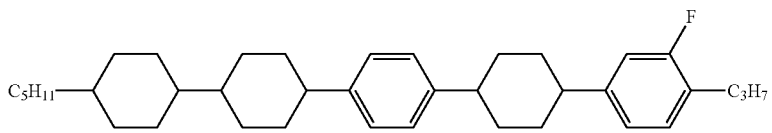 |
| 30 | 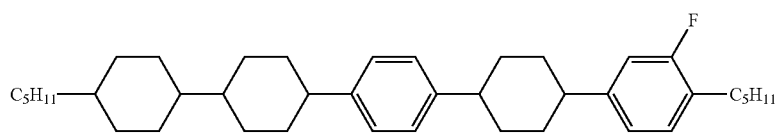 |
| 31 | 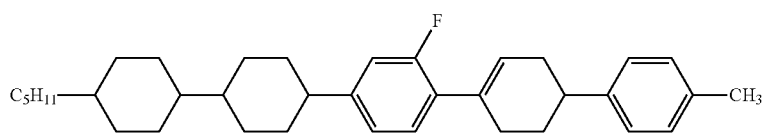 |
| 32 | 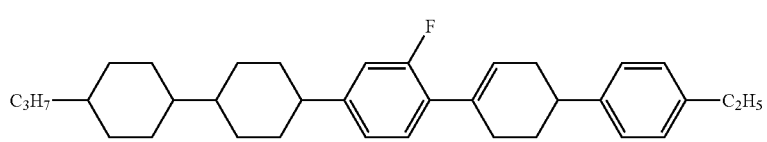 |

-continued
| No. | |
|---|---|
| 33 | 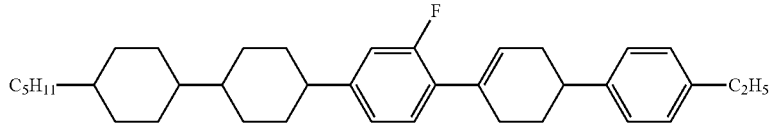<br>C 23.9 S_B 291.5 N >350 I<br>$T_{Ni}$; 245.7° C., Δ ε; 2.47, Δ n; 0.164 |
| 34 | 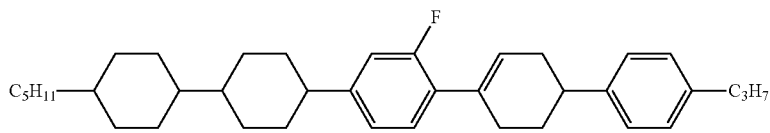 |
| 35 | 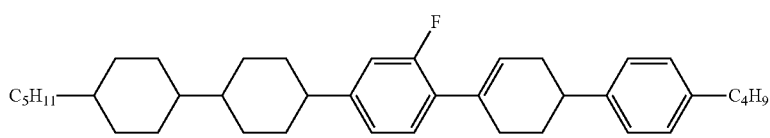 |
| 36 | 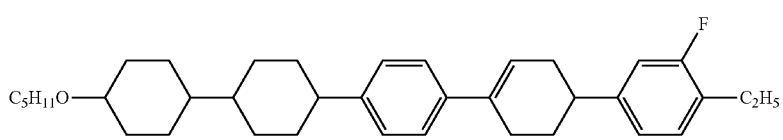 |
| 37 | 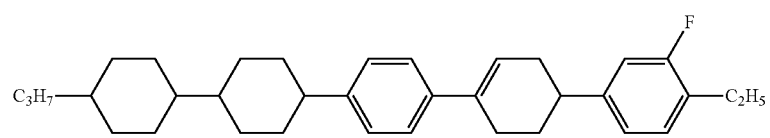 |
| 38 | 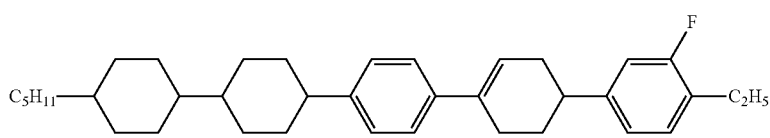 |
| 39 | 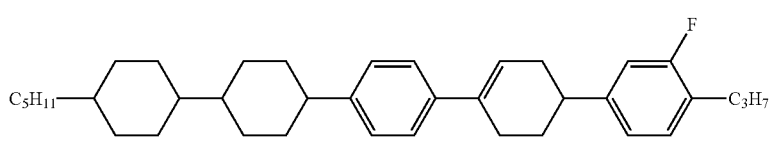 |
| 40 | 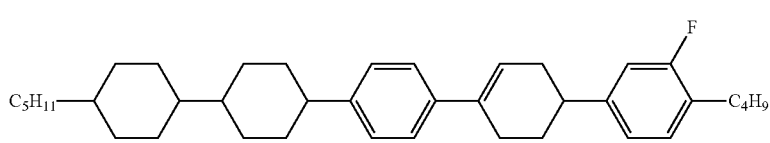 |
| 41 | 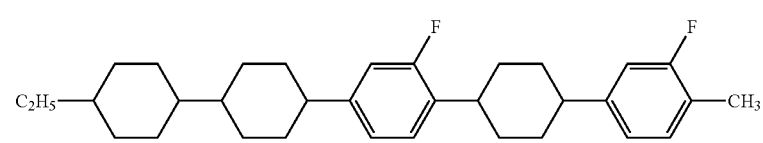 |
| 42 | 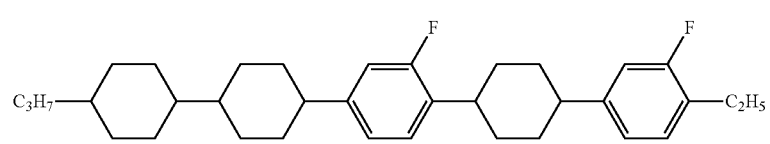 |

-continued
| No. | |
|---|---|
| 43 | 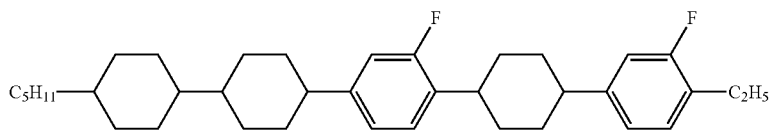 |
| 44 | 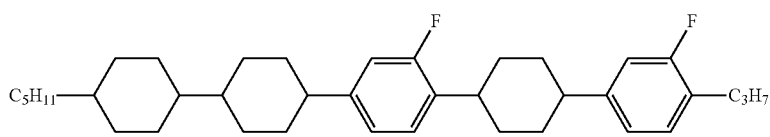 |
| 45 | 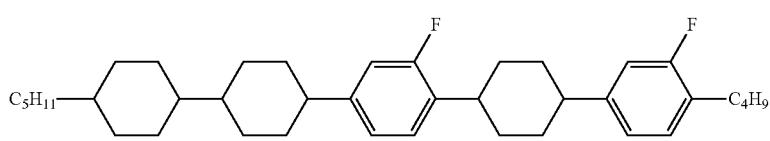 |
| 46 | 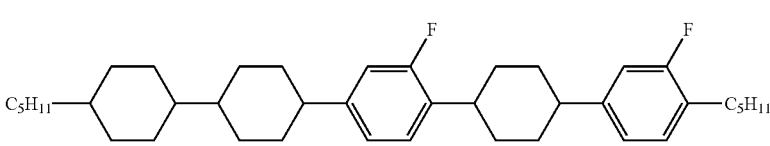 |
| 47 | 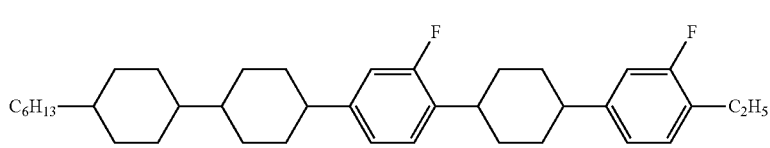 |
| 48 | 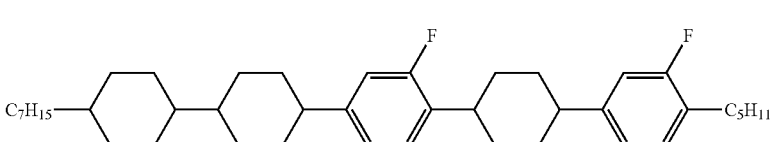 |
| 49 | 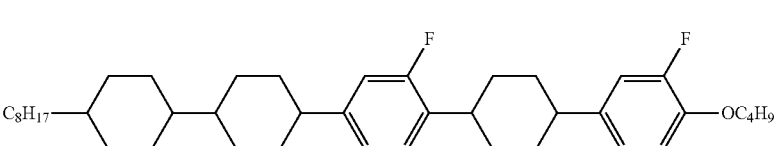 |
| 50 | 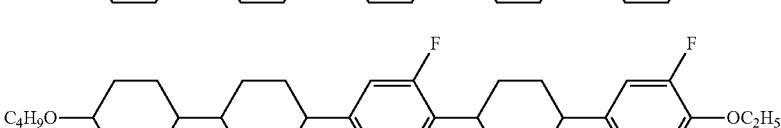 |
| 51 | 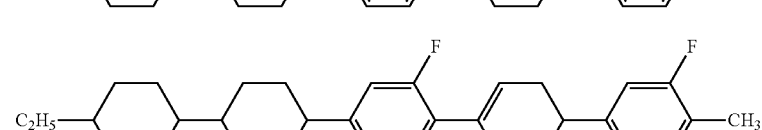 |
| 52 | 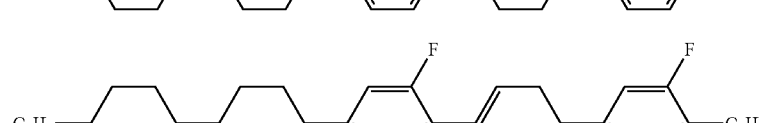 |
| 53 | 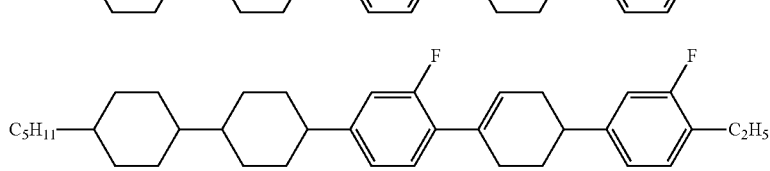 |

-continued
| No. | |
|---|---|
| 54 | 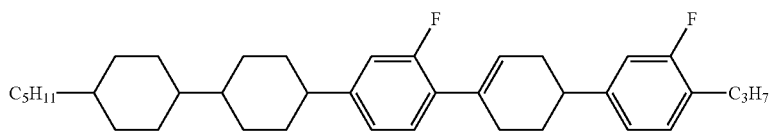 |
| 55 | 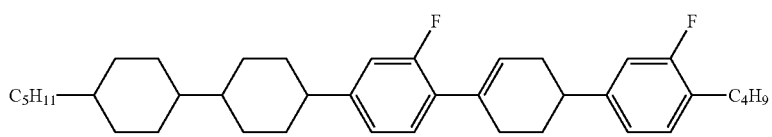 |
| 56 | 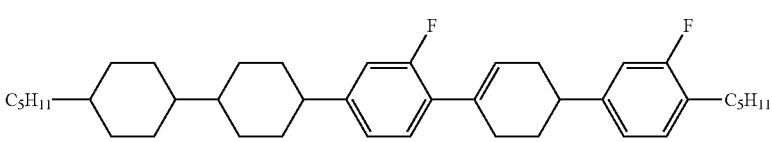 |
| 57 | 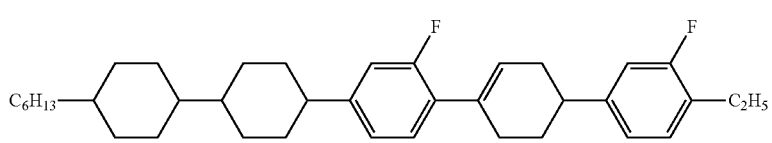 |
| 58 | 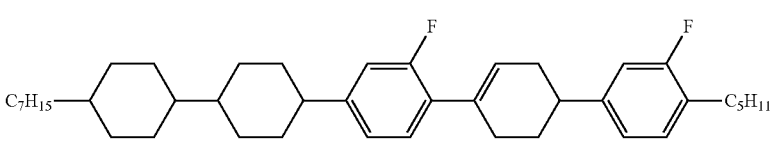 |
| 59 | 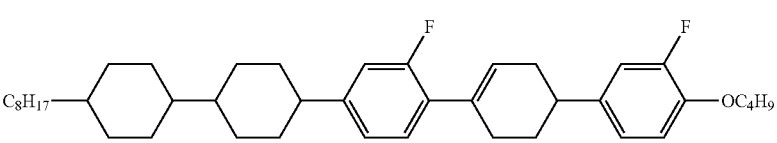 |
| 60 | 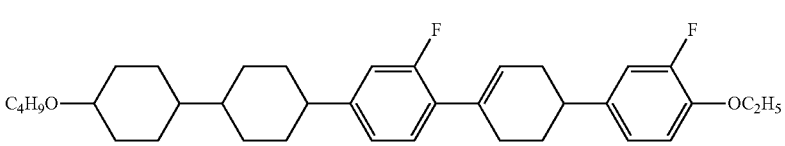 |
| 61 | 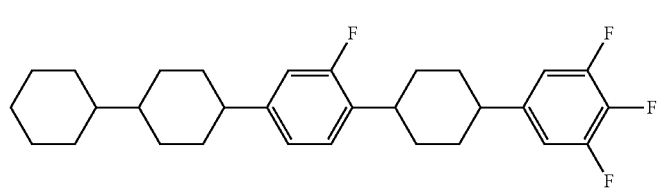 |
| 62 | 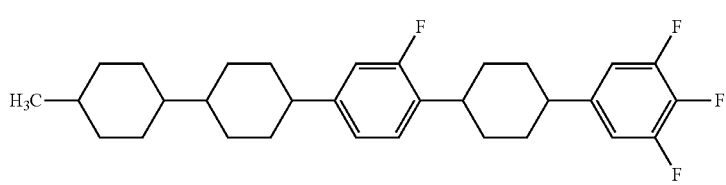 |
| 63 | 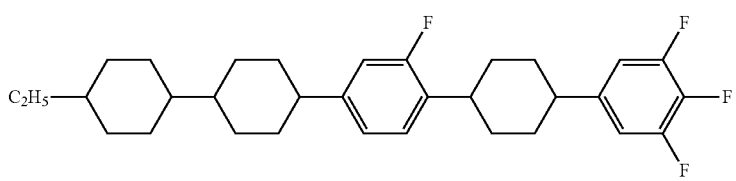 |

-continued
| No. |  |
|---|---|
| 64 | 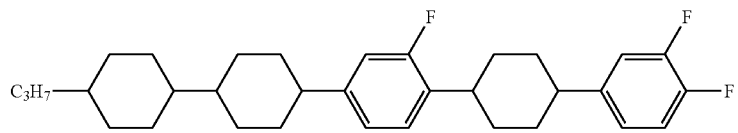 |
| 65 | 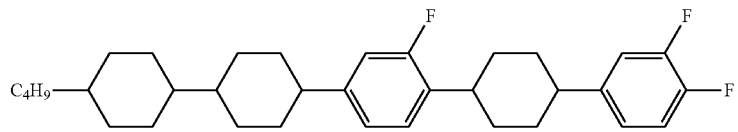 |
| 66 | 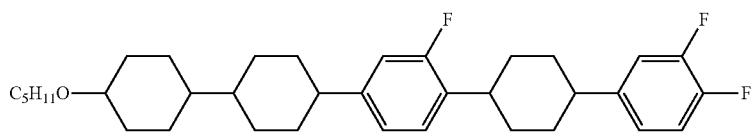 |
| 67 | 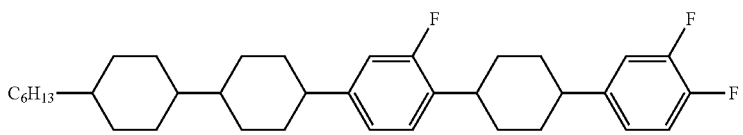 |
| 68 | 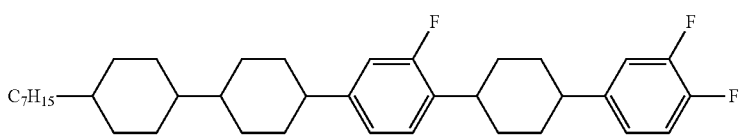 |
| 69 | 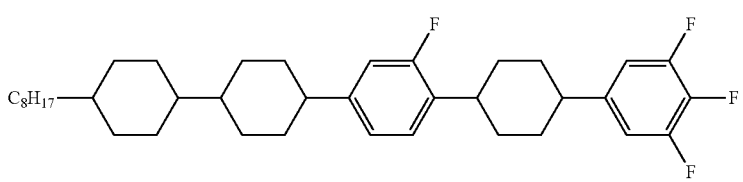 |
| 70 | 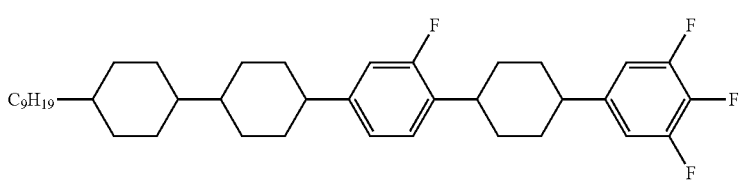 |
| 71 | 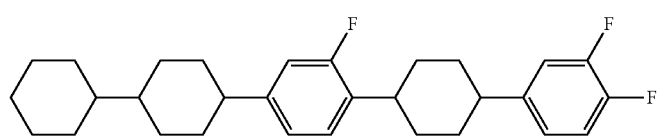 |
| 72 | 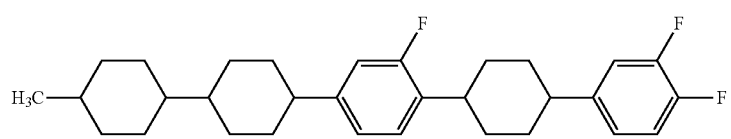 |
| 73 | 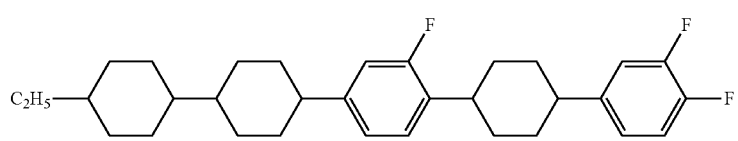 |

-continued
| No. |
|---|
| 74 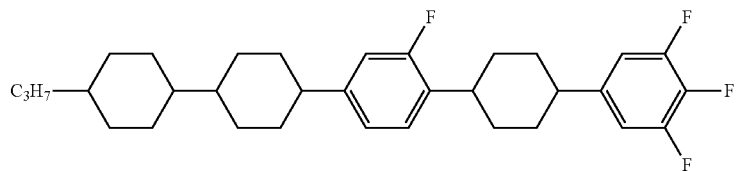 |
| 75 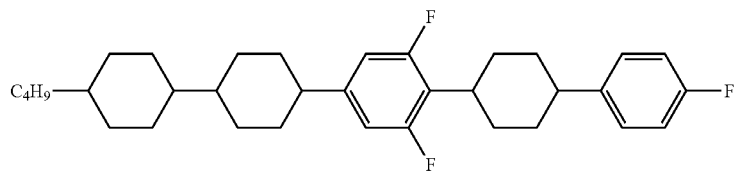 |
| 76 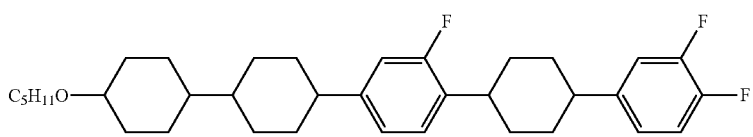 |
| 77 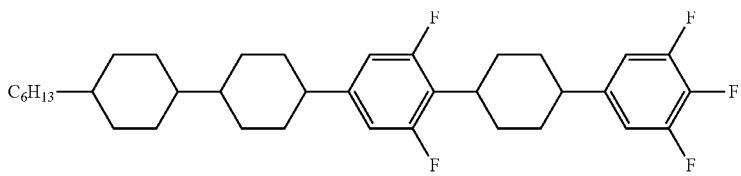 |
| 78 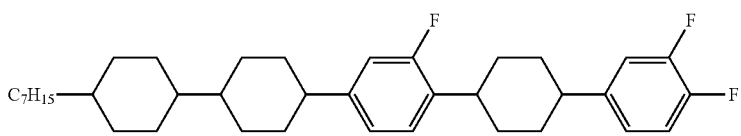 |
| 79 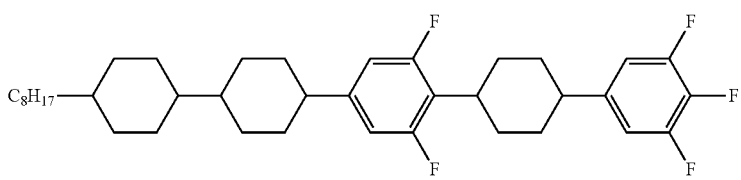 |
| 80 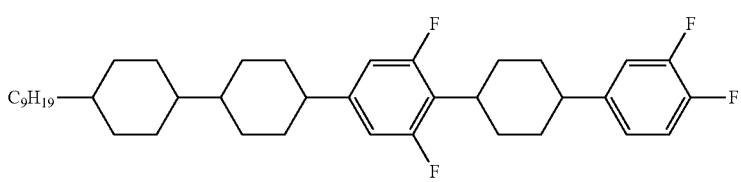 |
| 81 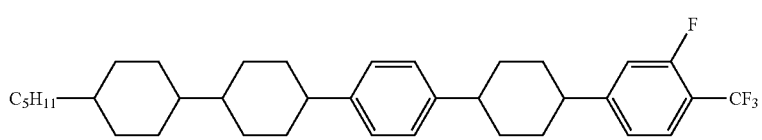 |
| 82 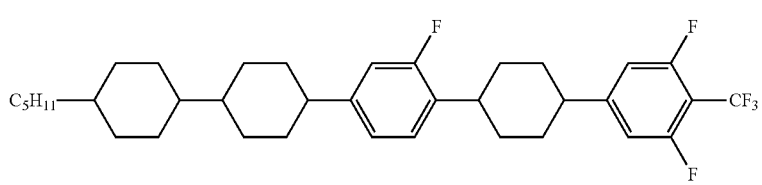 |

| No. | |
|---|---|
| 83 | 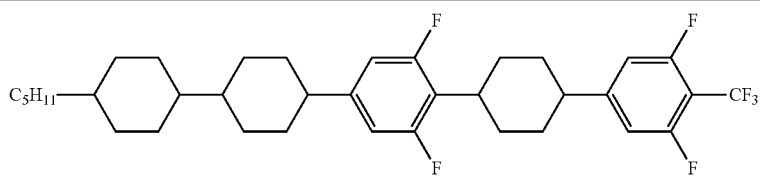 |
| 84 | 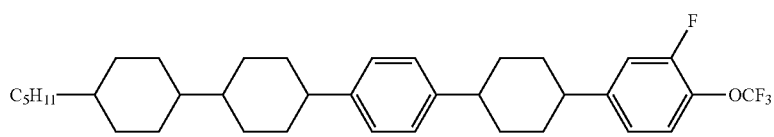 |
| 85 | 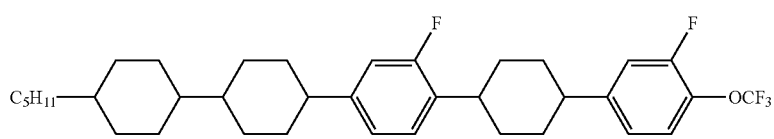 |
| 86 | 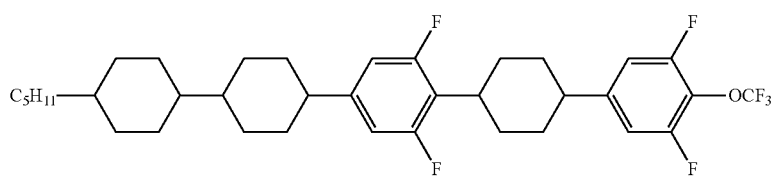 |
| 87 | 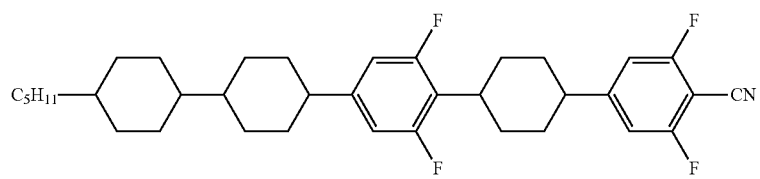 |
| 88 | 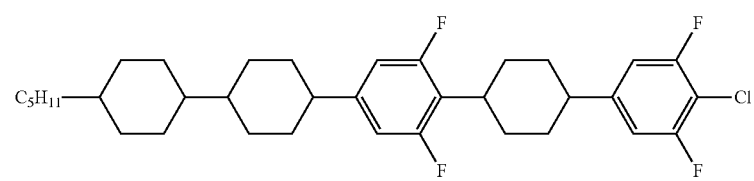 |
| 89 | 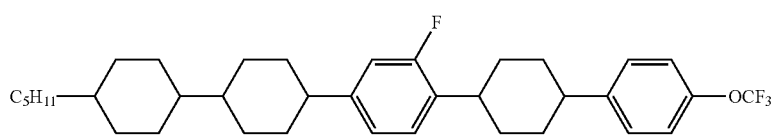<br>C 63.1 $S_B$ 290.1 N >350 I<br>$T_{NI}$; 219.7° C., Δ ε; 3.70, Δ n; 0.157 |
| 90 | 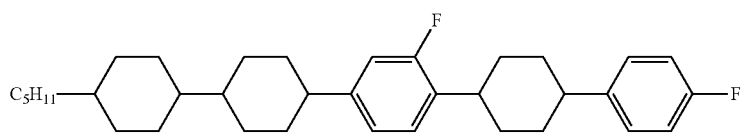 |
| 91 | 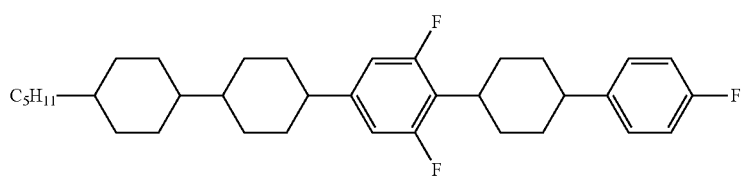 |

-continued
| No. |
|---|
| 92 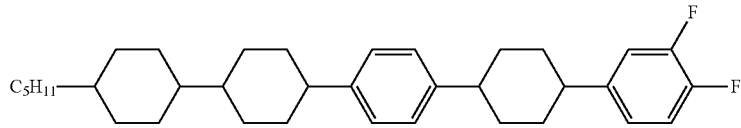 |
| 93 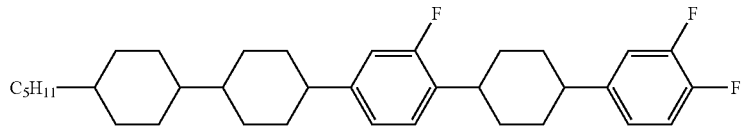 |
| 94 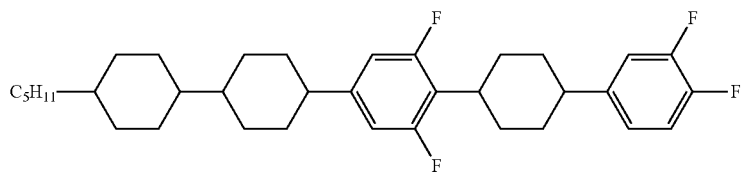 |
| 95 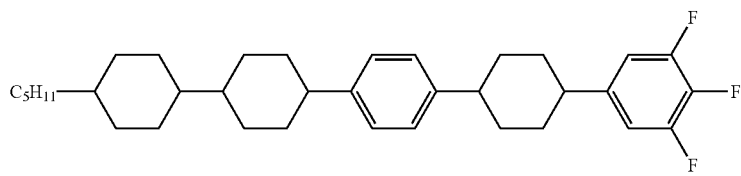 |
| 96 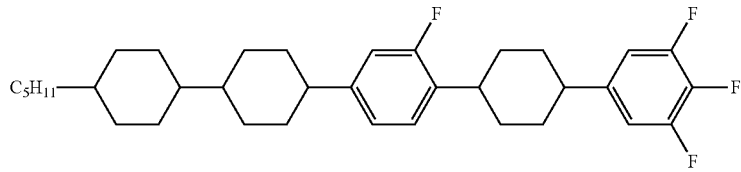
C 126.8 $S_B$ 179.3 N 343.7 I
$T_{NI}$; 217.7° C., Δ ε; 9.92, Δ n; 0.133 |
| 97 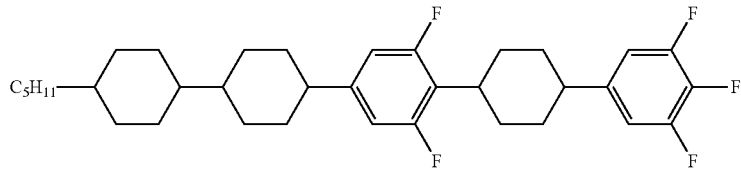
C 176.5 N 338.4 I
$T_{NI}$; 221.7° C., Δ ε; 17.3, Δ n; 0.117 |
| 98 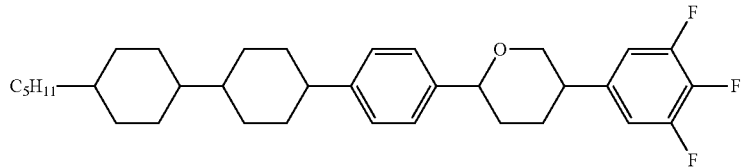 |
| 99 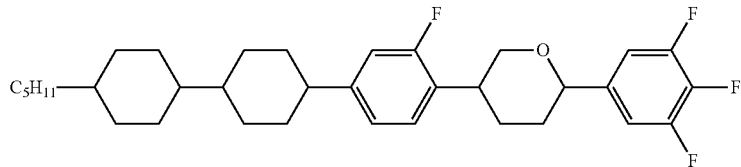 |

| No. |  |
|---|---|
| 100 | 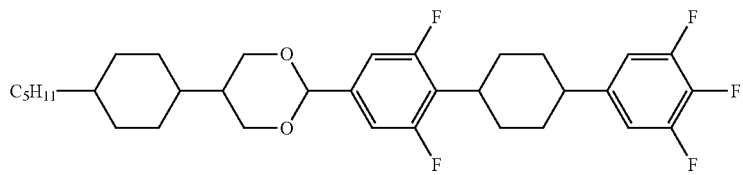 |
| 101 | 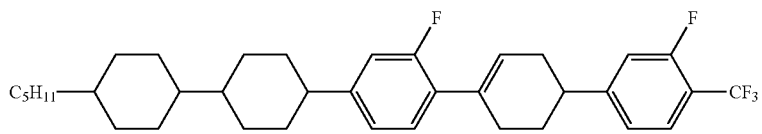 |
| 102 | 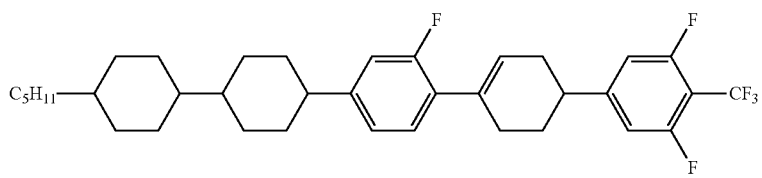 |
| 103 | 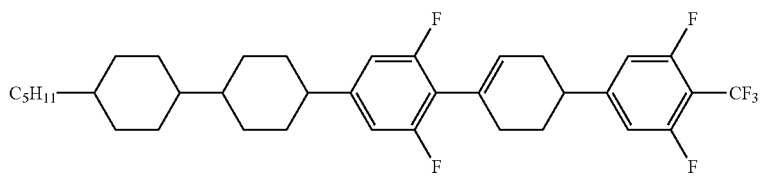 |
| 104 | 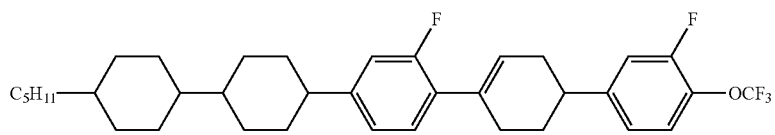 |
| 105 | 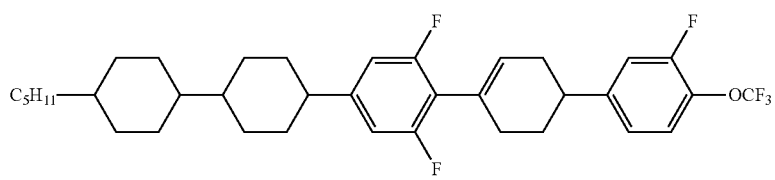 |
| 106 | 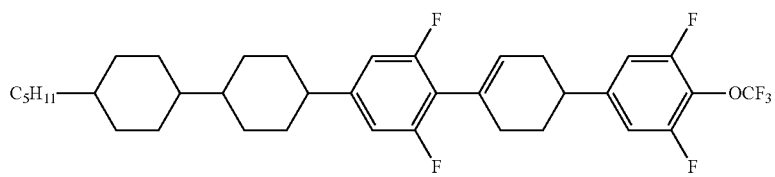 |
| 107 | 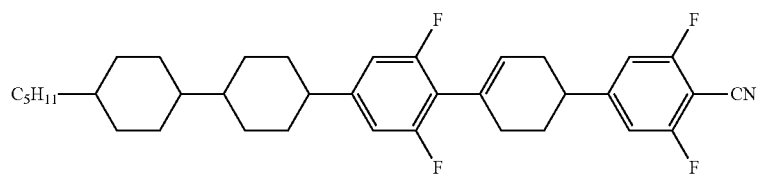 |

-continued
| No. | |
|---|---|
| 108 | 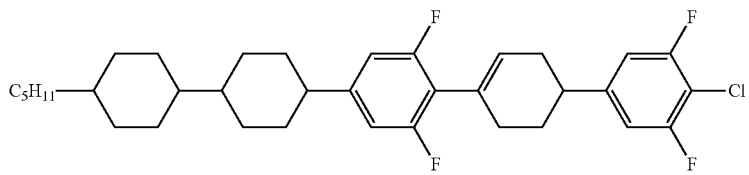 |
| 109 | 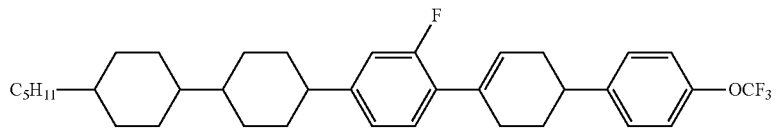
C 55.0 S$_B$ 271.3 N 280.9 I
T$_{NI}$; 232.4° C., Δ ε; 1.70, Δ n; 0.157 |
| 110 | 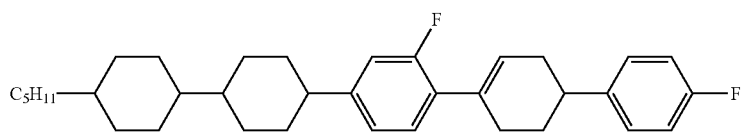 |
| 111 | 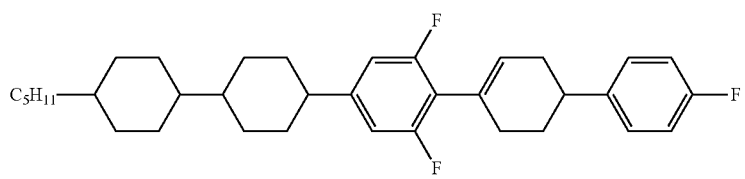 |
| 112 | 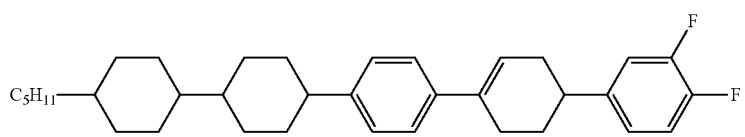 |
| 113 | 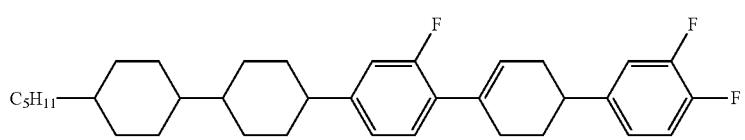 |
| 114 | 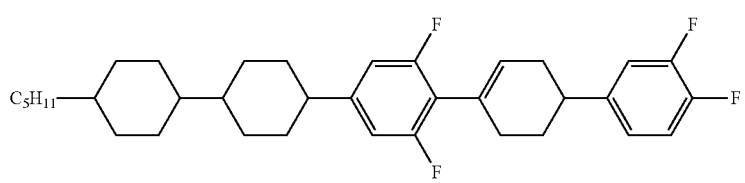 |
| 115 | 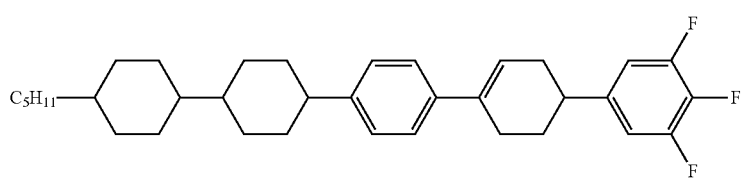 |

-continued
| No. | |
|---|---|
| 116 | 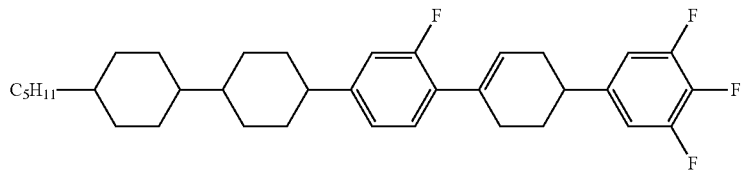 |
C 116.7 S$_B$ 153.1 N 309.3 I
T$_{NI}$; 226.4° C., Δ ϵ; 7.80, Δ n; 0.150
| 117 | 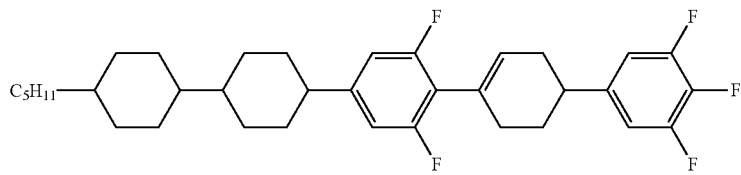 |
C 166.1 N 288.7 I
T$_{NI}$; 189.7° C., Δ ϵ; 17.6, Δ n; 0.137
| 118 | 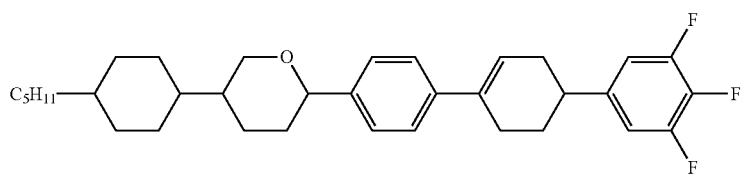 |
| 119 | 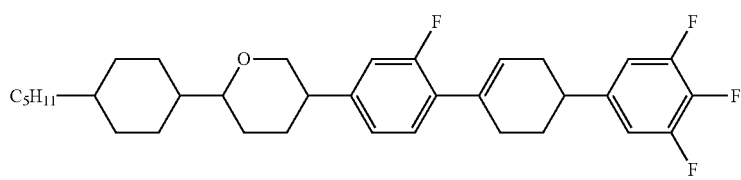 |
| 120 | 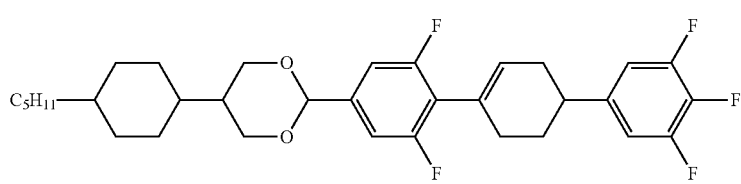 |
| 121 | 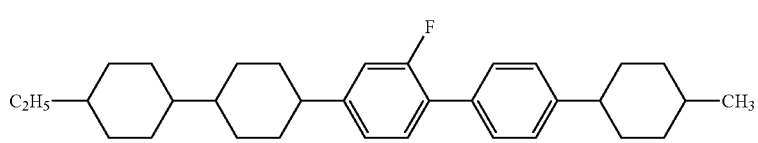 |
| 122 | 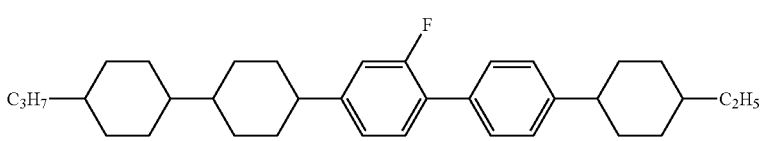 |
| 123 | 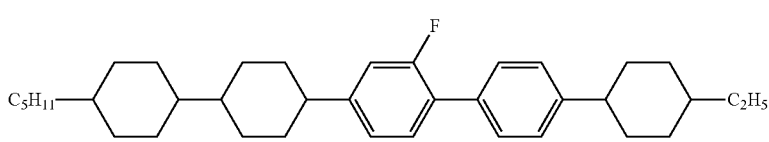 |
| 124 | 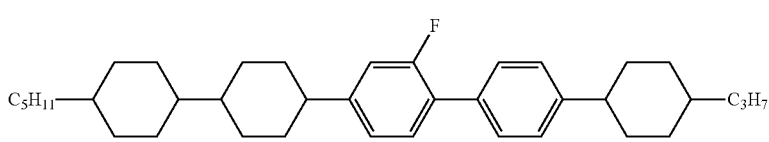 |

|     |     |
| --- | --- |
| No. | |
| 125 | 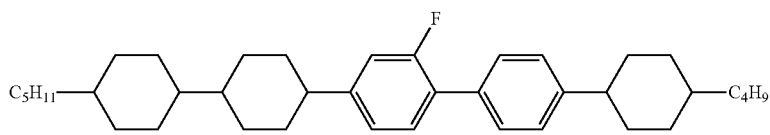 |
| 126 | 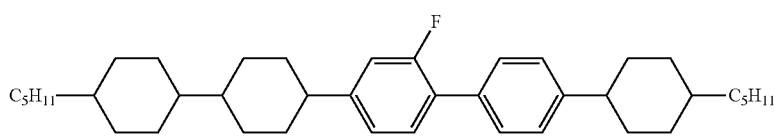 |
| 127 | 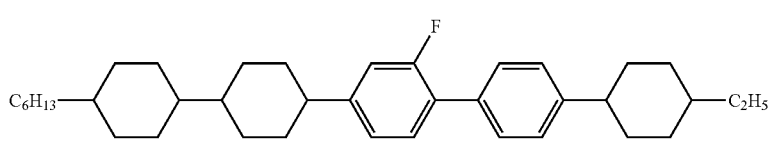 |
| 128 | 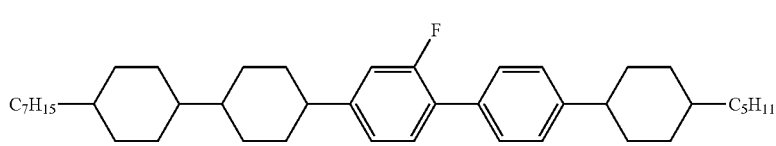 |
| 129 | 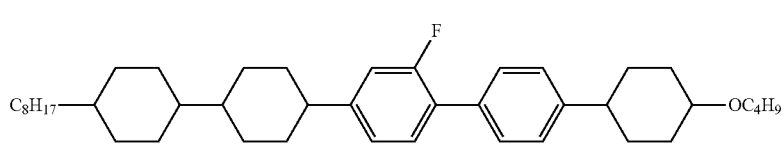 |
| 130 | 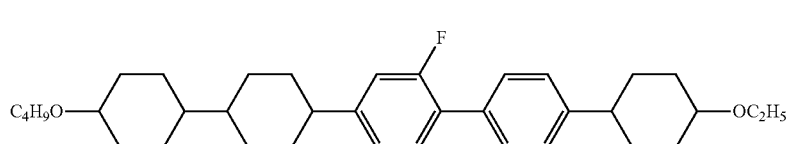 |
| 131 | 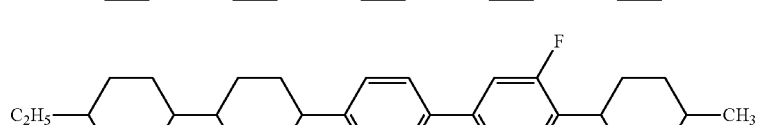 |
| 132 | 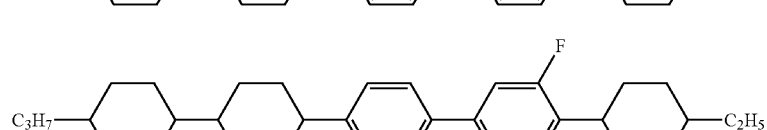 |
| 133 | 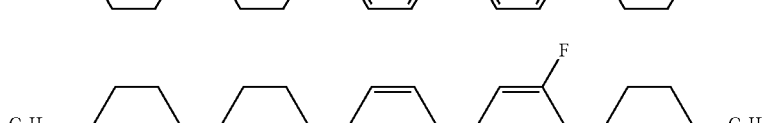 |
| 134 | 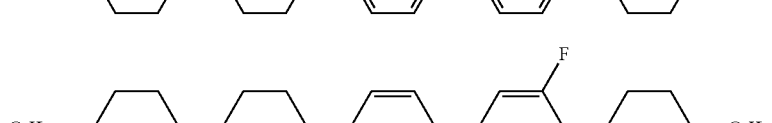 |
| 135 | 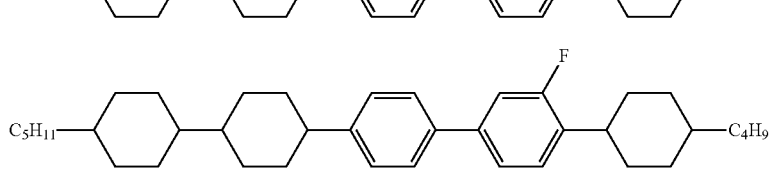 |

-continued
| No. | |
|---|---|
| 136 | 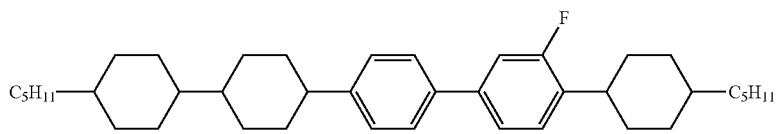 |
| 137 | 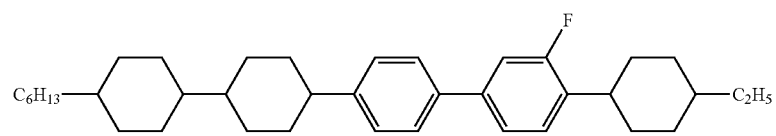 |
| 138 | 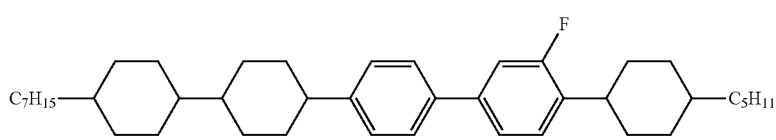 |
| 139 | 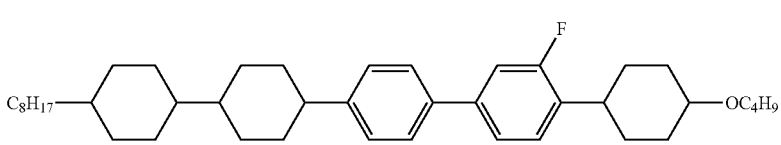 |
| 140 | 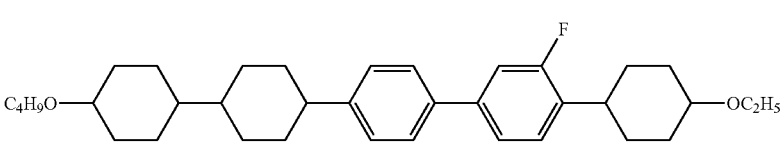 |
| 141 | 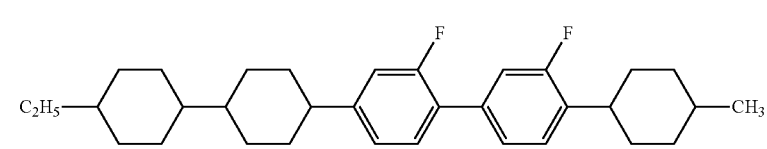 |
| 142 | 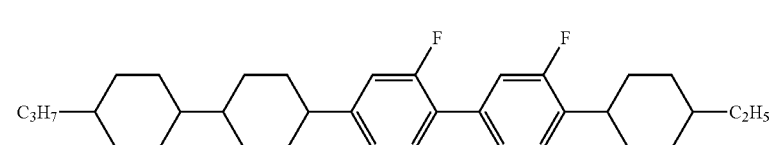 |
| 143 | 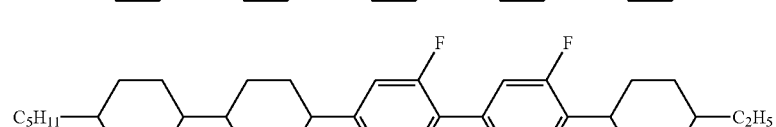 |
| 144 | 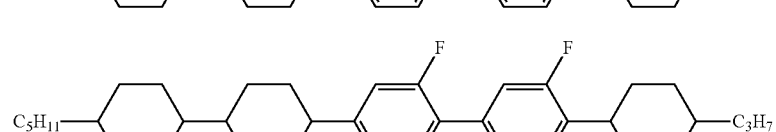 |
| 145 | 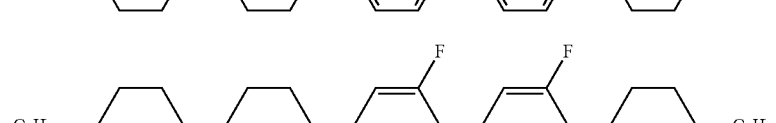 |
| 146 | 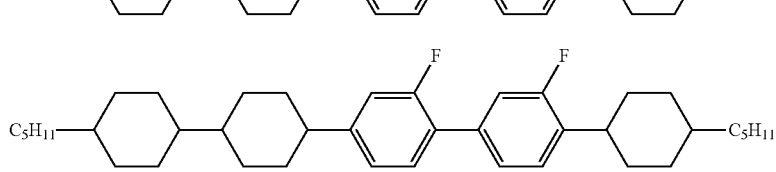 |

| No. | |
|---|---|
| 147 | 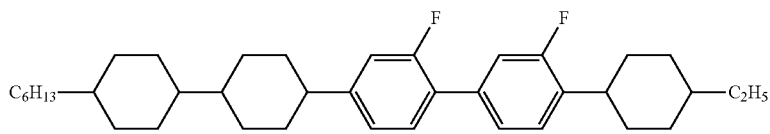 |
| 148 | 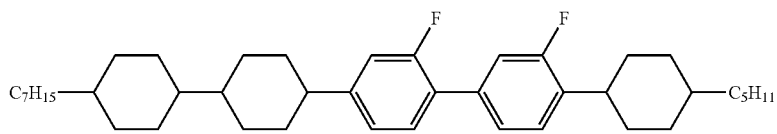 |
| 149 | 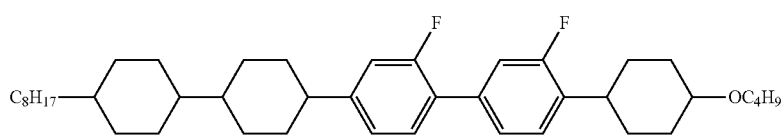 |
| 150 | 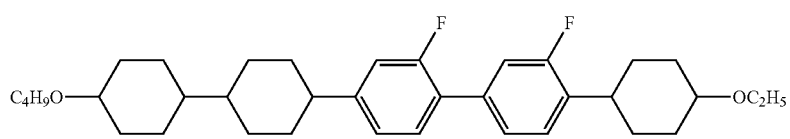 |
| 151 | 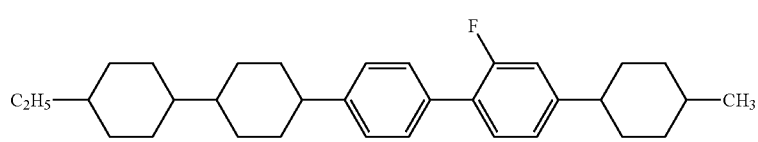 |
| 152 | 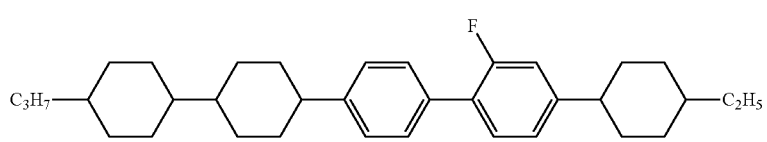 |
| 153 | 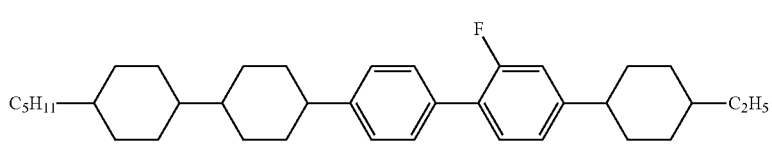 |
| 154 | 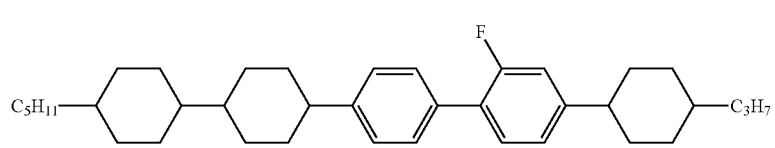 |
| 155 | 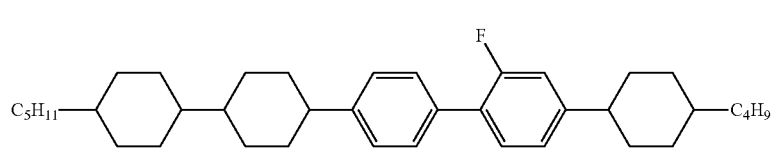 |
| 156 | 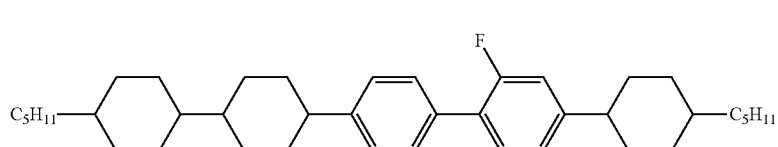 |
| 157 | 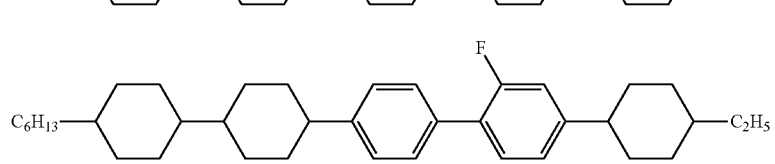 |

-continued
| No. | |
|---|---|
| 158 | 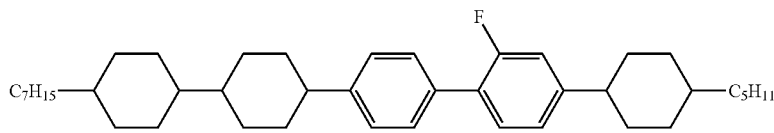 |
| 159 | 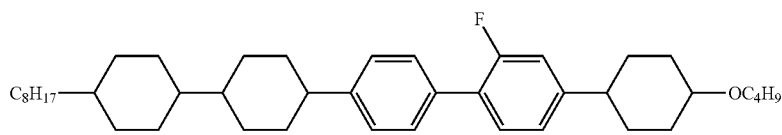 |
| 160 | 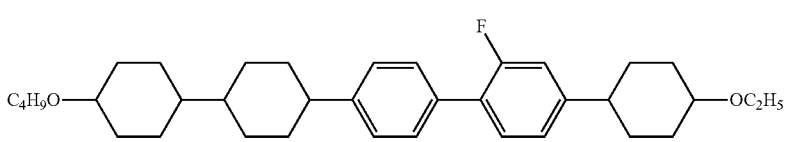 |
| 161 | 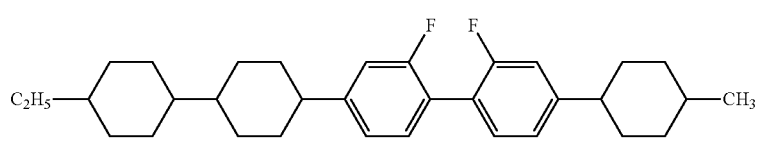 |
| 162 | 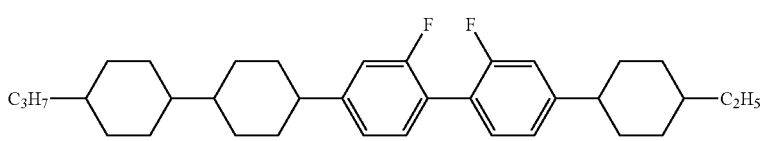 |
| 163 | 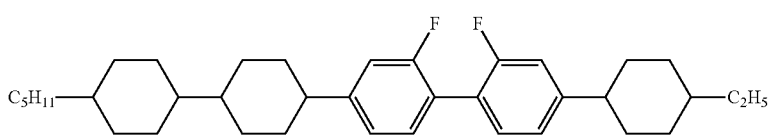 |
| 164 | 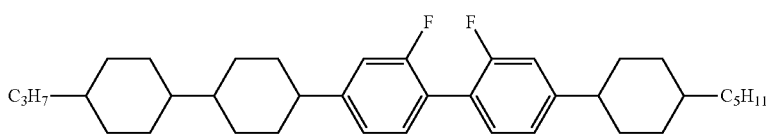<br>C 58.3 $S_X$ 92.7 $S_B$ 226.5 N >350 I<br>$T_{NI}$; 237.7° C., Δ ϵ; 3.80, Δ n; 0.177 |
| 165 | 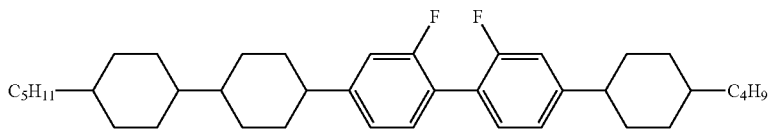 |
| 166 | 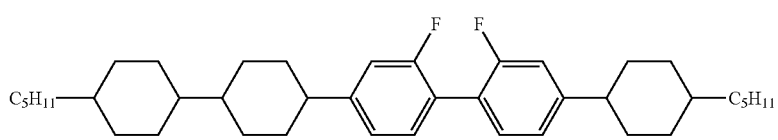 |
| 167 | 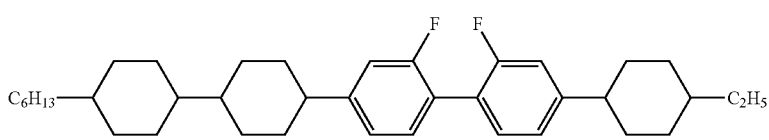 |
| 168 | 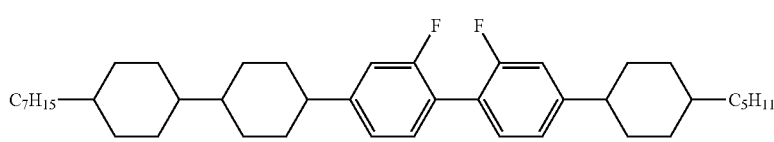 |

-continued
| No. | |
|---|---|
| 169 | 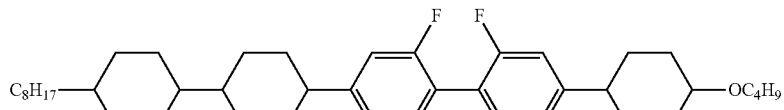 |
| 170 | 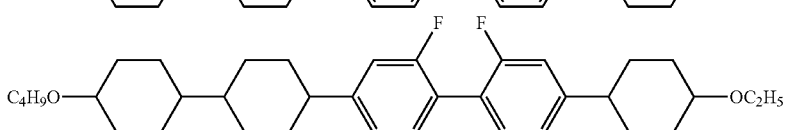 |
| 171 | 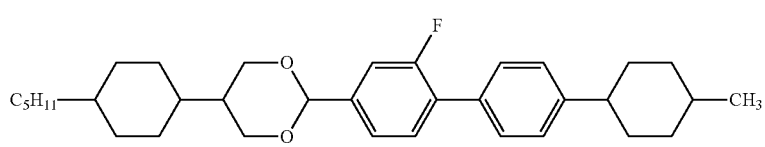 |
| 172 | 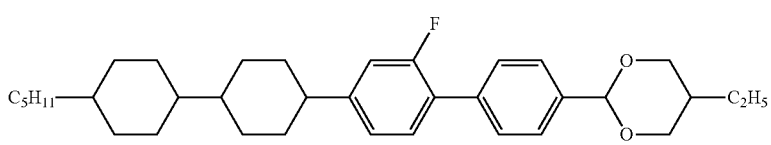 |
| 173 | 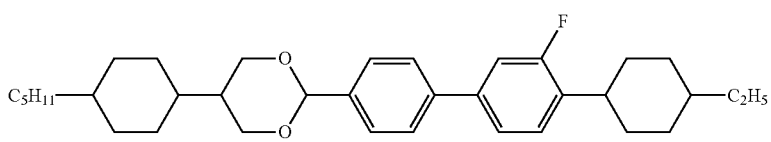 |
| 174 | 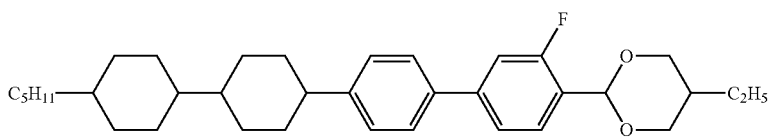 |
| 175 | 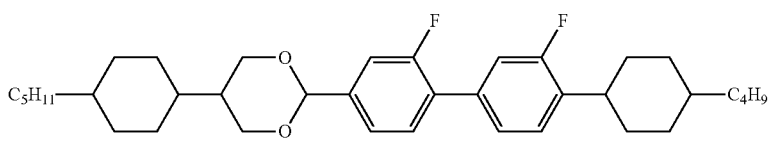 |
| 176 | 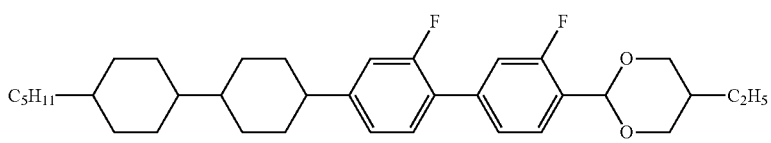 |
| 177 | 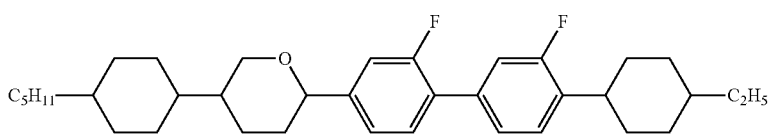 |
| 178 | 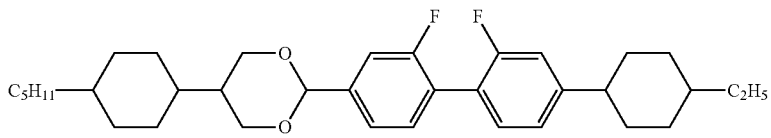 |
| 179 | 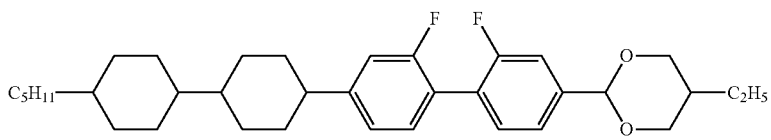 |

-continued
| No. |
|---|
| 180 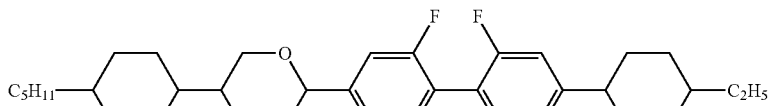 |
| 181 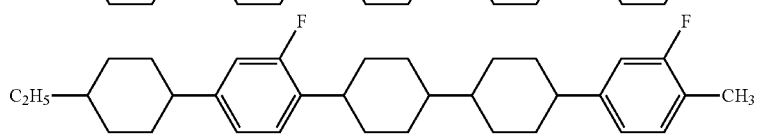 |
| 182 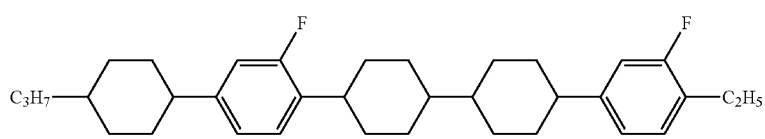 |
| 183 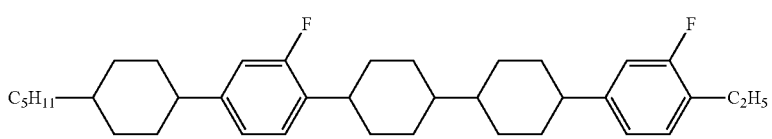 |
| 184 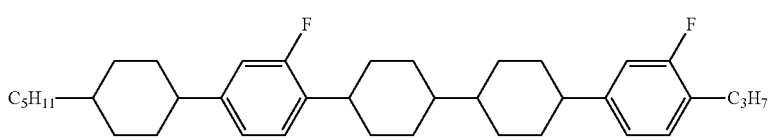 |
| 185 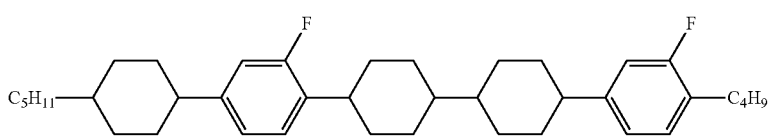 |
| 186 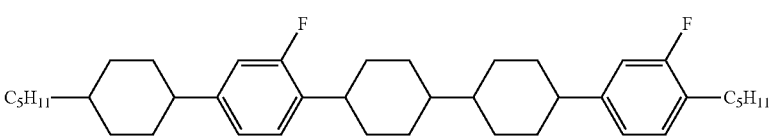 |
| 187 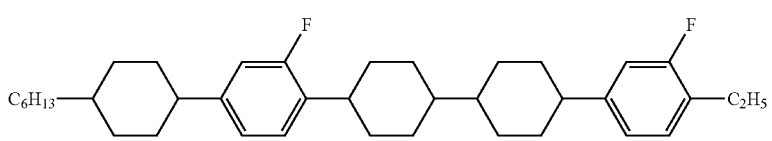 |
| 188 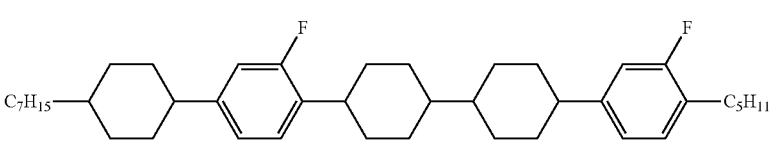 |
| 189 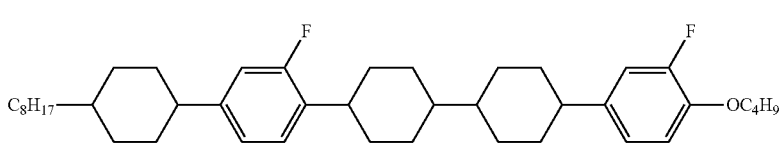 |
| 190 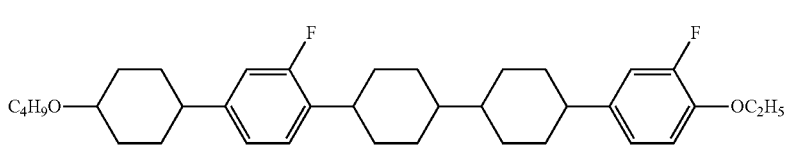 |

| No. |
|---|
| 191 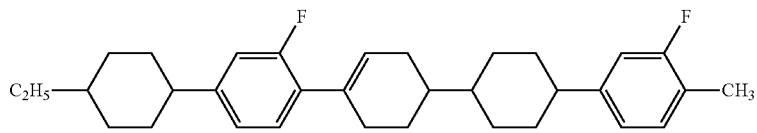 |
| 192 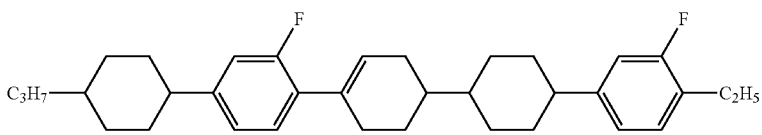 |
| 193 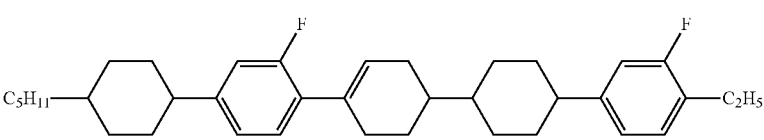 |
| 194 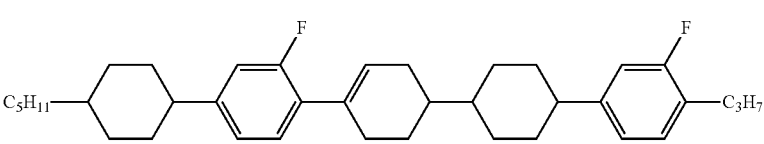 |
| 195 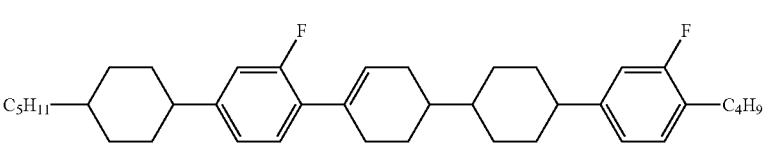 |
| 196 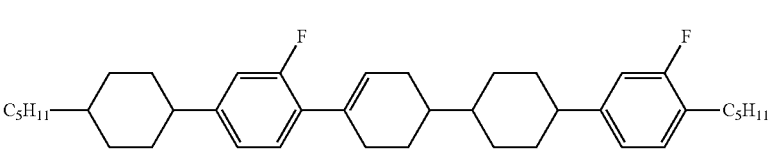 |
| 197 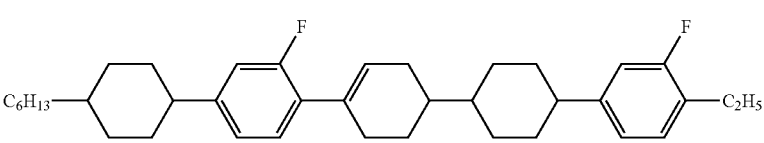 |
| 198 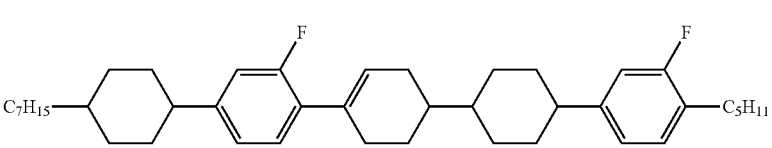 |
| 199 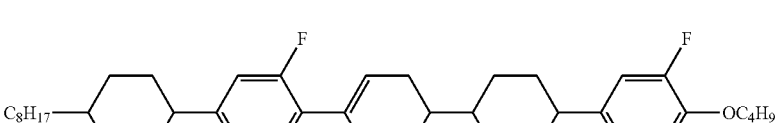 |
| 200 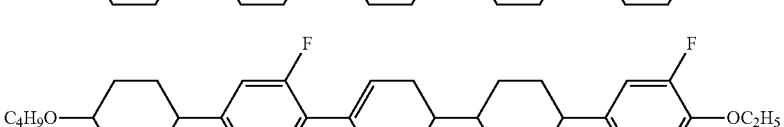 |
| 201 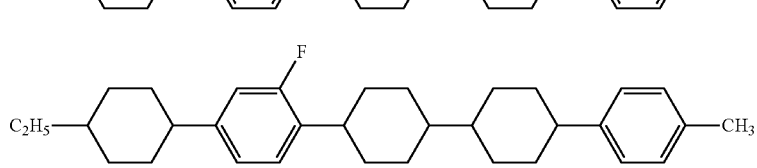 |

-continued
| No. | |
|---|---|
| 202 | 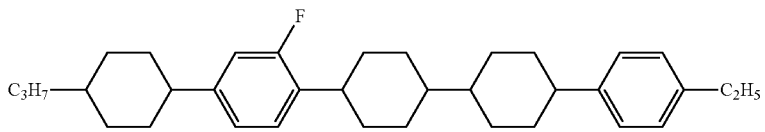 |
| 203 | 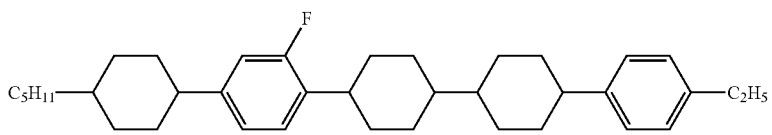
C 74.8 S$_B$ 323.1 N >350 I
T$_{NI}$; 245.0° C., Δ ε; 5.13, Δ n; 0.170 |
| 204 | 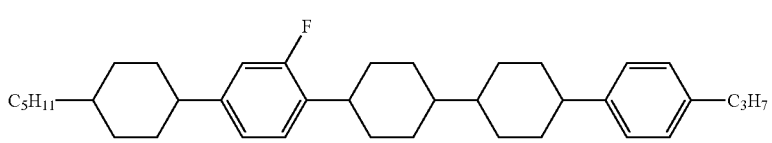 |
| 205 | 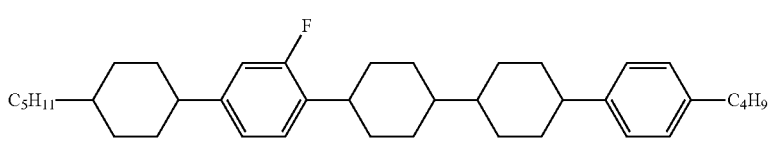 |
| 206 | 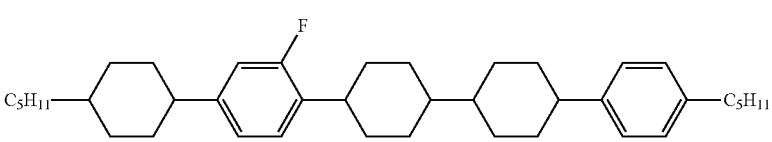 |
| 207 | 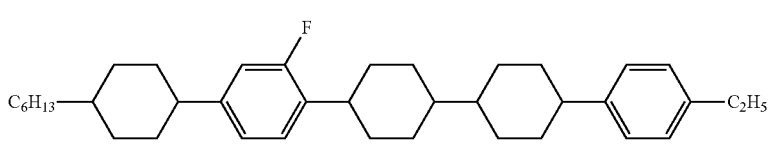 |
| 208 | 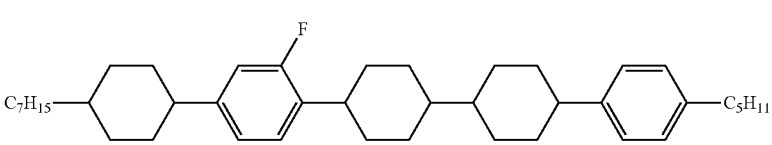 |
| 209 | 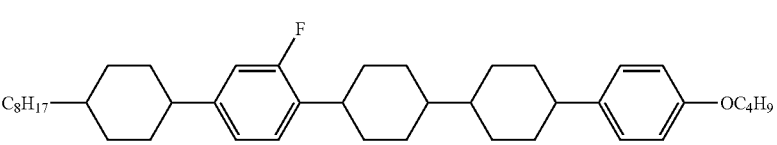 |
| 210 | 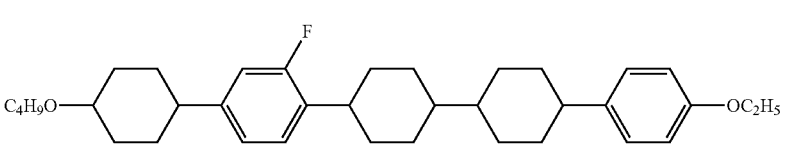 |
| 211 | 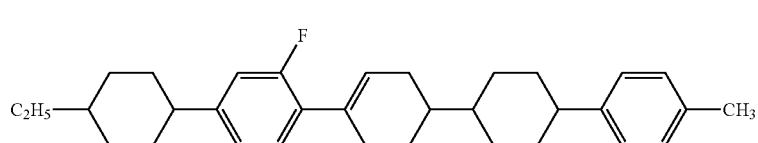 |
| 212 | 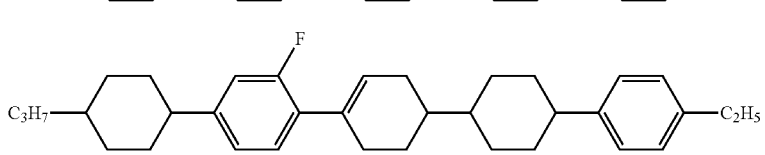 |

| No. | |
|---|---|
| 213 | 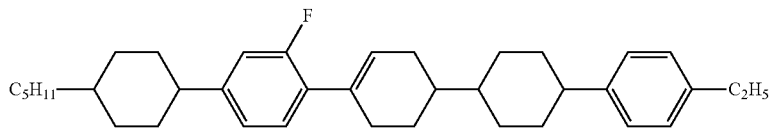 C 96.9 S$_B$ 288.0 N >350 I<br>T$_{Ni}$; 247.7° C., Δ ∈; 1.80, Δ n; 0.177 |
| 214 | 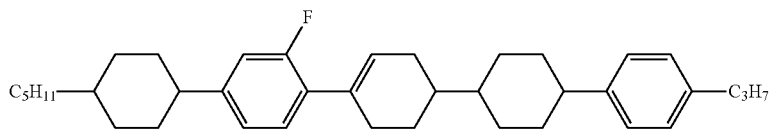 |
| 215 | 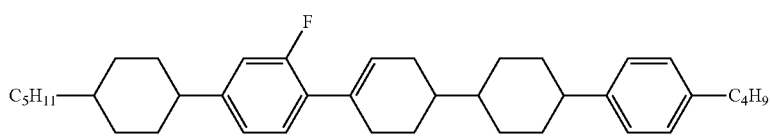 |
| 216 | 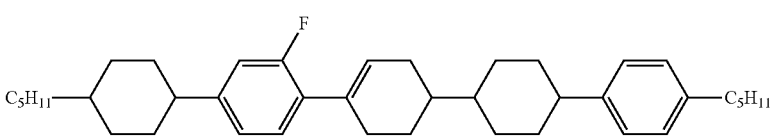 |
| 217 | 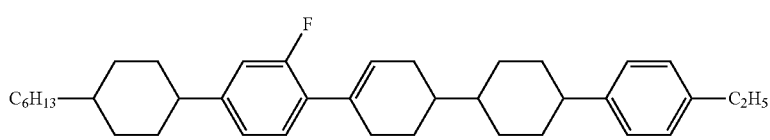 |
| 218 | 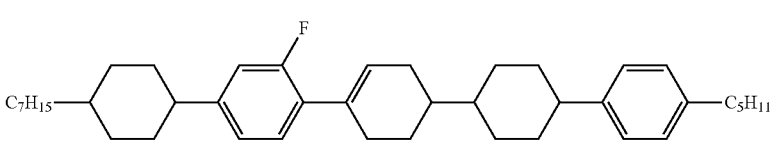 |
| 219 | 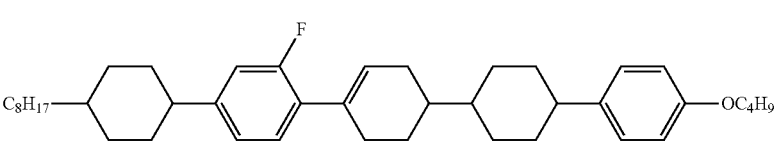 |
| 220 | 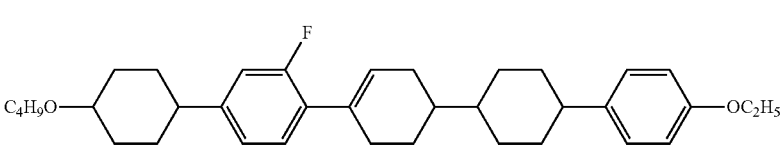 |
| 221 | 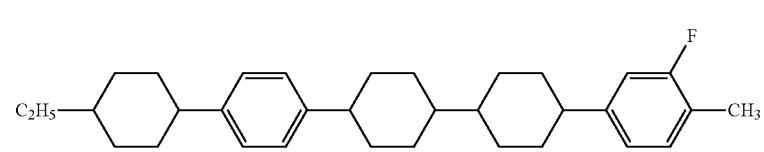 |
| 222 | 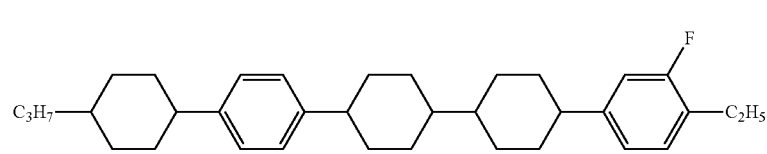 |

-continued
| No. | |
|---|---|
| 223 | 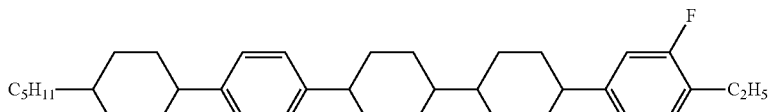 |
| 224 | 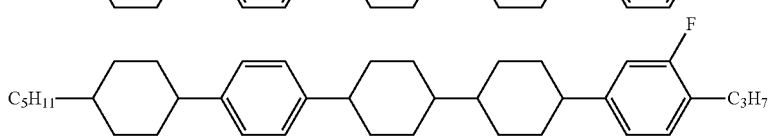 |
| 225 | 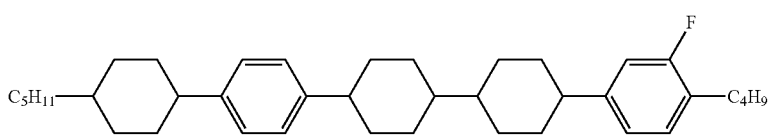 |
| 226 | 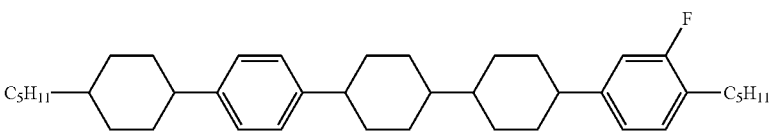 |
| 227 | 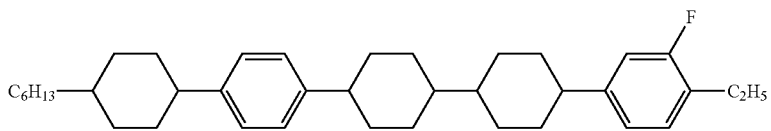 |
| 228 | 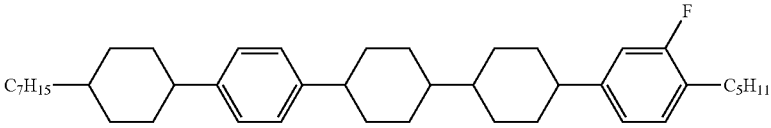 |
| 229 | 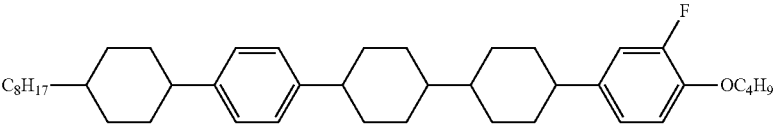 |
| 230 | 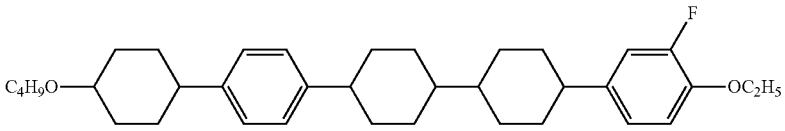 |
| 231 | 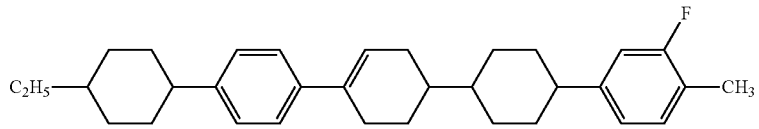 |
| 232 | 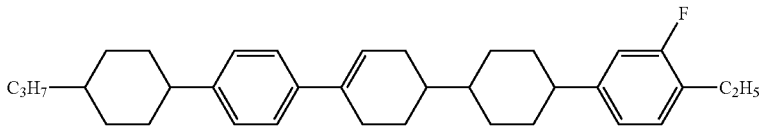 |
| 233 | 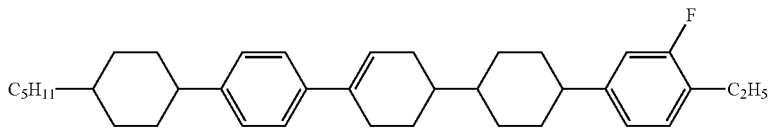 |

-continued
| No. |
|---|
| 234 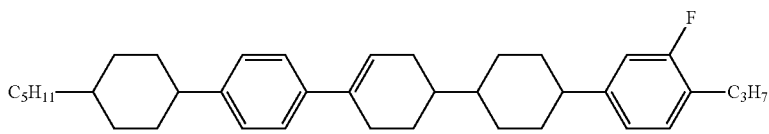 |
| 235 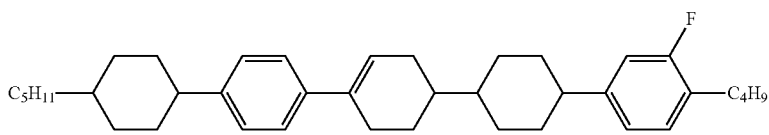 |
| 236 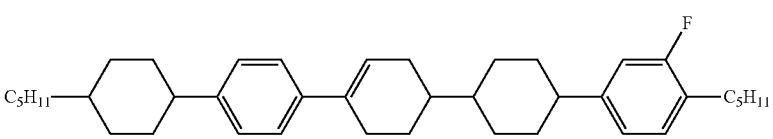 |
| 237 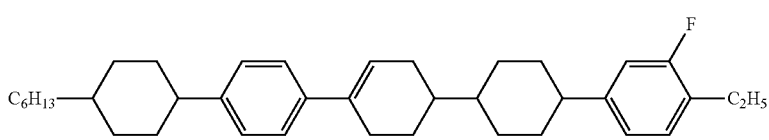 |
| 238 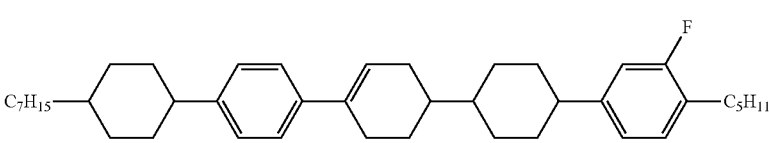 |
| 239 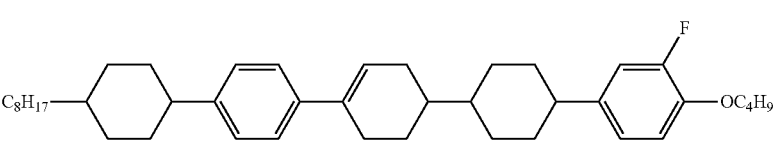 |
| 240 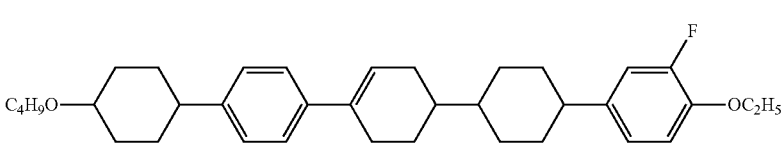 |
| 241 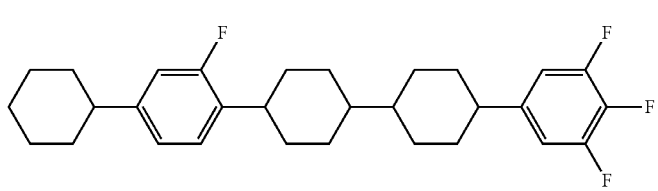 |
| 242 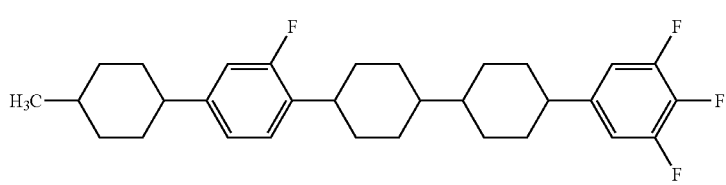 |
| 243 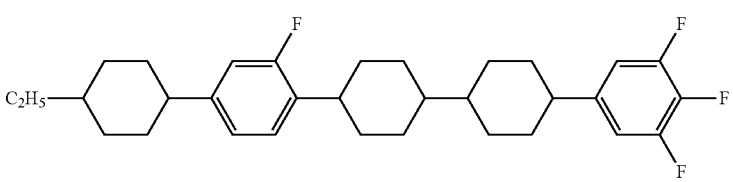 |

-continued
| No. | |
|---|---|
| 244 | 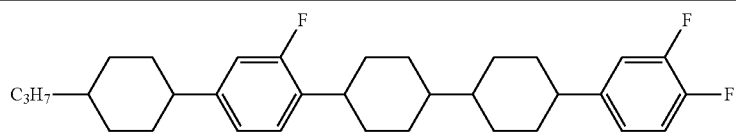 |
| 245 | 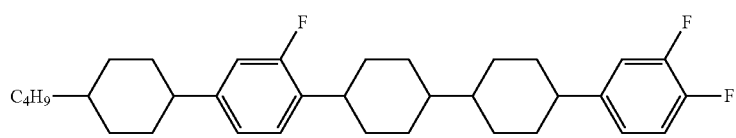 |
| 246 | 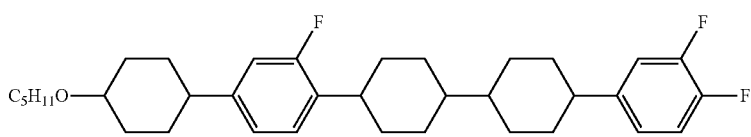 |
| 247 | 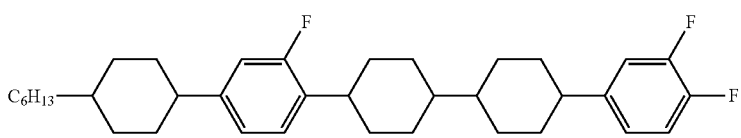 |
| 248 | 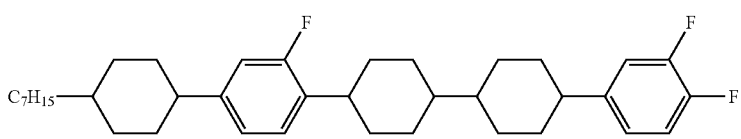 |
| 249 | 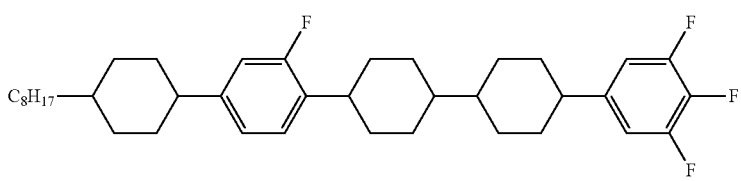 |
| 250 | 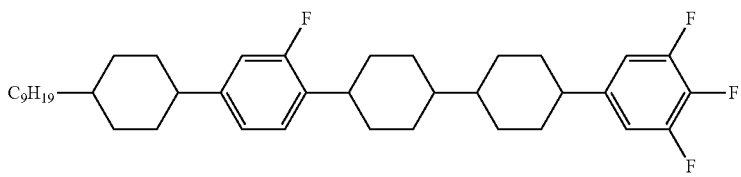 |
| 251 | 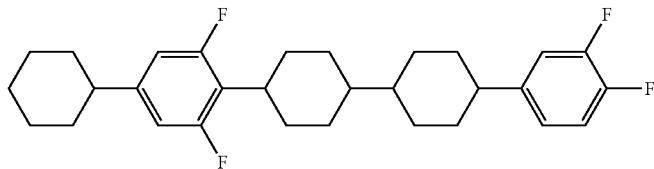 |
| 252 | 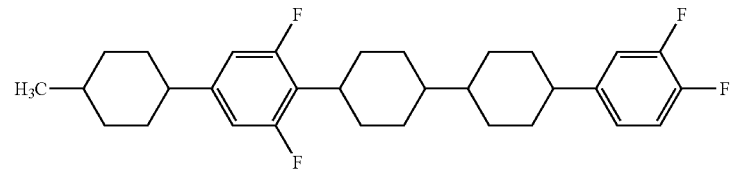 |
| 253 | 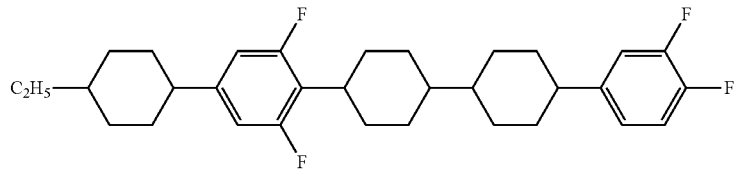 |

-continued
| No. | |
|---|---|
| 254 | 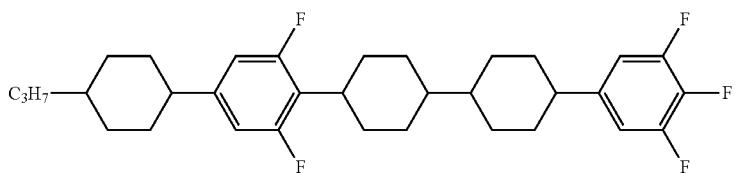 |
| 255 | 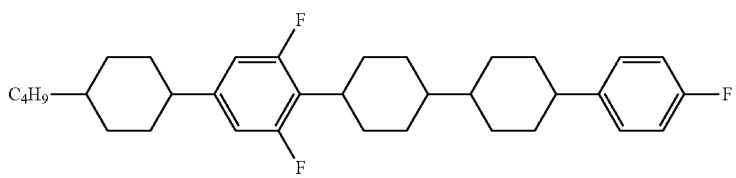 |
| 256 | 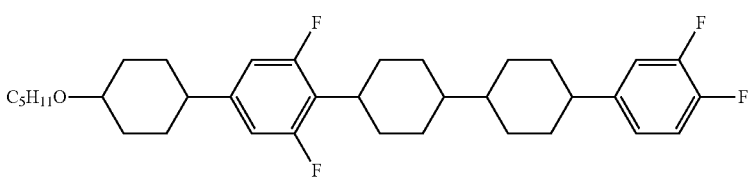 |
| 257 | 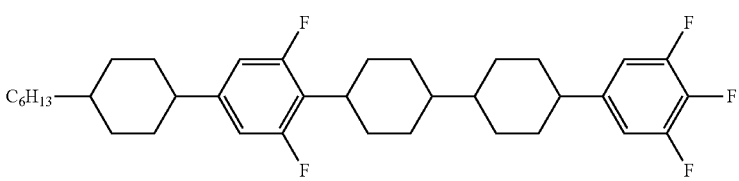 |
| 258 | 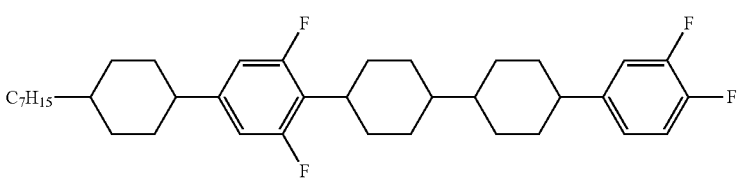 |
| 259 | 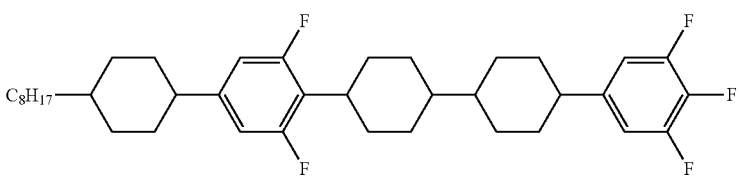 |
| 260 | 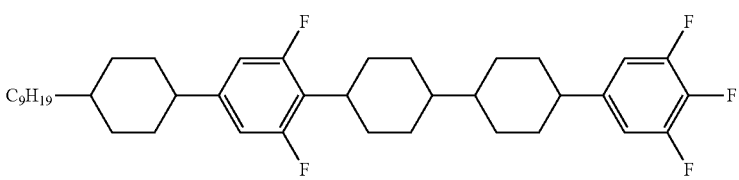 |
| 261 | 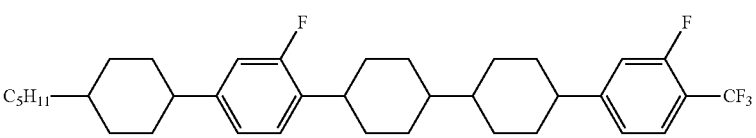 |
| 262 | 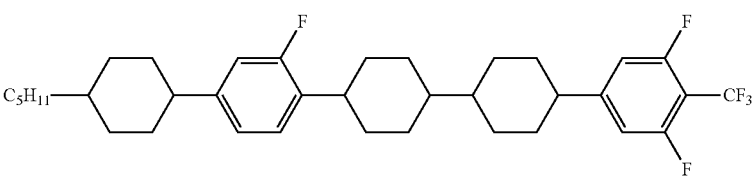 |

-continued
| No. | |
|---|---|
| 263 | 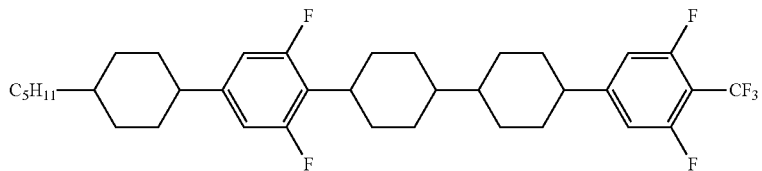 |
| 264 | 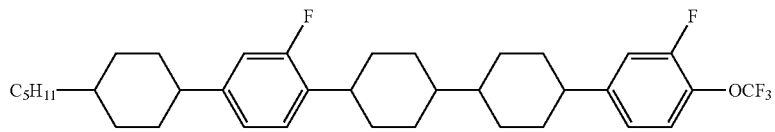 |
| 265 | 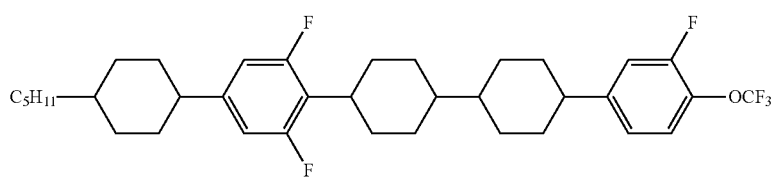 |
| 266 | 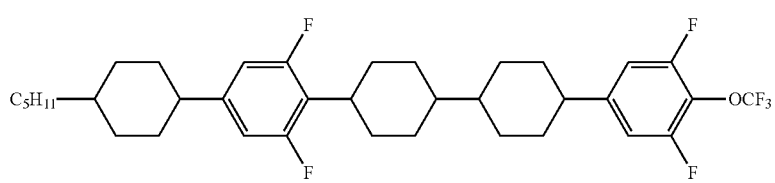 |
| 267 | 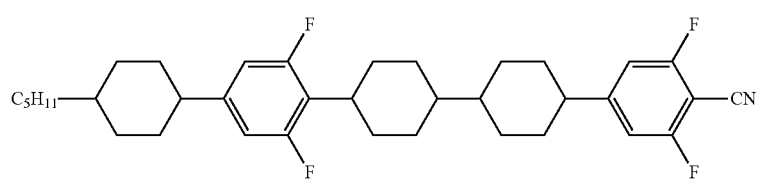 |
| 268 | 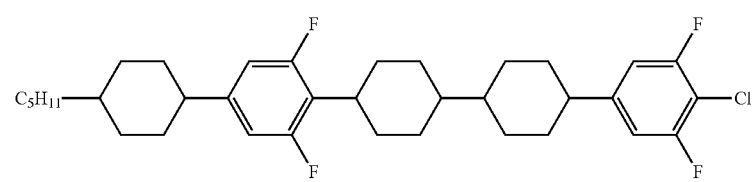 |
| 269 | 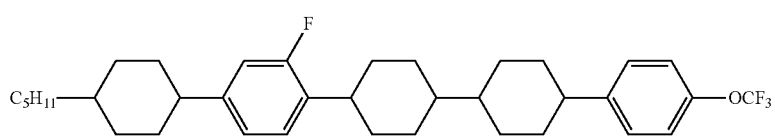 |
| 270 | 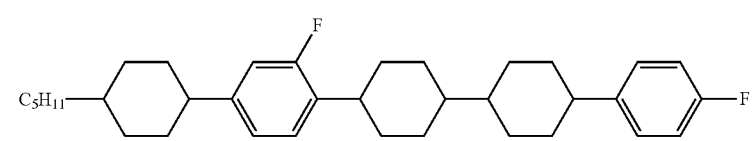 |
| 271 | 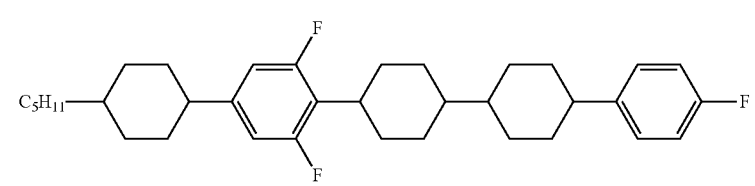 |

| No. | |
|---|---|
| 272 | 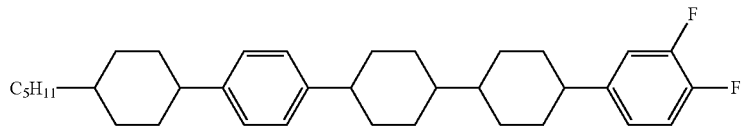 |
| 273 | 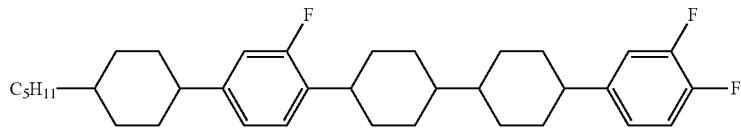 |
C 66.2 S$_B$ 172.0 N 324.6 I
T$_{NI}$; 198.7° C., Δ ε; 5.80, Δ n; 0.127
| 274 | 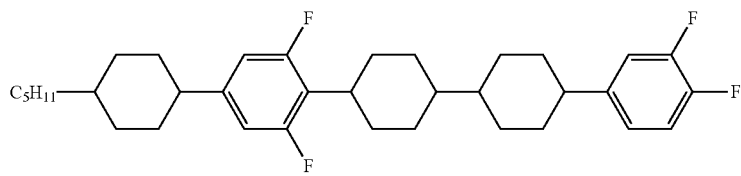 |
C 117.5 S$_B$ 182.0 N >350 I
T$_{NI}$; 208.4° C., Δ ε; 24.73, Δ n; 0.170
| 275 | 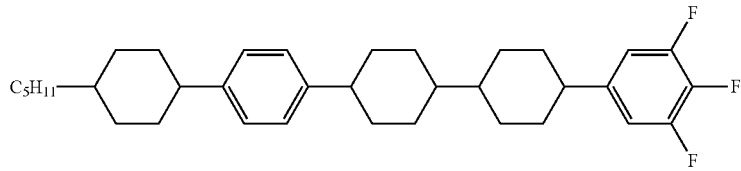 |
| 276 | 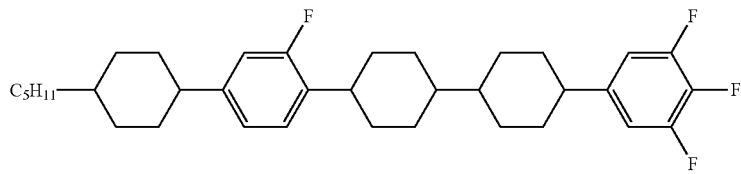 |
C 95.4 S$_B$ 169.0 N 337.3 I
T$_{NI}$; 213.7° C., Δ ε; 8.37, Δ n; 0.130
| 277 | 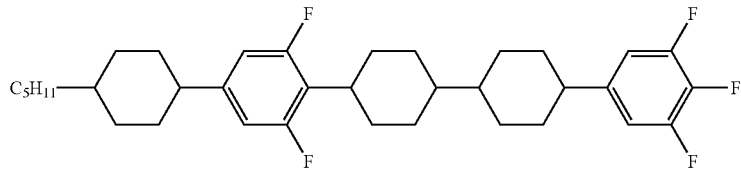 |
C 120.5 S$_B$ 145.3 N 341.0 I
T$_{NI}$; 201.7° C., Δ ε; 18.27, Δ n; 0.137
| 278 | 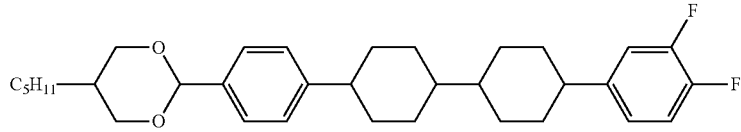 |
| 279 | 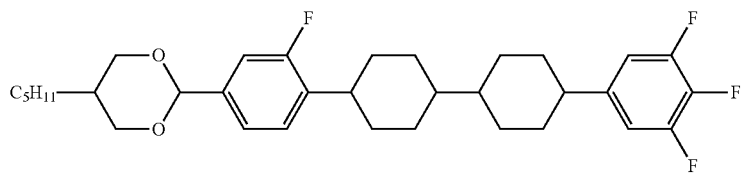 |

-continued
| No. | |
|---|---|
| 280 | 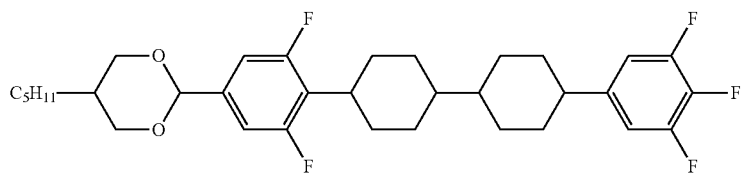 |
| 281 | 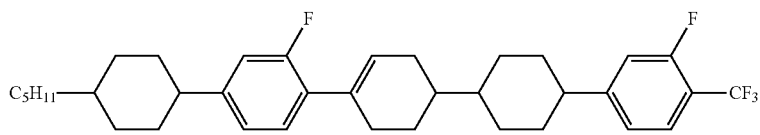 |
| 282 | 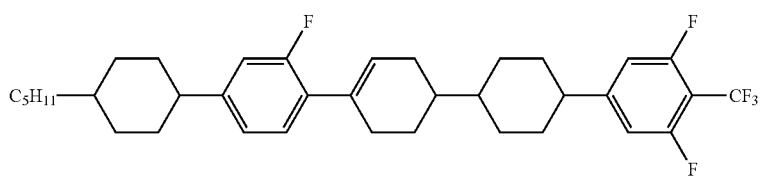 |
| 283 | 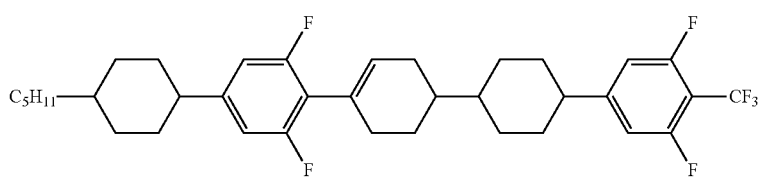 |
| 284 | 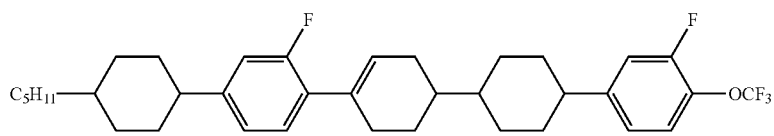 |
| 285 | 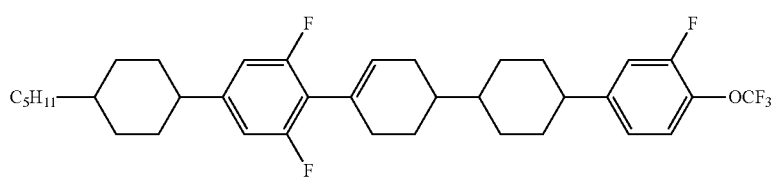 |
| 286 | 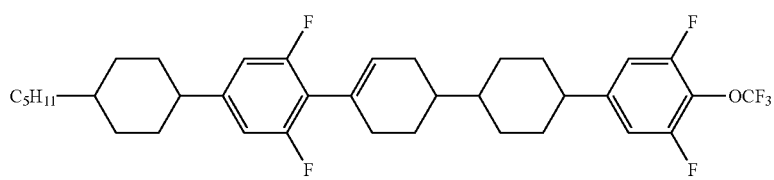 |
| 287 | 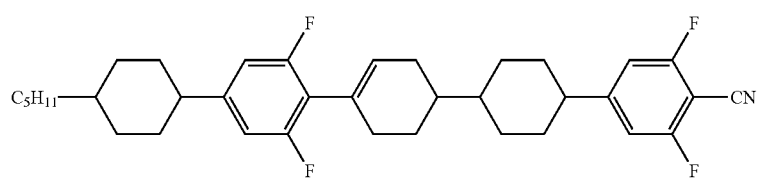 |
| 288 | 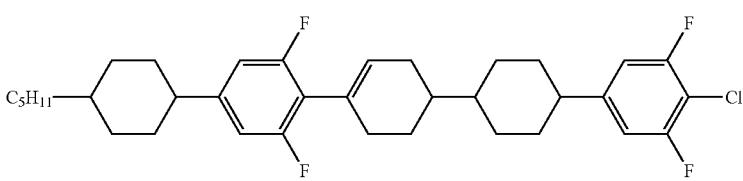 |

-continued
| No. |
|---|
289
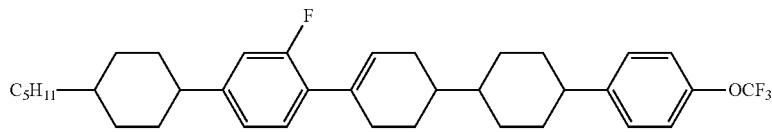
290
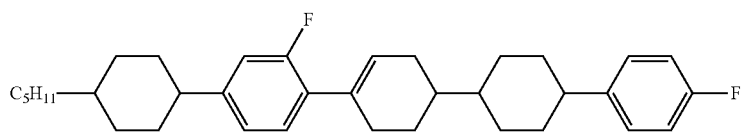
291
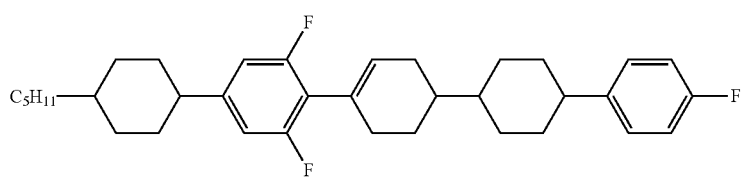
292
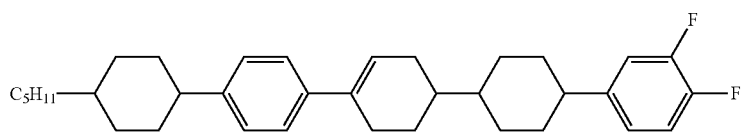
293
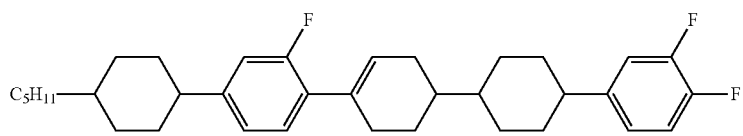
C 78.2 $S_B$ 171.1 $S_A$ 189.6 N 330.7 I
$T_{NI}$; 238.4° C., Δ ϵ; 5.80, Δ n; 0.164
294
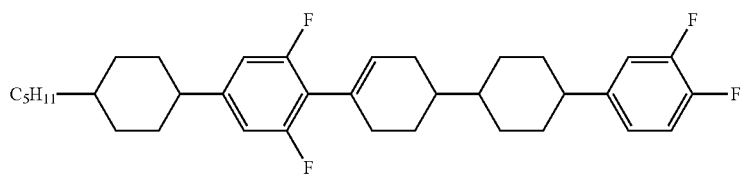
C 118.5 $S_B$ 129.0 N 318.0 I
$T_{NI}$; 210.7° C., Δ ϵ; 12.1, Δ n; 0.157
295
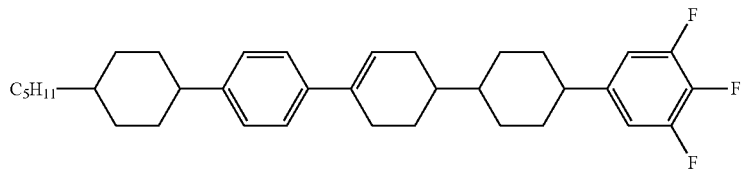

-continued
| No. | |
|---|---|
| 296 | 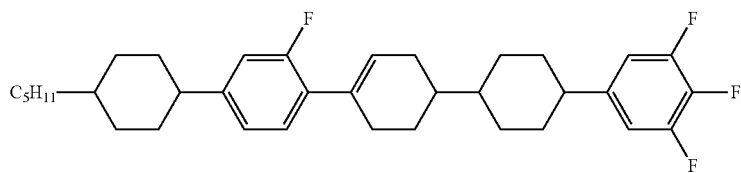 |
C 120.2 S$_B$ 127.7 S$_A$ 152.2 N 303.0 I
T$_{NI}$; 219.7° C., Δ ε; 9.13, Δ n; 0.150
| 297 | 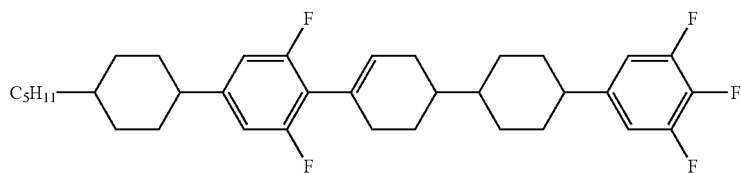 |
C 109.9 S$_B$ 126.8 S$_A$ 132.0 N 307.3 I
T$_{NI}$; 193.7° C., Δ ε; 18.1, Δ n; 0.147
| 298 | 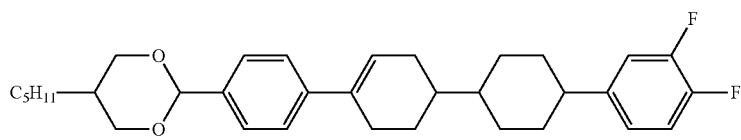 |
| 299 | 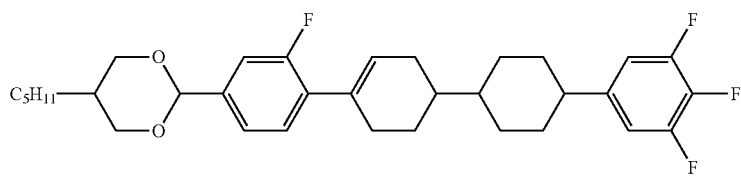 |
| 300 | 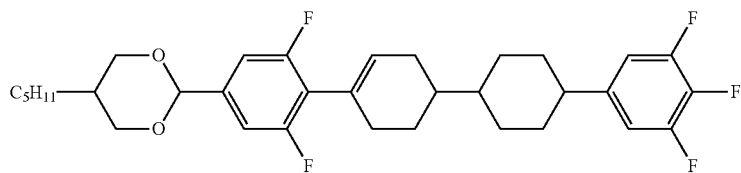 |
| 301 | 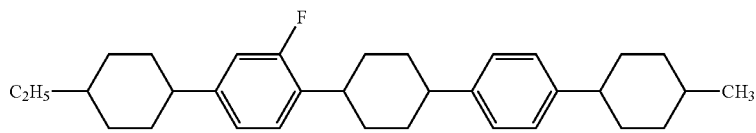 |
| 302 | 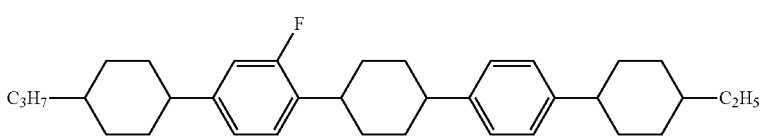 |
| 303 | 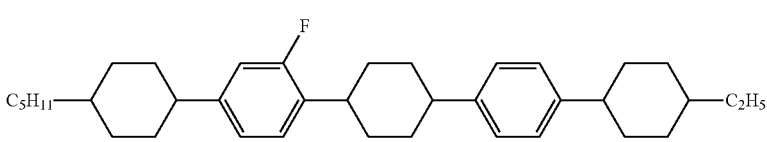 |
| 304 | 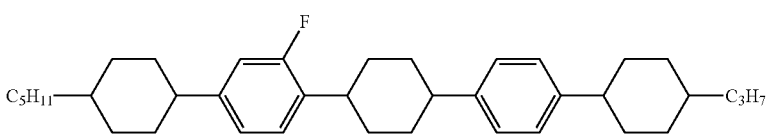 |

-continued
| No. | |
|---|---|
| 305 | 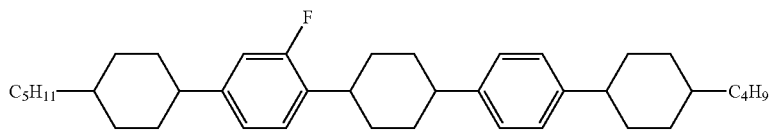 |
| 306 | 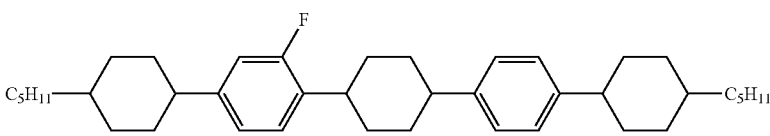 |
| 307 | 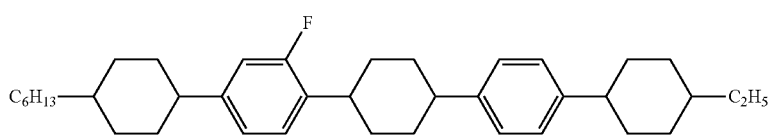 |
| 308 | 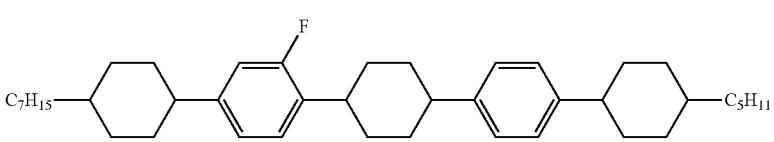 |
| 309 | 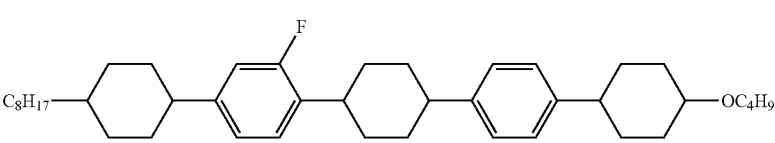 |
| 310 | 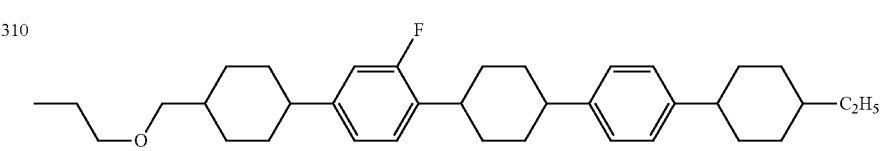 |
| 311 | 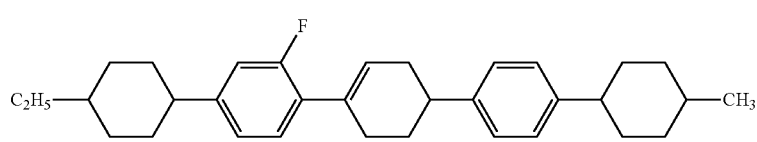 |
| 312 | 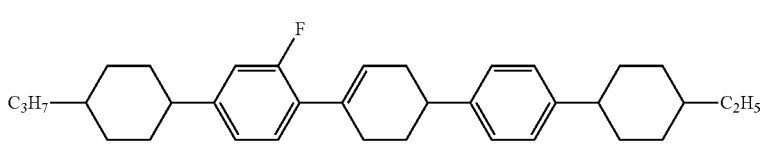 |
| 313 | 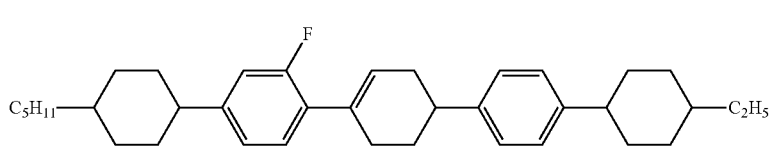 |
| 314 | 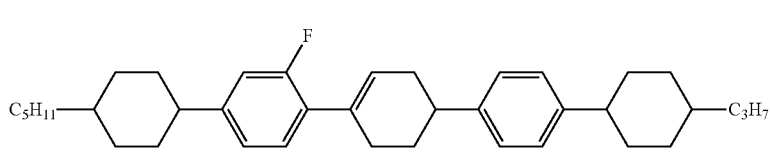 |
| 315 | 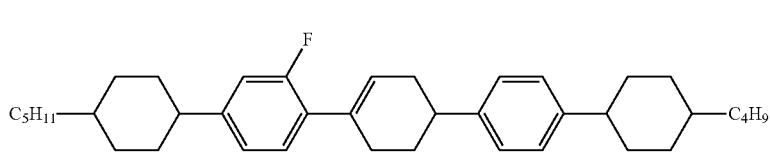 |

-continued
| No. | |
|---|---|
| 316 | 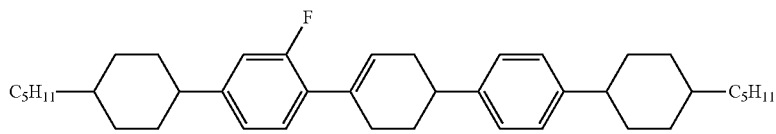 |
| 317 | 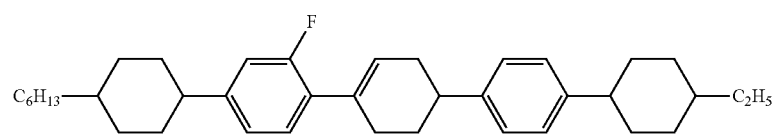 |
| 318 | 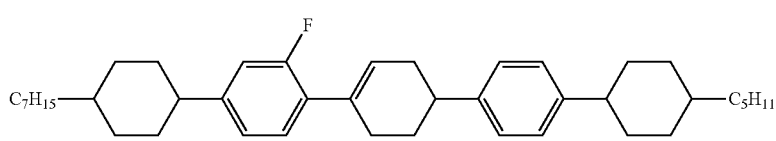 |
| 319 | 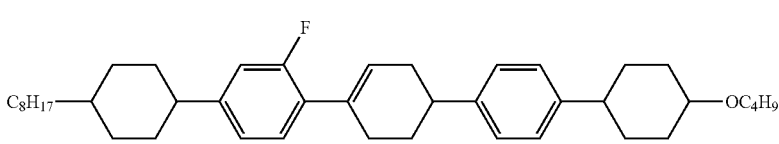 |
| 320 | 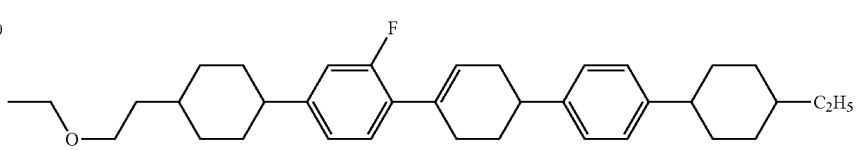 |
| 321 | 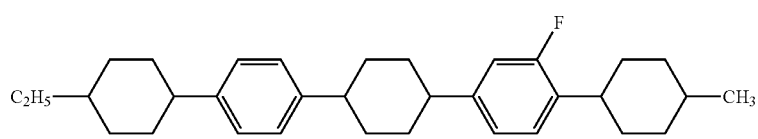 |
| 322 | 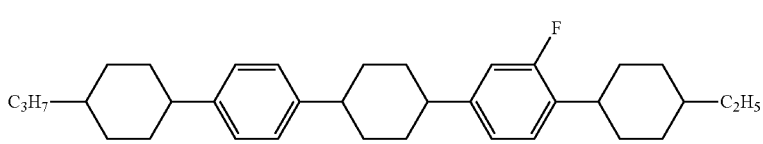 |
| 323 | 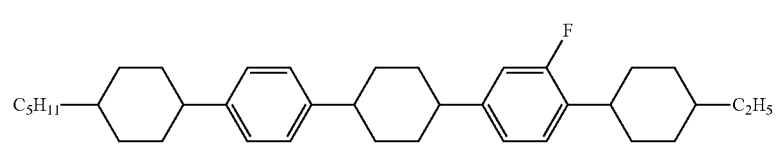 |
| 324 | 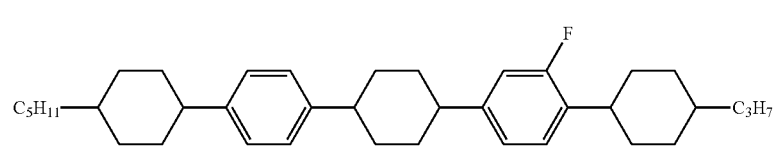 |
| 325 | 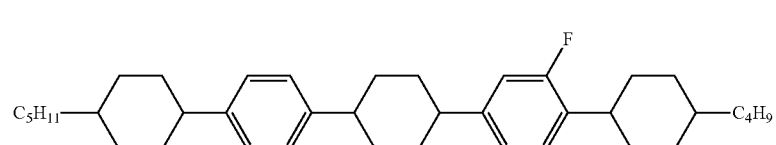 |
| 326 | 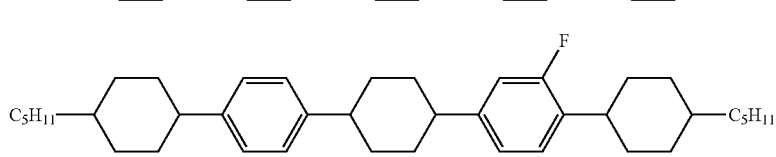 |

-continued
| No. | |
|---|---|
| 327 | 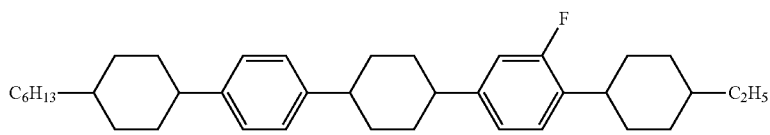 |
| 328 | 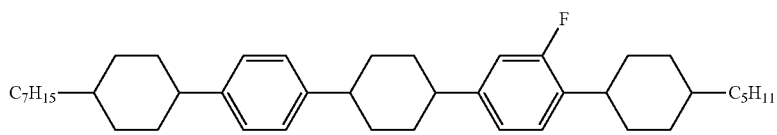 |
| 329 | 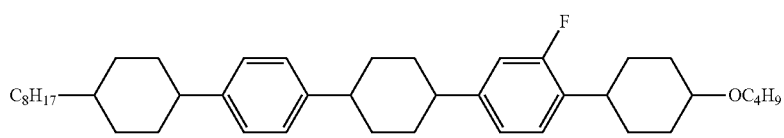 |
| 330 | 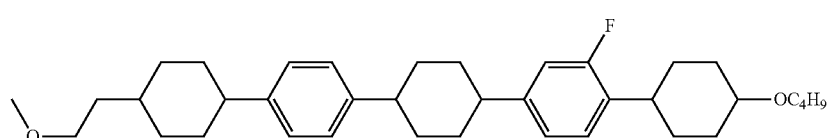 |
| 331 | 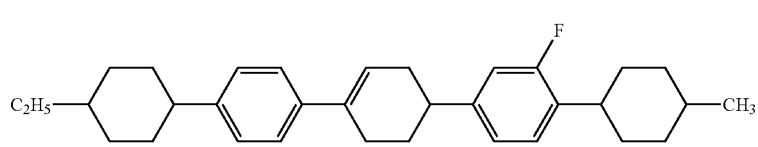 |
| 332 | 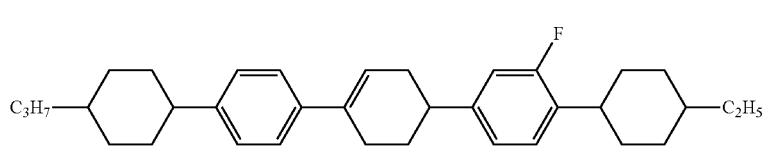 |
| 333 | 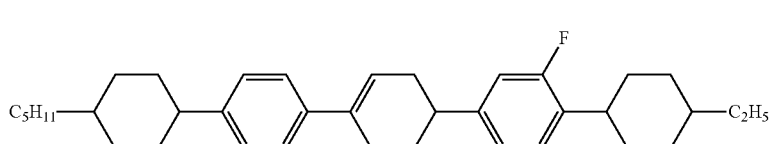 |
| 334 | 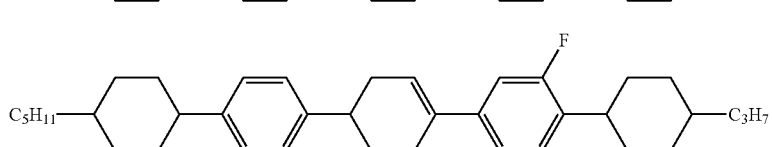 |
| 335 | 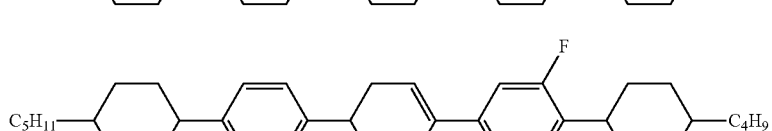 |
| 336 | 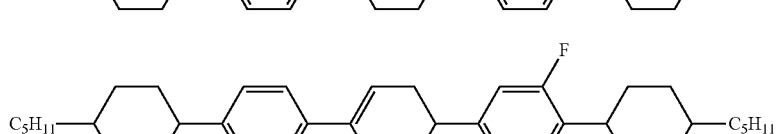 |
| 337 | 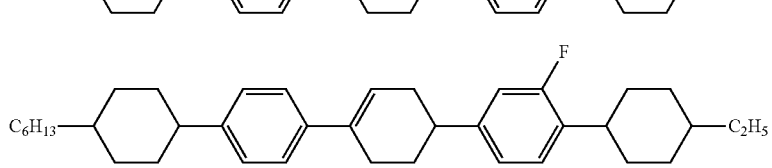 |

-continued
| No. |
|---|
| 338 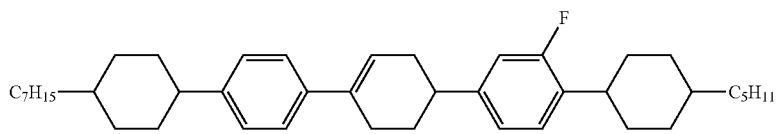 |
| 339 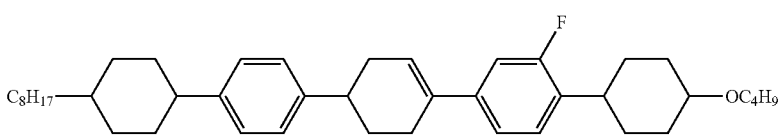 |
| 340 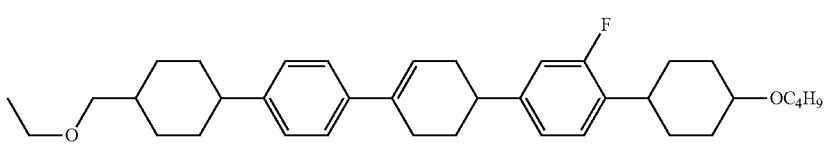 |
| 341 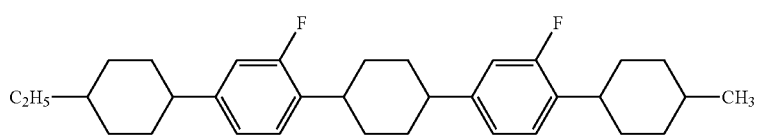 |
| 342 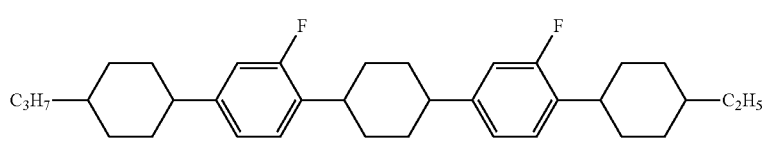 |
| 343 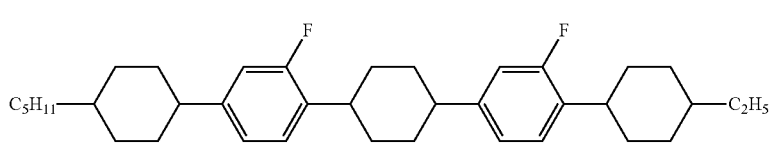 |
| 344 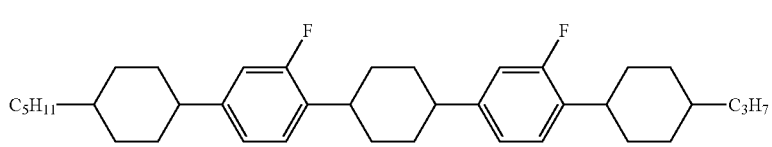 |
| 345 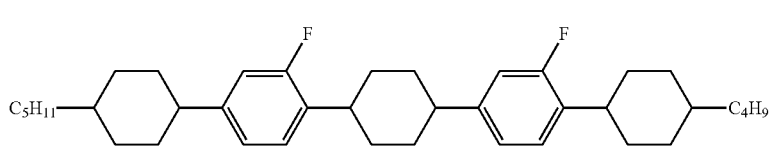 |
| 346 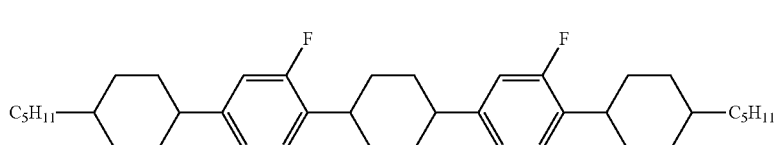 |
| 347 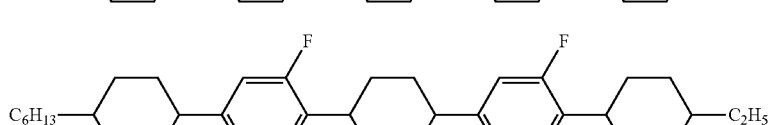 |
| 348 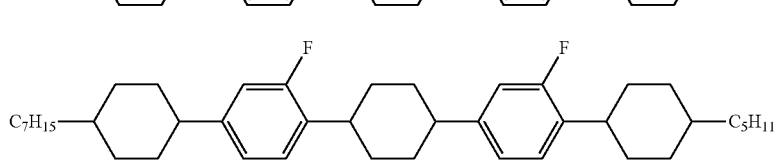 |

-continued
| No. | |
|---|---|
| 349 | 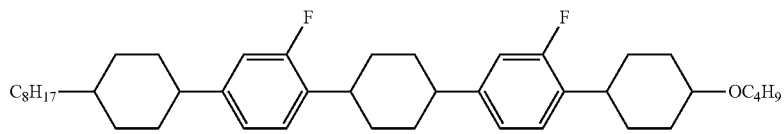 |
| 350 | 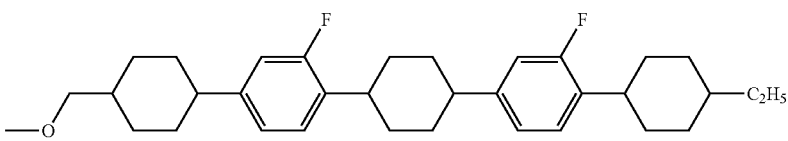 |
| 351 | 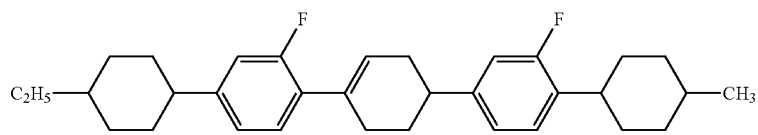 |
| 352 | 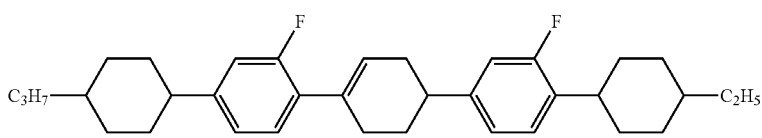 |
| 353 | 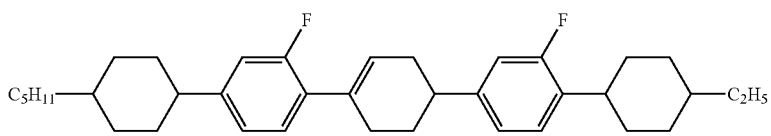 |
| 354 | 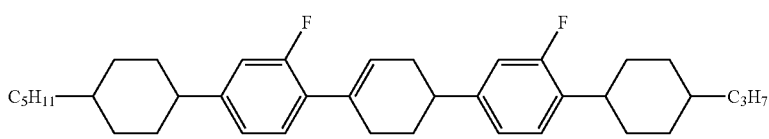 |
| 355 | 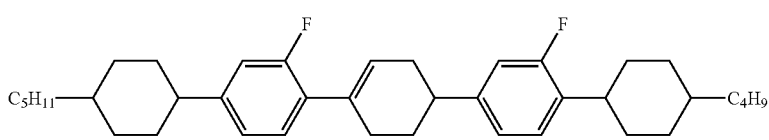 |
| 356 | 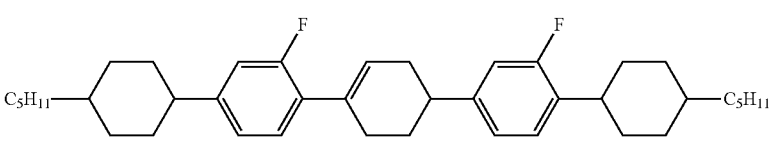 |
| 357 | 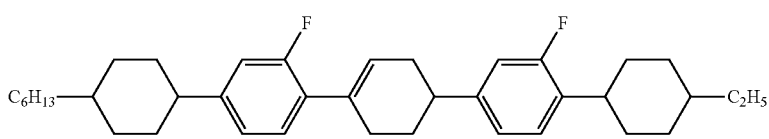 |
| 358 | 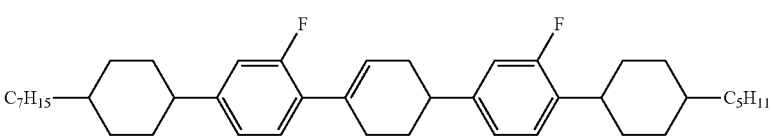 |
| 359 | 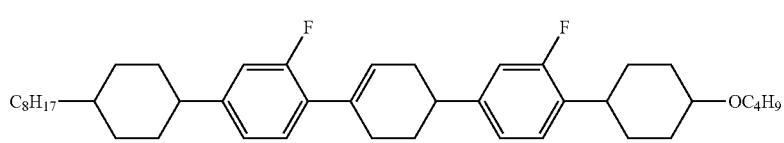 |

-continued
| No. |
|---|
| 360 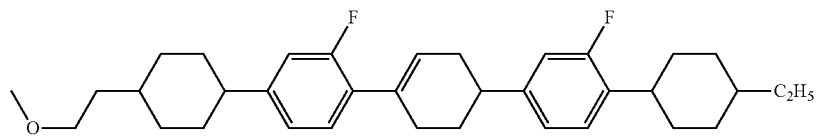 |
| 361 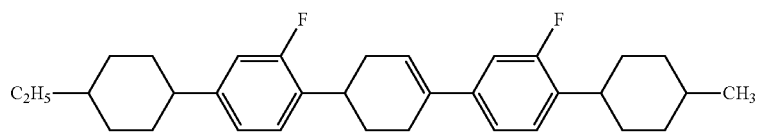 |
| 362 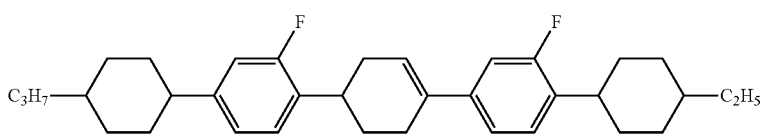 |
| 363 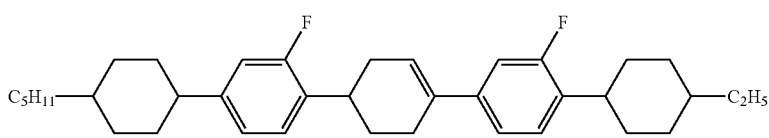 |
| 364 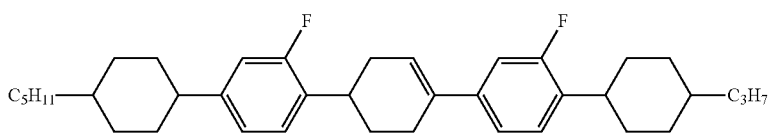 |
| 365 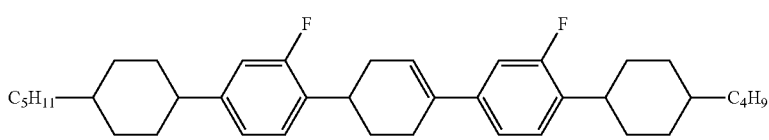 |
| 366 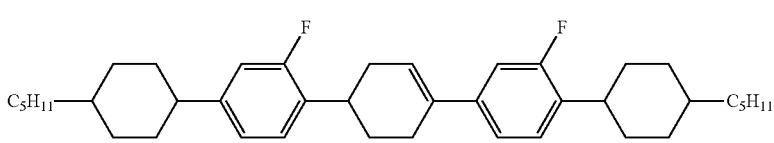 |
| 367 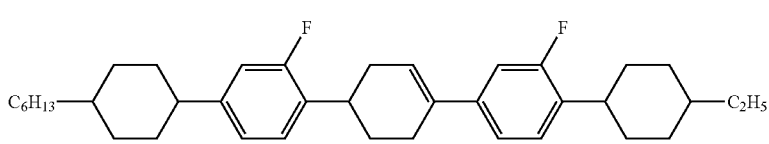 |
| 368 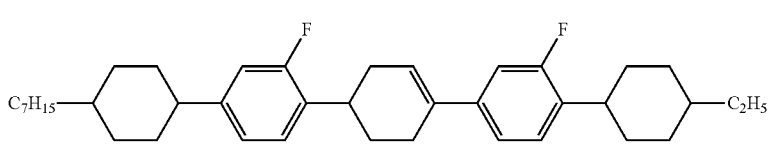 |
| 369 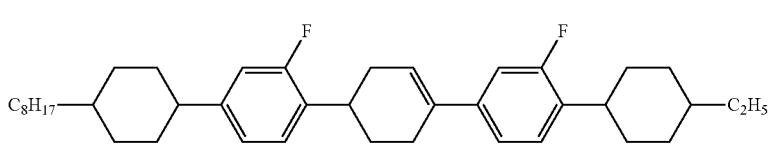 |
| 370 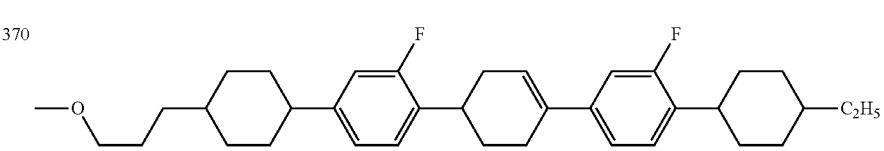 |

-continued
| No. | |
|---|---|
| 371 | 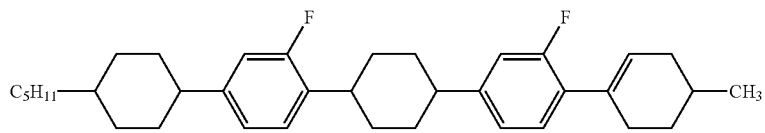 |
| 372 | 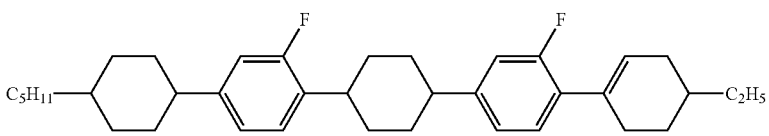 |
| 373 | 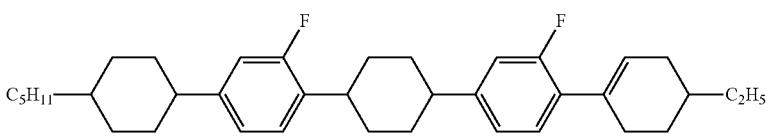 |
| 374 | 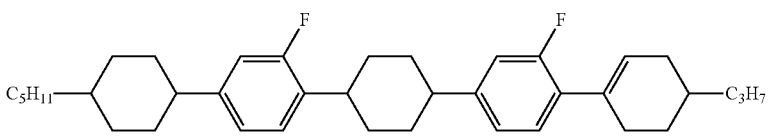 |
| 375 | 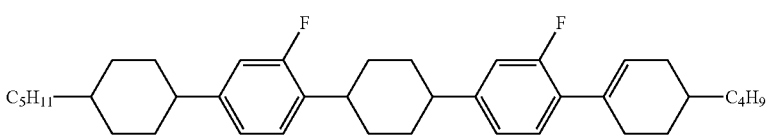 |
| 376 | 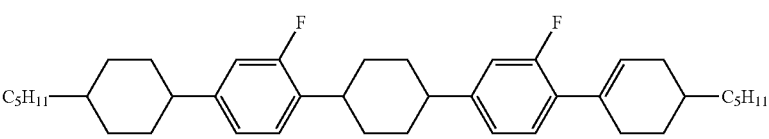 |
| 377 | 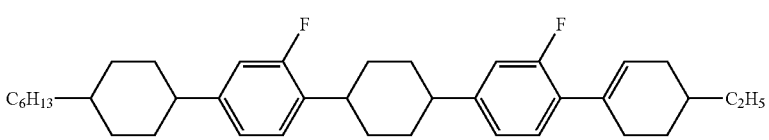 |
| 378 | 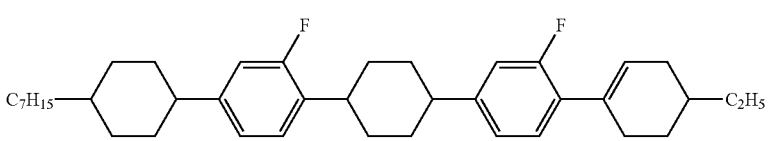 |
| 379 | 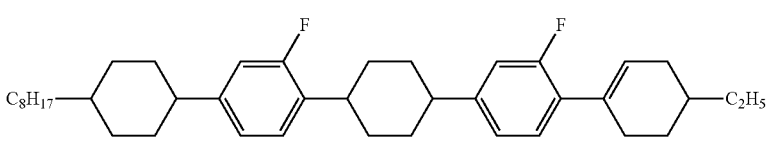 |
| 380 | 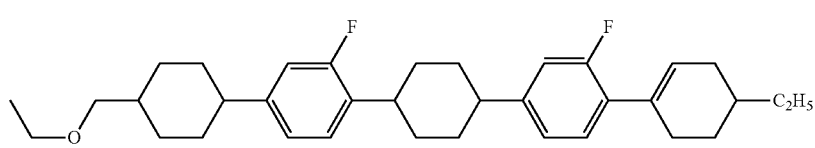 |

Comparative Example 1

4'-(trans-4-Propylcyclohexyl)-2-fluoro-4-(trans-4-pentyl cyclohexyl)biphenyl (A) was prepared as a comparative example.

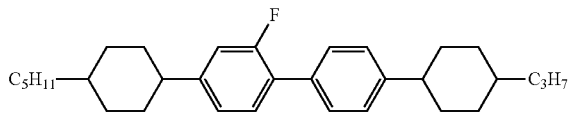

(A)

The chemical shift (δ; ppm) in $^1$H-NMR analysis was described below, and the resulting compound was identified as 4'-(trans-4-propylcyclohexyl)-2-fluoro-4-(trans-4-pentylcyclohexyl)biphenyl (A). The solvent for measurement was CDCl$_3$.

Chemical shift (δ ppm): 7.46 (d, 2H), 7.33 (t, 1H), 7.26 (d, 2H), 7.03 (d, 1H), 6.98 (d, 1H), 2.50 (m, 2H), 1.90 (m, 8H), 1.54-1.40 (m, 4H), 1.37-1.20 (m, 14H), 1.12-1.01 (m, 4H) and 0.90-0.79 (m, 6H).

The transition temperature of the compound (A) was as follows. Transition temperature: C 60.2 S$_X$ 76.2 S$_X$ 114.3 S$_X$ 138.3 N 290.4 I.

The mother liquid crystals (i) having a nematic phase were prepared by mixing four compounds, which were described above as the mother liquid crystals (i). The physical properties of the mother liquid crystals (i) were as follows. Maximum temperature (T$_{NI}$)=71.7° C.; viscosity (η$_{20}$)=26.9 mPa·s; optical anisotropy (Δn)=0.137; dielectric anisotropy (Δ∈)=11.0.

The liquid crystal composition (ii) consisting of 85% by weight of the mother liquid crystals (i) and 15% by weight of 4'-(trans-4-ethylcyclohexyl)-2-fluoro-4-(trans-4-pentylcyclohexyl)biphenyl (A) synthesized was prepared. The physical property values of the resulting liquid crystal composition (ii) were measured, and the extrapolated values of physical properties of the comparative compound (A) were calculated by extrapolating the measured values. The values were as follows. Maximum temperature (T$_{NI}$)=225.7° C.; dielectric anisotropy (Δ∈)=2.00. The elastic constant K$_{33}$ of the liquid crystal composition (ii) was 27.26 pN.

Example 8

Physical Properties of the Liquid Crystal Compound (No. 33)

The liquid crystal composition (iii) consisting of 85% by weight of the mother liquid crystals (i) and 15% by weight of trans-4-(4-(4-(4-ethylphenyl)cyclohex-1-enyl)-3-fluorophenyl)-4'-pentylbicyclohexane (No. 33) obtained in Example 6 was prepared. The physical property values of the resulting the liquid crystal composition (iii), and the extrapolated values of physical properties of the liquid crystal compound (No. 32) were calculated by extrapolating the measured values. The values were as follows. Maximum temperature (T$_{N1}$)= 245.7° C.; optical anisotropy (Δn)=0.141; dielectric anisotropy (Δ∈)=2.47. The elastic constant K$_{33}$ of the liquid crystal composition (iii) was 29.83 pN.

From these findings, it was found that the liquid crystal compound (No. 32) had a high maximum temperature (T$_{NI}$), a large elastic constant (K$_{33}$) and a large dielectric anisotropy (Δ∈).

It was also found that the compound had a high maximum temperature (T$_{NI}$), a large elastic constant (K$_{33}$), a large dielectric anisotropy (Δ∈) and a low melting point in comparison with Comparative compound (A).

Comparative Example 2 trans-4-(3-Fluoro-4-(trans-4-pentylcyclohexyl)phenyl)-trans-4'-ethylbicyclohexane (E), which is similar to the compound (D), was prepared as a comparative example.

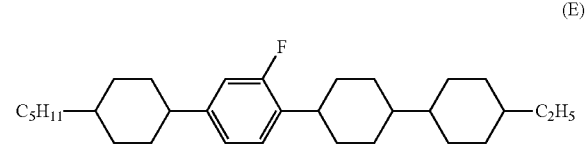

(E)

The chemical shift (δ; ppm) in $^1$H-NMR analysis was described below, and the resulting compound was identified as trans-4-(3-fluoro-4-(trans-4-pentylcyclohexyl)phenyl)-trans-4'-ethyl bicyclohexane (E). The solvent for measurement was CDCl$_3$.

Chemical shift (δ ppm): 7.11 (dd, 1H), 6.91 (dd, 1H), 6.84 (dd, 1H), 2.75 (m, 1H), 2.41 (m, 1H), 1.89-1.73 (m, 12H), 1.46-0.95 (m, 24H) and 0.90-0.84 (m, 8H).

The transition temperature of the compound (E) was as follows. Transition temperature: S 42.4 S$_B$ 206.2 N 273.8 I.

The liquid crystal composition (iv) consisting of 85% by weight of the mother liquid crystals (i) and 15% by weight trans-4-(3-fluoro-4-(trans-4-pentylcyclohexyl)phenyl)-trans-4'-ethylbicyclohexane (E) synthesized was prepared. The physical property values of the resulting liquid crystal composition (iv) were measured, and the extrapolated values of physical properties of the comparative compound (E) were calculated by extrapolating the measured values. The values were as follows. Maximum temperature (T$_{NI}$)=203.0° C.; optical anisotropy (Δn)=0.104; dielectric anisotropy (Δ∈)=0.77.

Example 9

Physical Properties of the Liquid Crystal Compound (No. 3)

The liquid crystal composition (v) consisting of 90% by weight of the mother liquid crystals (i) and 10% by weight of trans-4-(4-(4-(trans-4-ethylcyclohexyl)cyclohexyl)-3-fluorophenyl)-4'-pentylbicyclohexane (No. 3) obtained in Example 4 was prepared. The physical property values of the resulting liquid crystal composition (v) were measured, and the extrapolated values of physical properties of the liquid crystal compound (No. 3) were calculated by extrapolating the measured values. The values were as follows. Maximum temperature (T$_{N1}$)=251.7° C.; optical anisotropy (Δn)=0.109; dielectric anisotropy (Δ∈)=1.74.

From these findings, it was found that the liquid crystal compound (No. 3) had a high maximum temperature (T$_{NI}$), a large optical anisotropy (Δn) and a large dielectric anisotropy (Δ∈).

It was also found that the compound had a high maximum temperature (T$_{NI}$) and a large dielectric anisotropy (Δ∈) in comparison with Comparative compound (E).

Examples of the Liquid Crystal Composition

Hereinafter, the liquid crystal compositions of the invention will be explained in detail by way of examples. Liquid crystal compounds used in the examples are expressed by symbols according to the notations in the Table below. In the Table, 1,4-cyclohexylene has a trans-configuration. The ratio (percentage) of each compound means a weight percentage (% by weight) based on the total weight of the liquid crystal composition, unless otherwise indicated. The values of characteristics of the liquid crystal composition obtained are shown in the last part of each example.

A number described next to the name of a liquid crystal compound in each example corresponds to the formula number of the liquid crystal compound of the invention or of the liquid crystal compound used for the liquid crystal composition of the invention, those of which are described above. When only the symbol "-" is given instead of the formula number, it means another compound, which is different from these liquid crystal compounds.

The notations using symbols for compounds are shown below.

TABLE 1

Method of Description of Compounds using Symbols
R—(A$_1$)—Z$_1$—...—Z$_n$—(A$_n$)—R'

| | Symbol |
|---|---|
| 1) Left-terminal Group R— | |
| $C_nH_{2n+1}$— | n- |
| $C_nH_{2n+1}O$— | nO— |
| $C_nH_{2m+1}OC_nH_{2n}$— | mOn- |
| $CH_2$=CH— | V— |
| $C_nH_{2n+1}$—CH=CH— | nV— |
| $CH_2$=CH—$C_nH_{2n}$ | Vn- |
| $C_nH_{2m+1}$—CH=CH—$C_nH_{2n}$ | mVn- |
| $CF_2$=CH— | VFF— |
| $CF_2$=CH—$C_nH_{2n}$— | VFFn- |
| 2) Right-terminal Group —R' | |
| —$C_nH_{2n+1}$ | -n |
| —$OC_nH_{2n+1}$ | —On |
| —CH=$CH_2$ | —V |
| —$C_nH_{2n}$—CH=$CH_2$ | -nV |
| —$C_mH_{2m}$—CH=CH—$C_nH_{2n+1}$ | -mVn |
| —CH=$CF_2$ | —VFF |
| —$COOCH_3$ | —EMe |
| —F | —F |
| —Cl | —CL |
| —CN | —C |
| —$CF_3$ | —CF3 |
| —$OCF_3$ | —OCF3 |
| —$OCF_2H$ | —OCF2H |
| 3) Bonding Group —Z$_n$— | |
| —$C_nH_{2n}$— | n |
| —COO— | E |
| —CH=CH— | V |
| —$CH_2O$— | 1O |
| —$OCH_2$— | O1 |
| —$CF_2O$— | X |
| —C≡C— | T |
| 4) Ring Structure —A$_n$— | |
|  | B |
| 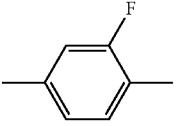 | B(F) |
| 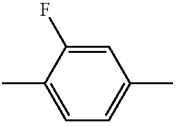 | B(2F) |
| 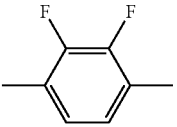 | B(2F,3F) |

TABLE 1-continued
Method of Description of Compounds using Symbols
R—(A₁)—Z₁—...—Zₙ—(Aₙ)—R'
| Structure | Symbol |
|---|---|
| 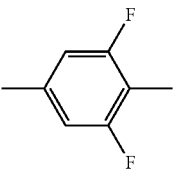 | B(F,F) |
| 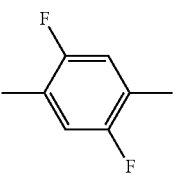 | B(2F,5F) |
| 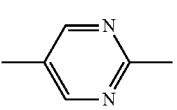 | Py |
|  | H |
|  | Ch |
| 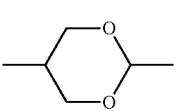 | G |
5) Examples of Description
Example 1. 5-HB(F)ChHB-2
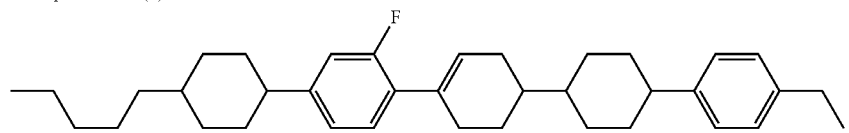
Example 2. 5-HB(F)HHB(F)—F
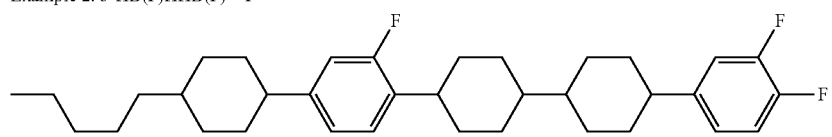
Example 3. 5-HBB(F)B-3
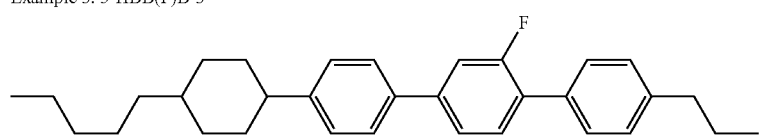
Example 4. 3-HH-4
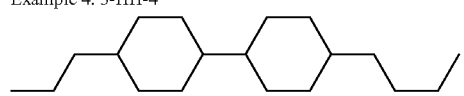

The values of characteristics were measured according to the following methods. Most were methods described in the Standard of Electronic Industries Association of Japan, EIAJ•ED-2521A, or the modified methods.

(1) Maximum Temperature of a Nematic Phase (NI; °C.)

A sample was placed on a hot plate in a melting point apparatus equipped with a polarizing microscope and was heated at the rate of 1° C. per minute. The temperature was measured when part of the sample began to change from a nematic phase to an isotropic liquid. A higher limit of the temperature range of a nematic phase may be abbreviated to "the maximum temperature."

(2) Minimum Temperature of a Nematic Phase (TC; °C.)

A sample having a nematic phase was in freezers at temperatures of 0° C., −10° C., −20° C., −30° C. and −40° C. for 10 days, and then the liquid crystal phases were observed. For example, when the sample maintained the nematic phase at −20° C. and changed to crystals or a smectic phase at −30° C., TC was expressed as ≦−20° C. A lower limit of the temperature range of a nematic phase may be abbreviated to "the minimum temperature."

(3) Optical Anisotropy (ΔN; Measured at 25° C.)

Measurement was carried out by use of an Abbe refractometer with a polarizing plate mounted on the ocular, using light at a wavelength of 589 nanometers. The surface of the main prism was rubbed in one direction, and then a sample was dropped on the main prism. The refractive index (n∥) was measured when the direction of polarized light was parallel to that of the rubbing. The refractive index (n⊥) was measured when the direction of polarized light was perpendicular to that of the rubbing. The value of optical anisotropy was calculated from the equation: Δn=n∥−n⊥.

(4) Viscosity (η Measured at 20° C.; mPa·s)

An E-type viscometer was used for measurement.

(5) Dielectric Anisotropy (Δ∈; Measured at 25° C.)

An ethanol (20 mL) solution of octadecyltriethoxysilane (0.16 mL) was applied to well-washed glass substrates. The glass substrates were rotated with a spinner, and then heated at 150° C. for 1 hour. A VA device in which the distance (cell gap) was 20 micrometers was assembled from the two glass substrates.

A polyimide alignment film was prepared on glass substrates in a similar manner. After a rubbing-treatment to the alignment film obtained on the glass substrates, a TN device in which the distance between the two glass substrates was 9 micrometers and the twist angle was 80 degrees was assembled.

A sample (a liquid crystal composition, or a mixture of a liquid crystal compound and mother liquid crystals) was put in the VA device obtained, a voltage of 0.5 V (1 kHz, sine waves) was applied to the sample, and then the dielectric constant (∈∥) in the major axis direction of the liquid crystal molecules was measured.

The sample (the liquid crystal composition or the mixture of the liquid crystal compound and the mother liquid crystals) was put in the TN device obtained, a voltage of 0.5 V (1 kHz, sine waves) was applied to the sample, and then the dielectric constant (∈⊥) in the minor axis direction of the liquid crystal molecules was measured.

The value of the dielectric anisotropy was calculated from the equation: Δ∈=∈∥−∈⊥.

A composition in which this value is negative has negative dielectric anisotropy.

(6) Voltage Holding Ratio (VHR; Measured at 25° C. and 100° C.; %)

A TN device was prepared by putting a sample in a cell having a polyimide alignment film, where the distance between the two glass substrates (cell gap) was 6 micrometers. The TN device was charged at 25° C. by applying pulse voltage (60 microseconds at 5V). The waveforms of the voltage applied to the TN device were observed with a cathode ray oscilloscope and the area between the voltage curve and the axis of abscissa in a unit period (16.7 milliseconds) was measured. An area was similarly measured based on the waveform of the applied voltage after the TN device had been removed. The value of the voltage holding ratio (%) was calculated from the value of (voltage holding ratio)=(value of the area in the presence of a TN device)/(value of the area in the absence of a TN device)×100.

The voltage holding ratio thus obtained was referred to as "VHR-1." Then, the TN device was heated at 100° C. for 250 hours. After the TN device had been allowed to return to 25° C., the voltage holding ratio was measured by a method similar to that described above. The voltage holding ratio obtained after the heating test was referred to as "VHR-2." The heating test means an acceleration test and was used as a test corresponding to a long-term durability test for the TN device.

Example 10

| | | |
|---|---|---|
| 5-HB(F)ChHB-2 | (No. 213) | 5% |
| 5-HB(F)HHB-2 | (No. 203) | 3% |
| 2-BEB(F)—C | (5-14) | 5% |
| 3-BEB(F)—C | (5-14) | 4% |
| 4-BEB(F)—C | (5-14) | 12% |
| 1V2-BEB(F, F)—C | (5-15) | 16% |
| 3-HB—O2 | (6-5) | 10% |
| 3-HH-4 | (6-1) | 3% |
| 3-HHB—F | (3-1) | 3% |
| 3-HHB-1 | (7-1) | 8% |
| 3-HHB—O1 | (7-1) | 4% |
| 3-HBEB—F | (3-37) | 4% |
| 3-HHEB—F | (3-10) | 7% |
| 5-HHEB—F | (3-10) | 7% |
| 3-H2BTB-2 | (7-17) | 4% |
| 3-HB(F)TB-2 | (7-18) | 5% |

NI=95.6° C.; Δn=0.138; Δ∈=28.2; Vth=1.18 V; η=43.2 mPa·sec.

Example 11

| | | |
|---|---|---|
| 5-HHB(F)ChH-2 | (No. 13) | 4% |
| 5-HHB(F)HH-2 | (No. 3) | 4% |
| 2-HB—C | (5-1) | 5% |
| 3-HB—C | (5-1) | 12% |
| 3-HB—O2 | (6-5) | 15% |
| 2-BTB-1 | (6-10) | 3% |
| 3-HHB—F | (3-1) | 4% |
| 3-HHB-1 | (7-1) | 8% |
| 3-HHB—O1 | (7-1) | 2% |
| 3-HHB-3 | (7-1) | 14% |
| 3-HHEB—F | (3-10) | 3% |
| 2-HHB(F)—F | (3-2) | 7% |
| 3-HHB(F)—F | (3-2) | 7% |
| 5-HHB(F)—F | (3-2) | 7% |
| 3-HHB(F, F)—F | (3-3) | 5% |

NI=103.2° C.; Δn=0.099; Δ∈=4.5; Vth=2.63 V; ηn=20.9 mPa·sec.

Example 12

| | | |
|---|---|---|
| 5-HB(F)ChHB(F)—F | (No. 293) | 3% |
| 5-HB(F)HHB(F)—F | (No. 273) | 3% |
| 3-BEB(F)—C | (5-14) | 8% |
| 3-HB—C | (5-1) | 8% |
| V—HB—C | (5-1) | 8% |
| 1V—HB—C | (5-1) | 8% |
| 3-HB—O2 | (6-5) | 3% |
| 3-HH-2V | (6-1) | 14% |
| 3-HH-2V1 | (6-1) | 7% |
| V2-HHB-1 | (7-1) | 15% |
| 3-HHB-1 | (7-1) | 5% |
| 3-HHEB—F | (3-10) | 7% |
| 3-H2BTB-2 | (7-17) | 6% |
| 3-H2BTB-4 | (7-17) | 5% |

NI=101.8° C.; Δn=0.127; Δ∈=8.5; Vth=2.27 V; η=20.4 mPa·sec.

The helical pitch was 61.2 μm when 0.25 part of the optically active compound (Op-5) was added to 100 parts of the preceding composition.

Example 13

| | | |
|---|---|---|
| 5-HB(F)ChHB(F, F)—F | (No. 296) | 5% |
| 5-HB(F)HHB(F, F)—F | (No. 276) | 5% |
| 5-BEB(F)—C | (5-14) | 5% |
| V—HB—C | (5-1) | 11% |
| 5-PyB—C | (5-9) | 6% |
| 4-BB-3 | (6-8) | 9% |
| 3-HH-2V | (6-1) | 10% |
| 5-HH—V | (6-1) | 11% |
| V—HHB-1 | (7-1) | 7% |
| V2-HHB-1 | (7-1) | 7% |
| 3-HHB-1 | (7-1) | 9% |
| 1V2-HBB-2 | (7-4) | 10% |
| 3-HHEBH-3 | (8-6) | 5% |

NI=100.8° C.; Δn=0.118; Δ∈=5.3; Vth=2.55 V; η=23.7 mPa·sec.

Example 14

| | | |
|---|---|---|
| 5-HHB(F)ChB-2 | (No. 33) | 5% |
| 5-HHB(F)HB-2 | (No. 23) | 3% |
| 1V2-BEB(F, F)—C | (5-15) | 3% |
| 3-HB—C | (5-1) | 13% |
| 2-BTB-1 | (6-10) | 10% |
| 5-HH—VFF | (—) | 30% |
| 3-HHB-1 | (7-1) | 4% |
| VFF—HHB-1 | (—) | 8% |
| VFF2-HHB-1 | (—) | 11% |
| 3-H2BTB-2 | (7-17) | 5% |
| 3-H2BTB-3 | (7-17) | 4% |
| 3-H2BTB-4 | (7-17) | 4% |

NI=91.2° C.; Δn=0.127; Δ∈=3.9; Vth=2.27 V; η=12.8 mPa·sec.

Example 15

| | | |
|---|---|---|
| 5-HHB(F)HB(F, F)—F | (No. 96) | 3% |
| 3-HHB(F)B(2F)H-5 | (No. 164) | 3% |
| 5-HB—CL | (2-2) | 16% |
| 3-HH-4 | (6-1) | 12% |
| 3-HH-5 | (6-1) | 4% |
| 3-HHB—F | (3-1) | 4% |
| 3-HHB—CL | (3-1) | 3% |
| 4-HHB—CL | (3-1) | 4% |
| 3-HHB(F)—F | (3-2) | 10% |
| 4-HHB(F)—F | (3-2) | 9% |
| 5-HHB(F)—F | (3-2) | 9% |
| 7-HHB(F)—F | (3-2) | 5% |
| 5-HBB(F)—F | (3-23) | 4% |
| 1O1-HBBH-5 | (8-1) | 3% |
| 3-HHBB(F, F)—F | (4-6) | 2% |
| 4-HHBB(F, F)—F | (4-6) | 3% |
| 3-HH2BB(F, F)—F | (4-15) | 3% |
| 4-HH2BB(F, F)—F | (4-15) | 3% |

NI=119.8° C.; Δn=0.094; Δ∈=3.7; Vth=2.69 V; η=20.7 mPa·sec.

Example 16

| | | |
|---|---|---|
| 5-HB(F)ChHB(F)—F | (No. 293) | 3% |
| 3-HHB(F)B(2F)H-5 | (No. 164) | 3% |
| 3-HHB(F, F)—F | (3-3) | 9% |
| 3-H2HB(F, F)—F | (3-15) | 8% |
| 4-H2HB(F, F)—F | (3-15) | 8% |
| 5-H2HB(F, F)—F | (3-15) | 8% |
| 3-HBB(F, F)—F | (3-24) | 21% |
| 5-HBB(F, F)—F | (3-24) | 20% |
| 3-H2BE(F, F)—F | (3-27) | 8% |
| 5-HHBB(F, F)—F | (4-6) | 3% |
| 5-HHEBB—F | (4-17) | 2% |
| 3-HH2BB(F, F)—F | (4-15) | 3% |
| 1O1-HBBH-5 | (8-1) | 4% |

NI=101.4° C.; Δn=0.117; Δ∈=8.9; Vth=1.84 V; η=36.5 mPa·sec.

Example 17

| | | |
|---|---|---|
| 5-HB(F)ChHB-2 | (No. 213) | 3% |
| 3-HHB(F)B(2F)H-5 | (No. 164) | 3% |
| 5-HB—F | (2-2) | 12% |
| 6-HB—F | (2-2) | 9% |
| 7-HB—F | (2-2) | 7% |
| 2-HHB—OCF3 | (3-1) | 7% |
| 3-HHB—OCF3 | (3-1) | 7% |
| 4-HHB—OCF3 | (3-1) | 7% |
| 5-HHB—OCF3 | (3-1) | 5% |
| 3-HH2B—OCF3 | (3-4) | 4% |
| 5-HH2B—OCF3 | (3-4) | 4% |
| 3-HHB(F, F)—OCF2H | (3-3) | 4% |
| 3-HHB(F, F)—OCF3 | (3-3) | 5% |
| 3-HH2B(F)—F | (3-5) | 3% |
| 3-HBB(F)—F | (3-23) | 7% |
| 5-HBB(F)—F | (3-23) | 7% |
| 5-HBBH-3 | (8-1) | 3% |
| 3-HB(F)BH-3 | (8-2) | 3% |

NI=94.6° C.; Δn=0.094; Δ∈=4.1; Vth=2.69 V; η=18.0 mPa·sec.

Example 18

| | | |
|---|---|---|
| 5-HB(F)ChHB-2 | (No. 213) | 3% |
| 5-HHB(F)ChH-2 | (No. 33) | 3% |
| 5-HB—CL | (2-2) | 8% |
| 3-HH-4 | (6-1) | 8% |
| 3-HHB-1 | (7-1) | 2% |
| 3-HHB(F, F)—F | (3-3) | 8% |
| 3-HBB(F, F)—F | (3-24) | 20% |
| 5-HBB(F, F)—F | (3-24) | 15% |
| 3-HHEB(F, F)—F | (3-12) | 10% |
| 4-HHEB(F, F)—F | (3-12) | 3% |
| 5-HHEB(F, F)—F | (3-12) | 3% |
| 2-HBEB(F, F)—F | (3-39) | 3% |
| 3-HBEB(F, F)—F | (3-39) | 5% |
| 5-HBEB(F, F)—F | (3-39) | 3% |
| 3-HHBB(F, F)—F | (4-6) | 6% |

NI=90.5° C.; Δn=0.108; Δ∈=8.6; Vth=1.73 V; η=26.6 mPa·sec.

Example 19

| | | |
|---|---|---|
| 5-HB(F)ChHB(F)—F | (No. 293) | 4% |
| 3-HHB(F)B(2F)H-5 | (No. 164) | 4% |
| 3-HB—CL | (2-2) | 3% |
| 5-HB—CL | (2-2) | 4% |
| 3-HHB—OCF3 | (3-1) | 5% |
| 3-H2HB—OCF3 | (3-13) | 5% |
| 5-H4HB—OCF3 | (3-19) | 15% |
| V-HHB(F)—F | (3-2) | 5% |
| 3-HHB(F)—F | (3-2) | 5% |
| 5-HHB(F)—F | (3-2) | 5% |
| 3-H4HB(F, F)—CF3 | (3-21) | 8% |
| 5-H4HB(F, F)—CF3 | (3-21) | 10% |
| 5-H2HB(F, F)—F | (3-15) | 5% |
| 5-H4HB(F, F)—F | (3-21) | 7% |
| 2-H2BB(F)—F | (3-26) | 5% |
| 3-H2BB(F)—F | (3-26) | 5% |
| 3-HBEB(F, F)—F | (3-39) | 5% |

NI=84.8° C.; Δn=0.102; Δ∈=8.1; Vth=2.08 V; η=30.2 mPa·sec.

Example 20

| | | |
|---|---|---|
| 5-HB(F)HHB(F)—F | (No. 273) | 5% |
| 5-HB(F)ChHB(F, F)—F | (No. 296) | 5% |
| 5-HB—CL | (2-2) | 7% |
| 7-HB(F, F)—F | (2-4) | 3% |
| 3-HH-4 | (6-1) | 10% |
| 3-HH-5 | (6-1) | 5% |
| 3-HB—O2 | (6-5) | 15% |
| 3-HHB-1 | (7-1) | 8% |
| 3-HHB—O1 | (7-1) | 5% |
| 2-HHB(F)—F | (3-2) | 7% |
| 3-HHB(F)—F | (3-2) | 7% |
| 5-HHB(F)—F | (3-2) | 7% |
| 3-HHB(F, F)—F | (3-3) | 6% |
| 3-H2HB(F, F)—F | (3-15) | 5% |
| 4-H2HB(F, F)—F | (3-15) | 5% |

NI=92.0° C.; Δn=0.081; Δ∈=2.9; Vth=2.44 V; η=24.3 mPa·sec.

Example 21

| | | |
|---|---|---|
| 5-HB(F)HHB(F, F)—F | (No. 276) | 4% |
| 5-HHB(F)ChB(F, F)—F | (No. 116) | 4% |
| 5-HB—CL | (2-2) | 3% |
| 7-HB(F)—F | (2-3) | 7% |
| 3-HH-4 | (6-1) | 9% |
| 3-HH—EMe | (6-2) | 15% |
| 3-HHEB—F | (3-10) | 8% |
| 5-HHEB—F | (3-10) | 8% |
| 3-HHEB(F, F)—F | (3-12) | 10% |
| 4-HHEB(F, F)—F | (3-12) | 5% |
| 4-HGB(F, F)—F | (3-103) | 5% |
| 5-HGB(F, F)—F | (3-103) | 6% |
| 2-H2GB(F, F)—F | (3-106) | 4% |
| 3-H2GB(F, F)—F | (3-106) | 5% |
| 5-GHB(F, F)—F | (3-109) | 7% |

NI=91.2° C.; Δn=0.070; Δ∈=6.3; Vth=1.73 V; η=27.1 mPa·sec.

Example 22

| | | |
|---|---|---|
| 5-HB(F)ChHB(F, F)—F | (No. 296) | 4% |
| 5-HHB(F)ChB(F, F)—F | (No. 116) | 3% |
| 3-HB—O2 | (6-5) | 10% |
| 5-HB—CL | (2-2) | 13% |
| 3-PyB(F)—F | (2-15) | 10% |
| 5-PyB(F)—F | (2-15) | 10% |
| 3-HBB(F, F)—F | (3-24) | 4% |
| 3-PyBB—F | (3-80) | 10% |
| 4-PyBB—F | (3-80) | 10% |
| 5-PyBB—F | (3-80) | 10% |
| 5-HBB(F)B-2 | (8-5) | 8% |
| 5-HBB(F)B-3 | (8-5) | 8% |

NI=104.1° C.; Δn=0.188; Δ∈=8.1; Vth=2.08 V; η=43.3 mPa·sec.

Example 23

| | | |
|---|---|---|
| 5-HHB(F)ChB—OCF3 | (No. 109) | 3% |
| 5-HHB(F)HB—OCF3 | (No. 89) | 3% |
| 5-HB(F, F)ChHB(F, F)—F | (No. 297) | 3% |
| 5-HB(F, F)HHB(F, F)—F | (No. 277) | 3% |
| 3-HH—V | (6-1) | 35% |
| 3-BB(F, F)XB(F, F)—F | (3-97) | 16% |
| 3-HHB-1 | (7-1) | 2% |
| 2-HBB—F | (3-22) | 3% |
| 3-HBB—F | (3-22) | 4% |
| 3-HHB—CL | (3-1) | 5% |
| 1-BB(F)B-2V | (7-6) | 6% |
| 2-BB(F)B-2V | (7-6) | 6% |
| 3-BB(F)B-2V | (7-6) | 3% |
| 2-HHB(F, F)—F | (3-3) | 4% |
| 3-HHB(F, F)—F | (3-3) | 4% |

NI=101.7° C.; Δn=0.128; Δ∈=4.9; Vth=2.30 V; η=18.1 mPa·sec.

Example 24

| | | |
|---|---|---|
| 5-HB(F, F)ChHB(F)—F | (No. 294) | 3% |
| 5-HB(F, F)HHB(F)—F | (No. 274) | 3% |
| 5-HHB(F, F)ChB(F, F)—F | (No. 117) | 3% |
| 5-HHHB(F, F)HB(F, F)—F | (No. 97) | 3% |
| 5-HB—CL | (2-2) | 7% |
| 7-HB(F, F)—F | (2-4) | 3% |
| 3-HH-4 | (6-1) | 10% |
| 3-HH-5 | (6-1) | 5% |
| 3-HB—O2 | (6-5) | 15% |
| 3-HHB-1 | (7-1) | 8% |
| 3-HHB—O1 | (7-1) | 5% |
| 2-HHB(F)—F | (3-2) | 7% |
| 3-HHB(F)—F | (3-2) | 7% |
| 5-HHB(F)—F | (3-2) | 7% |
| 3-HHB(F, F)—F | (3-3) | 6% |
| 3-H2HB(F, F)—F | (3-15) | 5% |
| 4-H2HB(F, F)—F | (3-15) | 3% |

NI=91.1° C.; Δn=0.083; Δ∈=4.0; Vth=2.03 V; η=25.3 mPa·sec.

INDUSTRIAL APPLICABILITY

The liquid crystal compound of the invention is superior in a wide temperature range of a nematic phase and a large elastic constant $K_{33}$. Furthermore, it is quite excellent in view of the fact that the dielectric anisotropy has a tendency to increase without an increase in the viscosity. The liquid crystal composition of the invention is effective for a device that needs a large optical anisotropy, since it has a large optical anisotropy.

What is claimed is:

1. A compound represented by formula (1-1):

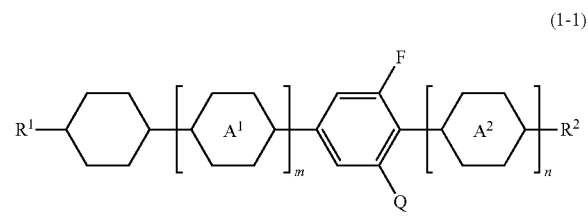

wherein $R^1$ is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons; $R^2$ is hydrogen, alkyl having 1 to 10 carbons, alkenyl having 2 to 10 carbons, alkoxy having 1 to 9 carbons, alkoxyalkyl having 2 to 9 carbons, alkenyloxy having 2 to 9 carbons, halogen, —C≡N, —SF$_5$, —CF$_3$, —CHF$_2$, —CH$_2$F, —OCF$_3$, —OCHF$_2$ or —OCH$_2$F; the ring $A^1$ and the ring $A^2$ are independently 2-fluoro-1,4-phenylene, 3-fluoro-1,4-phenylene, 3,5-difluoro-1,4-phenylene, 1,4-cyclohexenylene, tetrahydropyran-2,5-diyl, or tetrahydropyran-3,6-diyl; Q is hydrogen or fluorine; and m and n are independently 0, 1, 2 or 3, and the sum of m and n is 3, wherein arbitrary two of the ring $A^1$ may be the same or different when m is 2 or 3, and arbitrary two of the ring $A^2$ may be the same or different when n is 2 or 3.

2. A liquid crystal composition including a first component and a second component, wherein the first component is at least one compound selected from compounds according to claim 1.

3. The liquid crystal composition according to claim 2, including at least one compound selected from the group of compounds represented by formulas (2), (3) and (4), as the second component:

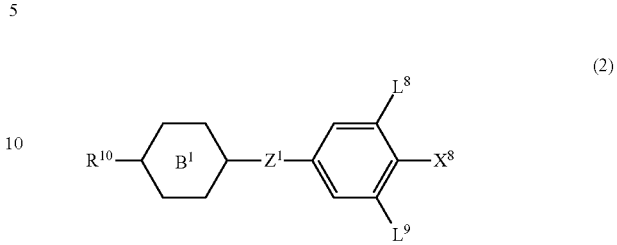

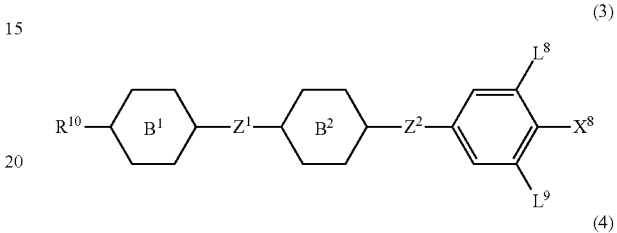

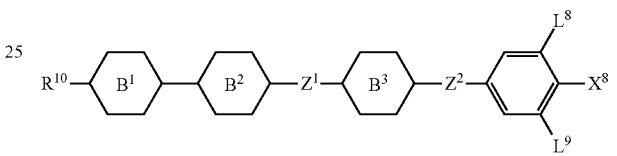

wherein $R^{10}$ is alkyl having 1 to 10 carbons or alkenyl having 2 to 10 carbons, and in the alkyl and alkenyl, arbitrary hydrogen may be replaced by fluorine and arbitrary —CH$_2$— may be replaced by —O—; $X^8$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$; the ring $B^1$, the ring $B^2$ and the ring $B^3$ are independently 1,4-cyclohexylene, 1,3-dioxane-2,5-diyl, pyrimidine-2,5-diyl, 1-tetrahydropyran-2,5-diyl, or 1,4-phenylene in which arbitrary hydrogen may be replaced by fluorine; $Z^1$ and $Z^2$ are independently —(CH$_2$)$_2$—, —(CH$_2$)$_4$—, —COO—, —CF$_2$O—, —OCF$_2$—, —CH=CH—, —C≡C—, —CH$_2$O— or a single bond; and $L^8$ and $L^9$ are independently hydrogen or fluorine; where in formula (4), the ring $B^3$ is not 1-tetrahydropyran-2,5-diyl when both the ring $B^1$ and the ring $B^2$ are 2,3-difluoro-1,4-phenylene, and the ring $B^1$ is not 1-tetrahydropyran-2,5-diyl when both the ring $B^2$ and the ring $B^3$ are 2,3-difluoro-1,4-phenylene and $Z^1$ is a single bond.

4. The liquid crystal composition according to claim 2, including at least one compound selected from the group of compounds represented by formula (5), as the second component:

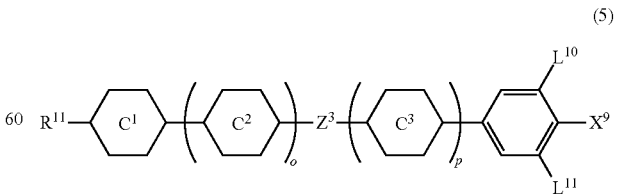

wherein $R^{11}$ is alkyl having 1 to 10 carbons or alkenyl having 2 to 10 carbons, and in the alkyl and alkenyl, arbitrary hydrogen may be replaced by fluorine and arbitrary —CH$_2$— may be replaced by —O—; X$^9$ is —C≡N or —C≡C—C≡N; the ring C$^1$, the ring C$^2$ and the ring C$^3$ are independently 1,4-cyclohexylene, 1,4-phenylene in which arbitrary hydrogen may be replaced by fluorine, 1,3-dioxane-2,5-diyl, 1-tetrahydropyran-2,5-diyl or pyrimidine-2,5-diyl; Z$^3$ is —(CH$_2$)$_2$—, —COO—, —CF$_2$O—, —OCF$_2$—, —C≡C—, —CH$_2$O— or a single bond; L$^{10}$ and L$^{11}$ are independently hydrogen or fluorine; and o is 0, 1 or 2, p is 0 or 1, and the sum of o and p is 2 or less.

5. The liquid crystal composition according to claim 2, including at least one compound selected from the group of compounds represented by formulas (6), (7) and (8), as the second component:

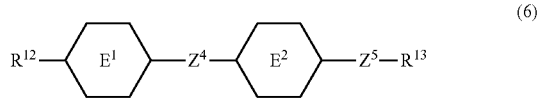

(6)

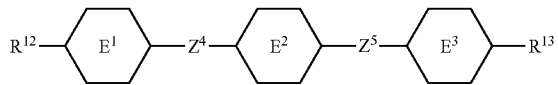

(7)

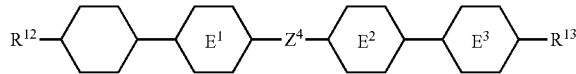

(8)

wherein R$^{12}$ and R$^{13}$ are independently alkyl having 1 to 10 carbons or alkenyl having 2 to 10 carbons, and in the alkyl and alkenyl, arbitrary —CH$_2$— may be replaced by —O—; the ring E$^1$, the ring E$^2$ and the ring E$^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and Z$^4$ and Z$^5$ are independently —C≡C—, —COO—, —(CH$_2$)$_2$—, —CH=CH— or a single bond.

6. The liquid crystal composition according to claim 2, further including at least one optically active compound and/or at least one polymerizable compound.

7. The liquid crystal composition according to claim 2, further including at least one antioxidant and/or at least one ultraviolet light absorber.

8. A liquid crystal display device containing the liquid crystal composition according to claim 2.

* * * * *